US011845791B2

(12) United States Patent
Dobson et al.

(10) Patent No.: US 11,845,791 B2
(45) Date of Patent: Dec. 19, 2023

(54) ANTIBODIES DIRECTED AGAINST GDF-15

(71) Applicant: MedImmune, LLC, Gaithersburg, MD (US)

(72) Inventors: Claire Dobson, Cambridge (GB); Fiona Cusdin, Cambridge (GB); Darren Schofield, Cambridge (GB); Peter Cariuk, Cambridge (GB); Elaine Hurt, Gaithersburg, MD (US); Margareta Ek, Södertälje (SE); Carina Johansson, Södertälje (SE); Jenny Sandmark, Södertälje (SE)

(73) Assignee: MEDIMMUNE, LLC, Gaithersburg, MD (US)

( * ) Notice: Subject to any disclaimer, the term of this patent is extended or adjusted under 35 U.S.C. 154(b) by 0 days.

(21) Appl. No.: 17/653,681

(22) Filed: Mar. 7, 2022

(65) Prior Publication Data

US 2022/0281965 A1 Sep. 8, 2022

Related U.S. Application Data

(60) Provisional application No. 63/158,274, filed on Mar. 8, 2021.

(51) Int. Cl.

| | |
|---|---|
| ***C07K 16/22*** | (2006.01) |
| ***A61P 35/00*** | (2006.01) |
| ***A61P 21/00*** | (2006.01) |
| ***A61K 39/00*** | (2006.01) |

(52) U.S. Cl.

CPC .............. *C07K 16/22* (2013.01); *A61P 21/00* (2018.01); *A61P 35/00* (2018.01); *A61K 2039/505* (2013.01); *C07K 2317/24* (2013.01); *C07K 2317/34* (2013.01); *C07K 2317/565* (2013.01); *C07K 2317/74* (2013.01); *C07K 2317/76* (2013.01); *C07K 2317/92* (2013.01)

(58) Field of Classification Search

CPC C07K 16/22; C07K 2317/24; C07K 2317/34; C07K 2317/565; C07K 2317/74; C07K 2317/76; C07K 2317/92; A61K 2039/505

See application file for complete search history.

(56) References Cited

U.S. PATENT DOCUMENTS

2021/0061916 A1* 3/2021 Reilly ................ C07K 16/2866

FOREIGN PATENT DOCUMENTS

| | | | | |
|---|---|---|---|---|
| WO | 2008/119567 A2 | | 10/2008 | |
| WO | WO-2008119565 A2 | * | 10/2008 | .............. A61P 31/00 |
| WO | 2014/100689 A1 | | 6/2014 | |
| WO | 2016/028672 A1 | | 2/2016 | |
| WO | WO-2016028672 A1 | * | 2/2016 | ........... A61K 39/395 |
| WO | WO-2021016128 A1 | * | 1/2021 | ............. A61K 45/06 |

* cited by examiner

*Primary Examiner* — Jeffrey Stucker
*Assistant Examiner* — Laura Ann Essex

(57) ABSTRACT

The present disclosure is directed to human GDF-15-binding antibodies and antigen-binding fragments thereof. The antibodies and fragments can be used, for example, to detect human GDF-15 and/or in methods of treating cancer or body weight loss, including cachexia, associated with over-expression of human GDF-15.

9 Claims, 25 Drawing Sheets

Specification includes a Sequence Listing.

A.

Protected regions

GDF15 sequence ARNGDHCPLGPGRCCRLHTVRASLEDLGWADWVLSPREVQVTMCIGACPSQFRAANMHAQIKTSLHRLKPDTVPAPCCVPASYNPMVLIQKTDTGVSLQTYDDLLAKDCHCI Peptide coverage Weak protection Strong protection Medium/strong protection 5 10 15 20 25 30 35 40 45 50 55 60 65 70 75 80 85 90 95 100 105 110

Missing regions
GDF15 sequence
Peptide coverage
Weak protection
Strong protection
Medium/strong protection

FIG. 21

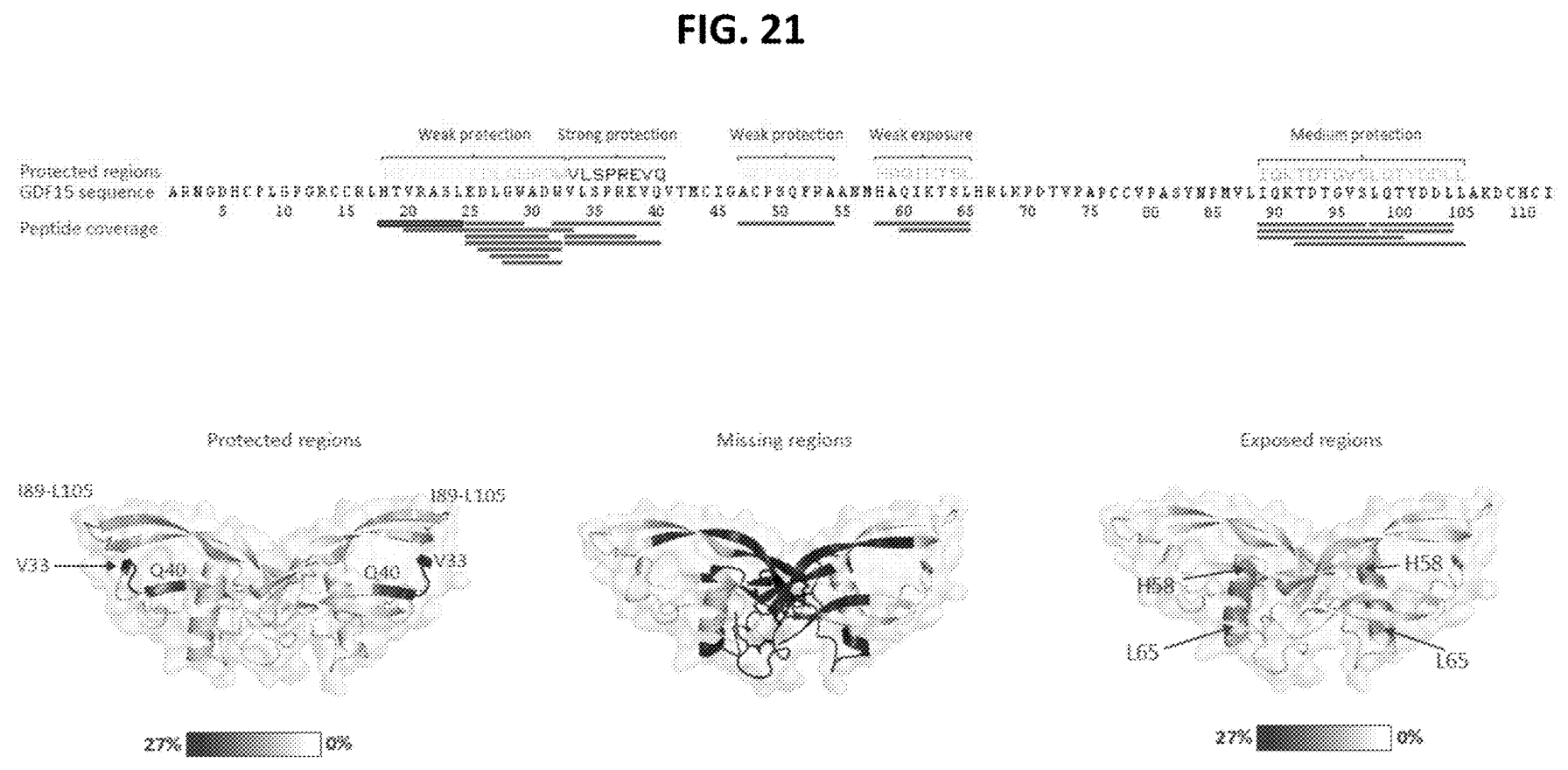

Protected regions
GDF15 sequence
Peptide coverage

Weak protection
Strong protection
VLSPREVQ
Weak protection
Weak exposure
Medium protection Protected regions
I89-L105
V33
Q40
27%
0%

Missing regions

Exposed regions
H58
L65
27%
0%

Protected regions
GDF15 sequence
Peptide coverage
Weak protection
Strong protection
Weak exposure
Medium/strong protection
Protected regions
Missing regions
Exposed regions
I89-L104
V33
Q40
H58
L65
23%
0%

ANTIBODIES DIRECTED AGAINST GDF-15

CROSS-REFERENCE RELATED APPLICATION

This application claims priority to U.S. Provisional Patent Application 63/158,274, filed on Mar. 8, 2021, which is hereby incorporated by reference in its entirety.

REFERENCE TO A SEQUENCE LISTING SUBMITTED ELECTRONICALLY VIA EFS-WEB

The content of the electronically submitted sequence listing (Name: GDF15-100-US-NP_Seqlisting_ST25; Size: 195,622 bytes; and Date of Creation: Mar. 2, 2022) is incorporated herein by reference in its entirety.

BACKGROUND

Growth/differentiation factor 15 (GDF-15; also known as macrophage inhibitory cytokine (MIC-1), NSAID-activated gene 1 protein (NAG-1), NSAID-regulated gene 1 protein (NRG-1), placental TGF-beta, placental bone morphogenetic protein, and prostate differentiation factor) is a secreted, homodimeric protein of the TGFβ superfamily. GDF-15 is known to have functional roles in inflammation, pregnancy, and body weight regulation. In healthy tissue, GDF-15 expression is highest in placenta and prostate epithelium. However, GDF-15 is also expressed in many solid malignancies, and expression has been associated with poor patient prognosis in several cancers.

There remains a significant need for antibodies useful for treating cancer. The present disclosure provides such anti-GDF-15 antibodies.

BRIEF SUMMARY

Provided herein are antibodies or antigen-binding fragments thereof that specifically bind to human GDF-15. In some aspects, an antibody or antigen-binding fragment thereof that specifically binds to human GDF-15 comprises a variable heavy chain (VH) complementarity determining region (CDR) 1, a VH CDR2, a VH CDR3, a variable light chain (VL) CDR1, a VL CDR2, and a VL CDR3, wherein the VH CDR1, VH CDR2, VH CDR3, VL CDR1, VL CDR2, and VL CDR3 comprise sequences selected from the group consisting of: (a) SEQ ID NOs:3-5, 12-14, respectively; (b) SEQ ID NOs:21-23, 30-32, respectively; (c) SEQ ID NOs:39-41, 48-50, respectively; (d) SEQ ID NOs:57-59, 66-68, respectively; (e) SEQ ID NOs:75-77, 84-86, respectively; (f) SEQ ID NOs:93-95, 102-104, respectively; (g) SEQ ID NOs:111-113, 120-122, respectively; (h) SEQ ID NOs:129-131, 138-140, respectively; (i) SEQ ID NOs:147-149, 156-158, respectively; (j) SEQ ID NOs:165-167, 174-176, respectively; (k) SEQ ID NOs:183-185, 192-194, respectively; (1) SEQ ID NOs:201-203, 210-212, respectively; (m) SEQ ID NOs:219-221, 228-230, respectively; (n) SEQ ID NOs:237-239, 246-248, respectively; (o) SEQ ID NOs:255-257, 264-266, respectively; (p) SEQ ID NOs:273-275, 282-284, respectively; (q) SEQ ID NOs:291-293, 300-302, respectively; (r) SEQ ID NOs:309-311, 318-320, respectively; (s) SEQ ID NOs:327-329, 336-338, respectively; (t) SEQ ID NOs:345-347, 354-356, respectively; (u) SEQ ID NOs:363-365, 372-374, respectively; (v) SEQ ID NOs:381-383, 390-392, respectively; (w) SEQ ID NOs:399-401, 408-410, respectively; (x) SEQ ID NOs:417-419, 426-428, respectively; (y) SEQ ID NOs:435-437, 444-446, respectively; and (z) SEQ ID NOs:453-455, 462-464, respectively.

In some aspects, an antibody or antigen-binding fragment thereof that specifically binds to human GDF-15 comprises the VH CDR1, VH CDR2, VH CDR3, VL CDR1, VL CDR2, and VL CDR3 of AB1170002, AB1170006, AB1170010, AB1170019, AB1170028, AB1170036, AB1170040, AB1170043, AB1170047, AB1170069, AB1170070, AB1170072, AB1170073, AB1170074, AB1170086, AB1170148, AB1170241, AB1170242, AB1170243, AB1170244, AB1170245, AB1170246, AB1170247, AB1170248, AB1170249, or AB1520085. In some aspects, the CDRs are the Kabat-defined CDRs, the Chothia-defined CDRs, the IMGT-defined CDRs, or the AbM-defined CDRs.

In some aspects, the antibody or antigen-binding fragment thereof comprises a VH and a VL, wherein the VH comprises the amino acid sequence of SEQ ID NO:2, 20, 38, 56, 74, 92, 110, 128, 146, 164, 182, 200, 218, 236, 254, 272, 290, 308, 326, 344, 362, 380, 398, 416, 434, or 452. In some aspects, the antibody or antigen-binding fragment thereof comprises a VH and a VL, wherein the VL comprises the amino acid sequence of SEQ ID NO:11, 29, 47, 65, 83, 101, 119, 137, 155, 173, 191, 209, 227, 245, 263, 281, 299, 317, 335, 353, 371, 389, 407, 425, 443, or 461.

In some aspects, an antibody or antigen-binding fragment thereof that specifically binds to human GDF-15 comprises a VH region and a VL, wherein VH comprises the amino acid sequence of SEQ ID NO:2, 20, 38, 56, 74, 92, 110, 128, 146, 164, 182, 200, 218, 236, 254, 272, 290, 308, 326, 344, 362, 380, 398, 416, 434, or 452.

In some aspects, an antibody or antigen-binding fragment thereof that specifically binds to human GDF-15, wherein the antibody or antigen-binding fragment thereof comprises a VH and a VL, wherein the light chain variable region comprises the amino acid sequence of SEQ ID NO:11, 29, 47, 65, 83, 101, 119, 137, 155, 173, 191, 209, 227, 245, 263, 281, 299, 317, 335, 353, 371, 389, 407, 425, 443, or 461.

In some aspects, the antibody or antigen-binding fragment thereof comprises a VH and a VL, wherein the VH and VL comprise sequences selected from the group consisting of: (a) SEQ ID NOs:2 and 11, respectively; (b) SEQ ID NOs:20 and 29, respectively; (c) SEQ ID NOs:38 and 47, respectively; (d) SEQ ID NOs:56 and 65, respectively; (e) SEQ ID NOs:74 and 83, respectively; (f) SEQ ID NOs:92 and 101, respectively; (g) SEQ ID NOs:110 and 119, respectively; (h) SEQ ID NOs:128 and 137, respectively; (i) SEQ ID NOs: 146 and 155, respectively; (j) SEQ ID NOs:164 and 173, respectively; (k) SEQ ID NOs:182 and 191, respectively; (1) SEQ ID NOs:200 and 209, respectively; (m) SEQ ID NOs:218 and 227, respectively; (n) SEQ ID NOs:236 and 245, respectively; (o) SEQ ID NOs:254 and 263, respectively; (p) SEQ ID NOs:272 and 281, respectively; (q) SEQ ID NOs:290 and 299, respectively; (r) SEQ ID NOs:308 and 317, respectively; (s) SEQ ID NOs:326 and 335, respectively; (t) SEQ ID NOs:344 and 353, respectively; (u) SEQ ID NOs:362 and 371, respectively; (v) SEQ ID NOs:380 and 389, respectively; (w) SEQ ID NOs:398 and 407, respectively; (x) SEQ ID NOs:416 and 425, respectively; (y) SEQ ID NOs:434 and 443, respectively; and (z) SEQ ID NOs:452 and 461, respectively. In some aspects, the antibody or antigen-binding fragment thereof comprises a VH comprising the sequence of SEQ ID NO:326 and/or a VL comprising the sequence of SEQ ID NO:335.

In some aspects, a monoclonal antibody or antigen-binding fragment thereof that specifically binds to human GDF-15 binds to the same epitope as a reference antibody comprising a VH comprising the sequence of SEQ ID NO:326 and a VL comprising the sequence of SEQ ID NO:335. In some aspects, the epitope is determined using a hydrogen/deuterium exchange assay.

In some aspects, a monoclonal antibody or antigen-binding fragment that specifically binds to human GDF-15 competitively inhibits binding of a reference antibody to GDF-15, wherein the reference antibody comprises a VH comprising the sequence of SEQ ID NO:326 and a VL comprising the sequence of SEQ ID NO:335.

In some aspects, a monoclonal antibody or antigen-binding fragment thereof binds to an epitope of GDF-15 comprising an amino acid in amino acids E25-W32 of mature GDF-15 (SEQ ID NO:485), an amino acid in amino acids V33-Q40 of mature GDF-15 (SEQ ID NO:486), and/or an amino acid in amino acids I89-L105 of mature GDF-15 (SEQ ID NO:487).

In some aspects, a monoclonal antibody or antigen-binding fragment thereof that specifically binds to human GDF-15 inhibits the interaction of GDF-15 with GFRAL and inhibits the interaction of GDF-15 with RET.

In some aspects, the antibody or antigen-binding fragment binds to cynomolgus GDF-15. In some aspects, the antibody or antigen-binding fragment binds to mouse GDF-15. In some aspects, the antibody or antigen-binding fragment binds to cynomolgus GDF-15 and mouse GDF-15.

In some aspects, the antibody or antigen-binding fragment thereof is capable of inhibiting proliferation of cancer cells. In some aspects, the proliferation is inhibited by at least 25%, at least 50%, or at least 75% as compared to the proliferation in the absence of the antibody or antigen-binding fragment thereof. The ability of an antibody or antigen-binding fragment thereof to inhibit proliferation of cancer cells can be determined by plating cancer cells (e.g., LNCaP cells) at a density of 5000 cells/well in a 96-well plate, treating the cells with the antibody or antigen-binding fragment thereof at a concentration from 400-25 nM, incubating the cells for 3 days, and measuring the viability of the cells based on ATP, wherein less viability in the presence of the antibody or antigen-binding fragment thereof as compared to in its absence indicates the antibody or antigen-binding fragment thereof is capable of inhibiting proliferation of the cancer cells. In some aspects, the antibody or antigen-binding fragment thereof is capable of activating dendritic cells. In some aspects, the activation is doubled as compared to activation in the absence of the antibody or antigen-binding fragment thereof. The ability of an antibody or antigen-binding fragment thereof to activate dendritic cells can be determined by plating monocytes at a density of 1 million cells/mL in a 6-well plate, treating the monocytes for 6 days with 100 ng/ml IL-4 and 100 ng/mL GM-CSF, adding 15 nM CD40L and 10 μg/ml of anti-GDF15 antibody to the wells for two days, and analyzing the cells by flow cytometry for expression of CD14 and CD1a to confirm differentiation to dendritic cells as well as CD83, CD86, along with IL-12p70 secretion to measure activation, wherein increased CD83, CD86, or IL-12p70 in the presence of the antibody or antigen-binding fragment thereof as compared to in its absence indicates the antibody or antigen-binding fragment thereof is capable of activating dendritic cells.

In some aspects, the antibody or antigen-binding fragment thereof is capable of increasing the proliferation of T cells. In some aspects, the increase is at least 25%, at least 30%, at least 35%, or at least 40% as compared to the proliferation in the absence of the antibody or antigen-binding fragment thereof. The ability of an antibody or antigen-binding fragment thereof to increase the proliferation of T cells can be determined by plating isolated CD3 cells at a density of 100,000 cells/well in a 96-well plate that is coated with 10 μg/ml anti-CD3 and 10 μg/ml anti-CD28 antibody, adding antibodies at a concentration from 33.3-0.05 nM, and measuring the proliferation of the cells using Cell Titer Glo (Promega), wherein greater viability in the presence of the antibody or antigen-binding fragment thereof as compared to in its absence indicates the antibody or antigen-binding fragment thereof is capable of inhibiting the proliferation of T cells.

In some aspects, the antibody or antigen-binding fragment thereof is capable of increasing differentiation of Th1 cells. In some aspects, the increase is at least 1.5-fold or by at least 2-fold as compared to the differentiation in the absence of the antibody or antigen-binding fragment thereof. The ability of an antibody or antigen-binding fragment thereof to increase differentiation of Th1 cells can be determined by plating isolated CD4+ T-cells at a density of 250,000 cells/well in a 24-well plate coated with 10 mg/mL mouse anti-CD3 antibody, adding 10 ug/mL of the antibody or antigen-binding fragment thereof for 5 days, and analyzing culture supernatants for TNF-alpha and IFNγ secretion by ELISA, wherein increased levels of TNF-alpha and IFNγ secretion in the presence of the antibody or antigen-binding fragment thereof as compared to in its absence indicates the antibody or antigen-binding fragment thereof is capable of increasing differentiation of Th1 cells.

In some aspects, the antibody or antigen-binding fragment thereof inhibits the interaction of GDF-15 with GFRAL. In some aspects, the antibody or antigen-binding fragment thereof inhibits the interaction of GDF-15 with RET.

In some aspects, the antibody or antigen-binding fragment thereof binds to an epitope comprising an amino acid in amino acids E25-W32 of mature GDF-15 (SEQ ID NO:485), an amino acid in amino acids V33-Q40 of mature GDF-15 (SEQ ID NO:486), and/or an amino acid in amino acids I89-L105 of mature GDF-15 (SEQ ID NO:487).

In some aspects, the antibody or antigen-binding fragment comprises a heavy chain comprising a heavy chain constant domain comprising the sequence of SEQ ID NO:474. In some aspects, the antibody or antigen-binding fragment comprises a light chain comprising a light chain constant domain comprising the sequence of SEQ ID NO:475.

In some aspects, the antibody or antigen-binding fragment further comprises a heavy chain constant region. In some aspects, the heavy chain constant region is selected from the group consisting of human immunoglobulin $IgG_1$, $IgG_2$, $IgG_3$, $IgG_4$, $IgA_1$, and $IgA_2$ heavy chain constant regions. In some aspects, the heavy chain constant region is a human $IgG_1$ constant region.

In some aspects, the antibody or antigen-binding fragment further comprises a light chain constant region. In some aspects, the light chain constant region is selected from the group consisting of human immunoglobulin IgGκ and IgGλ light chain constant regions. In some aspects, the light chain constant region is a human IgGκ light chain constant region.

In some aspects, the antibody or antigen-binding fragment thereof is an IgG antibody or antigen-binding fragment thereof.

In some aspects, the antibody or antigen-binding fragment thereof comprises an Fc region that has been engineered to improve half-life. In some aspects, the antibody or antigen-binding fragment thereof comprises an Fc region with a YTE mutation. In some aspects, the antibody or antigen-binding fragment thereof comprises an Fc region with a L234F/L235E/P331S triple mutation (TM).

In some aspects, the antibody or antigen-binding fragment is a monoclonal antibody or antigen-binding fragment.

In some aspects, antibody or antigen-binding fragment is a full-length antibody. In some aspects, the antibody or antigen-binding fragment is an antigen-binding fragment. In some aspects, the antigen-binding fragment comprises a Fab, Fab', $F(ab')_2$, single chain Fv (scFv), disulfide linked Fv, intrabody, IgGΔCH2, minibody, $F(ab')_3$, tetrabody, triabody, diabody, DVD-Ig, Fcab, $mAb^2$, $(scFv)_2$, or scFv-Fc.

In some aspects, the antibody or antigen-binding fragment thereof further comprises a detectable label.

Also provided herein are isolated polynucleotides. In some aspects, an isolated polynucleotide comprises a nucleic acid molecule encoding the VH or heavy chain of an antibody or antigen-binding fragment thereof provided herein. In some aspects, an isolated polynucleotide comprises a nucleic acid molecule encoding the VL or light chain of an antibody or antigen-binding fragment thereof provided herein.

Also provided herein are vectors. In some aspects, a vector comprises a polynucleotide provided herein. In some aspects, the vector is isolated.

Also provided herein are host cells. In some aspects, a host cell comprises a polynucleotide, vector, or combination of vectors provided herein. In some aspects, the host cell is selected from the group consisting of CHO, NS0, PER-C6, HEK-293, and HeLa cells. In some aspects, the host cell is isolated.

Also provided herein are methods or producing antibodies or antigen-binding fragments thereof. In some aspects, a method of producing an antibody or antigen-binding fragment thereof comprises culturing a host cell provided herein so that the antibody or antigen-binding fragment thereof is produced. In some aspects, the method further comprises isolating the antibody or antigen-binding fragment thereof from the culture.

Also provided herein are antibodies or antigen-binding fragments thereof produced by a method provided herein.

Also provided herein are compositions. In some aspects, a composition comprises an antibody or antigen-binding fragment provided herein. In some aspects, the composition further comprises a pharmaceutically-acceptable carrier.

Also provided herein are methods of using an antibody or antigen-binding fragment thereof provided herein. In some aspects, a method of treating cancer in a subject comprises administering to the subject an antibody or antigen-binding fragment or composition provided herein. In some aspects, the cancer is colorectal cancer (CRC), gastric (stomach) cancer, hepatoma (hepatocellular carcinoma (HCC)), renal cell cancer (RCC), bladder cancer, esophageal cancer, non-small cell lung cancer (NSCLC), small cell lung cancer, breast cancer, pancreatic ductal adenocarcinoma (PDAC), or prostate cancer. In some aspects, the cancer is a GDF-15-expressing cancer.

In some aspects, a method of inhibiting the proliferation of cancer cells comprises contacting the cancer cells with an antibody or antigen-binding fragment or composition provided herein. In some aspects, the proliferation is inhibited by at least 25%, at least 50%, or at least 75% as compared to the proliferation in the absence of the antibody or antigen-binding fragment thereof. In some aspects, the cancer cells are colorectal cancer (CRC), gastric (stomach) cancer, hepatoma (hepatocellular carcinoma (HCC)), renal cell cancer (RCC), bladder cancer, esophageal cancer, non-small cell lung cancer (NSCLC), or prostate cancer cells.

In some aspects, a method of activating dendritic cells comprises contacting the dendritic cells with an antibody or antigen-binding fragment or composition provided herein. In some aspects, the antibody or antigen-binding fragment thereof doubles the activation of dendritic cells as compared to activation in the absence of the antibody or antigen-binding fragment thereof.

In some aspects, a method of increasing the proliferation of T cells comprises contacting the T cells with an antibody or antigen-binding fragment or composition provided herein. In some aspects, the antibody or antigen-binding fragment thereof increases the proliferation of T cells by at least 25%, at least 30%, at least 35%, or at least 40% as compared to proliferation in the absence of the antibody or antigen-binding fragment thereof.

In some aspects, a method of increasing the differentiation of Th1 cells comprises contacting the Th1 cells with an antibody or antigen-binding fragment or composition provided herein. In some aspects, the antibody or antigen-binding fragment increases differentiation of Th1 cells by at least 1.5-fold or by at least 2-fold.

In some aspects, a method of inhibiting the interaction of GDF-15 with RET comprises contacting the GDF-15 and/or the RET with an antibody or antigen-binding fragment or composition provided herein.

In some aspects, a method of inhibiting the interaction of GDF-15 with GFRAL comprises contacting the GDF-15 and/or the GFRAL with an antibody or antigen-binding fragment or composition provided herein.

In some aspects of methods provided herein, the contacting occurs in vitro. In some aspects of the methods provided herein, the contacting occurs in a subject. In some aspects, the subject has a cancer, optionally wherein the cancer is colorectal cancer (CRC), gastric (stomach) cancer, hepatoma (hepatocellular carcinoma (HCC)), renal cell cancer (RCC), bladder cancer, esophageal cancer, non-small cell lung cancer (NSCLC), or prostate cancer.

In some aspects, a method of treating cachexia in a subject comprises administering an antibody or antigen-binding fragment or composition provided herein.

In some aspects, a method of inhibiting loss of muscle mass associated with cachexia in a subject comprises administering an antibody or antigen-binding fragment or composition provided herein. In some aspects, the loss of muscle mass is accompanied by a loss of fat mass.

In some aspects, a method of inhibiting or reducing involuntary weight loss associated with cachexia in a subject comprises administering an antibody or antigen-binding fragment or composition provided herein.

In some aspects, a method of inhibiting loss of organ mass associated with cachexia in a subject comprises administering an antibody or antigen-binding fragment or composition provided herein. In some aspects, the organ is kidney, liver, heart, or spleen. In some aspects, the loss of organ mass is accompanied by a loss of muscle mass, a loss of fat mass or involuntary weight loss.

In some aspects, a method of increasing appetite in a subject suffering from cachexia comprises administering an antibody or antigen-binding fragment or composition provided herein.

In some aspects, a method of decreasing the incidence and/or severity of cachexia in a subject, thereby increasing the maximum tolerated dose of an anti-cancer agent capable of causing cachexia in the subject, comprises administering to the subject an antibody or antigen-binding fragment or composition provided herein.

In some aspects, the cachexia is associated with an underlying disease selected from the group consisting of cancer, chronic heart failure, chronic kidney disease, COPD, AIDS, multiple sclerosis, rheumatoid arthritis, sepsis, and tuberculosis.

In some aspects, a method of treating sarcopenia associated with cachexia in a subject comprises administering to the subject an antibody or antigen-binding fragment or composition provided herein.

In some aspects, a method for detecting human GDF-15 in a sample comprises contacting the sample with an antibody or antigen-binding fragment provided herein. In some aspects, the sample is obtained from a subject. In some aspects, the subject has cancer.

BRIEF DESCRIPTION OF THE DRAWINGS/FIGURES

Figure 4:
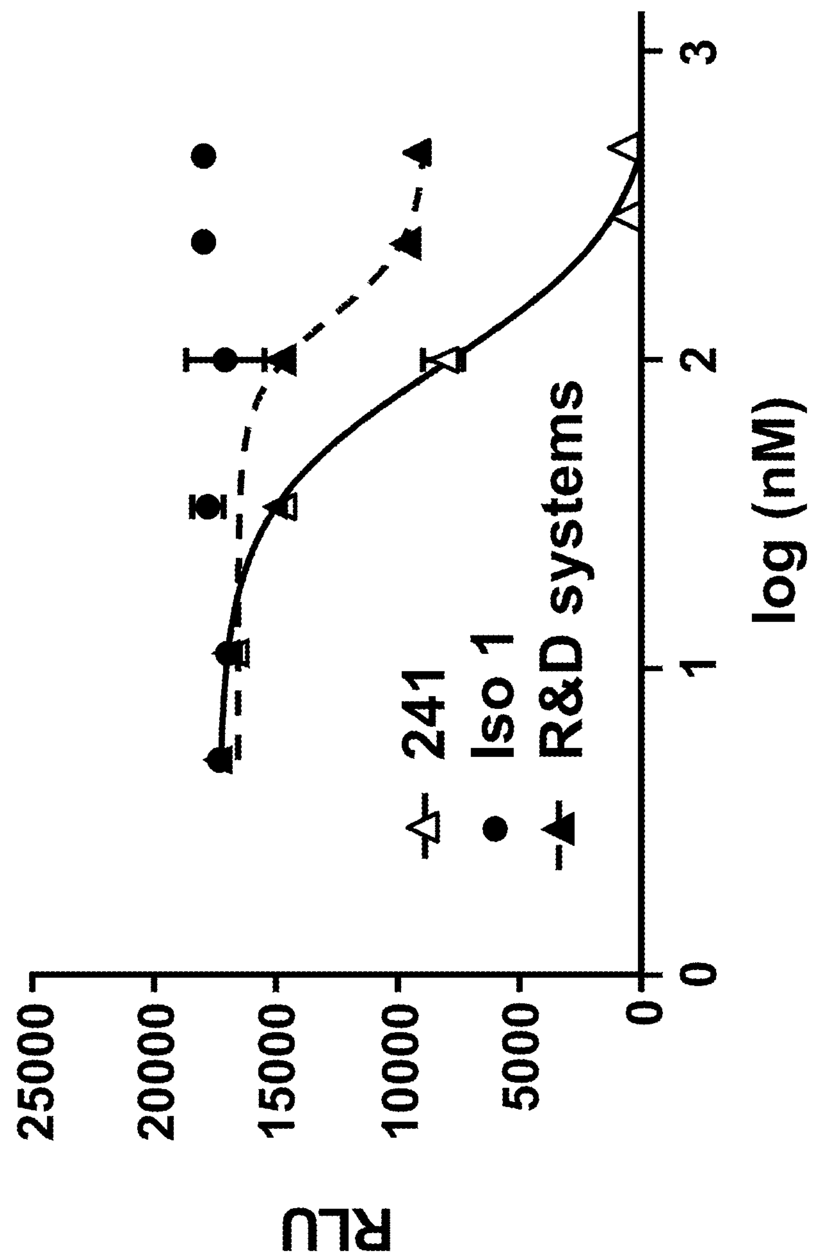

FIG. 4 shows the effect of GDF-15 antibodies on proliferation of prostate cells. "241" indicates AB1170241. R&D systems indicates control Antibody A. Iso 1 indicates a negative control antibody. (See Example 6.)

Figure 5A:
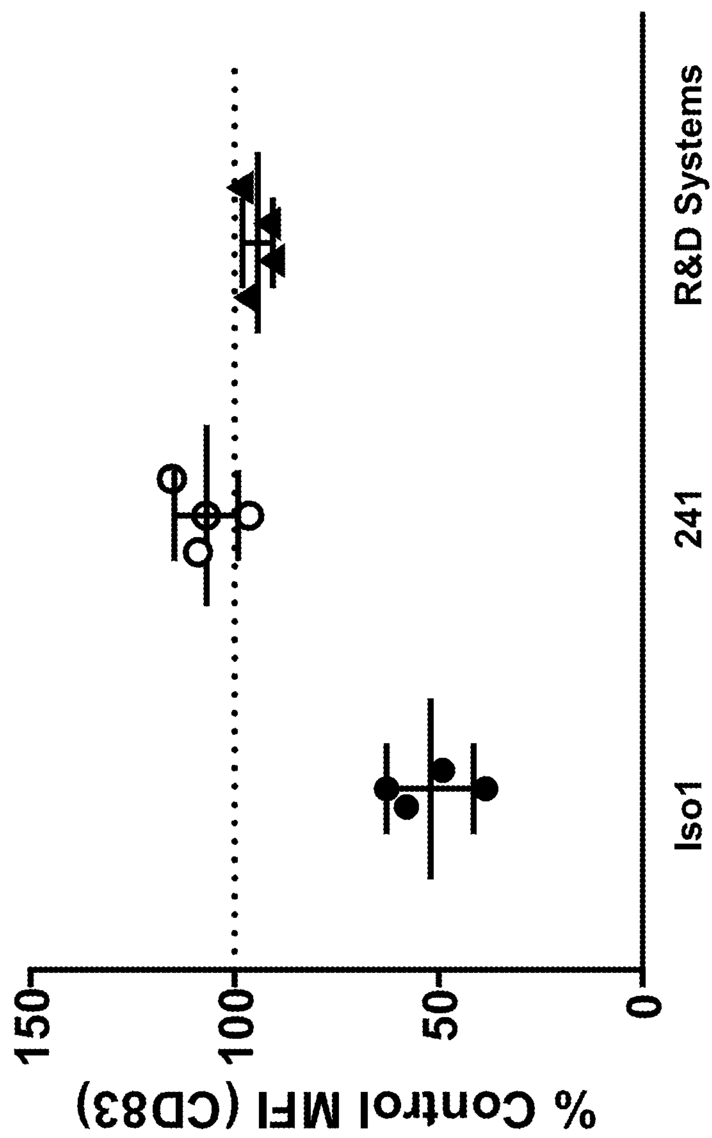
Figure 5B:
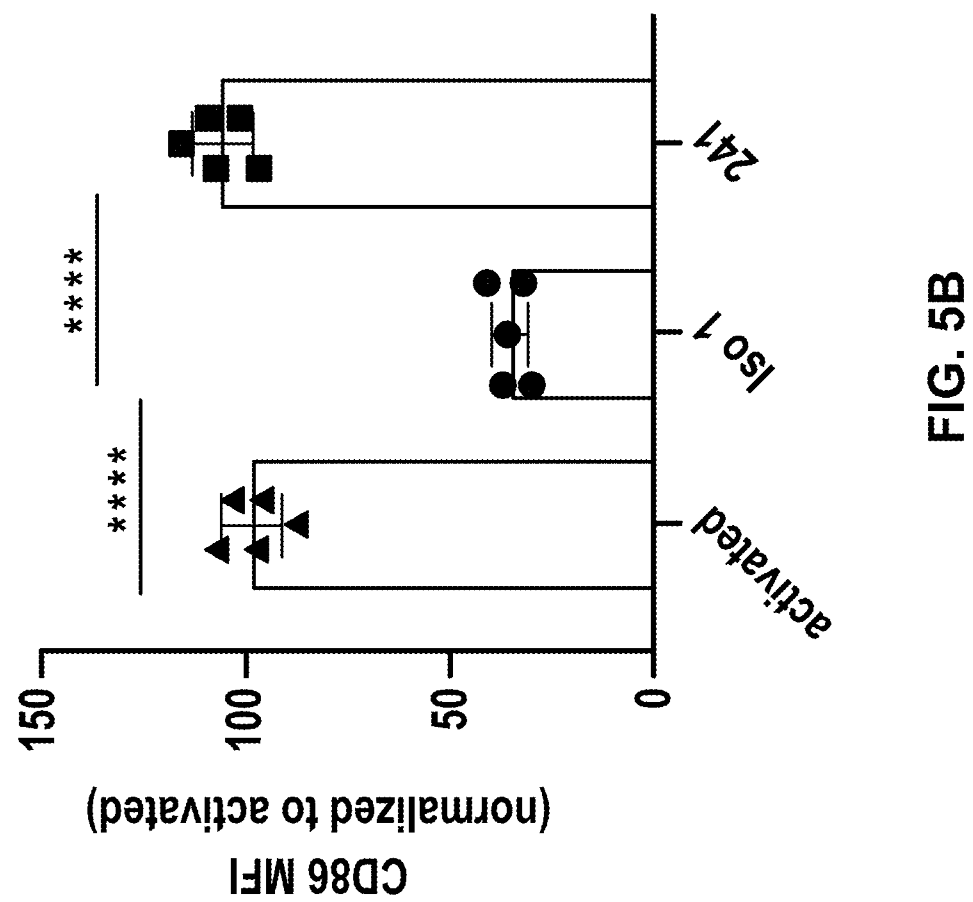
Figure 5C:
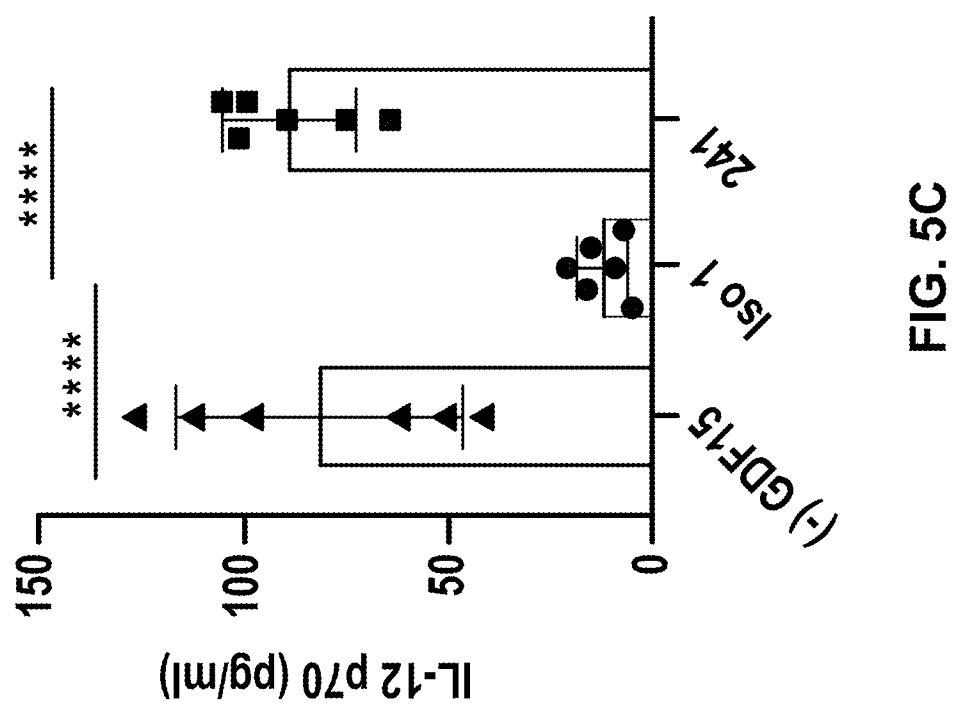

FIGS. 5A, 5B, and 5C show the effect of GDF-15 antibodies on the expression of costimulatory proteins in monocyte-derived dendritic cells. "241" indicates AB1170241. R&D systems indicates control Antibody A. Iso 1 indicates a negative control antibody. * indicates $p<0.005$, and ** indicates $p<0.001$. (See Example 7.)

Figure 6:
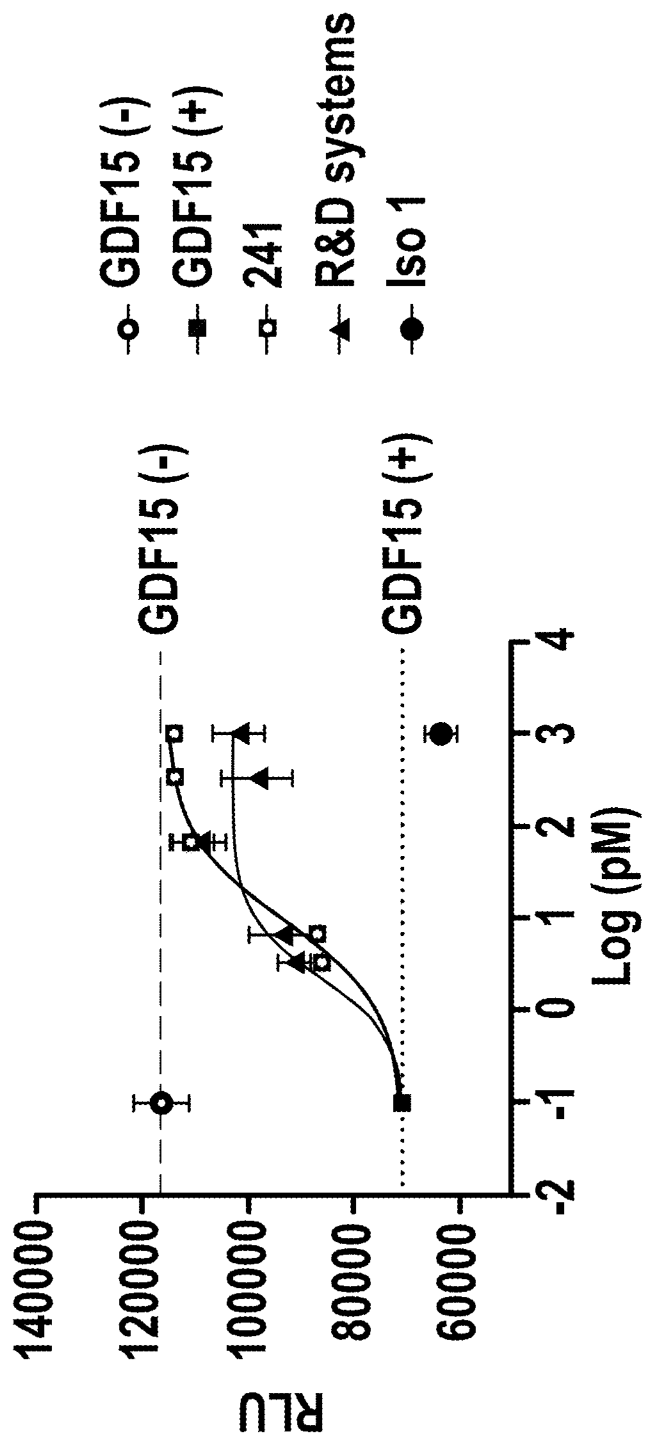

FIG. 6 shows the effect of GDF-15 antibodies on T cell proliferation. GDF15(−) shows the level of proliferation in the absence of recombinant hu-GDF15, while GDF15(+) shows the level of proliferation of T cells in the presence of recombinant hu-GDF15. "241" indicates AB1170241. (See Example 8.)

Figure 7A:
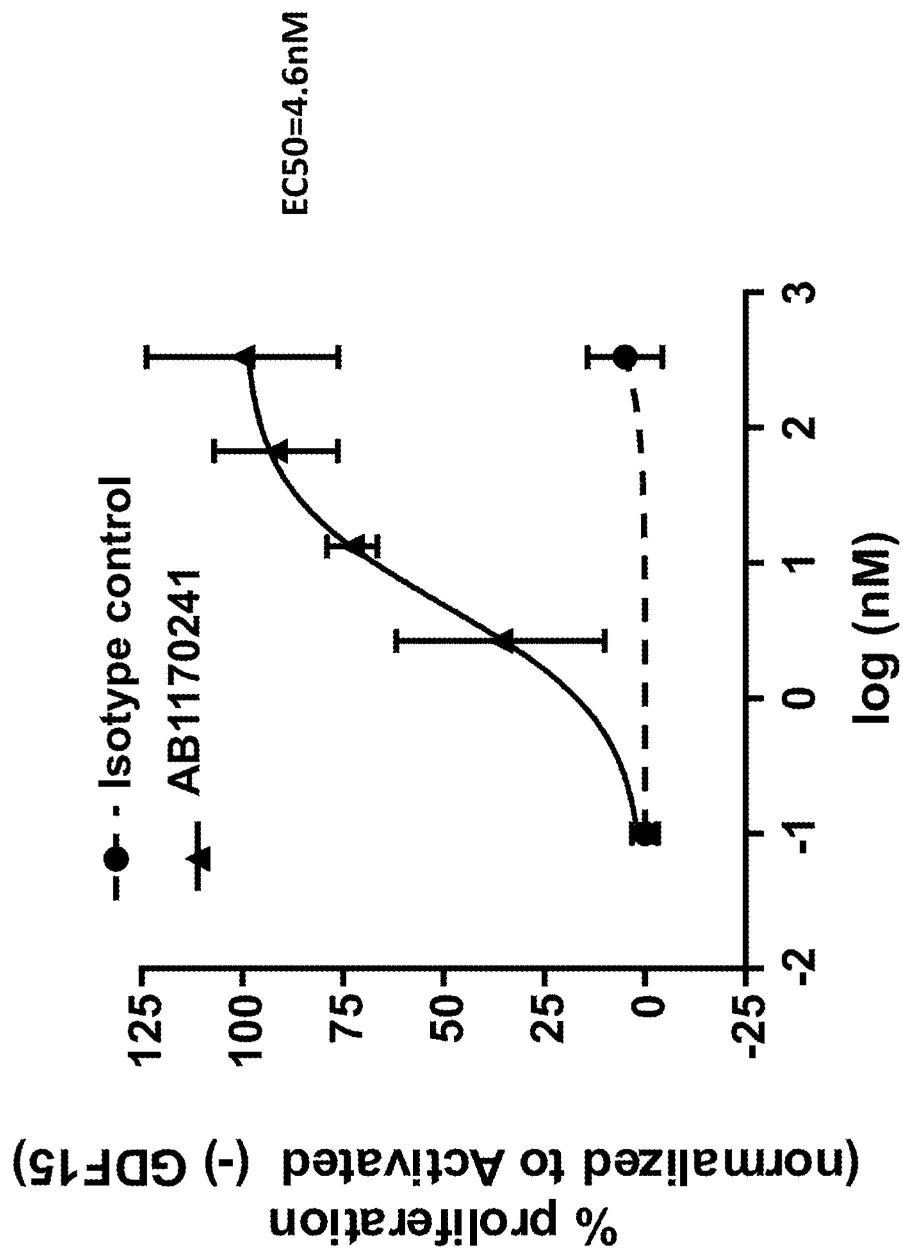
Figure 7B:
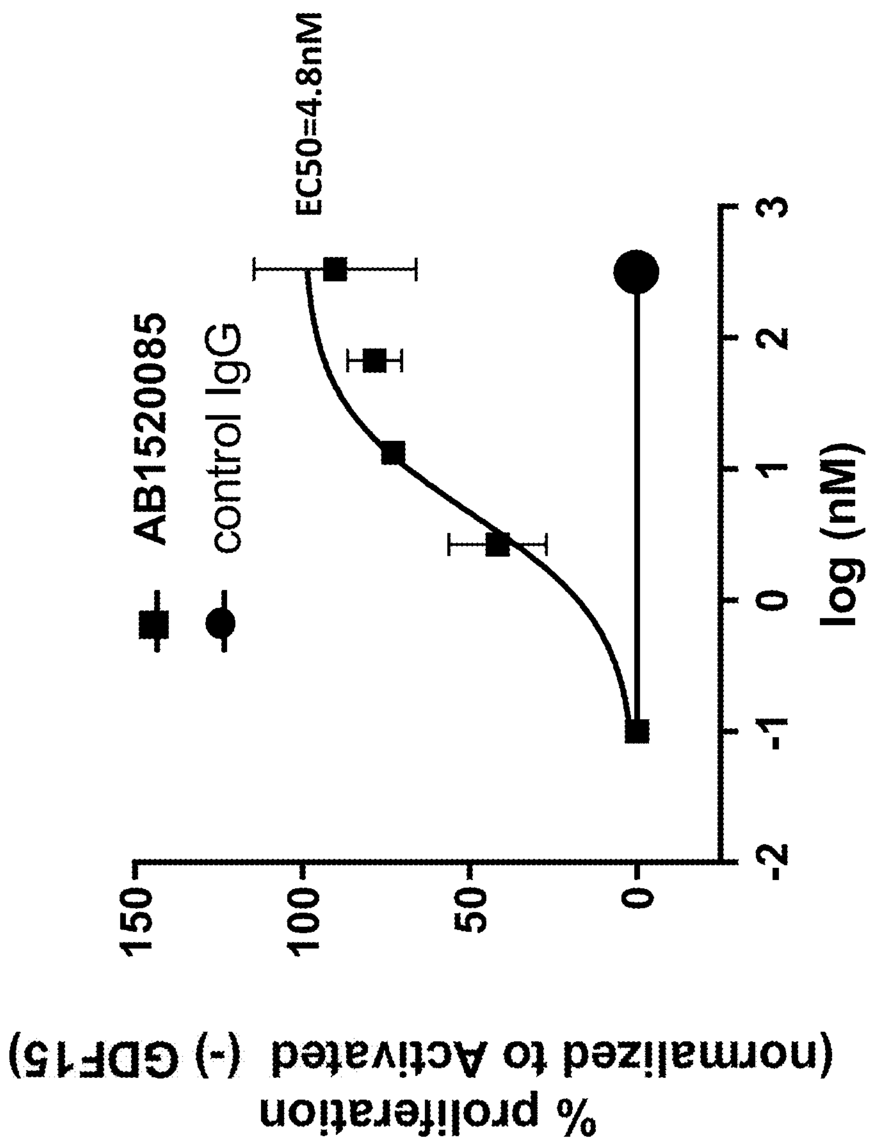

FIGS. 7A and 7B show the ability of GDF-15 antibodies to reverse GDF-15 inhibition of T cells. (See Example 8.)

Figure 8:
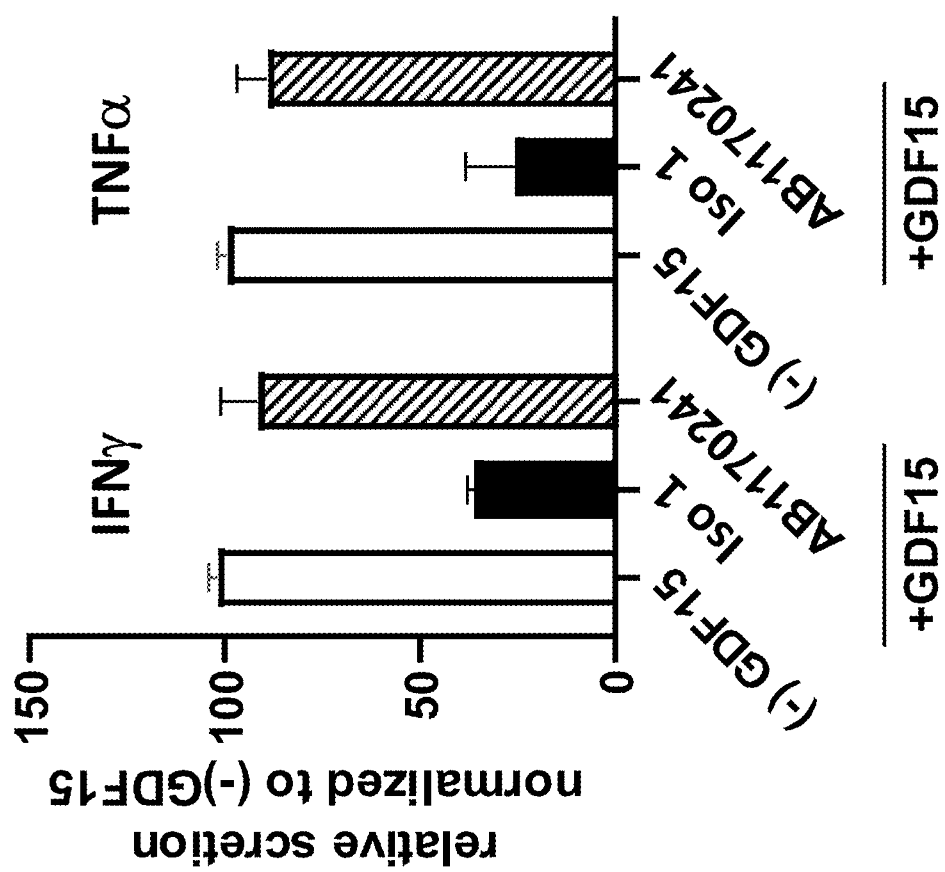

FIG. 8 shows the ability of GDF-15 antibodies to reverse GDF-15 inhibition of Th1 differentiation. (See Example 9.)

Figure 9:
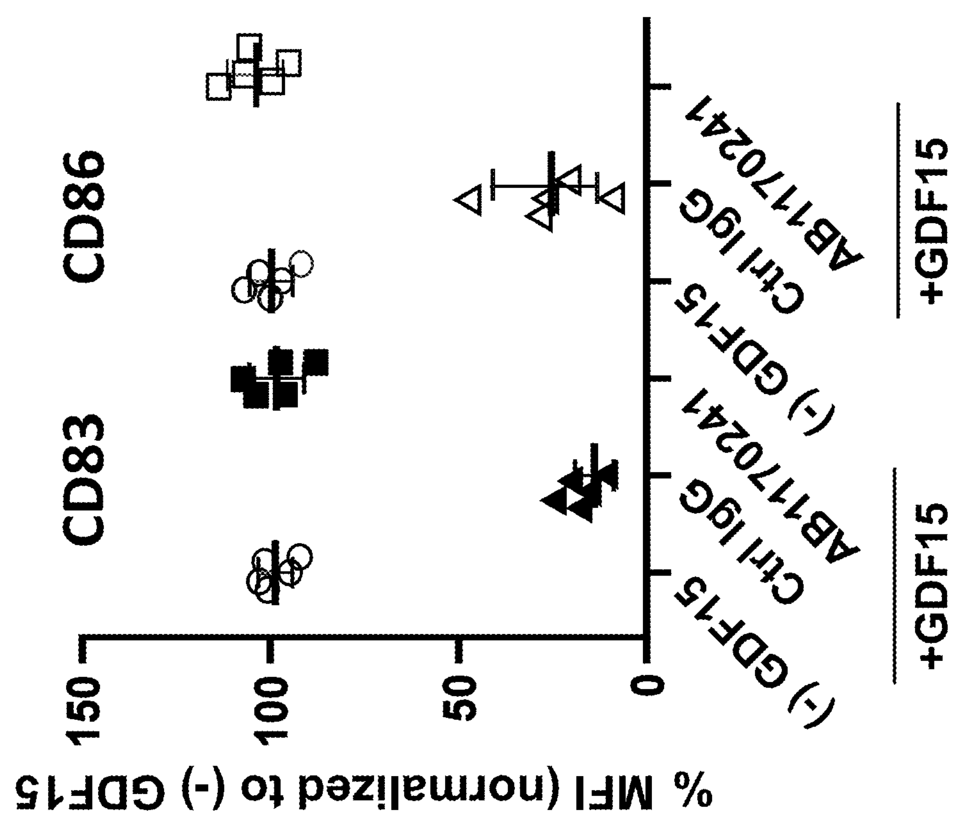

FIG. 9 shows the ability of GDF-15 antibodies to reverse GDF-15 downregulation of dendritic cell (DC) activation markers. (See Example 10.)

Figure 10:
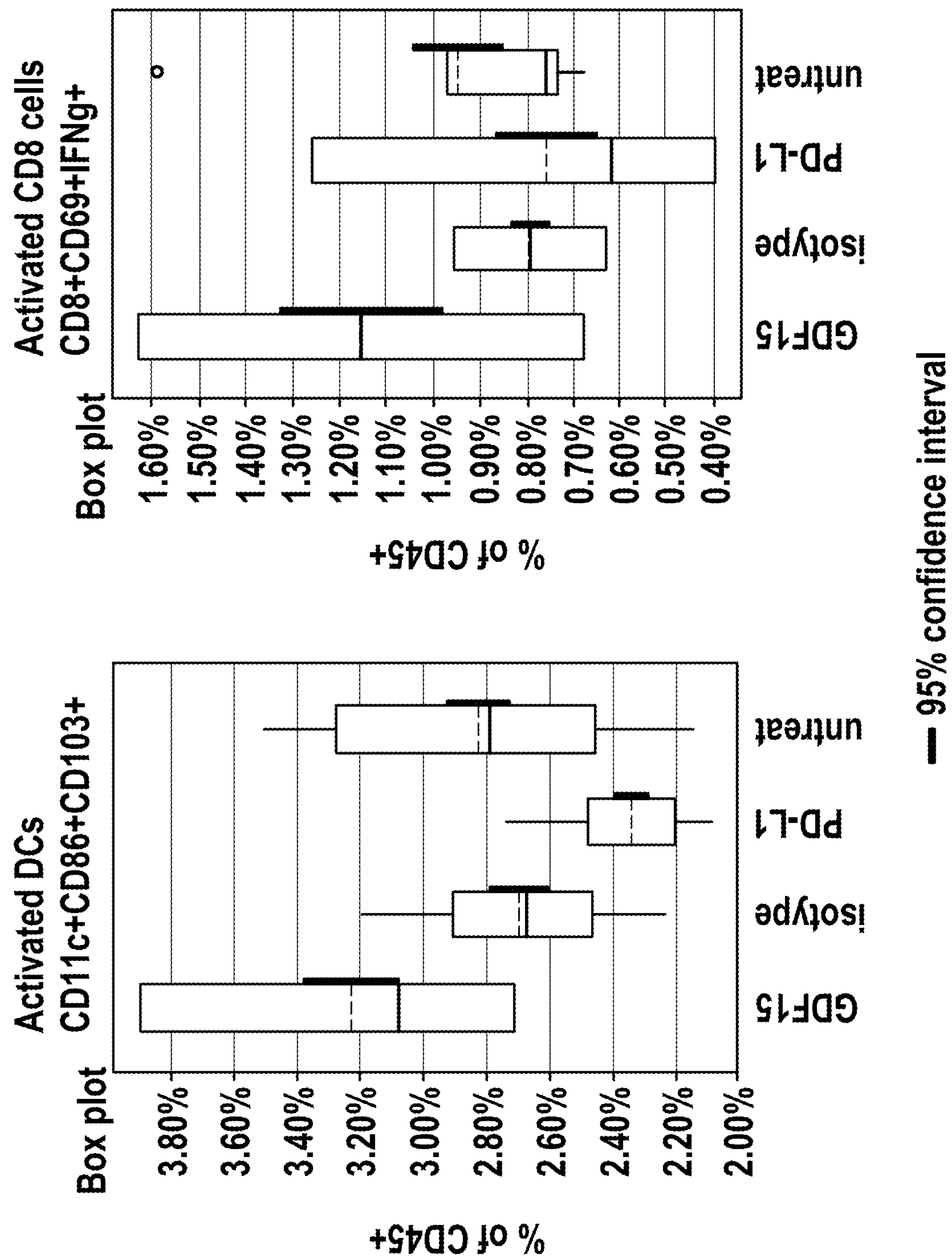

FIG. 10 shows flow cytometry data demonstrating activation of dendritic cells and CD8 cells in an LL/2 model. (See Example 11.)

Figure 11:
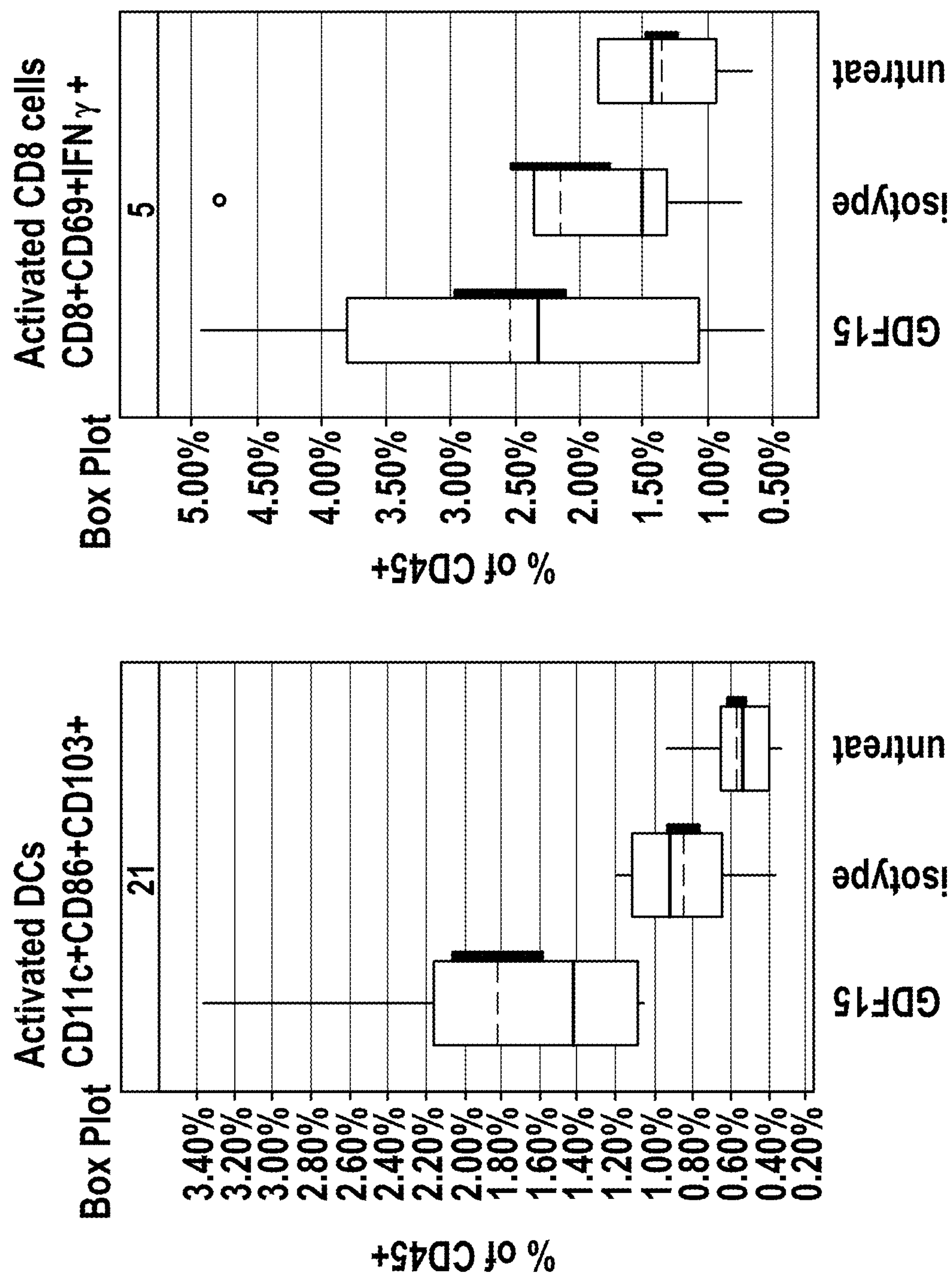

FIG. 11 shows flow cytometry data demonstrating activation of dendritic cells and CD8 cells in an MBT2 model. (See Example 11.)

Figure 12:
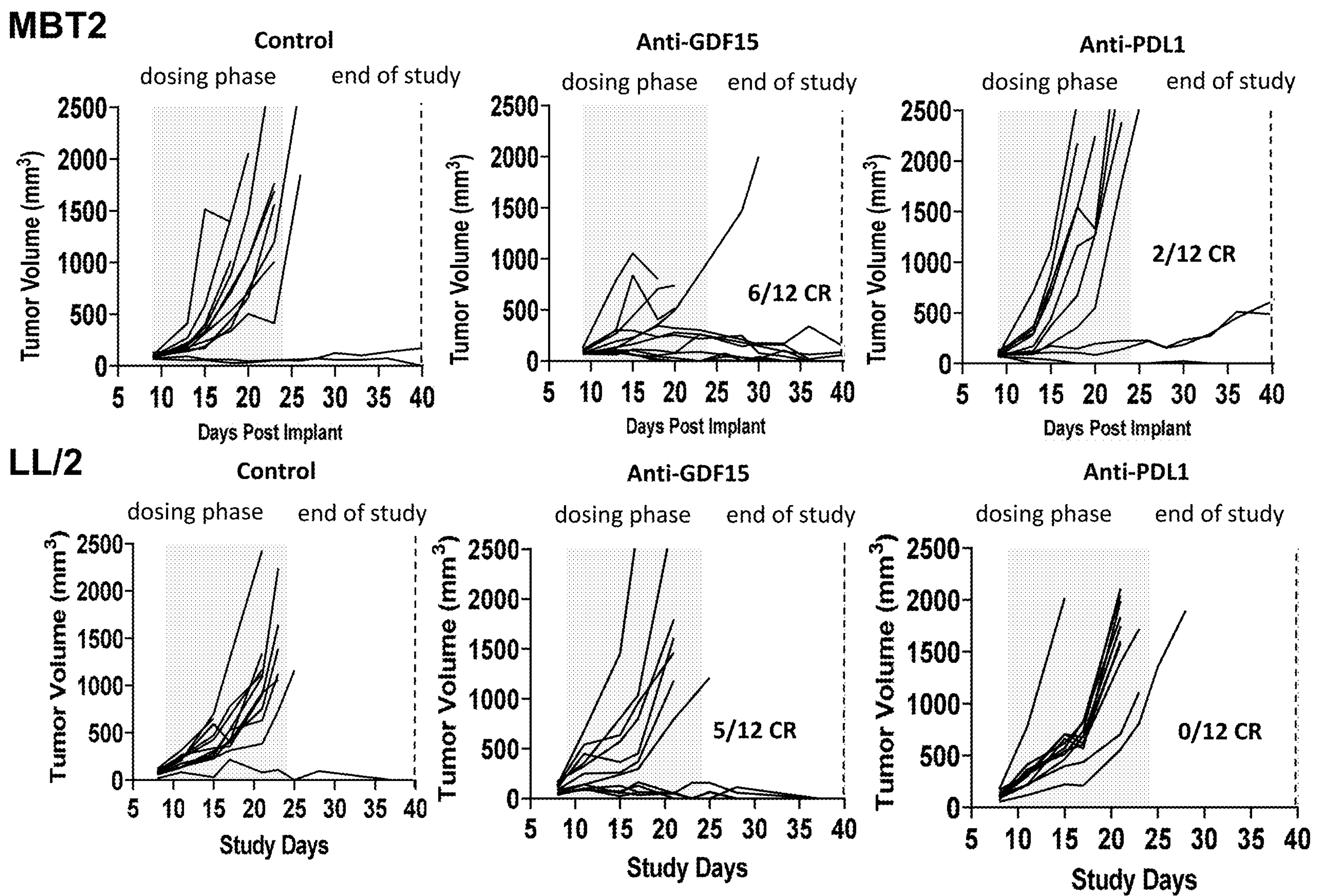

FIG. 12 shows that GDF-15 antibodies demonstrate antitumor activity in anti-PD-L1 refractory LL/2 and MBT2 syngeneic tumors with 50% of the animals showing complete tumor regressions. (See Example 11.)

Figure 13A:
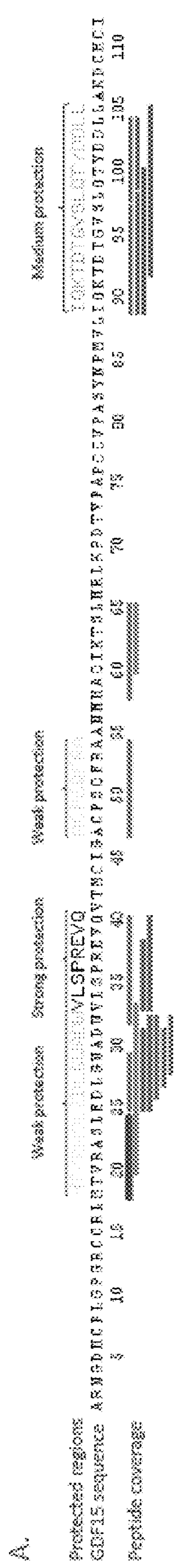
Figure 13B:
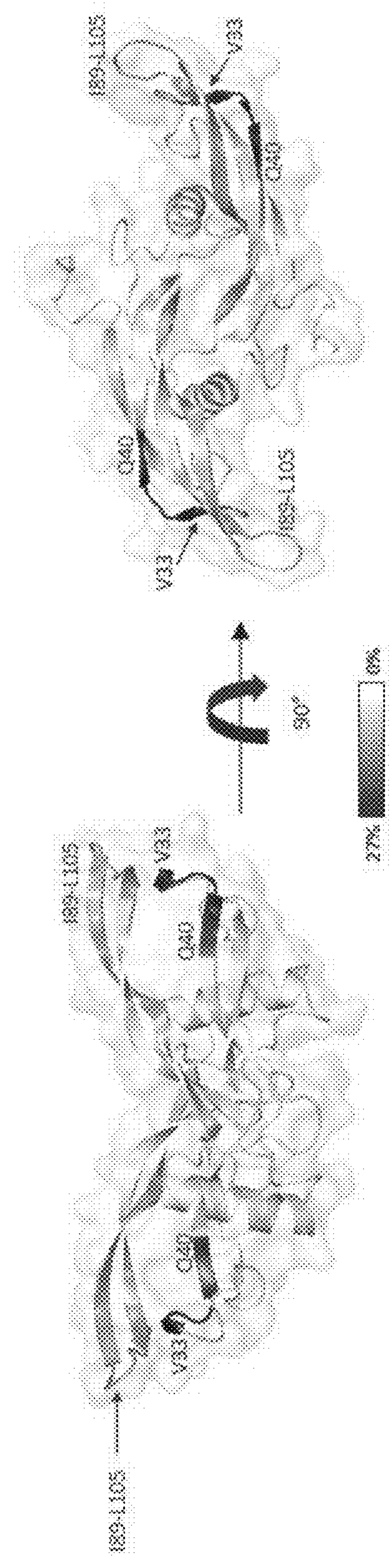

FIGS. 13A and 13B show increased protection in a mature GDF15-AB 1170241 Fab complex using HDX-MS difference data. In FIG. 13A, the top row shows normalized HDX-MS difference data (only increased protection displayed), corresponding to the mapping in FIG. 13B. Black/dark grey regions are more protected in the GDF15-Fab complex compared to in GDF15 alone. The bottom row shows GDF15 peptide coverage indicating which regions of the GDF15 protein that are represented in the data set. Mature GDF15 amino acid sequence shown is SEQ ID NO: 479. FIG. 13B shows normalized HDX-MS difference data mapped on PDB structure 5vz3 (GDF15). Two regions, V33-Q40 (SEQ ID NO: 486) and I89-L105 (black/dark grey) (SEQ ID NO:487) are more protected in the mature GDF15-AB1170241 Fab complex compared to GDF15 alone, indicating binding. The normalization is based on the peptide with the largest difference in deuterium uptake (27%, black and white bar). (See Example 12.)

Figure 14A:
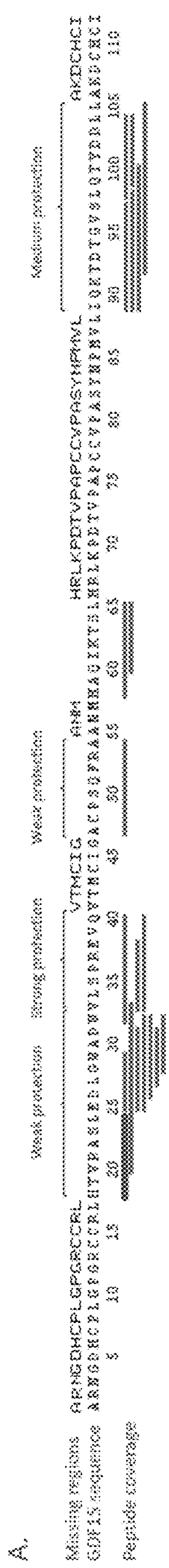
Figure 14B:
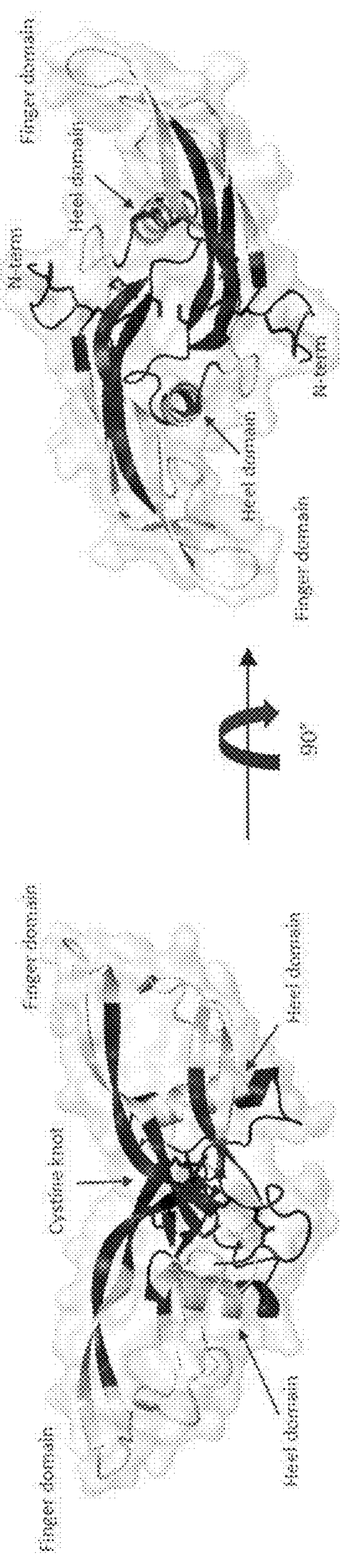

FIGS. 14A and 14B show HDX-MS missing regions. FIG. 14A is a GDF15 peptide coverage map highlighting regions of the mature GDF15 protein (SEQ ID NO:479) that are not detected in the HDX-MS dataset (top row, black) corresponding to the mapping in FIG. 14B. FIG. 14B shows GDF15 regions missing in the HDX-MS data set mapped on PDB structure 5vz3 (GDF15). The regions for which no peptides are detected (black) are mainly the N-terminus and the central cystine knot (cysteine sidechains shown as sticks). (See Example 12.)

Figure 15:
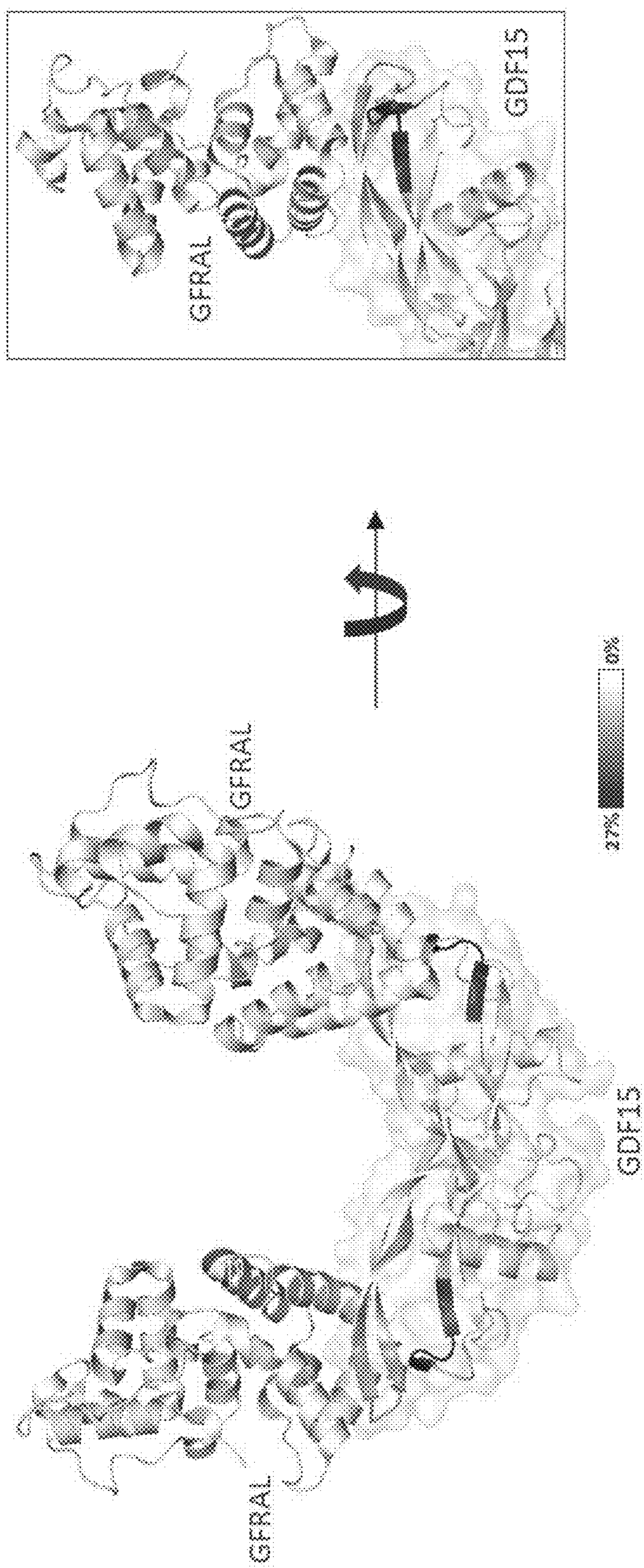

FIG. 15 shows that protected regions of mature GDF15 overlap with its GFRAL binding site. Normalized HDX-MS difference data is mapped on PDB structure 5vz3 (GDF15), and the crystal structure of GFRAL (5vz4) is overlayed. Black/dark grey regions are more protected in the mature GDF15-AB1170241 Fab complex compared to mature GDF15 alone, indicating binding. The normalization is based on the peptide with the largest difference in deuterium uptake (27%, black and white bar). (See Example 12.)

Figure 16A:
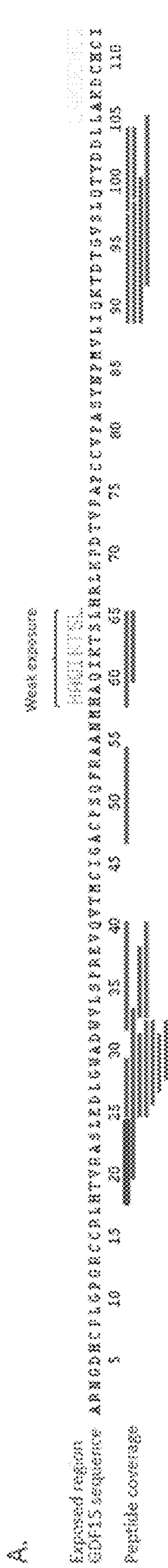
Figure 16B:
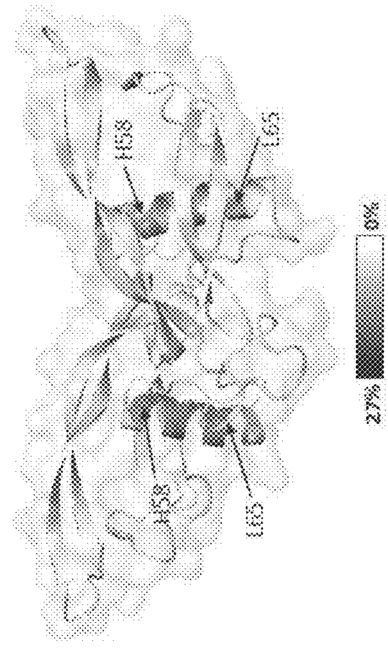

FIGS. 16A and 16B show increased exposure in a mature GDF15-AB 1170241 Fab complex using HDX-MS difference data. In FIG. 16A, the top row shows normalized HDX-MS difference data (only increased exposure displayed), corresponding to the mapping in FIG. 16B. One region, H58-L65 (the Heel domain), is more exposed in the GDF15-AB1170241 Fab complex compared to mature GDF15 alone. However, the difference is much weaker than the observed protection in FIGS. 13A and 13B. FIG. 16B shows normalized HDX-MS difference exposure data mapped on PDB structure 5vz3 (GDF15). Two regions, V33-Q40 (SEQ ID NO:486) and I89-L104 (black/dark grey) (SEQ ID NO:487), are more protected in the mature GDF15-AB 1170241 Fab complex compared to GDF15 alone, indicating binding. In addition, the E25-W32 stretch (SEQ ID NO:485) is weakly protected. The normalization is based on the peptide with the largest difference in deuterium uptake (27%, black and white bar). (See Example 12.)

Figures 17A, 17B:
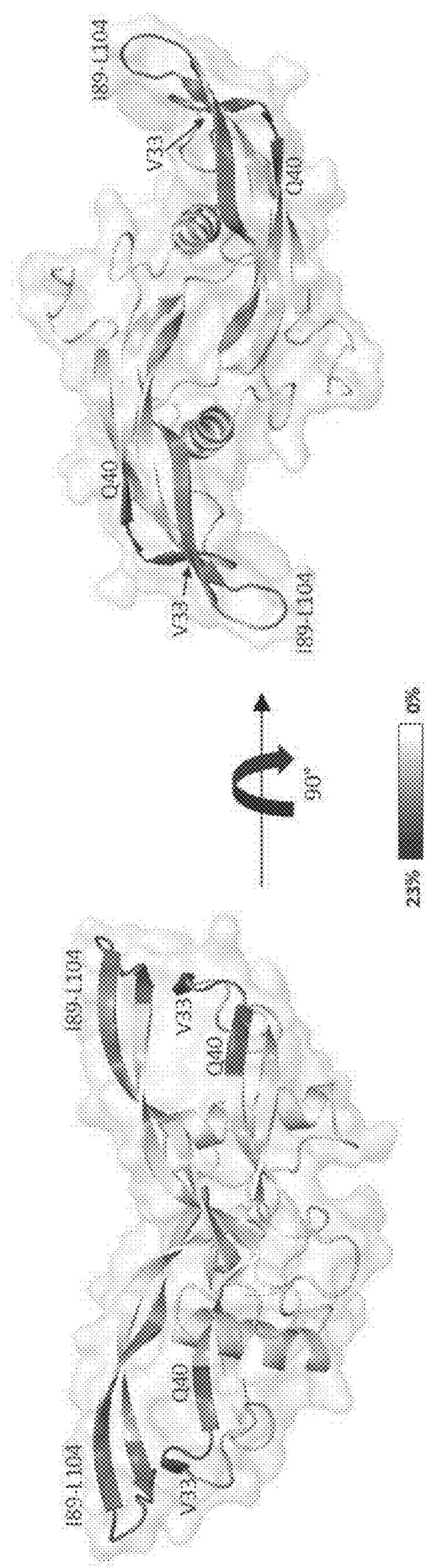

FIGS. 17A and 17B show increased protection in a mature GDF15-AB 1170241 Fab complex using HDX-MS difference data. In FIG. 17A, the top row shows normalized HDX-MS difference data (only increased protection displayed), corresponding to the mapping in FIG. 17A. Black/dark grey regions are more protected in the mature GDF15-AB 1170241 Fab complex compared to mature GDF15 alone. The bottom row shows GDF15 peptide coverage indicating which regions of the GDF protein are represented in the data set. FIG. 17B shows normalized HDX-MS difference data mapped on PDB structure 5vz3 (GDF15). Two regions, V33-Q40 (SEQ ID NO:486) and I89-L104 (black/dark grey) (SEQ ID NO:487) are more protected in the mature GDF15-AB1170241 Fab complex compared to mature GDF15 alone, indicating binding. In addition, the E25-W32 (SEQ ID NO:485) stretch is weakly protected. The normalization is based on the peptide with the largest difference in deuterium uptake in this dataset (23%, black and white bar). (See Example 12.)

Figures 18A, 18B:
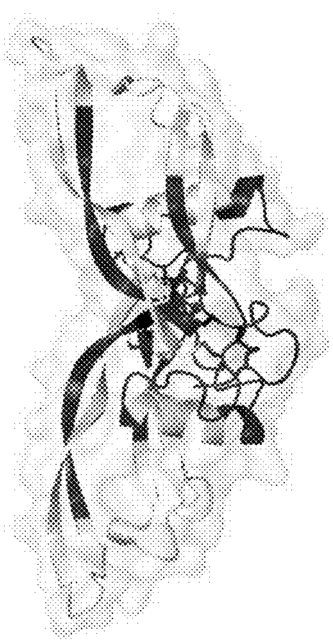

FIGS. 18A and 18B show HDX-MS missing regions. FIG. 18A is a GDF15 peptide (SEQ ID NO: 479) coverage map highlighting regions of the mature GDF15 protein that are not detected in the HDX-MS dataset (top row, black), corresponding to the mapping in FIG. 18B. FIG. 18B shows mature GDF15 regions missing in the HDX-MS data set mapped on PDB structure 5vz3 (GDF15). The regions for which no peptides are detected (black) are mainly the N-terminus and the central cysteine knot (cysteine side-chains shown as sticks). (See Example 12.)

Figure 19:
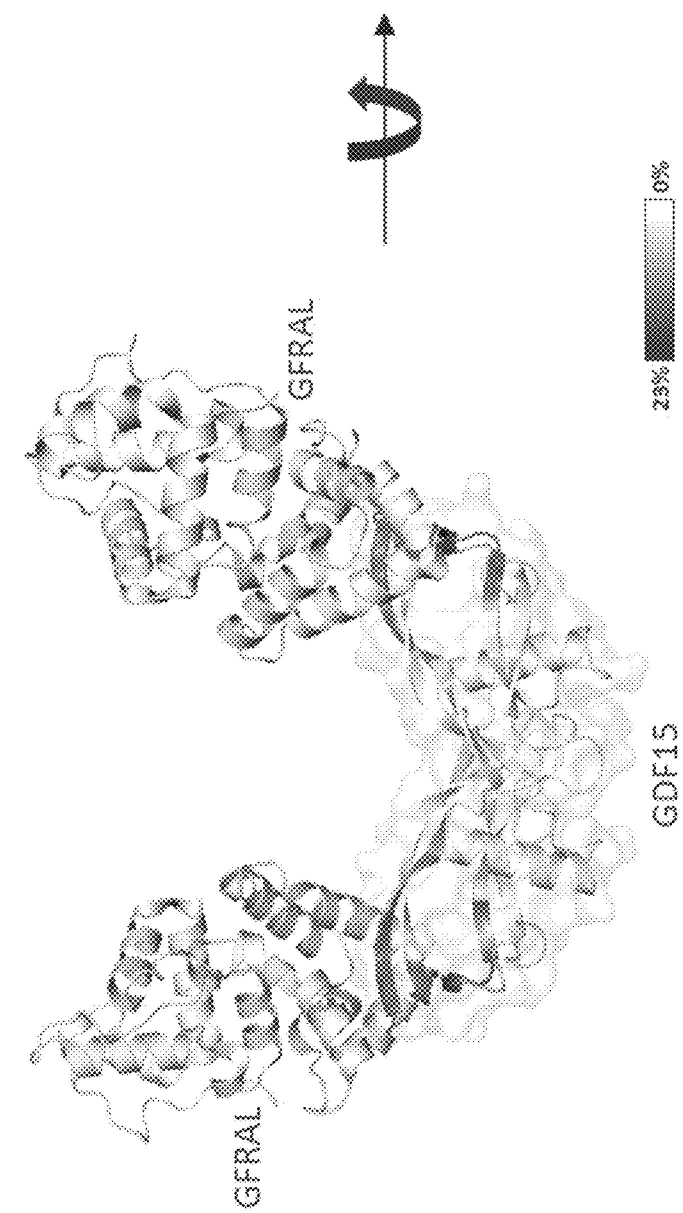

FIG. 19 shows that protected regions of mature GDF15 overlap with its GFRAL binding site. Normalized HDX-MS difference data is mapped on PDB structure 5vz3 (GDF15), and the crystal structure of GFRAL (5vz4) is overlayed. Black/dark grey regions are more protected in the mature GDF15-AB1170241 Fab complex compared to GDF15 alone, indicating binding. The normalization is based on the peptide with largest difference in deuterium uptake (23%, black and white bar). (See Example 12.)

Figure 20A:
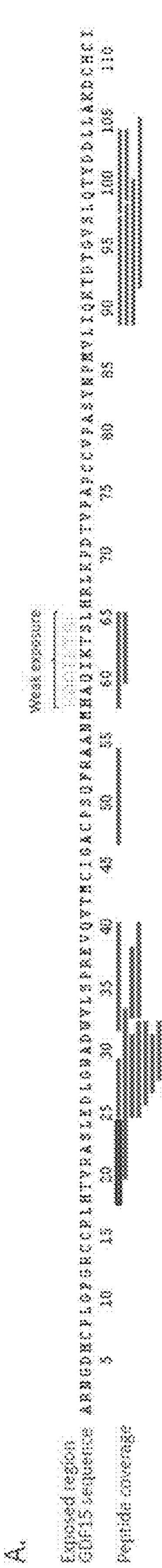
Figure 20B:
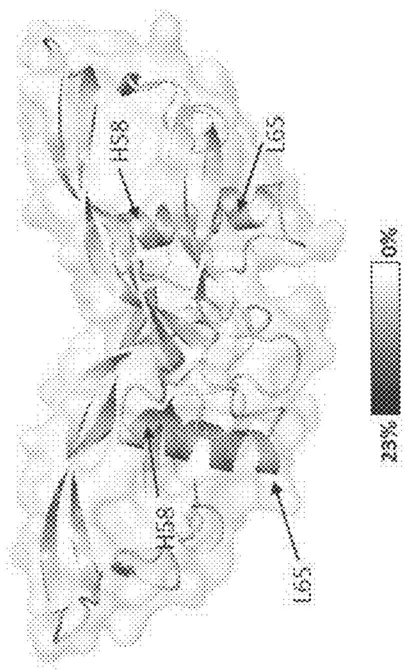

FIGS. 20A and 20B show increased exposure in a mature GDF15-AB 1170241 Fab complex using HDX-MS difference data. In FIG. 20A, the top row shows the normalized HDX-MS difference data (only increased exposure displayed), corresponding to the mapping in FIG. 20B. One region, the H58-L65 (the Heel domain), is more exposed in the mature GDF15-AB 1170241 Fab complex compared to in GDF15 alone (SEQ ID NO: 479). However, the difference is much weaker than the observed protection in FIGS. 17A and 17B. FIG. 20B shows normalized HDX-MS difference exposure data mapped on PDB structure 5vz3 (GDF15). The normalization is based on the peptide with largest difference in deuterium uptake (23%, black and white bar). (See Example 12.)

FIG. 21 summarizes the epitope mapping results obtained using mature GDF15 protein (SEQ ID NO: 479) and preformed mature GDF15-AB 1170241 Fab complex in Experiment 1 of Example 12.

Figure 22:
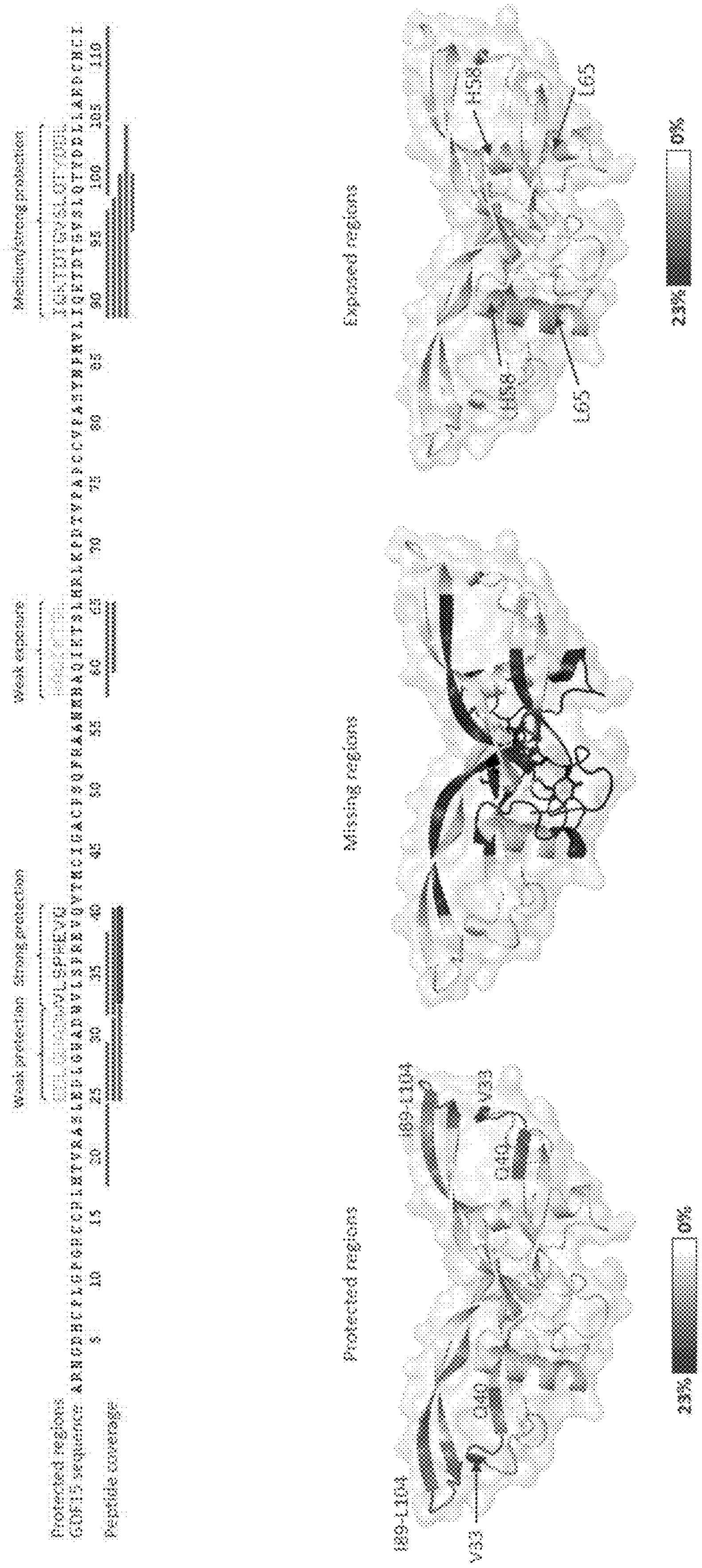

FIG. 22 summarizes the data obtained using mature GDF15 protein (SEQ ID NO: 479), preformed mature GDF15-AB1170241 Fab complex, and AB1170241 Fab in Experiment 2 of Example 12.

DETAILED DESCRIPTION

The present disclosure provides antibodies and antigen-binding fragments thereof human GDF-15.

I. Definitions

As used herein, the term “GDF-15” or “GDF15” refers to mammalian GDF-15 polypeptides including, but not limited to, native GDF-15 polypeptides and isoforms of GDF-15 polypeptides. “GDF-15” encompasses full-length, unprocessed GDF-15 polypeptides as well as forms of GDF-15 polypeptides that result from processing within the cell. As used herein, the term “human GDF-15” refers to a polypeptide comprising the amino acid sequence of SEQ ID NO:469; naturally occurring variants of SEQ ID NO:469, including but not limited to variants thereof in which either D is present at position 202 of SEQ ID NO:469 (i.e., SEQ ID NO:471); and processed forms of SEQ ID NO:469 or SEQ ID NO: 471, including but not limited to SEQ ID NO: 469 or SEQ ID NO: 471 lacking its signal peptide, e.g., from amino acids 1-29 or SEQ ID NO: 469 or SEQ ID NO: 471 lacking both signal peptide and pro domain (i.e., mature forms comprising amino acid SEQ ID NO:479 and SEQ ID NO: 480). A “GDF-15 polynucleotide,” “GDF-15 nucleotide,” or “GDF-15 nucleic acid” refers to a polynucleotide encoding any GDF-15, including those described above.

The term “antibody” means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term “antibody” encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The terms “anti-GDF-15 antibody,” “GDF-15 antibody” and “antibody that binds to GDF-15” refer to an antibody that is capable of binding GDF-15 with sufficient affinity and specificity such that the antibody is useful as a diagnostic, a therapeutic, and/or as a modulator of GDF-15 activity.

The term “monoclonal antibodies,” as used herein, refers to antibodies that are produced by a single clone of B-cells and bind to the same epitope. In contrast, the term “polyclonal antibodies” refers to a population of antibodies that are produced by different B-cells and bind to different epitopes of the same antigen.

The term “antibody fragment” refers to a portion of an intact antibody. An “antigen-binding fragment,” “antigen-binding domain,” or “antigen-binding region,” refers to a portion of an intact antibody that binds to an antigen. An antigen-binding fragment can contain the antigenic determining regions of an intact antibody (e.g., the complementarity determining regions (CDR)). Examples of antigen-binding fragments of antibodies include, but are not limited to Fab, Fab', F(ab')2, and Fv fragments, linear antibodies, and single chain antibodies. An antigen-binding fragment of an antibody can be derived from any animal species, such as rodents (e.g., mouse, rat, or hamster) and humans or can be artificially produced.

A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CH1, CH2 and CH3) regions, and each light chain contains one N-terminal variable (VL) region and one C-terminal constant (CL) region. The variable regions of each pair of light and heavy chains form the antigen binding site of an antibody. The VH and VL regions have the same general structure, with each region comprising four framework regions, whose sequences are relatively conserved. The term “framework region,” as used herein, refers to the relatively conserved amino acid sequences within the variable region which are located between the hypervariable or complementary determining regions (CDRs). There are four framework regions in each variable domain, which are designated FW1, FW2, FW3, and FW4. The framework regions form the R sheets that provide the structural framework of the variable region (see, e.g., C. A. Janeway et al. (eds.), Immunobiology, 5th Ed., Garland Publishing, New York, NY (2001)). The three CDRs, known as CDR1, CDR2, and CDR3, form the "hypervariable region" of an antibody, which is responsible for antigen binding.

The terms "VL" and "VL domain" are used interchangeably to refer to the light chain variable region of an antibody.

The terms "VH" and "VH domain" are used interchangeably to refer to the heavy chain variable region of an antibody.

The term "Kabat numbering" and like terms are recognized in the art and refer to a system of numbering amino acid residues in the heavy and light chain variable regions of an antibody or an antigen-binding fragment thereof. In some aspects, CDRs can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In some aspects, the CDRs of the antibodies described herein have been determined according to the Kabat numbering scheme.

Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and 1135B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32..34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

As used herein, the term "constant region" or "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., IgG1, IgG2, IgG3, and IgG4. Heavy chain amino acid sequences are well known in the art. In some aspects, the heavy chain is a human heavy chain.

As used herein, the term "light chain" when used in reference to an antibody can refer to any distinct type, e.g., kappa (κ) or lambda (λ) based on the amino acid sequence of the constant domains. Light chain amino acid sequences are well known in the art. In some aspects, the light chain is a human light chain.

The term "chimeric" antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g. mouse, rat, rabbit, etc.) with the desired specificity, affinity, and capability while the constant regions are homologous to the sequences in antibodies or antigen-binding fragments thereof derived from another (usually human) to avoid eliciting an immune response in that species.

A "humanized" antibody is an antibody comprising a human antibody scaffold and at least one CDR obtained or derived from a non-human antibody. Non-human antibodies include antibodies isolated from any non-human animal, such as, for example, a rodent (e.g., a mouse or rat). A humanized antibody can comprise, one, two, or three CDRs obtained or derived from a non-human antibody. A fully human antibody does not contain any amino acid residues obtained or derived from a non-human animal. It will be appreciated that fully human and humanized antibodies carry a lower risk for inducing immune responses in humans than mouse or chimeric antibodies (see, e.g., Harding et al., mAbs, 2(3): 256-26 (2010)).

The term "human" antibody or antigen-binding fragment thereof means an antibody or antigen-binding fragment thereof having an amino acid sequence derived from a human immunoglobulin gene locus, where such antibody or antigen-binding fragment is made using any technique known in the art. This definition of a human antibody or antigen-binding fragment thereof includes intact or full-length antibodies and fragments thereof.

"Binding affinity" generally refers to the strength of the sum total of non-covalent interactions between a single binding site of a molecule (e.g., an antibody or antigen-binding fragment thereof) and its binding partner (e.g., an antigen). Unless indicated otherwise, as used herein, "binding affinity" refers to intrinsic binding affinity which reflects a 1:1 interaction between members of a binding pair (e.g., antibody or antigen-binding fragment thereof and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody or antigen-binding fragment thereof to an antigen, and $k_{off}$ refers to the dissociation rate constant of, e.g., an antibody or antigen-binding fragment thereof from an antigen. The $k_{on}$ and $k_{off}$ can be determined by techniques known to one of ordinary skill in the art, such as BIAcore© or KinExA.

As used herein, an "epitope" is a term in the art and refers to a localized region of an antigen to which an antibody or antigen-binding fragment thereof can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In some aspects, the epitope to which an antibody or antigen-binding fragment thereof binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization can be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody/antigen-binding fragment thereof: antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al., U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies can be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

An antibody that "binds to the same epitope" as a reference antibody refers to an antibody that binds to the same amino acid residues as the reference antibody. The ability of an antibody to bind to the same epitope as a reference antibody can determined by a hydrogen/deuterium exchange assay (see Coales et al. Rapid Commun. Mass Spectrom. 2009; 23: 639-647) or x-ray crystallography.

As used herein, the terms "immunospecifically binds," "immunospecifically recognizes," "specifically binds," and "specifically recognizes" are analogous terms in the context of antibodies or antigen-binding fragments thereof. These terms indicate that the antibody or antigen-binding fragment thereof binds to an epitope via its antigen-binding domain and that the binding entails some complementarity between the antigen binding domain and the epitope. Accordingly, for example, an antibody that "specifically binds" to human GDF-5 may also bind to GDF-15 from other species (e.g., cynomolgus monkey and/or mouse GDF-15) and/or GDF-15 proteins produced from other human alleles, but the extent of binding to an un-related, non-GDF-15 protein (e.g., TGFβ1 or BMP7) is less than about 10% of the binding of the antibody to GDF-15 as measured, e.g., by an ELISA assay.

An antibody is said to "competitively inhibit" binding of a reference antibody to a given epitope if it preferentially binds to that epitope or an overlapping epitope to the extent that it blocks, to some degree, binding of the reference antibody to the epitope. Competitive inhibition may be determined by any method known in the art, for example, competition ELISA assays and the assays used in Example 4. An antibody may be said to competitively inhibit binding of the reference antibody to a given epitope by at least 90%, at least 80%, at least 70%, at least 60%, or at least 50%.

The term "nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some aspects, an antibody, polynucleotide, vector, cell, or composition which is isolated is substantially pure. As used herein, "substantially pure" refers to material which is at least 50% pure (i.e., free from contaminants), at least 90% pure, at least 95% pure, at least 98% pure, or at least 99% pure.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this disclosure are based upon antibodies, in some aspects, the polypeptides can occur as single chains or associated chains.

"Percent identity" refers to the extent of identity between two sequences (e.g., amino acid sequences or nucleic acid sequences). Percent identity can be determined by aligning two sequences, introducing gaps to maximize identity between the sequences. Alignments can be generated using programs known in the art. For purposes herein, alignment of nucleotide sequences can be performed with the blastn program set at default parameters, and alignment of amino acid sequences can be performed with the blastp program set at default parameters (see National Center for Biotechnology Information (NCBI) on the worldwide web, ncbi.nlm.nih.gov).

As used herein, the term "host cell" can be any type of cell, e.g., a primary cell, a cell in culture, or a cell from a cell line. In some aspects, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome.

"Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991)); DEAE-dextran; electroporation; cationic liposome-mediated transfection; tungsten particle-facilitated microparticle bombardment (Johnston, Nature, 346: 776-777 (1990)); and strontium phosphate DNA co-precipitation (Brash et al, Mol. Cell Biol., 7: 2031-2034 (1987)). Phage or viral vectors can be introduced into host cells, after growth of infectious particles in suitable packaging cells, many of which are commercially available.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

The terms "administer," "administering," "administration," and the like, as used herein, refer to methods that may be used to deliver a drug, e.g., an anti-GDF-15 antibody or antigen-binding fragment thereof, to the desired site of biological action. Administration techniques that can be employed with the agents and methods described herein are found in e.g., Goodman and Gilman, *The Pharmacological Basis of Therapeutics*, current edition, Pergamon; and Remington's, *Pharmaceutical Sciences*, current edition, Mack Publishing Co., Easton, Pa.

As used herein, the terms "subject" and "patient" are used interchangeably. The subject can be a mammal such as a non-human animal (e.g., cow, pig, horse, cat, dog, rat, mouse, monkey or other primate, etc.). In some aspects, the subject is a cynomolgus monkey. In some aspects, the subject is a human.

The term "therapeutically effective amount" refers to an amount of a drug, e.g., an anti-GDF-15 antibody or antigen-binding fragment thereof, effective to treat a disease or condition in a subject.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with or suspected of having the disorder.

As used herein, the terms "cancer" and "cancerous" refer to the physiological condition in mammals in which a population of cells are characterized by unregulated cell growth. Examples of cancer include but are not limited to, carcinoma, blastoma, and sarcoma. More particular examples of such cancers include squamous cell carcinoma, lung cancer, small-cell lung cancer, non-small cell lung cancer, glioma, gastrointestinal (tract) cancer, renal cancer, ovarian cancer, liver cancer, colorectal cancer, endometrial cancer, kidney cancer, prostate cancer, castration-resistant prostate cancer, thyroid cancer, melanoma, chondrosarcoma, neuroblastoma, pancreatic cancer, glioblastoma multiforme, cervical cancer, brain cancer, stomach cancer, bladder cancer, hepatoma (hepatocellular carcinoma (HCC)), breast cancer, colon carcinoma, head and neck cancer, squamous cell head and neck cancer, renal cell carcinoma, Merkel cell carcinoma, urothelial cancer, thymic cancer, epithelial cancer, salivary cancer, choriocarcinoma, oral cancer, skin cancer, and esophageal cancer. The cancer can be a "cancer that expresses GDF-15" or a "GDF-15 expressing cancer." Such terms refer to a cancer comprising cells that express GDF-15.

As used herein, "cachexia" means a metabolic syndrome associated with underlying disease and characterized by involuntary loss of muscle mass. Cachexia is often accompanied by involuntary weight loss, loss of fat mass, anorexia, inflammation, insulin resistance, fatigue, weakness, significant loss of appetite, and/or increased muscle protein breakdown. Cachexia is distinct from starvation, age-related loss of muscle mass, malabsorption, and hyperthyroidism. Underlying diseases associated with cachexia include cancer, chronic heart failure, chronic kidney disease, COPD, AIDS, multiple sclerosis, rheumatoid arthritis, sepsis, and tuberculosis.

As used herein, "sarcopenia" is understood to be a condition characterized primarily by loss of skeletal muscle mass and muscle strength. Sarcopenia is frequently associated with aging. See, Ruegg and Glass (2011) ANNUAL REV. PHARMACOL. TOXICOL. 51:373-395. In one approach, sarcopenia can be identified in a subject if a value of the appendicular skeletal muscle mass of a subject divided by the height of the subject in meters is more than two standard deviations below the young normal mean. (Thomas (2007) supra; see also Baumgartner et al. (1999) MECH. AGEING DEV. 147:755-763).

As used in the present disclosure and claims, the singular forms "a," "an," and "the" include plural forms unless the context clearly dictates otherwise.

It is understood that wherever aspects are described herein with the language "comprising," otherwise analogous aspects described in terms of "consisting of" and/or "consisting essentially of" are also provided. In this disclosure, "comprises," "comprising," "containing" and "having" and the like can mean "includes," "including," and the like; "consisting essentially of" or "consists essentially of" are open-ended, allowing for the presence of more than that which is recited so long as basic or novel characteristics of that which is recited is not changed by the presence of more than that which is recited, but excludes prior art aspects.

Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following: A, B, and C; A, B, or C; A or C; A or B; B or C; A and C; A and B; B and C; A (alone); B (alone); and C (alone). Use of the term "or" herein is not meant to imply that alternatives are mutually exclusive.

The term "about," as used herein, includes the recited number±10%. Thus, "about 10" means 9 to 11. As is understood by one skilled in the art, reference to "about" a value or parameter herein includes (and describes) aspects that are directed to that value or parameter per se. For example, description referring to "about X" includes description of "X."

Any compounds (e.g., antibodies or antigen-binding fragments thereof, polynucleotides, vectors, host cells), compositions, or methods provided herein can be combined with one or more of any of the other compounds, compositions, and methods provided herein II. Anti-GDF-15 Antibodies In some aspects, provided herein are antibodies (e.g., monoclonal antibodies, such as mouse, chimeric, humanized, or human antibodies) and antigen-binding fragments thereof which specifically bind to GDF-15 (e.g., human GDF-15).

In some aspects, an antibody or antigen-binding fragment thereof described herein binds to human GDF-15. In some aspects, an antibody or antigen-binding fragment thereof binds to human and cynomolgus monkey GDF-15. In some aspects, an antibody or antigen-binding fragment thereof binds to human and murine GDF-15. In some aspects, an antibody or antigen-binding fragment thereof binds to human, cynomolgus monkey, and murine GDF-15.

In some aspects, an antibody or antigen-binding fragment thereof described herein binds to human GDF-15 and comprises the six CDRs of an antibody listed in Tables 1 and 2 (i.e., the three VH CDRs of the antibody listed in Table 1 and the three VL CDRs of the same antibody listed in Table 2).

TABLE 1

VH CDR Amino Acid Sequences

| Antibody Name | VH CDR1 (SEQ ID NO:) | VH CDR2 (SEQ ID NO:) | VH CDR3 (SEQ ID NO:) |
|---|---|---|---|
| AB1170002 | SEQ ID NO: 3 | SEQ ID NO: 4 | SEQ ID NO: 5 |
| AB1170006 | SEQ ID NO: 21 | SEQ ID NO: 22 | SEQ ID NO: 23 |
| AB1170010 | SEQ ID NO: 39 | SEQ ID NO: 40 | SEQ ID NO: 41 |
| AB1170019 | SEQ ID NO: 57 | SEQ ID NO: 58 | SEQ ID NO: 59 |
| AB1170028 | SEQ ID NO: 75 | SEQ ID NO: 76 | SEQ ID NO: 77 |
| AB1170036 | SEQ ID NO: 93 | SEQ ID NO: 94 | SEQ ID NO: 95 |
| AB1170040 | SEQ ID NO: 111 | SEQ ID NO: 112 | SEQ ID NO: 113 |
| AB1170043 | SEQ ID NO: 129 | SEQ ID NO: 130 | SEQ ID NO: 131 |
| AB1170047 | SEQ ID NO: 147 | SEQ ID NO: 148 | SEQ ID NO: 149 |
| AB1170069 | SEQ ID NO: 165 | SEQ ID NO: 166 | SEQ ID NO: 167 |
| AB1170070 | SEQ ID NO: 183 | SEQ ID NO: 184 | SEQ ID NO: 185 |
| AB1170072 | SEQ ID NO: 201 | SEQ ID NO: 202 | SEQ ID NO: 203 |
| AB1170073 | SEQ ID NO: 219 | SEQ ID NO: 220 | SEQ ID NO: 221 |
| AB1170074 | SEQ ID NO: 237 | SEQ ID NO: 238 | SEQ ID NO: 239 |
| AB1170086 | SEQ ID NO: 255 | SEQ ID NO: 256 | SEQ ID NO: 257 |
| AB1170148 | SEQ ID NO: 273 | SEQ ID NO: 274 | SEQ ID NO: 275 |
| AB1170242 | SEQ ID NO: 291 | SEQ ID NO: 292 | SEQ ID NO: 293 |
| AB1170243 | SEQ ID NO: 309 | SEQ ID NO: 310 | SEQ ID NO: 311 |
| AB1170241 | SEQ ID NO: 327 | SEQ ID NO: 328 | SEQ ID NO: 329 |
| AB1170244 | SEQ ID NO: 345 | SEQ ID NO: 346 | SEQ ID NO: 347 |
| AB1170245 | SEQ ID NO: 363 | SEQ ID NO: 364 | SEQ ID NO: 365 |
| AB1170246 | SEQ ID NO: 381 | SEQ ID NO: 382 | SEQ ID NO: 383 |
| AB1170247 | SEQ ID NO: 399 | SEQ ID NO: 400 | SEQ ID NO: 401 |
| AB1170248 | SEQ ID NO: 417 | SEQ ID NO: 418 | SEQ ID NO: 419 |
| AB1170249 | SEQ ID NO: 435 | SEQ ID NO: 436 | SEQ ID NO: 437 |
| AB1520085 | SEQ ID NO: 453 | SEQ ID NO: 454 | SEQ ID NO: 455 |

TABLE 2

VL CDR Amino Acid Sequences

| Antibody Name | VL CDR1 (SEQ ID NO:) | VL CDR2 (SEQ ID NO:) | VL CDR3 (SEQ ID NO:) |
|---|---|---|---|
| AB1170002 | SEQ ID NO: 12 | SEQ ID NO: 13 | SEQ ID NO: 14 |
| AB1170006 | SEQ ID NO: 30 | SEQ ID NO: 31 | SEQ ID NO: 32 |
| AB1170010 | SEQ ID NO: 48 | SEQ ID NO: 49 | SEQ ID NO: 50 |
| AB1170019 | SEQ ID NO: 66 | SEQ ID NO: 67 | SEQ ID NO: 68 |
| AB1170028 | SEQ ID NO: 84 | SEQ ID NO: 85 | SEQ ID NO: 86 |
| AB1170036 | SEQ ID NO: 102 | SEQ ID NO: 103 | SEQ ID NO: 104 |
| AB1170040 | SEQ ID NO: 120 | SEQ ID NO: 121 | SEQ ID NO: 122 |
| AB1170043 | SEQ ID NO: 138 | SEQ ID NO: 139 | SEQ ID NO: 140 |
| AB1170047 | SEQ ID NO: 156 | SEQ ID NO: 157 | SEQ ID NO: 158 |
| AB1170069 | SEQ ID NO: 174 | SEQ ID NO: 175 | SEQ ID NO: 176 |
| AB1170070 | SEQ ID NO: 192 | SEQ ID NO: 193 | SEQ ID NO: 194 |
| AB1170072 | SEQ ID NO: 210 | SEQ ID NO: 211 | SEQ ID NO: 212 |
| AB1170073 | SEQ ID NO: 228 | SEQ ID NO: 229 | SEQ ID NO: 230 |
| AB1170074 | SEQ ID NO: 246 | SEQ ID NO: 247 | SEQ ID NO: 248 |
| AB1170086 | SEQ ID NO: 264 | SEQ ID NO: 265 | SEQ ID NO: 266 |
| AB1170148 | SEQ ID NO: 282 | SEQ ID NO: 283 | SEQ ID NO: 284 |
| AB1170242 | SEQ ID NO: 300 | SEQ ID NO: 301 | SEQ ID NO: 302 |
| AB1170243 | SEQ ID NO: 318 | SEQ ID NO: 319 | SEQ ID NO: 320 |
| AB1170241 | SEQ ID NO: 336 | SEQ ID NO: 337 | SEQ ID NO: 338 |
| AB1170244 | SEQ ID NO: 354 | SEQ ID NO: 355 | SEQ ID NO: 356 |
| AB1170245 | SEQ ID NO: 372 | SEQ ID NO: 373 | SEQ ID NO: 374 |
| AB1170246 | SEQ ID NO: 390 | SEQ ID NO: 391 | SEQ ID NO: 392 |
| AB1170247 | SEQ ID NO: 408 | SEQ ID NO: 409 | SEQ ID NO: 410 |
| AB1170248 | SEQ ID NO: 426 | SEQ ID NO: 427 | SEQ ID NO: 428 |
| AB1170249 | SEQ ID NO: 444 | SEQ ID NO: 445 | SEQ ID NO: 446 |
| AB1520085 | SEQ ID NO: 462 | SEQ ID NO: 463 | SEQ ID NO: 464 |

In some aspects, an antibody or antigen-binding fragment thereof described herein binds to human GDF-15 and comprises the VH of an antibody listed in Table 3.

TABLE 3

Variable Heavy Chain (VH) Amino Acid Sequences

| Antibody | VH Amino Acid Sequence (SEQ ID NO) |
|---|---|
| AB1170002 | SEQ ID NO: 2 |
| AB1170006 | SEQ ID NO: 20 |
| AB1170010 | SEQ ID NO: 38 |
| AB1170019 | SEQ ID NO: 56 |
| AB1170028 | SEQ ID NO: 74 |
| AB1170036 | SEQ ID NO: 92 |
| AB1170040 | SEQ ID NO: 110 |
| AB1170043 | SEQ ID NO: 128 |
| AB1170047 | SEQ ID NO: 146 |
| AB1170069 | SEQ ID NO: 164 |
| AB1170070 | SEQ ID NO: 182 |
| AB1170072 | SEQ ID NO: 200 |
| AB1170073 | SEQ ID NO: 218 |
| AB1170074 | SEQ ID NO: 236 |
| AB1170086 | SEQ ID NO: 254 |
| AB1170148 | SEQ ID NO: 272 |
| AB1170242 | SEQ ID NO: 290 |
| AB1170243 | SEQ ID NO: 308 |
| AB1170241 | SEQ ID NO: 326 |
| AB1170244 | SEQ ID NO: 344 |
| AB1170245 | SEQ ID NO: 362 |
| AB1170246 | SEQ ID NO: 380 |
| AB1170247 | SEQ ID NO: 398 |
| AB1170248 | SEQ ID NO: 416 |
| AB1170249 | SEQ ID NO: 434 |
| AB1520085 | SEQ ID NO: 452 |

In some aspects, an antibody or antigen-binding fragment thereof described herein binds to human GDF-15 and comprises the VL of an antibody listed in Table 4.

TABLE 4

| Variable Light Chain (VL) Amino Acid Sequences | |
|---|---|
| Antibody | VL Amino Acid Sequence (SEQ ID NO) |
| AB1170002 | SEQ ID NO: 11 |
| AB1170006 | SEQ ID NO: 29 |
| AB1170010 | SEQ ID NO: 47 |
| AB1170019 | SEQ ID NO: 65 |
| AB1170028 | SEQ ID NO: 83 |
| AB1170036 | SEQ ID NO: 101 |
| AB1170040 | SEQ ID NO: 119 |
| AB1170043 | SEQ ID NO: 137 |
| AB1170047 | SEQ ID NO: 155 |
| AB1170069 | SEQ ID NO: 173 |
| AB1170070 | SEQ ID NO: 191 |
| AB1170072 | SEQ ID NO: 209 |
| AB1170073 | SEQ ID NO: 227 |
| AB1170074 | SEQ ID NO: 245 |
| AB1170086 | SEQ ID NO: 263 |
| AB1170148 | SEQ ID NO: 281 |
| AB1170242 | SEQ ID NO: 299 |
| AB1170243 | SEQ ID NO: 317 |
| AB1170241 | SEQ ID NO: 335 |

TABLE 4-continued

| Variable Light Chain (VL) Amino Acid Sequences | |
|---|---|
| Antibody | VL Amino Acid Sequence (SEQ ID NO) |
| AB1170244 | SEQ ID NO: 353 |
| AB1170245 | SEQ ID NO: 371 |
| AB1170246 | SEQ ID NO: 389 |
| AB1170247 | SEQ ID NO: 407 |
| AB1170248 | SEQ ID NO: 425 |
| AB1170249 | SEQ ID NO: 443 |
| AB1520085 | SEQ ID NO: 461 |

In some aspects, an antibody or antigen-binding fragment thereof described herein binds to human GDF-15 and comprises the VH and the VL of an antibody listed in Tables 3 and 4 (i.e., the VH of the antibody listed in Table 3 and the VL of the same antibody listed in Table 4).

In some aspects, an antibody or antigen-binding fragment thereof described herein binds to human GDF-15 and comprises the VH framework regions of an antibody listed in Table 5.

TABLE 5

| VH Framework Amino Acid Sequences | | | | |
|---|---|---|---|---|
| Antibody | VH FW1 (SEQ ID NO:) | VH FW2 (SEQ ID NO:) | VH FW3 (SEQ ID NO:) | VH FW4 (SEQ ID NO:) |
| AB1170002 | SEQ ID NO: 6 | SEQ ID NO: 7 | SEQ ID NO: 8 | SEQ ID NO: 9 |
| AB1170006 | SEQ ID NO: 24 | SEQ ID NO: 25 | SEQ ID NO: 26 | SEQ ID NO: 27 |
| AB1170010 | SEQ ID NO: 42 | SEQ ID NO: 43 | SEQ ID NO: 44 | SEQ ID NO: 45 |
| AB1170019 | SEQ ID NO: 60 | SEQ ID NO: 61 | SEQ ID NO: 62 | SEQ ID NO: 63 |
| AB1170028 | SEQ ID NO: 78 | SEQ ID NO: 79 | SEQ ID NO: 80 | SEQ ID NO: 81 |
| AB1170036 | SEQ ID NO: 96 | SEQ ID NO: 97 | SEQ ID NO: 98 | SEQ ID NO: 99 |
| AB1170040 | SEQ ID NO: 114 | SEQ ID NO: 115 | SEQ ID NO: 116 | SEQ ID NO: 117 |
| AB1170043 | SEQ ID NO: 132 | SEQ ID NO: 133 | SEQ ID NO: 134 | SEQ ID NO: 135 |
| AB1170047 | SEQ ID NO: 150 | SEQ ID NO: 151 | SEQ ID NO: 152 | SEQ ID NO: 153 |
| AB1170069 | SEQ ID NO: 168 | SEQ ID NO: 169 | SEQ ID NO: 170 | SEQ ID NO: 171 |
| AB1170070 | SEQ ID NO: 186 | SEQ ID NO: 187 | SEQ ID NO: 188 | SEQ ID NO: 189 |
| AB1170072 | SEQ ID NO: 204 | SEQ ID NO: 205 | SEQ ID NO: 206 | SEQ ID NO: 207 |
| AB1170073 | SEQ ID NO: 222 | SEQ ID NO: 223 | SEQ ID NO: 224 | SEQ ID NO: 225 |
| AB1170074 | SEQ ID NO: 240 | SEQ ID NO: 241 | SEQ ID NO: 242 | SEQ ID NO: 243 |
| AB1170086 | SEQ ID NO: 258 | SEQ ID NO: 259 | SEQ ID NO: 260 | SEQ ID NO: 261 |
| AB1170148 | SEQ ID NO: 276 | SEQ ID NO: 277 | SEQ ID NO: 278 | SEQ ID NO: 279 |
| AB1170242 | SEQ ID NO: 294 | SEQ ID NO: 295 | SEQ ID NO: 296 | SEQ ID NO: 297 |
| AB1170243 | SEQ ID NO: 312 | SEQ ID NO: 313 | SEQ ID NO: 314 | SEQ ID NO: 315 |
| AB1170241 | SEQ ID NO: 330 | SEQ ID NO: 331 | SEQ ID NO: 332 | SEQ ID NO: 333 |
| AB1170244 | SEQ ID NO: 348 | SEQ ID NO: 349 | SEQ ID NO: 350 | SEQ ID NO: 351 |
| AB1170245 | SEQ ID NO: 366 | SEQ ID NO: 367 | SEQ ID NO: 368 | SEQ ID NO: 369 |
| AB1170246 | SEQ ID NO: 384 | SEQ ID NO: 385 | SEQ ID NO: 386 | SEQ ID NO: 387 |
| AB1170247 | SEQ ID NO: 402 | SEQ ID NO: 403 | SEQ ID NO: 404 | SEQ ID NO: 405 |
| AB1170248 | SEQ ID NO: 420 | SEQ ID NO: 421 | SEQ ID NO: 422 | SEQ ID NO: 423 |
| AB1170249 | SEQ ID NO: 438 | SEQ ID NO: 439 | SEQ ID NO: 440 | SEQ ID NO: 441 |
| AB1520085 | SEQ ID NO: 456 | SEQ ID NO: 457 | SEQ ID NO: 458 | SEQ ID NO: 459 |

In some aspects, an antibody or antigen-binding fragment thereof described herein binds to human GDF-15 and comprises the VL framework regions of an antibody listed in Table 6.

TABLE 6

| VL Framework Amino Acid Sequences | | | | |
|---|---|---|---|---|
| Antibody | VL FW1 (SEQ ID NO:) | VL FW2 (SEQ ID NO:) | VL FW3 (SEQ ID NO:) | VL FW4 (SEQ ID NO:) |
| AB1170002 | SEQ ID NO: 15 | SEQ ID NO: 16 | SEQ ID NO: 17 | SEQ ID NO: 18 |
| AB1170006 | SEQ ID NO: 33 | SEQ ID NO: 34 | SEQ ID NO: 35 | SEQ ID NO: 36 |
| AB1170010 | SEQ ID NO: 51 | SEQ ID NO: 52 | SEQ ID NO: 53 | SEQ ID NO: 54 |
| AB1170019 | SEQ ID NO: 69 | SEQ ID NO: 70 | SEQ ID NO: 71 | SEQ ID NO: 72 |

TABLE 6-continued

| VL Framework Amino Acid Sequences | | | | |
|---|---|---|---|---|
| Antibody | VL FW1 (SEQ ID NO:) | VL FW2 (SEQ ID NO:) | VL FW3 (SEQ ID NO:) | VL FW4 (SEQ ID NO:) |
| AB1170028 | SEQ ID NO: 87 | SEQ ID NO: 88 | SEQ ID NO: 89 | SEQ ID NO: 90 |
| AB1170036 | SEQ ID NO: 105 | SEQ ID NO: 106 | SEQ ID NO: 107 | SEQ ID NO: 108 |
| AB1170040 | SEQ ID NO: 123 | SEQ ID NO: 124 | SEQ ID NO: 125 | SEQ ID NO: 126 |
| AB1170043 | SEQ ID NO: 141 | SEQ ID NO: 142 | SEQ ID NO: 143 | SEQ ID NO: 144 |
| AB1170047 | SEQ ID NO: 159 | SEQ ID NO: 160 | SEQ ID NO: 161 | SEQ ID NO: 162 |
| AB1170069 | SEQ ID NO: 177 | SEQ ID NO: 178 | SEQ ID NO: 179 | SEQ ID NO: 180 |
| AB1170070 | SEQ ID NO: 195 | SEQ ID NO: 196 | SEQ ID NO: 197 | SEQ ID NO: 198 |
| AB1170072 | SEQ ID NO: 213 | SEQ ID NO: 214 | SEQ ID NO: 215 | SEQ ID NO: 216 |
| AB1170073 | SEQ ID NO: 231 | SEQ ID NO: 232 | SEQ ID NO: 233 | SEQ ID NO: 234 |
| AB1170074 | SEQ ID NO: 249 | SEQ ID NO: 250 | SEQ ID NO: 251 | SEQ ID NO: 252 |
| AB1170086 | SEQ ID NO: 267 | SEQ ID NO: 268 | SEQ ID NO: 269 | SEQ ID NO: 270 |
| AB1170148 | SEQ ID NO: 285 | SEQ ID NO: 286 | SEQ ID NO: 287 | SEQ ID NO: 288 |
| AB1170242 | SEQ ID NO: 303 | SEQ ID NO: 304 | SEQ ID NO: 305 | SEQ ID NO: 306 |
| AB1170243 | SEQ ID NO: 321 | SEQ ID NO: 322 | SEQ ID NO: 323 | SEQ ID NO: 324 |
| AB1170241 | SEQ ID NO: 339 | SEQ ID NO: 340 | SEQ ID NO: 341 | SEQ ID NO: 342 |
| AB1170244 | SEQ ID NO: 357 | SEQ ID NO: 358 | SEQ ID NO: 359 | SEQ ID NO: 360 |
| AB1170245 | SEQ ID NO: 375 | SEQ ID NO: 376 | SEQ ID NO: 377 | SEQ ID NO: 378 |
| AB1170246 | SEQ ID NO: 393 | SEQ ID NO: 394 | SEQ ID NO: 395 | SEQ ID NO: 396 |
| AB1170247 | SEQ ID NO: 411 | SEQ ID NO: 412 | SEQ ID NO: 413 | SEQ ID NO: 414 |
| AB1170248 | SEQ ID NO: 429 | SEQ ID NO: 430 | SEQ ID NO: 431 | SEQ ID NO: 432 |
| AB1170249 | SEQ ID NO: 447 | SEQ ID NO: 448 | SEQ ID NO: 449 | SEQ ID NO: 450 |
| AB1520085 | SEQ ID NO: 465 | SEQ ID NO: 466 | SEQ ID NO: 467 | SEQ ID NO: 468 |

In some aspects, an antibody or antigen-binding fragment thereof described herein binds to human GDF-15 and comprises the four VH framework regions and the four VL framework regions of an antibody listed in Tables 5 and 6 (i.e., the four VH framework regions of the antibody listed in Table 5 and the four VL framework regions of the same antibody listed in Table 6.)

The amino acid sequences of antibodies used in the Examples below are summarized in Table 7.

TABLE 7

| SEQ ID NOs of Antibody CDR, Variable Regions, and VH and VL Frameworks | | | | | | |
|---|---|---|---|---|---|---|
| Antibody | H CDRs | L CDRs | VH | VL | VH FWs | VL FWs |
| AB1170002 | 3-5 | 12-14 | 2 | 11 | 6-9 | 15-18 |
| AB1170006 | 21-23 | 30-32 | 20 | 29 | 24-27 | 33-36 |
| AB1170010 | 39-41 | 48-50 | 38 | 47 | 42-45 | 51-54 |
| AB1170019 | 57-59 | 66-68 | 56 | 65 | 60-63 | 69-72 |
| AB1170028 | 75-77 | 84-86 | 74 | 83 | 78-81 | 87-90 |
| AB1170036 | 93-95 | 102-104 | 92 | 101 | 96-99 | 105-108 |
| AB1170040 | 111-113 | 120-122 | 110 | 119 | 114-117 | 123-126 |
| AB1170043 | 129-131 | 138-140 | 128 | 137 | 132-135 | 141-144 |
| AB1170047 | 147-149 | 156-158 | 146 | 155 | 150-153 | 159-162 |
| AB1170069 | 165-167 | 174-176 | 164 | 173 | 168-171 | 177-180 |
| AB1170070 | 183-185 | 192-194 | 182 | 191 | 186-189 | 195-198 |
| AB1170072 | 201-203 | 210-212 | 200 | 209 | 204-207 | 213-216 |
| AB1170073 | 219-221 | 228-230 | 218 | 227 | 222-225 | 231-234 |
| AB1170074 | 237-239 | 246-248 | 236 | 245 | 240-243 | 249-252 |
| AB1170086 | 255-257 | 264-266 | 254 | 263 | 258-261 | 267-270 |
| AB1170148 | 273-275 | 282-284 | 272 | 281 | 276-279 | 285-288 |
| AB1170242 | 291-293 | 300-302 | 290 | 299 | 294-297 | 303-306 |
| AB1170243 | 309-311 | 318-320 | 308 | 317 | 312-315 | 321-324 |
| AB1170241 | 327-329 | 336-338 | 326 | 335 | 330-333 | 339-342 |
| AB1170244 | 345-347 | 354-356 | 344 | 353 | 348-351 | 357-360 |
| AB1170245 | 363-365 | 372-374 | 362 | 371 | 366-369 | 375-378 |
| AB1170246 | 381-383 | 390-392 | 380 | 389 | 384-387 | 393-396 |
| AB1170247 | 399-401 | 408-410 | 398 | 407 | 402-405 | 411-414 |
| AB1170248 | 417-419 | 426-428 | 416 | 425 | 420-423 | 429-432 |
| AB1170249 | 435-437 | 444-446 | 434 | 443 | 438-441 | 447-450 |
| AB1520085 | 453-455 | 462-464 | 452 | 461 | 456-459 | 465-468 |

In some aspects, an antibody or antigen-binding fragment thereof described herein is described by its VL domain alone, or its VH domain alone, or by its 3 VL CDRs alone, or its 3 VH CDRs alone. See, for example, Rader C et al., (1998) PNAS 95: 8910-8915, which is incorporated herein by reference in its entirety, describing the humanization of the mouse anti-αvβ3 antibody by identifying a complementing light chain or heavy chain, respectively, from a human light chain or heavy chain library, resulting in humanized antibody variants having affinities as high or higher than the affinity of the original antibody. See also Clackson T et al., (1991) Nature 352: 624-628, which is incorporated herein by reference in its entirety, describing methods of producing antibodies that bind a specific antigen by using a specific VL domain (or VH domain) and screening a library for the complementary variable domains. The screen produced 14 new partners for a specific VH domain and 13 new partners for a specific VL domain, which were strong binders, as determined by ELISA. See also Kim S J & Hong H J, (2007) J Microbiol 45: 572-577, which is incorporated herein by reference in its entirety, describing methods of producing antibodies that bind a specific antigen by using a specific VH domain and screening a library (e.g., human VL library) for complementary VL domains; the selected VL domains in turn could be used to guide selection of additional complementary (e.g., human) VH domains.

In some aspects, the CDRs of an antibody or antigen-binding fragment thereof can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In some aspects, provided herein antibodies and antigen-binding fragments thereof that comprise the Chothia VH and VL CDRs of the GDF-15 antibody. In some aspects, antibodies or antigen-binding fragments thereof comprise one or more CDRs, in which the Chothia and Kabat CDRs have the same amino acid sequence. In some aspects, provided herein are antibodies and antigen-binding fragments thereof comprise combinations of Kabat CDRs and Chothia CDRs.

In some aspects, the CDRs of an antibody or antigen-binding fragment thereof can be determined according to the IMGT numbering system as described in Lefranc M-P, (1999) The Immunologist 7: 132-136 and Lefranc M-P et al., (1999) Nucleic Acids Res 27: 209-212. According to the IMGT numbering scheme, VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97. In some aspects, provided herein are antibodies and antigen-binding fragments thereof that comprise the IMGT VH and VL CDRs of the GDF-15 antibody, for example, as described in Lefranc M-P (1999) supra and Lefranc M-P et al., (1999) supra).

In some aspects, the CDRs of an antibody or antigen-binding fragment thereof can be determined according to MacCallum R M et al., (1996) J Mol Biol 262: 732-745. See also, e.g., Martin A. "Protein Sequence and Structure Analysis of Antibody Variable Domains," in Antibody Engineering, Kontermann and Dubel, eds., Chapter 31, pp. 422-439, Springer-Verlag, Berlin (2001). In some aspects, provided herein are antibodies or antigen-binding fragments thereof that comprise the VH and VL CDRs of the GDF-15 antibody determined by the method in MacCallum R M et al.

In some aspects, the CDRs of an antibody or antigen-binding fragment thereof can be determined according to the AbM numbering scheme, which refers AbM hypervariable regions which represent a compromise between the Kabat CDRs and Chothia structural loops, and are used by Oxford Molecular's AbM antibody modeling software (Oxford Molecular Group, Inc.). In some aspects, provided herein are antibodies or antigen-binding fragments that comprise the VH and VL CDRs of the GDF-15 antibody as determined by the AbM numbering scheme.

In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), and comprises a VH comprising a sequence at least 80% identical to the VH sequence of the same antibody in Table 3 and a VL comprising a sequence at least 80% identical to the VL sequence of the same antibody in Table 4. In some aspects, an antibody or antigen-binding fragment thereof described herein binds to human GDF-15, comprises the six CDRs of an antibody an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), and comprises a VH comprising a sequence at least 85% identical to the VH sequence of the same antibody in Table 3 and a VL comprising a sequence at least 85% identical to the VL sequence of the same antibody in Table 4.

In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), and comprises a VH comprising a sequence at least 90% identical to the VH sequence of the same antibody in Table 3 and a VL comprising a sequence at least 90% identical to the VL sequence of the same antibody in Table 4. In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), and comprises a VH comprising a sequence at least 95% identical to the VH sequence of the same antibody in Table 3 and a VL comprising a sequence at least 95% identical to the VL sequence of the same antibody in Table 4.

In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), and comprises a VH comprising a sequence at least 96% identical to the VH sequence of the same antibody in Table 3 and a VL comprising a sequence at least 96% identical to the VL sequence of the same antibody in Table 4. In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), and comprises a VH comprising a sequence at least 97% identical to the VH sequence of the same antibody in Table 3 and a VL comprising a sequence at least 97% identical to the VL sequence of the same antibody in Table 4. In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), and comprises a VH comprising a sequence at least 98% identical to the VH sequence of the same antibody in Table 3 and a VL comprising a sequence at least 98% identical to the VL sequence of the same antibody in Table 4. In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), and comprises a VH comprising a sequence at least 99% identical to the VH sequence of the same antibody in Table 3 and a VL comprising a sequence at least 99% identical to the VL sequence of the same antibody in Table 4.

In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 80% identical to the VH sequence of the same antibody in Table 3 and a VL comprising a sequence at least 80% identical to the VL sequence of the same antibody in Table 4, and is capable of inhibiting the proliferation of cancer cells, e.g., by at least 25%, at least 50%, or at least 75% as compared to the proliferation in the absence of the antibody or antigen-binding fragment thereof. In some aspects, an antibody or antigen-binding fragment thereof described herein binds to human GDF-15, comprises the six CDRs of an antibody an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 85% identical to the VH sequence of the same antibody in Table 3 and a VL comprising a sequence at least 85% identical to the VL sequence of the same antibody in Table 4, and is capable of inhibiting the proliferation of cancer cells, e.g., by at least 25%, at least 50%, or at least 75% as compared to the proliferation in the absence of the antibody or antigen-binding fragment thereof.

In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 90% identical to the VH sequence of the same antibody in Table 3 and a VL comprising a sequence at least 90% identical to the VL sequence of the same antibody in Table 4, and is capable of inhibiting the proliferation of cancer cells, e.g., by at least 25%, at least 50%, or at least 75% as compared to the proliferation in the absence of the antibody or antigen-binding fragment thereof. In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 95% identical to the VH sequence of the same antibody in Table 3 and a VL comprising a sequence at least 95% identical to the VL sequence of the same antibody in Table 4, and is capable of inhibiting the proliferation of cancer cells, e.g., by at least 25%, at least 50%, or at least 75% as compared to the proliferation in the absence of the antibody or antigen-binding fragment thereof.

In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 96% identical to the VH sequence of the same antibody in Table 3 and a VL comprising a sequence at least 96% identical to the VL sequence of the same antibody in Table 4, and is capable of inhibiting the proliferation of cancer cells, e.g., by at least 25%, at least 50%, or at least 75% as compared to the proliferation in the absence of the antibody or antigen-binding fragment thereof. In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 97% identical to the VH sequence of the same antibody in Table 3 and a VL comprising a sequence at least 97% identical to the VL sequence of the same antibody in Table 4, and is capable of inhibiting the proliferation of cancer cells, e.g., by at least 25%, at least 50%, or at least 75% as compared to the proliferation in the absence of the antibody or antigen-binding fragment thereof. In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 98% identical to the VH sequence of the same antibody in Table 3 and a VL comprising a sequence at least 98% identical to the VL sequence of the same antibody in Table 4, and is capable of inhibiting the proliferation of cancer cells, e.g., by at least 25%, at least 50%, or at least 75% as compared to the proliferation in the absence of the antibody or antigen-binding fragment thereof. In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 99% identical to the VH sequence of the same antibody in Table 3 and a VL comprising a sequence at least 99% identical to the VL sequence of the same antibody in Table 4, and is capable of inhibiting the proliferation of cancer cells, e.g., by at least 25%, at least 50%, or at least 75% as compared to the proliferation in the absence of the antibody or antigen-binding fragment thereof.

In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 80% identical to the VH sequence of the same antibody in Table 3 and a VL comprising a sequence at least 80% identical to the VL sequence of the same antibody in Table 4, and is capable of activating dendritic cells, e.g., doubling the activation of dendritic cells as compared to activation in the absence of the antibody or antigen-binding fragment thereof. In some aspects, an antibody or antigen-binding fragment thereof described herein binds to human GDF-15, comprises the six CDRs of an antibody an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 85% identical to the VH sequence of the same antibody in Table 3 and a VL comprising a sequence at least 85% identical to the VL sequence of the same antibody in Table 4, and is capable of activating dendritic cells, e.g., doubling the activation of dendritic cells as compared to activation in the absence of the antibody or antigen-binding fragment thereof.

In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 90% identical to the VH sequence of the same antibody in Table 3 and a VL comprising a sequence at least 90% identical to the VL sequence of the same antibody in Table 4, and is capable of activating dendritic cells, e.g., doubling the activation of dendritic cells as compared to activation in the absence of the antibody or antigen-binding fragment thereof. In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 95% identical to the VH sequence of the same antibody in Table 3 and a VL comprising a sequence at least 95% identical to the VL sequence of the same antibody in Table 4, and is capable of activating dendritic cells, e.g., doubling the activation of dendritic cells as compared to activation in the absence of the antibody or antigen-binding fragment thereof.

In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 96% identical to the VH sequence of the same antibody in Table 3 and a VL comprising a sequence at least 96% identical to the VL sequence of the same antibody in Table 4, and is capable of activating dendritic cells, e.g., doubling the activation of dendritic cells as compared to activation in the absence of the antibody or antigen-binding fragment thereof. In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 97% identical to the VH sequence of the same antibody in Table 3 and a VL comprising a sequence at least 97% identical to the VL sequence of the same antibody in Table 4, and is capable of activating dendritic cells, e.g., doubling the activation of dendritic cells as compared to activation in the absence of the antibody or antigen-binding fragment thereof. In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 98% identical to the VH sequence of the same antibody in Table 3 and a VL comprising a sequence at least 98% identical to the VL sequence of the same antibody in Table 4, and is capable of activating dendritic cells, e.g., doubling the activation of dendritic cells as compared to activation in the absence of the antibody or antigen-binding fragment thereof. In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 99% identical to the VH sequence of the same antibody in Table 3 and a VL comprising a sequence at least 99% identical to the VL sequence of the same antibody in Table 4, and is capable of activating dendritic cells, e.g., doubling the activation of dendritic cells as compared to activation in the absence of the antibody or antigen-binding fragment thereof.

In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 80% identical to the VH sequence of the same antibody in Table 3 and a VL comprising a sequence at least 80% identical to the VL sequence of the same antibody in Table 4, and is capable of increasing the proliferation of T cells, e.g., by at least 25%, at least 30%, at least 35%, or at least 40% as compared to the proliferation in the absence of the antibody or antigen-binding fragment thereof. In some aspects, an antibody or antigen-binding fragment thereof described herein binds to human GDF-15, comprises the six CDRs of an antibody an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 85% identical to the VH sequence of the same antibody in Table 3 and a VL comprising a sequence at least 85% identical to the VL sequence of the same antibody in Table 4, and is capable of increasing the proliferation of T cells, e.g., by at least 25%, at least 30%, at least 35%, or at least 40% as compared to the proliferation in the absence of the antibody or antigen-binding fragment thereof.

In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 90% identical to the VH sequence of the same antibody in Table 3 and a VL comprising a sequence at least 90% identical to the VL sequence of the same antibody in Table 4, and is capable of increasing the proliferation of T cells, e.g., by at least 25%, at least 30%, at least 35%, or at least 40% as compared to the proliferation in the absence of the antibody or antigen-binding fragment thereof. In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 95% identical to the VH sequence of the same antibody in Table 3 and a VL comprising a sequence at least 95% identical to the VL sequence of the same antibody in Table 4, and is capable of increasing the proliferation of T cells, e.g., by at least 25%, at least 30%, at least 35%, or at least 40% as compared to the proliferation in the absence of the antibody or antigen-binding fragment thereof.

In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 96% identical to the VH sequence of the same antibody in Table 3 and a VL comprising a sequence at least 96% identical to the VL sequence of the same antibody in Table 4, and is capable of increasing the proliferation of T cells, e.g., by at least 25%, at least 30%, at least 35%, or at least 40% as compared to the proliferation in the absence of the antibody or antigen-binding fragment thereof. In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 97% identical to the VH sequence of the same antibody in Table 3 and a VL comprising a sequence at least 97% identical to the VL sequence of the same antibody in Table 4, and is capable of increasing the proliferation of T cells, e.g., by at least 25%, at least 30%, at least 35%, or at least 40% as compared to the proliferation in the absence of the antibody or antigen-binding fragment thereof. In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 98% identical to the VH sequence of the same antibody in Table 3 and a VL comprising a sequence at least 98% identical to the VL sequence of the same antibody in Table 4, and is capable of increasing the proliferation of T cells, e.g., by at least 25%, at least 30%, at least 35%, or at least 40% as compared to the proliferation in the absence of the antibody or antigen-binding fragment thereof. In some aspects, an antibody or antigen-binding fragment thereof described herein binds to human GDF-15, comprises the six CDRs of an antibody provided herein (e.g., the three VH CDRs of the antibody listed in Table 1 and the three VL CDRs of the same antibody listed in Table 2, or the Kabat-defined, Chothia-defined, IMGT-defined, or AbM-defined CDRs of a VH listed in Table 3 and the corresponding VL listed in Table 4), comprises a VH comprising a sequence at least 99% identical to the VH sequence of the same antibody in Table 3 and a VL comprising a sequence at least 99% identical to the VL sequence of the same antibody in Table 4, and is capable of increasing the proliferation of T cells, e.g., by at least 25%, at least 30%, at least 35%, or at least 40% as compared to the proliferation in the absence of the antibody or antigen-binding fragment thereof.

In some aspects, provided herein are antibodies or antigen-binding fragments thereof that comprise a heavy chain constant region and/or a light chain constant region. With respect to the heavy chain, in some aspects, the heavy chain of an antibody described herein can be an alpha (α), delta (δ), epsilon (ε), gamma (γ) or mu (μ) heavy chain.

In some aspects, the heavy chain can comprise a human alpha (α), delta (δ), epsilon (ε), gamma (γ) or mu (μ) heavy chain. In some aspects, an antibody or antigen-binding fragment thereof described herein, which immunospecifically binds to GDF-15 (e.g., human GDF-15), comprises a heavy chain wherein the amino acid sequence of the VH domain comprises an amino acid sequence set forth in Table 3 and wherein the constant region of the heavy chain comprises the amino acid sequence of a human gamma (γ) heavy chain constant region. In some aspects, an antibody or antigen-binding fragment thereof described herein, which immunospecifically binds to GDF-15 (e.g., human GDF-15), comprises a heavy chain wherein the amino acid sequence of the VH domain comprises an amino acid sequence set forth in Table 3 and wherein the constant region of the heavy chain comprises the amino acid sequence of SEQ ID NO:473. In some aspects, an antibody or antigen-binding fragment thereof described herein, which immunospecifically binds to GDF-15 (e.g., human GDF-15), comprises a heavy chain wherein the amino acid sequence of the VH domain comprises an amino acid sequence set forth in Table 3 and wherein the constant region of the heavy chain comprises the amino acid sequence of SEQ ID NO:474. Non-limiting examples of human constant region sequences have been described in the art, e.g., see U.S. Pat. No. 5,693,780 and Kabat E A et al., (1991) supra.

In some aspects, the light chain of an antibody or antigen-binding fragment thereof described herein is a human kappa light chain or a human lambda light chain. In some aspects, an antibody or antigen-binding fragment thereof described herein, which immunospecifically binds to GDF-15 (e.g., human GDF-15) comprises a light chain wherein the amino acid sequence of the VL domain comprises a sequence set forth in Table 4 and wherein the constant region of the light chain comprises the amino acid sequence of a human kappa or lambda light chain constant region. In some aspects, an antibody or antigen-binding fragment thereof described herein, which immunospecifically binds to GDF-15 (e.g., human GDF-15) comprises a light chain wherein the amino acid sequence of the VL domain comprises a sequence set forth in Table 4 and wherein the constant region of the light chain comprises the amino acid sequence of a human kappa light chain constant region. In some aspects, an antibody or antigen-binding fragment thereof described herein, which immunospecifically binds to GDF-15 (e.g., human GDF-15), comprises a light chain wherein the amino acid sequence of the VL domain comprises an amino acid sequence set forth in Table 4 and wherein the constant region of the light chain comprises the amino acid sequence of SEQ ID NO:475.

Exemplary heavy and light chain constant regions are provided in Table 8. Table 8. Constant Region Sequences Constant Sequence (SEQ ID NO) Region

TABLE 8

Constant Region Sequences

| Constant Region | Sequence (SEQ ID NO) |
|---|---|
| Human IgG1 (heavy) | ASTKGPSVFPLAPSSKSTSG<br>GTAALGCLVKDYFPEPVTVS<br>WNSGALTSGVHTFPAVLQSS<br>GLYSLSSVVTVPSSSLGTQT<br>YICNVNHKPSNTKVDKKVEP<br>KSCDKTHTCPPCPAPELLGG<br>PSVFLFPPKPKDTLMISRTP<br>EVTCVVVDVSHEDPEVKFNW<br>YVDGVEVHNAKTKPREEQYN<br>STYRVVSVLTVLHQDWLNGK<br>EYKCKVSNKALPAPIEKTIS<br>KAKGQPREPQVYTLPPSRDE<br>LTKNQVSLTCLVKGFYPSDI<br>AVEWESNGQPENNYKTTPPV<br>LDSDGSFFLYSKLTVDKSRW<br>QQGNVFSCSVMHEALHNHYT<br>QKSLSLSPGK<br>(SEQ ID NO: 473) |
| Human IgG1 TMF allotype (heavy) | ASTKGPSVFPLAPSSKSTSG<br>GTAALGCLVKDYFPEPVTVS<br>WNSGALTSGVHTFPAVLQSS<br>GLYSLSSVVTVPSSSLGTQT<br>YICNVNHKPSNTKVDKRVEP<br>KSCDKTHTCPPCPAPEFEGG<br>PSVFLFPPKPKDTLMISRTP<br>EVTCVVVDVSHEDPEVKFNW<br>YVDGVEVHNAKTKPREEQYN<br>STYRVVSVLTVLHQDWLNGK<br>EYKCKVSNKALPASIEKTIS<br>KAKGQPREPQVYTLPPSREE<br>MTKNQVSLTCLVKGFYPSDI<br>AVEWESNGQPENNYKTTPPV<br>LDSDGSFFLYSKLTVDKSRW<br>QQGNVFSCSVMHEALHNHYT<br>QKSLSLSPGK<br>(SEQ ID NO: 474) |
| Human IgG1 TM F allotype (heavy) | GCCTCCACCAAGGGCCCATC<br>GGTCTTCCCCCTGGCACCCT<br>CCTCCAAGAGCACCTCTGGG<br>GGCACAGCGGCCCTGGGCTG<br>CCTGGTCAAGGACTACTTCC<br>CCGAACCGGTGACGGTGTCG<br>TGGAACTCAGGCGCCCTGAC<br>CAGCGGCGTGCACACCTTCC<br>CGGCTGTCCTACAGTCCTCA<br>GGACTCTACTCCCTCAGCAG<br>CGTGGTGACAGTGCCCTCCA |

TABLE 8-continued

Constant Region Sequences

| Constant Region | Sequence (SEQ ID NO) |
|---|---|
| | GCAGCTTGGGCACCCAGACC<br>TACATCTGCAACGTGAATCA<br>CAAGCCCAGCAACACCAAGG<br>TGGACAAGAGAGTTGAGCCC<br>AAATCTTGTGACAAAACTCA<br>CACATGCCCACCGTGCCCAG<br>CACCTGAATTCGAGGGGGGA<br>CCGTCAGTCTTCCTCTTCCC<br>CCCAAAACCCAAGGACACCC<br>TCATGATCTCCCGGACCCCT<br>GAGGTCACATGCGTGGTGGT<br>GGACGTGAGCCACGAAGACC<br>CTGAGGTCAAGTTCAACTGG<br>TACGTGGACGGCGTGGAGGT<br>GCATAATGCCAAGACAAAGC<br>CGCGGGAGGAGCAGTACAAC<br>AGCACGTACCGTGTGGTCAG<br>CGTCCTCACCGTCCTGCACC<br>AGGACTGGCTGAATGGCAAG<br>GAGTACAAGTGCAAGGTCTC<br>CAACAAAGCCCTCCCAGCCT<br>CCATCGAGAAAACCATCTCC<br>AAAGCCAAAGGGCAGCCCCG<br>AGAACCACAGGTGTACACCC<br>TGCCCCCATCCCGGGAGGAG<br>ATGACCAAGAACCAGGTCAG<br>CCTGACCTGCCTGGTCAAAG<br>GCTTCTATCCCAGCGACATC<br>GCCGTGGAGTGGGAGAGCAA<br>TGGGCAGCCGGAGAACAACT<br>ACAAGACCACGCCTCCCGTG<br>CTGGACTCCGACGGCTCCTT<br>CTTCCTCTATAGCAAGCTCA<br>CCGTGGACAAGAGCAGGTGG<br>CAGCAGGGGAACGTCTTCTC<br>ATGCTCCGTGATGCATGAGG<br>CTCTGCACAACCACTACACG<br>CAGAAGAGCCTCTCCCTGTC<br>TCCGGGTAAA<br>(SEQ ID NO:481) |
| Human kappa (light) | RTVAAPSVFDFPPSDEQLKS<br>GTASWCLLNNFYPREAKVQW<br>KVDNALQSGNSQESVTEQDS<br>KDSTYSLSSTLTLSKADYEK<br>HKVYACEVTHQGLSSPVTKS<br>FNRGEC<br>(SEQ ID NO: 475) |
| Human kappa (light) | CGAACTGTGGCTGCACCATC<br>TGTCTTCATCTTCCCGCCAT<br>CTGATGAGCAGTTGAAATCT<br>GGAACTGCCTCTGTTGTGTG<br>CCTGCTGAATAACTTCTATC<br>CCAGAGAGGCCAAAGTACAG<br>TGGAAGGTGGATAACGCCCT<br>CCAATCGGGTAACTCCCAGG<br>AGAGTGTCACAGAGCAGGAC<br>AGCAAGGACAGCACCTACAG<br>CCTCAGCAGCACCCTGACGC<br>TGAGCAAAGCAGACTACGAG<br>AAACACAAAGTCTACGCCTG<br>CGAAGTCACCCATCAGGGCC<br>TGAGCTCGCCCGTCACAAAG<br>AGCTTCAACAGGGGAGAGTG<br>T (SEQ ID NO: 482) |
| Murine IgG1 (heavy) | AKTTPPSVYPLAPGSAAQTN<br>SMVTLGCLVKGYFPEPVTVT<br>WNSGSLSSGVHTFPAVLQSD<br>LYTLSSSVTVPSSTWPSQTV<br>TCNVAHPASSTKVDKKIVPR<br>DCGCKPCICTVPEVSSVFIF<br>PPKPKDVLTITLTPKVTCVV<br>VDISKDDPEVQFSWFVDDVE |

TABLE 8-continued

Constant Region Sequences

| Constant Region | Sequence (SEQ ID NO) |
| --- | --- |
| | VHTAQTKPREEQINSTFRSV<br>SELPIMHQDWLNGKEFKCRV<br>NSAAFPAPIEKTISKTKGRP<br>KAPQVYTIPPPKEQMAKDKV<br>SLTCMITDFFPEDITVEWQW<br>NGQPAENYKNTQPIMDTDGS<br>YFVYSKLNVQKSNWEAGNTF<br>TCSVLHEGLHNHHTEKSLSH<br>SPGK<br>(SEQ ID NO: 476) |
| Murine D265A IgG1 (heavy) | AKTTPPSVYPLAPGSAAQTN<br>SMVTLGCLVKGYFPEPVTVT<br>WNSGSLSSGVHTFPAVLQSD<br>LYTLSSSVTVPSSTWPSQTV<br>TCNVAHPASSTKVDKKIVPR<br>DCGCKPCICTVPEVSSVFIF<br>PPKPKDVLTITLTPKVTCVV<br>VAISKDDPEVQFSWFVDDVE<br>VHTAQTKPREEQINSTFRSV<br>SELPIMHQDWLNGKEFKCRV<br>NSAAFPAPIEKTISKTKGRP<br>KAPQVYTIPPPKEQMAKDKV<br>SLTCMITDFFPEDITVEWQW<br>N<br>GQPAENYKNTQPIMDTDGSY<br>FVYSKLNVQKSNWEAGNTFT<br>CSVLHEGLHNHHTEKSLSHS<br>PGK<br>(SEQ ID NO: 477) |
| Murine D265A IgG1 (heavy) | GCCAAAACGACACCCCCTTC<br>CGTGTACCCTCTGGCCCCTG<br>GCTCTGCCGCCCAGACCAAC<br>TCCATGGTCACACTGGGCTG<br>CCTGGTCAAGGGCTACTTCC<br>CTGAGCCTGTGACCGTGACC<br>TGGAACTCCGGCTCCCTGTC<br>CTCCGGCGTGCATACCTTCC<br>CTGCCGTGCTGCAGTCCGAC<br>CTGTACACCCTGTCCAGCTC<br>CGTGACCGTGCCTTCCTCCA<br>CCTGGCCTTCCCAGACCGTG<br>ACATGCAACGTGGCCCACCC<br>TGCCAGCAGCACCAAGGTGG<br>ACAAGAAAATTGTGCCCAGG<br>GATTGTGGTTGTAAGCCTTG<br>CATATGCACAGTCCCAGAAG<br>TATCATCCGTCTTTATCTTC<br>CCTCCTAAGCCTAAGGACGT<br>GCTGACCATCACCCTGACAC<br>CTAAGGTCACATGCGTGGTG<br>GTGGCCATCTCCAAGGACGA<br>TCCTGAGGTGCAGTTCAGTT<br>GGTTCGTGGACGACGTGGAG<br>GTCCACACCGCTCAGACCAA<br>GCCTCGGGAAGAGCAGATCA<br>ACTCCACCTTCAGATCCGTG<br>TCCGAGCTGCCTATCATGCA<br>CCAGGACTGGCTGAACGGCA<br>AAGAGTTCAAGTGCAGAGTC<br>AACAGCGCCGCCTTCCCTGC<br>TCCCATCGAGAAAACCATCT<br>CCAAAACCAAAGGCAGACCG<br>AAGGCTCCACAGGTGTACAC<br>CATTCCACCTCCTAAAGAGC<br>AGATGGCCAAGGACAAGGTG<br>TCCCTGACCTGCATGATCAC<br>CGATTTCTTCCCTGAGGACA<br>TCACCGTGGAGTGGCAGTGG<br>AACGGCCAGCCTGCCGAGAA<br>CTACAAGAATACCCAGCCCA<br>TCATGGACACCGACGGCTCC<br>TACTTCGTGTACTCCAAGCT<br>GAACGTGCAGAAGTCCAACT<br>GGGAGGCCGGCAACACCTTC<br>ACCTGTAGCGTGCTGCACGA<br>GGGCCTGCACAACCACCACA<br>CCGAGAAGTCCCTGTCCCAC<br>TCCCCCGGCAAG<br>(SEQ ID NO: 483) |
| Murine kappa (light) | RADAAPTVSIFPPSSEQLTS<br>GGASVVCFLNNFYPKDINVK<br>WKIDGSERQNGVLNSWTDQD<br>SKDSTYSMSSTLTLTKDEYE<br>RHNSYTCEATHKTSTSPIVK<br>SFNRNEC<br>(SEQ ID NO: 478) |
| Murine kappa (light) | CGGGCTGATGCTGCACCAAC<br>CGTGTCCATCTTCCCTCCCT<br>CCTCCGAGCAGCTGACCTCT<br>GGCGGCGCTTCCGTCGTCTG<br>CTTCCTGAACAACTTCTACC<br>CCAAGGACATCAACGTGAAG<br>TGGAAGATCGACGGCTCCGA<br>GCGGCAGAACGGCGTGCTGA<br>ACTCCTGGACCGACCAGGAC<br>TCCAAGGACAGCACCTACTC<br>CATGTCCTCCACCCTGACCC<br>TGACCAAGGACGAGTACGAG<br>CGGCACAACTCCTACACCTG<br>CGAGGCCACCCACAAGACCT<br>CCACCTCCCCCATCGTGAAG<br>TCCTTCAACCGGAACGAGTG<br>C<br>(SEQ ID NO: 484) |

In some aspects, an antibody described herein, which immunospecifically binds to GDF-15 (e.g., human GDF-15) comprises a VH domain and a VL domain comprising any amino acid sequence described herein, and wherein the constant regions comprise the amino acid sequences of the constant regions of an IgG, IgE, IgM, IgD, IgA, or IgY immunoglobulin molecule, or a human IgG, IgE, IgM, IgD, IgA, or IgY immunoglobulin molecule. In some aspects, an antibody described herein, which immunospecifically binds to GDF-15 (e.g., human GDF-15) comprises a VH domain and a VL domain comprising any amino acid sequence described herein, and wherein the constant regions comprise the amino acid sequences of the constant regions of an IgG, IgE, IgM, IgD, IgA, or IgY immunoglobulin molecule, any class (e.g., IgG1, IgG2, IgG3, IgG4, IgA1, and IgA2), or any subclass (e.g., IgG2a and IgG2b) of immunoglobulin molecule. In some aspects, the constant regions comprise the amino acid sequences of the constant regions of a human IgG, IgE, IgM, IgD, IgA, or IgY immunoglobulin molecule, any class (e.g., IgG1, IgG2, IgG3, IgG4, IgA1, and IgA2), or any subclass (e.g., IgG2a and IgG2b) of immunoglobulin molecule.

In some aspects, the antibody or antigen-binding fragment thereof (e.g., monoclonal antibody or fragment) described herein can comprise a constant region (Fc) of any suitable class (e.g., IgG, IgA, IgD, IgM, and IgE) that has been modified in order to improve the half-life of the antibody or antigen-binding fragment (e.g., monoclonal antibody or fragment). For example, the antibody or antigen-binding fragment thereof (e.g., monoclonal antibody or fragment) described herein can comprise an Fc that comprises a mutation that extends half-life relative to the same antibody without the mutation.

Fc region engineering is widely used in the art to extend the half-life of therapeutic antibodies and protect from degradation in vivo. In some aspects, the Fc region of an IgG antibody or antigen-binding fragment can be modified in order to increase the affinity of the IgG molecule for the Fc Receptor-neonate (FcRn), which mediates IgG catabolism and protects IgG molecules from degradation. Suitable Fc region amino acid substitutions or modifications are known in the art and include, for example, the triple substitution methionine (M) to tyrosine (Y) substitution in position 252, a serine (S) to threonine (T) substitution in position 254, and a threonine (T) to glutamic acid (E) substitution in position 256, numbered according to the EU index as in Kabat (M252Y/S254T/T256E; referred to as "YTE") (see, e.g., U.S. Pat. No. 7,658,921; U.S. Patent Application Publication 2014/0302058; and Yu et al., Antimicrob. Agents Chemother., 61(1): e01020-16 (2017), each of which is herein incorporated by reference in its entirety).

The triple mutation (TM) L234F/L235E/P331S (according to European Union numbering convention; Sazinsky et al. *Proc Natl Acad Sci USA,* 105:20167-20172 (2008)) in the heavy chain constant region can significantly reduce IgG effector function. In some aspects, an IgG1 sequence comprising the triple mutation comprises the of SEQ ID NO:474.

In some aspects, one, two, or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain can be altered to, e.g., facilitate assembly of the light and heavy chains, or to alter (e.g., increase or decrease) the stability of the antibody or antigen-binding fragment thereof.

In some aspects, one, two, or more mutations (e.g., amino acid substitutions) are introduced into the Fc region of an antibody or antigen-binding fragment thereof described herein (e.g., CH2 domain (residues 231-340 of human IgG1) and/or CH3 domain (residues 341-447 of human IgG1) and/or the hinge region, with numbering according to the Kabat numbering system (e.g., the EU index in Kabat)) to increase or decrease the affinity of the antibody or antigen-binding fragment thereof for an Fc receptor (e.g., an activated Fc receptor) on the surface of an effector cell. Mutations in the Fc region that decrease or increase affinity for an Fc receptor and techniques for introducing such mutations into the Fc receptor or fragment thereof are known to one of skill in the art. Examples of mutations in the Fc receptor that can be made to alter the affinity of the antibody or antigen-binding fragment thereof for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In some aspects, one, two, or more amino acid mutations (i.e., substitutions, insertions or deletions) are introduced into an IgG constant domain, or FcRn-binding fragment thereof (preferably an Fc or hinge-Fc domain fragment) to alter (e.g., decrease or increase) half-life of the antibody or antigen-binding fragment thereof in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody or antigen-binding fragment thereof in vivo. In some aspects, one, two or more amino acid mutations (i.e., substitutions, insertions, or deletions) are introduced into an IgG constant domain, or FcRn-binding fragment thereof (preferably an Fc or hinge-Fc domain fragment) to decrease the half-life of the antibody or antigen-binding fragment thereof in vivo. In some aspects, one, two or more amino acid mutations (i.e., substitutions, insertions or deletions) are introduced into an IgG constant domain, or FcRn-binding fragment thereof (e.g., an Fc or hinge-Fc domain fragment) to increase the half-life of the antibody or antigen-binding fragment thereof in vivo. In some aspects, the antibodies or antigen-binding fragments thereof may have one or more amino acid mutations (e.g., substitutions) in the second constant (CH2) domain (residues 231-340 of human IgG1) and/or the third constant (CH3) domain (residues 341-447 of human IgG1), with numbering according to the EU index in Kabat (Kabat E A et al., (1991) supra). In some aspects, an antibody or antigen-binding fragment thereof comprises an IgG constant domain comprising one, two, three or more amino acid substitutions of amino acid residues at positions 251-257, 285-290, 308-314, 385-389, and 428-436, numbered according to the EU index as in Kabat.

In some aspects, one, two, or more amino acid substitutions are introduced into an IgG constant domain Fc region to alter the effector function(s) of the antibody or antigen-binding fragment thereof. For example, one or more amino acids selected from amino acid residues 234, 235, 236, 237, 297, 318, 320 and 322, numbered according to the EU index as in Kabat, can be replaced with a different amino acid residue such that the antibody or antigen-binding fragment thereof has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260. In some aspects, the deletion or inactivation (through point mutations or other means) of a constant region domain can reduce Fc receptor binding of the circulating antibody or antigen-binding fragment thereof thereby increasing tumor localization. See, e.g., U.S. Pat. Nos. 5,585,097 and 8,591,886 for a description of mutations that delete or inactivate the constant domain. In some aspects, one or more amino acid substitutions can be introduced into the Fc region to remove potential glycosylation sites on Fc region, which may reduce Fc receptor binding (see, e.g., Shields R L et al., (2001) J Biol Chem 276: 6591-604).

In some aspects, one or more amino acids selected from amino acid residues 322, 329, and 331 in the constant region, numbered according to the EU index as in Kabat, can be replaced with a different amino acid residue such that the antibody or antigen-binding fragment thereof has altered C1q binding and/or reduced or abolished complement dependent cytotoxicity (CDC). This approach is described in further detail in U.S. Pat. No. 6,194,551 (Idusogie et al). In some aspects, one or more amino acid residues within amino acid positions 231 to 238 in the N-terminal region of the CH2 domain are altered to thereby alter the ability of the antibody to fix complement. This approach is described further in International Publication No. WO 94/29351. In some aspects, the Fc region is modified to increase or decrease the ability of the antibody or antigen-binding fragment thereof to mediate antibody dependent cellular cytotoxicity (ADCC) and/or to increase or decrease the affinity of the antibody or antigen-binding fragment thereof for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU index as in Kabat. This approach is described further in International Publication No. WO 00/42072.

In some aspects, an antibody or antigen-binding fragment thereof described herein comprises the constant domain of an IgG1 with a mutation (e.g., substitution) at position 267, 328, or a combination thereof, numbered according to the EU index as in Kabat. In some aspects, an antibody or antigen-binding fragment thereof described herein comprises the constant domain of an IgG1 with a mutation (e.g., substitution) selected from the group consisting of S267E, L328F, and a combination thereof. In some aspects, an antibody or antigen-binding fragment thereof described herein comprises the constant domain of an IgG1 with a S267E/L328F mutation (e.g., substitution). In some aspects, an antibody or antigen-binding fragment thereof described herein comprising the constant domain of an IgG1 with a S267E/L328F mutation (e.g., substitution) has an increased binding affinity for FcγRIIA, FcγRIIB, or FcγRIIA and FcγRIIB.

Engineered glycoforms may be useful for a variety of purposes, including but not limited to enhancing or reducing effector function. Methods for generating engineered glycoforms in an antibody or antigen-binding fragment thereof described herein include but are not limited to those disclosed, e.g., in Umana P et al., (1999) Nat Biotechnol 17: 176-180; Davies J et al., (2001) Biotechnol Bioeng 74: 288-294; Shields R L et al., (2002) J Biol Chem 277: 26733-26740; Shinkawa T et al., (2003) J Biol Chem 278: 3466-3473; Niwa R et al., (2004) Clin Cancer Res 1: 6248-6255; Presta L G et al., (2002) Biochem Soc Trans 30: 487-490; Kanda Y et al., (2007) Glycobiology 17: 104-118; U.S. Pat. Nos. 6,602,684; 6,946,292; and 7,214,775; U.S. Patent Publication Nos. US 2007/0248600; 2007/0178551; 2008/0060092; and 2006/0253928; International Publication Nos. WO 00/61739; WO 01/292246; WO 02/311140; and WO 02/30954; Potillegent™ technology (Biowa, Inc. Princeton, N.J.); and GlycoMAb® glycosylation engineering technology (Glycart biotechnology AG, Zurich, Switzerland). See also, e.g., Ferrara C et al., (2006) Biotechnol Bioeng 93: 851-861; International Publication Nos. WO 07/039818; WO 12/130831; WO 99/054342; WO 03/011878; and WO 04/065540.

In some aspects, any of the constant region mutations or modifications described herein can be introduced into one or both heavy chain constant regions of an antibody or antigen-binding fragment thereof described herein having two heavy chain constant regions.

In some aspects, provided herein are antibodies or antigen-binding fragments thereof that bind the same epitope of GDF-15 (e.g., an epitope of human GDF-15) as an antibody or antigen-binding fragment thereof described herein (e.g., AB1170002, AB1170006, AB1170010, AB1170019, AB1170028, AB1170036, AB1170040, AB1170043, AB1170047, AB1170069, AB1170070, AB1170072, AB1170073, AB1170074, AB1170086, AB1170148, AB1170241, AB1170242, AB1170243, AB1170244, AB1170245, AB1170246, AB1170247, AB 1170248, AB 1170249, or AB1520085). In some aspects, provided herein are antibodies or antigen-binding binding fragments thereof that bind to the same GDF-15 epitope as AB 1170241 (an antibody comprising a VH of SEQ ID NO:326 and a VL of SEQ ID NO:335).

Competition binding assays can be used to determine whether two antibodies bind to overlapping epitopes. Competitive binding can be determined in an assay in which the immunoglobulin under test inhibits specific binding of a reference antibody to a common antigen, such as GDF-15. Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using I-125 label (see Morel G A et al., (1988) Mol Immunol 25(1): 7-15); solid phase direct biotin-avidin EIA (Cheung R C et al., (1990) Virology 176: 546-52); and direct labeled RIA. (Moldenhauer G et al., (1990) Scand J Immunol 32: 77-82). Typically, such an assay involves the use of purified antigen (e.g., GDF-15 such as human GDF-15) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389.

In some aspects, a competition assay is performed using surface plasmon resonance (BIAcore®), e.g., by an 'in tandem approach' such as that described by Abdiche Y N et al., (2009) Analytical Biochem 386: 172-180, whereby GDF-15 antigen is immobilized on the chip surface, for example, a CM5 sensor chip and the anti-GDF-15 antibodies are then run over the chip. To determine if an antibody or antigen-binding fragment thereof competes with an anti-GDF-15 antibody described herein, the anti-GDF-15 antibody is first run over the chip surface to achieve saturation and then the potential, competing antibody is added. Binding of the competing antibody or antigen-binding fragment thereof can then be determined and quantified relative to a non-competing control.

In some aspects, Fortebio Octet competition binding is used to determine that a GDF-15 antibody or antigen-binding fragment thereof competitively inhibits the binding of another GDF-15 antibody or antigen-binding fragment thereof to GDF-15.

In some aspects, provided herein are antibodies that competitively inhibit (e.g., in a dose dependent manner) an antibody or antigen-binding fragment thereof described herein (e.g., 20502, 20502.1 or 22213) from binding to GDF-15 (e.g., human GDF-15), as determined using assays known to one of skill in the art or described herein (e.g., ELISA competitive assays, suspension array or surface plasmon resonance assay, or the methods used in Example 4).

An antibody or antigen-binding fragment (e.g. monoclonal antibody or fragment) described herein can be, or can be obtained from, a human antibody, a humanized antibody, a non-human antibody, or a chimeric antibody. In one aspect, an antibody described herein, or antigen-binding fragment thereof, is a fully human antibody. In some aspects, an antigen-binding fragment as described herein that specifically binds to GDF-15, is selected from the group consisting of a Fab, Fab', $F(ab')_2$, and scFv, wherein the Fab, Fab', $F(ab')_2$, or scFv comprises a heavy chain variable region sequence and a light chain variable region sequence of an antibody or antigen-binding fragment thereof described herein that specifically binds to GDF-15. A Fab, Fab', $F(ab')_2$, or scFv can be produced by any technique known to those of skill in the art. In some aspects, the Fab, Fab', $F(ab')_2$, or scFv further comprises a moiety that extends the half-life of the antibody in vivo. The moiety is also termed a "half-life extending moiety." Any moiety known to those of skill in the art for extending the half-life of a Fab, Fab', $F(ab')_2$, or scFv in vivo can be used. For example, the half-life extending moiety can include a Fc region, a polymer, an albumin, or an albumin binding protein or compound. The polymer can include a natural or synthetic, optionally substituted straight or branched chain polyalkylene, polyalkenylene, polyoxylalkylene, polysaccharide, polyethylene glycol, polypropylene glycol, polyvinyl alcohol, methoxypolyethylene glycol, lactose, amylose, dextran, glycogen, or derivative thereof. Substituents can include one or more hydroxy, methyl, or methoxy groups. In some aspects, the Fab, Fab', $F(ab')_2$, or scFv can be modified by the addition of one or more C-terminal amino acids for attachment of the half-life extending moiety. In some aspects the half-life extending moiety is polyethylene glycol or human serum albumin. In some aspects, the Fab, Fab', $F(ab')_2$, or scFv is fused to a Fc region.

An antibody or antigen-binding fragment thereof that binds to GDF-15 can be fused or conjugated (e.g., covalently or noncovalently linked) to a detectable label or substance. Examples of detectable labels or substances include enzyme labels, such as, glucose oxidase; radioisotopes, such as iodine ($^{125}I$, $^{121}I$), carbon (C), sulfur ($^{35}S$), tritium ($^{3}H$), indium ($^{121}In$), and technetium ($^{99}Tc$); luminescent labels, such as luminol; and fluorescent labels, such as fluorescein and rhodamine, and biotin. Such labeled antibodies or antigen-binding fragments thereof can be used to detect GDF-15.

In some aspects, an antibody or antigen-binding fragment thereof described herein is isolated or purified. Generally, an isolated antibody or antigen-binding fragment thereof is one that is substantially free of other antibodies or antigen-binding fragments thereof with different antigenic specificities than the isolated antibody or antigen-binding fragment thereof. For example, in some aspects, a preparation of an antibody or antigen-binding fragment thereof described herein is substantially free of cellular material and/or chemical precursors.

III. Nucleic Acids, Vectors, Host Cells, and Methods of Producing Antibodies

Antibodies and antigen-binding fragments thereof that immunospecifically bind to GDF-15 can be produced by any method known in the art for the synthesis of antibodies and antigen-binding fragments thereof, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Sambrook J et al., (2001) Molecular Cloning: A Laboratory Manual, Cold Spring Harbor Laboratory Press, Cold Spring Harbor, NY; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, TRL Press; Eckstein (ed.) (1991) Oligonucleotides and Analogues: A Practical Approach, TRL Press; Birren B et al., (eds.) (1999) Genome Analysis: A Laboratory Manual, Cold Spring Harbor Laboratory Press.

In some aspects, provided herein is a method of making an antibody or antigen-binding fragment which immunospecifically binds to GDF-15 comprising culturing a cell or host cell described herein. In some aspects, provided herein is a method of making an antibody or antigen-binding fragment thereof which immunospecifically binds to GDF-15 comprising expressing (e.g., recombinantly expressing) the antibody or antigen-binding fragment thereof using a cell or host cell described herein (e.g., a cell or a host cell comprising polynucleotides encoding an antibody or antigen-binding fragment thereof described herein). In some aspects, the cell is an isolated cell. In some aspects, the exogenous polynucleotides have been introduced into the cell. In some aspects, the method further comprises the step of separating or purifying the antibody or antigen-binding fragment obtained from the cell, host cell, or culture.

Methods for producing polyclonal antibodies are known in the art (see, for example, Chapter 11 in: Short Protocols in Molecular Biology, (2002) 5th Ed., Ausubel F M et al., eds., John Wiley and Sons, New York).

Monoclonal antibodies or antigen-binding fragments thereof can be prepared using a wide variety of techniques known in the art including the use of hybridoma, recombinant, and phage display technologies, yeast-based presentation technologies, or a combination thereof. For example, monoclonal antibodies or antigen-binding fragments thereof can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), or as described in Kohler G & Milstein C (1975) Nature 256: 495. Examples of yeast-based presentation methods that can be employed to select and generate the antibodies described herein include those disclosed in, for example, WO2009/036379A2; WO2010/105256; and WO2012/009568, each of which is herein incorporated by reference in its entirety.

In some aspects, a monoclonal antibody or antigen-binding fragment is an antibody or antigen-binding fragment produced by a clonal cell (e.g., hybridoma or host cell producing a recombinant antibody or antigen-binding fragment), wherein the antibody or antigen-binding fragment immunospecifically binds to GDF-15 as determined, e.g., by ELISA or other antigen-binding assays known in the art or in the Examples provided herein. In some aspects, a monoclonal antibody or antigen-binding fragment thereof can be a human antibody or antigen-binding fragment thereof. In some aspects, a monoclonal antibody or antigen-binding fragment thereof can be a Fab fragment or a $F(ab')_2$ fragment. Monoclonal antibodies or antigen-binding fragments thereof described herein can, for example, be made by the hybridoma method as described in Kohler G & Milstein C (1975) Nature 256: 495 or can, e.g., be isolated from phage libraries using the techniques as described herein, for example. Other methods for the preparation of clonal cell lines and of monoclonal antibodies and antigen-binding fragments thereof expressed thereby are well known in the art (see, for example, Chapter 11 in: Short Protocols in Molecular Biology, (2002) 5th Ed., Ausubel F M et al., supra).

Antigen-binding fragments of antibodies described herein can be generated by any technique known to those of skill in the art. For example, Fab and $F(ab')_2$ fragments described herein can be produced by proteolytic cleavage of immunoglobulin molecules, using enzymes such as papain (to produce Fab fragments) or pepsin (to produce $F(ab')_2$ fragments). A Fab fragment corresponds to one of the two identical arms of a tetrameric antibody molecule and contains the complete light chain paired with the VH and CH1 domains of the heavy chain. A $F(ab')_2$ fragment contains the two antigen-binding arms of a tetrameric antibody molecule linked by disulfide bonds in the hinge region.

Further, the antibodies or antigen-binding fragments thereof described herein can also be generated using various phage display and/or yeast-based presentation methods known in the art. In phage display methods, proteins are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in *E. coli* and the *E. coli* is infected with helper phage. Phage used in these methods are typically filamentous phage including fd and M13, and the VH and VL domains are usually recombinantly fused to either the phage gene III or gene VIII. Phage expressing an antibody or antigen-binding fragment thereof that binds to a particular antigen can be selected or identified with antigen, e.g., using labeled antigen or antigen bound or captured to a solid surface or bead. Examples of phage display methods that can be used to make the antibodies or fragments described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108

A human antibody, a non-human antibody, a chimeric antibody, or a humanized antibody can be obtained by any means, including via in vitro sources (e.g., a hybridoma or a cell line producing an antibody recombinantly) and in vivo sources (e.g., rodents, human tonsils). Methods for generating antibodies are known in the art and are described in, for example, Kohler and Milstein, Eur. J. Immunol., 5: 511-519 (1976); Harlow and Lane (eds.), Antibodies: A Laboratory Manual, CSH Press (1988); and Janeway et al. (eds.), Immunobiology, 5th Ed., Garland Publishing, New York, N.Y. (2001)). In some aspects, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin TC MOUSE™, and the Kyowa Kirin KM-MOUSE™ (see, e.g., Lonberg, Nat. Biotechnol., 23(9): 1117-25 (2005), and Lonberg, Handb. Exp. Pharmacol., 181: 69-97 (2008)). A humanized antibody can be generated using any suitable method known in the art (see, e.g., An, Z. (ed.), Therapeutic Monoclonal Antibodies: From Bench to Clinic, John Wiley & Sons, Inc., Hoboken, N.J. (2009)), including, e.g., grafting of non-human CDRs onto a human antibody scaffold (see, e.g., Kashmiri et al., Methods, 36(1): 25-34 (2005); and Hou et al., J. Biochem., 144(1): 115-120 (2008)). In some aspects, a humanized antibody can be produced using the methods described in, e.g., U.S. Patent Application Publication 2011/0287485 A1.

III(a). Nucleic Acids

Provided herein are one or more isolated polynucleotides comprising nucleic acid sequences that encode the antibody or antigen-binding fragment thereof that binds to human GDF-15 (optionally wherein the antibody or antigen-binding fragment thereof is a monoclonal antibody or fragment) or a fragment thereof (e.g., a VH and/or a VL).

Also provided herein is a polynucleotide comprising a nucleotide sequence encoding a polypeptide comprising a sequence selected from the group consisting of SEQ ID NOs:2, 20, 38, 56, 74, 92, 110, 128, 146, 164, 182, 200, 218, 236, 254, 272, 290, 308, 326, 344, 362, 380, 398, 416, 434, and 452. In some aspects, an antibody or antigen-binding fragment thereof comprising the polypeptide immunospecifically binds to GDF-15.

Also provided herein is a polynucleotide comprising a nucleotide sequence encoding a polypeptide comprising a sequence selected from the group consisting of SEQ ID NOs:11, 29, 47, 65, 83, 101, 119, 137, 155, 173, 191, 209, 227, 245, 263, 281, 299, 317, 335, 353, 371, 389, 407, 425, 443, and 461. In some aspects, an antibody or antigen-binding fragment thereof comprising the polypeptide immunospecifically binds to GDF-15.

In some aspects, provided herein are polynucleotides comprising a nucleotide sequence encoding the light chain or heavy chain of an antibody or an antigen-binding fragment described herein. The polynucleotides can comprise nucleotide sequences encoding a heavy chain comprising the VH FRs and CDRs of antibodies described herein (see, e.g., Tables 1 and 5). The polynucleotides can comprise nucleotide sequences encoding a light chain comprising the VL FRs and CDRs of antibodies described herein (see, e.g., Tables 2 and 6).

In some aspects, a polynucleotide or combination of polynucleotides provided herein comprises a nucleotide sequence or combination of nucleotide sequences encoding an antibody or antigen-binding fragment thereof that immunospecifically binds to GDF-15 (e.g., human GDF-15), wherein the antibody or antigen-binding fragment thereof comprises a heavy chain, wherein the heavy chain comprises a heavy chain variable domain comprising an amino acid sequence set forth in Table 3 and a heavy chain constant region comprising a heavy chain constant region sequence set forth in Table 8 (e.g., SEQ ID NO:473 or 474).

In some aspects, a polynucleotide or combination of polynucleotides provided herein comprises a nucleotide sequence or combination of nucleotide sequences encoding an antibody or antigen-binding fragment thereof that immunospecifically binds to GDF-15 (e.g., human GDF-15), wherein the antibody or antigen-binding fragment thereof comprises a light chain, wherein the light chain comprises a light chain variable domain comprising an amino acid sequence set forth in Table 4 and a light chain constant region comprising a light chain constant region sequence set forth in Table 8 (e.g., SEQ ID NO:475).

In some aspects, a polynucleotide or combination of polynucleotides provided herein comprises a nucleotide sequence or combination of nucleotide sequences encoding an antibody or antigen-binding fragment thereof that immunospecifically binds to GDF-15 (e.g., human GDF-15), wherein the antibody or antigen-binding fragment thereof comprises (i) a heavy chain, wherein the heavy chain comprises a heavy chain variable domain comprising an amino acid sequence set forth in Table 3 and a heavy chain constant region comprising a heavy chain constant region sequence set forth in Table 8 (e.g., SEQ ID NO:473 or 474) and (ii) a light chain, wherein the light chain comprises a light chain variable domain comprising an amino acid sequence set forth in Table 4 and a light chain constant region comprising a light chain constant region sequence set forth in Table 8 (e.g., SEQ ID NO:475).

In some aspects, an antibody or antigen-binding fragment thereof described herein binds to human GDF-15 and is encoded by a VH and/or VL-encoding DNA sequence listed in Table 9. Accordingly, also provided herein are polynucleotides comprising a nucleic acid comprising the VH and/or VL-encoding sequence listed in Table 9.

TABLE 9

SEQ ID NOs of VH- and VL-Encoding DNA Sequences

| Antibody | VH DNA (SEQ ID. NO:) | VL DNA (SEQ ID. NO:) |
|---|---|---|
| AB1170002 | 1 | 10 |
| AB1170006 | 19 | 28 |
| AB1170010 | 37 | 46 |
| AB1170019 | 55 | 64 |
| AB1170028 | 73 | 82 |
| AB1170036 | 91 | 100 |
| AB1170040 | 109 | 118 |
| AB1170043 | 127 | 136 |
| AB1170047 | 145 | 154 |
| AB1170069 | 163 | 172 |
| AB1170070 | 181 | 190 |
| AB1170072 | 199 | 208 |
| AB1170073 | 217 | 226 |
| AB1170074 | 235 | 244 |
| AB1170086 | 253 | 262 |
| AB1170148 | 271 | 280 |
| AB1170242 | 289 | 298 |
| AB1170243 | 307 | 316 |
| AB1170241 | 325 | 334 |
| AB1170244 | 343 | 352 |
| AB1170245 | 361 | 370 |
| AB1170246 | 379 | 388 |
| AB1170247 | 397 | 406 |
| AB1170248 | 415 | 424 |
| AB1170249 | 433 | 442 |
| AB1520085 | 451 | 460 |

In some aspects, a polynucleotide comprises a nucleotide comprising a VH-encoding sequence listed in Table 9 and nucleotide comprising a sequence encoding a heavy chain constant region (e.g., SEQ ID NO:473 and 474). In some aspects, a polynucleotide comprises a nucleotide comprising a VL-encoding sequence listed in Table 9 and nucleotide comprising a sequence encoding a light chain constant region (e.g., SEQ ID NO:475).

Also provided herein are polynucleotides encoding an antibody or antigen-binding fragment thereof described herein that specifically binds to GDF-15 that are optimized, e.g., by codon/RNA optimization, replacement with heterologous signal sequences, and elimination of mRNA instability elements. Methods to generate optimized nucleic acids encoding an antibody or antigen-binding fragment thereof that specifically binds to GDF-15 or a domain thereof (e.g., heavy chain, light chain, VH domain, or VL domain) for recombinant expression by introducing codon changes (e.g., a codon change that encodes the same amino acid due to the degeneracy of the genetic code) and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly.

A polynucleotide encoding an antibody or antigen-binding fragment thereof described herein or a domain thereof can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody or antigen-binding fragment thereof. Such PCR amplification methods can be used to obtain nucleic acids comprising the sequence encoding the variable light chain region and/or the variable heavy chain region of an antibody or antigen-binding fragment thereof. The amplified nucleic acids can be cloned into vectors for expression in host cells and for further cloning, for example, to generate chimeric and humanized antibodies or antigen-binding fragments thereof.

Polynucleotides provided herein can be, e.g., in the form of RNA or in the form of DNA. DNA includes cDNA, genomic DNA, and synthetic DNA, and DNA can be double-stranded or single-stranded. If single stranded, DNA can be the coding strand or non-coding (anti-sense) strand. In some aspects, the polynucleotide is a cDNA or a DNA lacking one more endogenous introns. In some aspects, a polynucleotide is a non-naturally occurring polynucleotide. In some aspects, a polynucleotide is recombinantly produced. In some aspects, the polynucleotides are isolated. In some aspects, the polynucleotides are substantially pure. In some aspects, a polynucleotide is purified from natural components.

III(b). Vectors and Host Cells

The disclosure further provides one or more vectors comprising one or more nucleic acid sequences encoding an antibody or antigen-binding fragment thereof that binds to human GDF-15 (optionally wherein one or more of the antibodies or antigen-binding fragments thereof is a monoclonal antibody or fragment). The vector can be, for example, a plasmid, episome, cosmid, viral vector (e.g., retroviral or adenoviral), or phage. Suitable vectors and methods of vector preparation are well known in the art (see, e.g., Sambrook et al., Molecular Cloning, a Laboratory Manual, 3rd edition, Cold Spring Harbor Press, Cold Spring Harbor, N.Y. (2001), and Ausubel et al., Current Protocols in Molecular Biology, Greene Publishing Associates and John Wiley & Sons, New York, N.Y. (1994)).

In addition to the nucleic acid sequence encoding the antibody or antigen-binding fragment thereof that binds to human GDF-15 (optionally wherein the antibody or antigen-binding fragments thereof is a monoclonal antibody or fragment), the vector desirably comprises expression control sequences, such as promoters, enhancers, polyadenylation signals, transcription terminators, internal ribosome entry sites (IRES), and the like, that provide for the expression of the coding sequence in a host cell. Exemplary expression control sequences are known in the art and described in, for example, Goeddel, Gene Expression Technology: Methods in Enzymology, Vol. 185, Academic Press, San Diego, Calif. (1990).

The vector(s) comprising the nucleic acid(s) the antibody or antigen-binding fragment thereof that binds to human GDF-15 (optionally wherein one or more of the antibodies or antigen-binding fragments thereof is a monoclonal antibody or fragment) can be introduced into a host cell that is capable of expressing the polypeptides encoded thereby, including any suitable prokaryotic or eukaryotic cell. As such, the present disclosure provides an isolated cell comprising the vector. Host cells that may be used include those that can be easily and reliably grown, have reasonably fast growth rates, have well characterized expression systems, and can be transformed or transfected easily and efficiently. Examples of suitable prokaryotic cells include, but are not limited to, cells from the genera *Bacillus* (such as *Bacillus subtilis* and *Bacillus brevis*), *Escherichia* (such as *E. coli*), *Pseudomonas, Streptomyces, Salmonella*, and *Erwinia*. Particularly useful prokaryotic cells include the various strains of *Escherichia coli* (e.g., K12, HB101 (ATCC No. 33694), DH5a, DH10, MC1061 (ATCC No. 53338), and CC102). Suitable eukaryotic cells are known in the art and include, for example, yeast cells, insect cells, and mammalian cells. In some aspects, the vector is expressed in mammalian cells. A number of suitable mammalian host cells are known in the art, and many are available from the American Type Culture Collection (ATCC, Manassas, VA). Examples of suitable mammalian cells include, but are not limited to, Chinese hamster ovary cells (CHO) (ATCC No. CCL61), CHO DHFR-cells (Urlaub et al, Proc. Natl. Acad. Sci. USA, 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70). The mammalian cell desirably is a human cell. For example, the mammalian cell can be a human lymphoid or lymphoid derived cell line, such as a cell line of pre-B lymphocyte origin, a PER.C6® cell line (Crucell Holland B.V., The Netherlands), or human embryonic kidney (HEK) 293 or 293T cells (ATCC No. CRL1573).

A nucleic acid sequence encoding amino acids of any of the antibodies or antigen-binding fragments (optionally monoclonal antibodies or fragments) described herein can be introduced into a cell by transfection, transformation, or transduction.

Once an antibody or antigen-binding fragment thereof described herein has been produced by recombinant expression, it can be purified by any method known in the art for purification of an immunoglobulin molecule, for example, by chromatography (e.g., ion exchange, affinity, particularly by affinity for the specific antigen after Protein A, and size exclusion chromatography), centrifugation, differential solubility, or by any other standard technique for the purification of proteins. Further, the antibodies or antigen-binding fragments thereof described herein can be fused to heterologous polypeptide sequences described herein or otherwise known in the art to facilitate purification.

IV. Pharmaceutical Compositions

Provided herein are compositions comprising an anti-GDF-15 antibody or antigen-binding fragment thereof, as described herein. In some aspects, the antibody or antigen-binding fragment thereof having the desired degree of purity is present in a formulation comprising, e.g., a physiologically acceptable carrier, excipient or stabilizer (Remington's Pharmaceutical Sciences (1990) Mack Publishing Co., Easton, PA). Acceptable carriers, excipients, or stabilizers are nontoxic to recipients at the dosages and concentrations employed. Formulations suitable for parenteral administration include aqueous and non-aqueous, isotonic sterile injection solutions, which can comprise antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

In some aspects, a pharmaceutical composition comprises an anti-GDF-15 antibody or antigen-binding fragment thereof as described herein, and a pharmaceutically acceptable carrier (see, e.g., Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)). Pharmaceutical compositions described herein are, in some aspects, for use as a medicament. The compositions to be used for in vivo administration can be sterile. This is readily accomplished by filtration through, e.g., sterile filtration membranes.

A pharmaceutical composition described herein can be used to exert a biological effect in vivo or in vitro.

A pharmaceutical composition described herein can be used to treat cancer. In some aspects, the cancer is squamous cell carcinoma, lung cancer, small-cell lung cancer, non-small cell lung cancer, glioma, gastrointestinal (tract) cancer, renal cancer, ovarian cancer, liver cancer, colorectal cancer, endometrial cancer, kidney cancer, prostate cancer, castration-resistant prostate cancer, thyroid cancer, melanoma, chondrosarcoma, neuroblastoma, pancreatic cancer, glioblastoma multiforme, cervical cancer, brain cancer, stomach cancer, bladder cancer, hepatoma (hepatocellular carcinoma (HCC)), breast cancer, colon carcinoma, head and neck cancer, squamous cell head and neck cancer, renal cell carcinoma, Merkel cell carcinoma, urothelial cancer, thymic cancer, epithelial cancer, salivary cancer, choriocarcinoma, oral cancer, skin cancer, or esophageal cancer. In some aspects, the cancer is colorectal cancer (CRC), gastric (stomach) cancer, hepatoma (hepatocellular carcinoma (HCC)), renal cell cancer (RCC), bladder cancer, esophageal cancer, non-small cell lung cancer (NSCLC), or prostate cancer. The cancer can be a GDF-15 expressing cancer.

A pharmaceutical composition described herein can be used in inhibit the proliferation of cancer cells. The cancer cells can be squamous cell carcinoma, lung cancer, small-cell lung cancer, non-small cell lung cancer, glioma, gastrointestinal (tract) cancer, renal cancer, ovarian cancer, liver cancer, colorectal cancer, endometrial cancer, kidney cancer, prostate cancer, castration-resistant prostate cancer, thyroid cancer, melanoma, chondrosarcoma, neuroblastoma, pancreatic cancer, glioblastoma multiforme, cervical cancer, brain cancer, stomach cancer, bladder cancer, hepatoma (hepatocellular carcinoma (HCC)), breast cancer, colon carcinoma, head and neck cancer, squamous cell head and neck cancer, renal cell carcinoma, Merkel cell carcinoma, urothelial cancer, thymic cancer, epithelial cancer, salivary cancer, choriocarcinoma, oral cancer, skin cancer, or esophageal cancer cells. In some aspects, the cancer cells are colorectal cancer (CRC), gastric (stomach) cancer, hepatoma (hepatocellular carcinoma (HCC)), renal cell cancer (RCC), bladder cancer, esophageal cancer, non-small cell lung cancer (NSCLC), or prostate cancer cells. The cancer cells can be a GDF-15 expressing cancer cells.

A pharmaceutical composition described herein can be used to activate dendritic cells, to increase proliferation of T cells, and/or to increase differentiation of Th1 cells. The dendritic cells, T cells, and/or Th1 cells can be in vitro. The dendritic cells, T cells, and/or Th1 cells can be in a subject, e.g., a human subject. In some aspects, the subject, e.g., human subject, has cancer.

A pharmaceutical composition described herein can be used to treat cachexia. In some aspects, a pharmaceutical composition provided herein is used to treat diseases or conditions such as cachexia. In some aspects, the cachexia is associated with an underlying disease selected from the group consisting of cancer, chronic heart failure, chronic kidney disease, COPD, AIDS, multiple sclerosis, rheumatoid arthritis, sepsis, and tuberculosis.

In some aspects, a pharmaceutical composition provided herein is used to inhibit loss of muscle mass and a loss of fat mass associated with cachexia. In some aspects, the cachexia is associated with an underlying disease selected from the group consisting of cancer, chronic heart failure, chronic kidney disease, COPD, AIDS, multiple sclerosis, rheumatoid arthritis, sepsis, and tuberculosis.

In some aspects, a pharmaceutical composition provided herein is used to inhibit or reduce involuntary weight loss associated with cachexia.

In some aspects, a pharmaceutical composition provided herein is used to inhibit loss of organ mass, a loss of muscle mass, a loss of fat mass, and involuntary weight loss associated with cachexia. In some aspects, the cachexia is associated with an underlying disease selected from the group consisting of cancer, chronic heart failure, chronic kidney disease, COPD, AIDS, multiple sclerosis, rheumatoid arthritis, sepsis, and tuberculosis. In some aspects, the organ is kidney, liver, heart, or spleen.

In some aspects, a pharmaceutical composition provided herein is used to treat sarcopenia associated with cachexia.

In some aspects, a pharmaceutical composition provided herein is used to decrease the incidence and/or severity of cachexia, thereby increasing the maximum tolerated dose of an anti-cancer agent capable of causing cachexia.

In some aspects, a pharmaceutical composition provided herein is used to increase the appetite in a subject suffering from cachexia. In some aspects, the cachexia is associated with an underlying disease selected from the group consisting of cancer, chronic heart failure, chronic kidney disease, COPD, AIDS, multiple sclerosis, rheumatoid arthritis, sepsis, and tuberculosis.

V. Therapeutic Uses and Methods

In various aspects, provided herein are in vitro and in vivo methods of using anti-GDF-15 antibodies or antigen-binding fragments thereof as described herein, or pharmaceutical compositions thereof as described herein.

In some aspects, provided herein are methods of treating cancer. A method of treating cancer can comprise administering an anti-GDF-15 antibody or antigen-binding fragment thereof as described herein, or a pharmaceutical composition thereof as described herein, to a subject in need thereof.

In some aspects, provided herein are methods of inhibiting the proliferation of cancer cells in a subject. A method of inhibiting the proliferation of cancer cells in a subject can comprise administering an anti-GDF-15 antibody or antigen-binding fragment thereof as described herein, or a pharmaceutical composition thereof as described herein, to a subject in need thereof. The subject can be, e.g., a subject with cancer.

In some aspects, provided herein are methods of increasing the activation of dendritic cells in a subject. A method of increasing the activation of dendritic cells in a subject can comprise administering an anti-GDF-15 antibody or antigen-binding fragment thereof as described herein, or a pharmaceutical composition thereof as described herein, to a subject in need thereof. The subject can be, e.g., a subject with cancer.

In some aspects, provided herein are methods of increasing the proliferation of T cells in a subject. A method of increasing the proliferation of T cells in a subject can comprise administering an anti-GDF-15 antibody or antigen-binding fragment thereof as described herein, or a pharmaceutical composition thereof as described herein, to a subject in need thereof. The subject can be, e.g., a subject with cancer.

In some aspects, provided herein are methods of increasing the differentiation of Th1 cells in a subject. A method of increasing the differentiation of Th1 cells in a subject can comprise administering an anti-GDF-15 antibody or antigen-binding fragment thereof as described herein, or a pharmaceutical composition thereof as described herein, to a subject in need thereof. The subject can be, e.g., a subject with cancer.

In some aspects, provided herein are methods of treating cachexia. A method of treating cachexia can comprise administering an anti-GDF-15 antibody or antigen-binding fragment thereof as described herein, or a pharmaceutical composition thereof as described herein, to a subject in need thereof. In some aspects, the cachexia is associated with an underlying disease selected from the group consisting of cancer, chronic heart failure, chronic kidney disease, COPD, AIDS, multiple sclerosis, rheumatoid arthritis, sepsis, and tuberculosis.

In some aspects, provided herein are methods of inhibiting loss of muscle mass and a loss of fat mass associated with cachexia. A method of inhibiting loss of muscle mass and a loss of fat mass associated with cachexia can comprise administering an anti-GDF-15 antibody or antigen-binding fragment thereof as described herein, or a pharmaceutical composition thereof as described herein, to a subject in need thereof. In some aspects, the cachexia is associated with an underlying disease selected from the group consisting of cancer, chronic heart failure, chronic kidney disease, COPD, AIDS, multiple sclerosis, rheumatoid arthritis, sepsis, and tuberculosis.

In some aspects, provided herein are methods of inhibiting or reducing involuntary weight loss associated with cachexia. A method of inhibiting or reducing involuntary weight loss associated with cachexia can comprise administering an anti-GDF-15 antibody or antigen-binding fragment thereof as described herein, or a pharmaceutical composition thereof as described herein, to a subject in need thereof.

In some aspects, provided herein are methods of inhibiting loss of organ mass, a loss of muscle mass, a loss of fat mass, and involuntary weight loss associated with cachexia. A method of inhibiting loss of organ mass, a loss of muscle mass, a loss of fat mass, and involuntary weight loss associated with cachexia can comprise administering an anti-GDF-15 antibody or antigen-binding fragment thereof as described herein, or a pharmaceutical composition thereof as described herein, to a subject in need thereof. In some aspects, the cachexia is associated with an underlying disease selected from the group consisting of cancer, chronic heart failure, chronic kidney disease, COPD, AIDS, multiple sclerosis, rheumatoid arthritis, sepsis, and tuberculosis. In some aspects, the organ is kidney, liver, heart, or spleen.

In some aspects, provided herein are methods of treating sarcopenia associated with cachexia. A method of treating sarcopenia associated with cachexia can comprise administering an anti-GDF-15 antibody or antigen-binding fragment thereof as described herein, or a pharmaceutical composition thereof as described herein, to a subject in need thereof.

In some aspects, provided herein are methods of decreasing the incidence and/or severity of cachexia, thereby increasing the maximum tolerated dose of an anti-cancer agent capable of causing cachexia. A method of decreasing the incidence and/or severity of cachexia, thereby increasing the maximum tolerated dose of an anti-cancer agent capable of causing cachexia can comprise administering an anti-GDF-15 antibody or antigen-binding fragment thereof as described herein, or a pharmaceutical composition thereof as described herein, to a subject in need thereof.

In some aspects, provided herein are methods of increasing the appetite in a subject suffering from cachexia. A method of increasing the appetite in a subject suffering from cachexia can comprise administering an anti-GDF-15 antibody or antigen-binding fragment thereof as described herein, or a pharmaceutical composition thereof as described herein, to a subject in need thereof. In some aspects, the cachexia is associated with an underlying disease selected from the group consisting of cancer, chronic heart failure, chronic kidney disease, COPD, AIDS, multiple sclerosis, rheumatoid arthritis, sepsis, and tuberculosis.

An anti-GDF-15 antibody or antigen-binding fragment thereof as provided herein, or a pharmaceutical composition thereof as provided herein, can be administered by any suitable means.

The appropriate dosage and dosing regimen of an anti-GDF-15 antibody or antigen-binding fragment thereof as provided herein, or a pharmaceutical composition thereof as provided herein, when used alone or in combination with one or more other additional therapeutic agents, will depend on the disease to be treated, the severity and course of the disease, the route of administration and other factors.

In some aspects, provided herein is an antibody or antigen-binding fragment thereof or pharmaceutical composition provided herein for use as a medicament.

In some aspects, provided herein is an antibody or antigen-binding fragment thereof or pharmaceutical composition provided herein, for use in a method for the treatment of cancer. In some aspects, provided herein is an antibody or antigen-binding fragment thereof or pharmaceutical composition provided herein, for use in a method for the treatment of cancer in a subject, comprising administering to the subject an effective amount of an antibody or antigen-binding fragment thereof or pharmaceutical composition provided herein.

In some aspects, provided herein is an antibody or antigen-binding fragment thereof or pharmaceutical composition provided herein, for use in a method for the treatment of cachexia. In some aspects, provided herein is an antibody or antigen-binding fragment thereof or pharmaceutical composition provided herein, for use in a method for the treatment of cachexia in a subject, comprising administering to the subject an effective amount of an antibody or antigen-binding fragment thereof or pharmaceutical composition provided herein.

In some aspects, provided herein is an antibody or antigen-binding fragment thereof or pharmaceutical composition provided herein, for use in a method for inhibiting loss of muscle mass and fat mass associated with cachexia. In some aspects, provided herein is an antibody or antigen-binding fragment thereof or pharmaceutical composition provided herein, for use in a method for inhibiting loss of muscle mass and fat mass associated with cachexia in a subject, comprising administering to the subject an effective amount of an antibody or antigen-binding fragment thereof or pharmaceutical composition provided herein.

In some aspects, provided herein is an antibody or antigen-binding fragment thereof or pharmaceutical composition provided herein, for use in a method for inhibiting or reducing involuntary weight loss associated with cachexia. In some aspects, provided herein is an antibody or antigen-binding fragment thereof or pharmaceutical composition provided herein, for use in a method for inhibiting or reducing involuntary weight loss associated with cachexia in a subject, comprising administering to the subject an effective amount of an antibody or antigen-binding fragment thereof or pharmaceutical composition provided herein.

In some aspects, provided herein is an antibody or antigen-binding fragment thereof or pharmaceutical composition provided herein, for use in a method for inhibiting loss of organ mass, a loss of muscle mass, a loss of fat mass, and involuntary weight loss associated with cachexia. In some aspects, provided herein is an antibody or antigen-binding fragment thereof or pharmaceutical composition provided herein, for use in a method for inhibiting loss of organ mass, a loss of muscle mass, a loss of fat mass, and involuntary weight loss associated with cachexia in a subject, comprising administering to the subject an effective amount of an antibody or antigen-binding fragment thereof or pharmaceutical composition provided herein.

In some aspects, provided herein is an antibody or antigen-binding fragment thereof or pharmaceutical composition provided herein, for use in a method for the treatment of sarcopenia associated with cachexia. In some aspects, provided herein is an antibody or antigen-binding fragment thereof or pharmaceutical composition provided herein, for use in a method for the treatment of sarcopenia associated with cachexia in a subject, comprising administering to the subject an effective amount of an antibody or antigen-binding fragment thereof or pharmaceutical composition provided herein.

In some aspects, provided herein is an antibody or antigen-binding fragment thereof or pharmaceutical composition provided herein, for use in a method for decreasing the incidence and/or severity of cachexia, thereby increasing the maximum tolerated dose of an anti-cancer agent capable of causing cachexia. In some aspects, provided herein is an antibody or antigen-binding fragment thereof or pharmaceutical composition provided herein, for use in a method for decreasing the incidence and/or severity of cachexia, thereby increasing the maximum tolerated dose of an anti-cancer agent capable of causing cachexia, comprising administering to the subject an effective amount of an antibody or antigen-binding fragment thereof or pharmaceutical composition provided herein.

In some aspects, provided herein is an antibody or antigen-binding fragment thereof or pharmaceutical composition provided herein, for use in a method for increasing the appetite in a subject suffering from cachexia. In some aspects, provided herein is an antibody or antigen-binding fragment thereof or pharmaceutical composition provided herein, for use in a method for increasing the appetite in a subject suffering from cachexia, comprising administering to the subject an effective amount of an antibody or antigen-binding fragment thereof or pharmaceutical composition provided herein.

VI. Detection and Diagnostic Uses

An anti-GDF-15 antibody or antigen-binding fragment thereof described herein can be used to assay GDF-15 protein (e.g., human GDF-15 protein) levels in a biological sample using classical methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine (125I, 121I), carbon (14C), sulfur (35S), tritium (3H), indium (121In), and technetium (99Tc); luminescent labels, such as luminol; and fluorescent labels, such as fluorescein and rhodamine, and biotin. Such labels can be used to label an antibody or antigen-binding fragment thereof described herein. Alternatively, a second antibody or antigen-binding fragment thereof that recognizes an anti-GDF-15 antibody or antigen-binding fragment thereof described herein can be labeled and used in combination with an anti-GDF-15 antibody or antigen-binding fragment thereof to detect GDF-15 protein (e.g., human GDF-15 protein) levels.

Assaying for the expression level of GDF-15 protein (e.g., human GDF-15 protein) is intended to include qualitatively or quantitatively measuring or estimating the level of a GDF-15 protein (e.g., human GDF-15 protein) in a first biological sample either directly (e.g., by determining or estimating absolute protein level) or relatively (e.g., by comparing to the disease associated protein level in a second biological sample). GDF-15 protein (e.g., human GDF-15 protein) expression level in the first biological sample can be measured or estimated and compared to a standard GDF-15 protein (e.g., human GDF-15 protein) level, the standard being taken from a second biological sample obtained from an individual not having the disorder or being determined by averaging levels from a population of individuals not having the disorder. As will be appreciated in the art, once the "standard" GDF-15 protein (e.g., human GDF-15 protein) level is known, it can be used repeatedly as a standard for comparison.

As used herein, the term "biological sample" refers to any biological sample obtained from a subject, cell line, tissue, or other source of cells potentially expressing GDF-15 protein (e.g., human GDF-15 protein). Methods for obtaining tissue biopsies and body fluids from animals (e.g., humans) are well known in the art.

Elevated GDF-15 levels have been associated with reduced overall survival in cancers (e.g., colorectal cancer and non-small cell lung cancer). Accordingly, an anti-GDF-15 antibody described herein can be used for prognostic, diagnostic, monitoring and screening applications, including in vitro and in vivo applications well known and standard to the skilled artisan and based on the present description.

Anti-GDF-15 antibodies and antigen-binding fragments thereof described herein can carry a detectable or functional label. When fluorescence labels are used, currently available microscopy and fluorescence-activated cell sorter analysis (FACS) or combination of both methods procedures known in the art may be utilized to identify and to quantitate the specific binding members. Anti-GDF-15 antibodies or antigen-binding fragments thereof described herein can carry a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-GDF-15 antibody can carry a radioactive label, such as the isotopes 3H, 14C, 32P, 35S, 36Cl, 51Cr, 57Co, 58Co, 59Fe, 67Cu, 90Y, 99Tc, 111In, 117Lu, 121I, 124I, 125I, 131I, 198Au, 211At, 213Bi, 225Ac and 186Re. When radioactive labels are used, currently available counting procedures known in the art may be utilized to identify and quantitate the specific binding of anti-GDF-15 antibody or antigen-binding fragment to GDF-15 protein (e.g., human GDF-15 protein). Where the label is an enzyme, detection can be accomplished by any of the presently utilized colorimetric, spectrophotometric, fluorospectrophotometric, amperometric or gasometric techniques as known in the art. This can be achieved by contacting a sample or a control sample with an anti-GDF-15 antibody or antigen-binding fragment thereof under conditions that allow for the formation of a complex between the antibody or antigen-binding fragment thereof and GDF-15 protein (e.g., human GDF-15 protein). Any complexes formed between the antibody or antigen-binding fragment thereof and GDF-15 protein (e.g., human GDF-15 protein) are detected and compared in the sample and the control. In light of the specific binding of the antibodies or antigen-binding fragments thereof described herein to human GDF-15, the antibodies or antigen-binding fragments thereof can be used to specifically detect GDF-15 protein (e.g., human GDF-15 protein) expression in samples. The antibodies or antigen-binding fragments thereof described herein can also be used to purify GDF-15 protein (e.g., human GDF-15 protein) via immunoaffinity purification.

Also included herein is an assay system which can be prepared in the form of a test kit for the quantitative analysis of the extent of the presence of GDF-15 protein (e.g., human GDF-15 protein). The system or test kit may comprise a labeled component, e.g., a labeled antibody or antigen-binding fragment, and one or more additional immunochemical reagents. See, e.g., Section VII below for more on kits.

In some aspects, methods for in vitro detection of GDF-15 protein (e.g., human GDF-15 protein) in a sample, comprising contacting said sample with an antibody or antigen-binding fragment thereof, are provided herein. In some aspects, provided herein is the use of an antibody or antigen-binding fragment thereof provided herein, for in vitro detection of GDF-15 protein (e.g., human GDF-15 protein) in a sample. In some aspects, provided herein is an antibody or antigen-binding fragment thereof or composition provided herein for use in the detection of GDF-15 protein (e.g., human GDF-15 protein) in a subject or a sample obtained from a subject. In some aspects, provided herein is an antibody or antigen-binding fragment thereof provided herein for use as a diagnostic. In some aspects, the antibody comprises a detectable label.

VII. Kits

Provided herein are kits comprising one or more antibodies or antigen-binding fragments thereof described herein. In some aspects, provided herein is a pharmaceutical pack or kit comprising one or more containers filled with one or more of the ingredients of the pharmaceutical compositions described herein, such as one or more antibodies or antigen-binding fragments thereof provided herein. Optionally associated with such container(s) can be a notice in the form prescribed by a governmental agency regulating the manufacture, use, or sale of pharmaceuticals or biological products, which notice reflects approval by the agency of manufacture, use or sale for human administration.

Also provided herein are kits that can be used in detection methods. In some aspects, a kit comprises an antibody or antigen-binding fragment thereof described herein, preferably a purified antibody or antigen-binding fragment thereof, in one or more containers. In some aspects, kits described herein contain a substantially isolated GDF-15 protein (e.g., human GDF-15 protein) that can be used as a control. In some aspects, the kits described herein further comprise a control antibody or antigen-binding fragment thereof which does not react with GDF-15 protein (e.g., human GDF-15 protein). In some aspects, kits described herein contain one or more elements for detecting the binding of an antibody or antigen-binding fragment thereof to GDF-15 protein (e.g., human GDF-15 protein) (e.g., the antibody or antigen-binding fragment thereof can be conjugated to a detectable substrate such as a fluorescent compound, an enzymatic substrate, a radioactive compound or a luminescent compound, or a second antibody or antigen-binding fragment thereof which recognizes the first antibody or antigen-binding fragment thereof can be conjugated to a detectable substrate). In some aspects, a kit provided herein can include a recombinantly produced or chemically synthesized GDF-15 protein (e.g., human GDF-15 protein). The GDF-15 protein (e.g., human GDF-15 protein) provided in the kit can also be attached to a solid support. In some aspects, the detecting means of the above described kit includes a solid support to which a GDF-15 protein (e.g., human GDF-15 protein) is attached. Such a kit can also include a non-attached reporter-labeled anti-GDF-15 antibody or antigen-binding fragment thereof or anti-mouse/rat antibody or antigen-binding fragment thereof. In this aspect, binding of the antibody or antigen-binding fragment thereof to the GDF-15 protein (e.g., human GDF-15 protein) can be detected by binding of the said reporter-labeled antibody or antigen-binding fragment thereof.

EXAMPLES

The examples in this Section are offered by way of illustration, and not by way of limitation.

Example 1: Methods for the Expression and Purification of Human, Cynomolgus, and Mouse GDF-15 Proteins The protein sequences used in the design of constructs for expression of human and cynomolgus mature GDF-15 proteins were derived from UniProt entries Q99988 (human; SEQ ID NO:469) and G7PWZ3 (cynomolgus (cyno); SEQ ID NO:470). In addition to the wild type human GDF-15 protein, a common variant H202D (MAF=0.231; SEQ ID NO:471) was produced (Ensembl ENST00000252809.3). The mouse GDF-15 sequence was derived from Uniprot entry Q9Z0J7 (SEQ ID NO:472).

```
MPGQELRTVNGSQMLLVLLVLSWLPHGGALSLAEA

SRASFPGPSELHSEDSRFRELRKRYEDLLTRLRAN

QSWEDSNTDLVPAPAVRILTPEVRLGSGGHLHLRI

SRAALPEGLPEASRLHRALFRLSPTASRSWDVTRP

LRRQLSLARPQAPALHLRLSPPPSQSDQLLAESSS

ARPQLELHLRPQAARGRRRARARNGDHCPLGPGRC

CRLFITVRASLEDLGWADWVLSPREVQVTMCIGAC

PSQFRAANMHAQIKTSLHRLKPDTVPAPCCVPASY

NPMVLIQKTDTGVSLQTYDDLLAKDCHCI
(SEQ ID NO: 469; signal peptide
(amino acids 1-29) underlined)

ARNGDHCPLGPGRCCRLHTVRASLEDLGWADWVLS

PREVQVTMCIGACPSQFRAANMHAQIKTSLHRLK

PDTVPAPCCVPASYNPMVLIQKTDTGVSLQTYDDL

LAKDCH
C1
(SEQ ID NO: 479; Mature GDF-15)

ARNGDDCPLGPGRCCRLHTVRASLEDLGWADWVLS

PREVQVTMCIGACPSQFRAANMHAQIKTSLHRLK

PDTVPAPCCVPASYNPMVLIQKTDTGVSLQTYDDL

LAKDCH
C1
(SEQ ID NO: 480; Mature GDF-15 H202D)

MPGQELKTLNGSQMLLVLLVLLWPPHGGAVSLAEA

SRASFPGPSDLHSEDSRFRELRKRYEDLLTRLRAN

QSWEDSNTDLIQAPEVRELTPEVRLGSGGHLHLRI

SRAVLPEGLPEACRIHRALFRLSPTASRSRDVTRP

LRRQLRLARPQAPALHLRLSPPPSQSDQLLVKSSS

SRPQLALHLRPRASRGRRRARARNGDRCPLGPGRC

CRLHTVHASLEDLGWADWVLSPREVQVTMCIGACP

SQFREANMHAQIKMNLHRLKPDTVPAPCCVPASYN

PMVLIQKTDTGVSLQTYDDLLAKDCHCV
(SEQ ID NO: 470; signal peptide
(amino acids 1-29) underlined)

MPGQELRTVNGSQMLLVLLVLSWLPHGGALSLAEA

SRASFPGPSELHSEDSRFRELRKRYEDLLTRLRAN

QSWEDSNTDLVPAPAVRILTPEVRLGSGGHLHLRI

SRAALPEGLPEASRLHRALFRLSPTASRSWDVTRP

LRRQLSLARPQAPALHLRLSPPPSQSDQLLAESSS

ARPQLELHLRPQAARGRRRARARNGDDCPLGPGRC

CRLHTVRASLEDLGWADWVLSPREVQVTMCIGACP

SQFRAANMHAQIKTSLHRLKPDTVPAPCCVPASYN

PMVLIQKTDTGVSLQTYDDLLAKDCHCI
```

-continued (SEQ ID NO: 471; signal peptide (amino acids 1-29) underlined; H202D bold and underlined)

```
MAPPALQAQPPGGSQLRFLLFLLLLLLLLSWPSQG

DALAMPEQRPSGPESQLNADELRGRFQDLLSRLHA

NQSREDSNSEPSPDPAVRILSPEVRLGSHGQLLLR

VNRASLSQGLPEAYRVHRALLLLTPTARPWDITRP

LKRALSLRGPRAPALRLRLTPPPDLAMLPSGGTQL

ELRLRVAAGRGRRSAHAHPRDSCPLGPGRCCHLET

VQATLEDLGWSDWVLSPRQLQLSMCVGECPHLYRS

ANTHAQIKARLHGLQPDKVPAPCCVPSSYTPVVLM

HRTDSGVSLQTYDDLVARGCHCA
```

(SEQ ID NO: 472; signal peptide (amino acids 1-30) underlined)

Non-Tagged Human and Cynomolgus GDF-15 Proteins

The sequences corresponding to the mature peptides of human and cynomolgus GDF-15 (residues 197-308) were cloned into the pET-28a (Merck) bacterial expression vector. The constructs were expressed in BL21(DE3) cells (Life Technologies), extracted from inclusion bodies, and refolded using standard techniques. The proteins underwent cation exchange and size exclusion chromatography purification using standard techniques.

Mammalian Expressed his- and FLAG-Tagged Human and Cynomolgus GDF-15 Proteins

Mature human and cynomolgus GDF-15 proteins encoding N-terminal poly-histidine (poly-His) and FLAG tags were cloned into the pDEST12.2 OriP (Thermo Fisher) vector. The constructs were expressed in Expi293F cells (Thermo Fisher) and purified from the conditioned media using standard immobilized metal affinity chromatography and size exclusion chromatography purification.

Cloning, Expression and Purification of his- and FLAG-Tagged Mouse GDF-15 Protein A full-length mouse GDF-15 construct was designed with FLAG and poly-His tags immediately C-terminal to the furin cleavage site and cloned into the pDEST12.2 OriP (Thermo Fisher) vector. The mouse GDF-15 plasmid and a plasmid encoding a furin protein were co-transfected into Chinese Hamster Ovary (CHO) cells. Mature dimeric mouse GDF-15 protein was purified from the conditioned medium using standard immobilized metal affinity chromatography and size exclusion chromatography purification.

Pro-Human GDF-15

A full length human GDF-15 (Pro-GDF-15) Fc fusion construct was designed with a deletion of GDF-15 residues 190-196 (Bauskin et al. 2010) and with an N-terminal Fc and poly-His tags. The construct was cloned into pDEST12.2 OriP (Thermo Scientific) and co-transfected with a complementary Fc construct into CHO cells. Dimeric Pro-GDF-15 protein was purified from the conditioned medium using a MabSelect PrismA column (GE Healthcare). The Fc tags were cleaved using TEV protease, and the released His-Pro-GDF-15 protein was further purified using standard immobilized metal affinity chromatography and size exclusion chromatography.

Toxin-Fused Forms of Mouse GDF-15 for Tolerance Breaking Upon Immunization of Rodents In order to break tolerance upon immunization of mice with recombinant mouse GDF-15, the protein was fused to antigens containing T-cell epitopes. First, a mature mouse GDF-15 (residues 189-303) construct was designed that was fused at the N-terminus to an Fc tag with a TEV cleavage site placed between the Fc tag and GDF-15. The construct was cloned into pDEST12.2 OriP (Thermo Scientific) and co-transfected with a complementary Fc construct into CHO cells. Dimeric Fc tagged GDF-15 protein was purified from the conditioned medium using a MabSelect PrismA column and then cleaved using TEV protease to produce dimeric mouse GDF-15. The mouse GDF15 was covalently fused to modified forms of bacterial toxins, either Diptheria toxin fragment A (DTA) or a dipeptide derived from tetanus toxin (TT) (described by Percival-Alwyn et al., 2015) to produce the immunogens His-TT-mouseGDF-15 and His-DTA-mouseGDF-15. The His-tagged-DTA was produced using a bacterial expression system and the His-tagged-TT was produced using CHO cells. The antigens were purified using standard immobilized metal affinity chromatography and size exclusion chromatography techniques.

Example 2: Methods for Generation of Anti-Human GDF-15 Antibodies by Hybridoma Technology Immunizations Recombinant human GDF-15 (hGDF-15) was used to immunize CD1 mice. Two groups of mice were used. For Group 1, mice were immunized with untagged hGDF-15 and Group 2 mice were immunized with 10 histidine tagged hGDF-15.

The recombinant proteins were diluted in PBS, emulsified with equal volumes of complete Freund's adjuvant, and injected into the mice at two sites. For the subsequent three injections, the proteins were emulsified in Freund's incomplete adjuvant and injections were performed as above. The final boost was carried out on day 24 by injecting recombinant protein in PBS intraperitoneally.

Tail vein bleeds were obtained from mice before immunization, on day 13 after the first immunization, and on day 20 after second immunization. The IgG titres to human GDF-15 were determined by serum ELISA. The animals with the highest titres were taken forward for hybridoma generation.

Assessment of Mouse Immune Response to hGDF-15

The serum IgG titres to human GDF-15 and an irrelevant protein control were determined by ELISA in 96-well microtitre plates using standard techniques. Antibodies were detected using an HRP labelled polyclonal goat anti-mouse IgG specific secondary antibody (Jackson Immunolabs), and the assay was developed using TMB substrate (Sigma) followed by the addition of 0.5 M sulphuric acid to stop the reaction. The plates were then read using a PerkinElmer EnVision 2103 multilabel plate reader.

The serum titration curves for human GDF-15 and the irrelevant protein were plotted and the respective area under the curves (AUC) were calculated.

Monoclonal Mouse IgG Isolation

Four days after the final boost, lymph nodes were aseptically harvested, and cells were isolated by mechanical disruption and then counted. These cells were mixed with SP2/0 myeloma cells and fused using an electrofusion apparatus. The resultant fusions were mixed with a methylcellulose-based semi-solid media and plated out into OmniTray plates. The semi-solid media comprised CloneMatrix and DMEM supplemented with 20% FCS, 10% BM Condimed H1, 1 mM sodium pyruvate and OPI media supplement, 2% hypoxanthine azaserine, and FITC conjugated goat anti-rat IgG. The cells in semi-solid media were cultured for 13 days at 37° C. in a 5% $CO_2$ incubator. During this incubation period, clonal colonies are formed from a single progenitor hybridoma cell. These colonies secrete IgG that is trapped in the vicinity of the colony by the FITC conjugated anti-IgG present in the semi-solid media. The resultant immune complex formation can be observed around the cell as a fluorescent 'halo' when visualized by ClonePix FL colony picker (Molecular Devices). These haloed colonies are then picked into 96 well microtitre plates.

After 3-5 days in culture, the supernatants of the picked colonies were harvested and screened for human GDF-15 binding.

DNA Sequencing and Purification of Mouse IgGs

Messenger RNA (mRNA) was extracted from hybridoma cells using magnetic oligo (dT) particles and reverse transcribed into cDNA. PCR amplification was performed using poly-C and constant region VH or VL primers specific to all mouse IgG subclasses.

Mouse IgG Purifications

Cells were propagated in 24-well plates and overgrown in serum free HL-1 medium supplemented with HyperZero and glutamine. After 10 days, the supernatants were transferred to 96-well master blocks, and mouse IgGs of all subclasses (IgG1, IgG2a, IgG2b and IgG3) were purified from overgrown cell culture supernatants on ProPlus resin (Phynexus) using Perkin Elmer Minitrack. The captured mouse IgGs were eluted with 100 mM HEPES, 140 mM NaCl pH 3.0 and then neutralised with an equal volume of 200 mM HEPES pH 8.0. The purified IgGs were quantified using an absorbance reading at 280 nm in UV-Star 384 well plate.

Reformatting of Mouse IgGs

Mouse hybridoma IgG clones were molecularly reformatted to generate constructs expressing mouse VH and VL domains and the relevant mouse IgG constant domains for each hybridoma essentially as described by Persic et al., 1997. The VH domain was cloned into the relevant vector containing the mouse heavy chain constant domains and regulatory elements to express whole IgG1 heavy chain in mammalian cells. Similarly, the VL domain was cloned into a vector for the expression of the appropriate mouse light chain (lambda or kappa) constant domains and regulatory elements to express whole IgG light chain in mammalian cells. To obtain IgGs, mammalian suspension CHO cells were transiently transfected with the heavy and light chain IgG vectors. IgGs were expressed and secreted into the medium. IgGs were purified from clarified supernatants using MabSelect SuRe chromatography columns (GE Healthcare Lifesciences Cat no: 11003493 for 1 ml columns; 11003495 for 5 ml columns) and the AktaXpress™ purification system from GE Healthcare Lifesciences. The eluted material was buffer exchanged into PBS using PD-10 desalting columns (GE Healthcare Lifesciences; Cat no: 17085101). The concentration of IgG was determined spectrophotometrically using extinction coefficients based on the amino acid sequences of the IgGs (Pace et al., 1995), and the purified IgGs were analyzed for purity using SDS-PAGE and HP-SEC analysis.

Humanization of a Panel of Mouse Anti-Human GDF-15 IgGs

Anti-human GDF-15 mouse IgGs were chosen for humanization based on in vitro binding and activity data i.e., replacing the mouse variable heavy and light chain framework regions with the nearest human IgG variable domains.

The amino acid sequence of each of the hybridoma clone (VH and VL) was analyzed against the IMGT human heavy and light chain germline sequences. For each antibody V-gene, the closest single human V-gene sequence to the murine V-gene (excluding Vernier residues and CDRs) was identified. In addition, for each V-gene the closest individual framework region (FW1, FW2, FW3 and FW4; again, excluding Vernier residues and CDRs) was also identified. For each hybridoma clone, either the single human germline or composite human germline was chosen that gave the fewest amino acid changes from the mouse germline was chosen.

Following codon optimization, each humanized V-gene sequence was synthesized and molecularly reformatted to generate into human IgG1 TM antibodies as described above with the following modifications. The VH domain was cloned into a vector containing the human heavy chain constant domains and regulatory elements to express whole IgG1 heavy chain in mammalian cells. This constant region contained the triple mutations (TM) L234F/L235E/P331S (SEQ ID NO: 474) resulting in an effector null human IgG1. Similarly, the VL domain was cloned into a vector for the expression of the human light chain (kappa) constant domains and regulatory elements to express whole IgG light chain in mammalian cells. To obtain IgGs, mammalian suspension CHO cells were transiently transfected with the heavy and light chain IgG vectors. IgGs were expressed and secreted into the medium. IgGs were purified from clarified supernatants using MabSelect SuRe chromatography columns (GE Healthcare Lifesciences Cat no: 11003493 for 1 ml columns; 11003495 for 5 ml columns) and the AktaXpress™ purification system from GE Healthcare Lifesciences. The eluted material was buffer exchanged into PBS using PD-10 desalting columns (GE Healthcare Lifesciences; Cat no: 17085101). The concentration of IgG was determined spectrophotometrically using extinction coefficients based on the amino acid sequences of the IgGs (Pace et al., 1995), and the purified IgGs were analyzed for purity using SDS-PAGE and HP-SEC analysis.

Antibody AB1170243 was mutated within heavy chain CDR2 to remove a deamidation liability within the sequence NNG. Mutation to NQG at this location generated clone AB 1170241 which demonstrated superior stability upon heat stress.

Example 3: Methods for Generation of Anti-Murine GDF-15 Antibodies by Hybridoma Technology Immunizations Recombinant murine GDF-15 (mGDF-15) was used to immunize CD1 mice. Two groups of mice were used. In order to break tolerance and generate a robust immune response to the mouse version of GDF-15 in mice, T helper epitopes were incorporated into the immunogens as described in Percival-Alwyn et al. (2015). For Group 1, mice were immunized with His-TT-mGDF-15, and Group 2 mice were immunized with His-DTA-mGDF-15. The immunizations were performed as described previously. Mouse hybridoma IgG clones were molecularly reformatted, as described above, to generate constructs expressing mouse VH and VL domains in an IgG1(D265A; SEQ ID NO:477) format.

Example 4: Methods for Profiling Antibodies

Screening Hybridoma IgGs for Specific Binding to Recombinant GDF-15 Proteins

Supernatants generated from the immunizations with human GDF-15 and purified IgGs were screened to identify IgGs with specific binding to human, cynomolgus, or mouse GDF-15. The HTRF (Homogeneous Time Resolved Fluorescence) assay is based on detection of a measurable FRET signal upon binding of a titration of test antibody to biotinylated human H202D GDF-15 variant, cynomolgus GDF-15 and mouse GDF-15. Europium cryptate (EuK) labelled Streptavidin and anti-human IgG XL665 (Cis Bio) were used as secondary detection reagents serving as energy donor and acceptor respectively. In the absence of test antibody binding, there is no detectable FRET fluorescence. When test antibody binds to GDF-15, the resulting physical proximity between the secondary reagent donor/acceptor pair results in FRET. FRET was measured ratiometrically [665 nm (acceptor)/620 nm (donor)] on an Envision plate reader, and data plotted using PRISM 6® software (Graphpad). Data are presented in Table 10.

Screening Hybridoma IgGs for Competitive Binding to Recombinant Human GDF-15 Protein in Homogeneous Assay Format Antibodies from the immunizations with human GDF-15, in the form of crude supernatants from the immunization or in the form of purified IgGs, were chosen on the basis that they bind and compete with an epitope recognized by a control anti-GDF-15 antibody "Antibody A". A biochemical epitope competition format was applied using an HTRF epitope competition assay that measured the binding of DyLight 650 labelled Antibody A to Europium labelled human GDF-15 (Prospec). In the absence of Antibody A binding, there is no detectable FRET fluorescence. When Antibody A binds to GDF-15, the resulting physical proximity between the secondary reagent donor/acceptor pair results in FRET. Competition with an antibody that recognizes the same or similar epitope will result in a dose dependent reduction of the FRET signal. FRET was measured ratiometrically [665 nm (acceptor)/620 nm (donor)] on an Envision plate reader, and $IC_{50}$ values were determined by curve fitting the data to a four parameter logistic equation using PRISM 6® software (Graphpad). Data are presented in Table 10 and Table 11.

TABLE 10

| Mouse hybridoma IgGs | | | | | | |
|---|---|---|---|---|---|---|
| | HTRF Binding Assays | | | | | |
| | Human GDF-15 H202D | Mouse GDF-15 | Cyno GDF-15 | HTRF Competition Assay for Antibody A Epitope | | |
| Clone ID | Binding | Binding | Binding | $IC_{50}$ (M) | SD | n |
| AB1170002 | Yes | No | Yes | 6.10E−09 | 4.38E−09 | 3 |
| AB1170006* | Yes | Yes | Yes | 9.71E−08 | 7.98E−07 | 3 |
| AB1170010 | Yes | Yes | Yes | 7.58E−10 | 1.86E−10 | 3 |
| AB1170019* | Yes | Yes | Yes | 8.64E−10 | 1.15E−09 | 4 |
| AB1170028* | Yes | Yes | Yes | 4.85E−10 | 4.61E−11 | 4 |
| AB1170036 | Yes | Yes | Yes | 6.222E−10 | 2.256E−10 | 4 |
| AB1170040 | Yes | Yes | Yes | 1.42E−09 | 8.66E−10 | 4 |
| AB1170043 | Yes | Yes | Yes | 1.95E−09 | 1.295E−09 | 4 |
| AB1170047 | Yes | Yes | Yes | 1.363E−09 | 8.454E−10 | 5 |
| AB1170069 | Yes | Yes | Yes | 7.59E−10 | 4.33E−10 | 3 |
| AB1170070 | Yes | Yes | Yes | 6.83E−09 | 6.70E−09 | 3 |
| AB1170072 | Yes | Yes | Yes | 6.93E−10 | 3.45E−10 | 4 |
| AB1170073 | Yes | Yes | Yes | 2.11E−09 | 1.555E−09 | 4 |
| AB1170074* | not tested | Yes | Yes | 1.37E−09 | 6.89E−10 | 3 |
| AB1170086 | Yes | Yes | Yes | 1.108E−09 | 4.733E−10 | 4 |
| AB1170148 | Yes | Yes | Yes | 6.83E−08 | 2.40E−07 | 2 |

$IC_{50}$ values represent the geometric mean.

SD = standard deviation and n = number of experiments.

Antibodies were reformatted to mIgG1 except those marked with * which were bulked up hybridoma clones.

TABLE 11

| Purified humanized hybridoma IgGs | | | |
|---|---|---|---|
| | HTRF Competition Assay for Antibody A Epitope | | |
| Clone ID | $IC_{50}$ (M) | SD | n |
| AB1170241 | 2.117E−10 | 8.674E−11 | 17 |
| AB1170242 | 2.88E−10 | ND | 1.0 |
| AB1170243 | 1.55E−10 | 6.19E−11 | 9 |
| AB1170244 | 1.17E−09 | ND | 1.0 |
| AB1170245 | 2.23E−09 | ND | 1.0 |
| AB1170246 | 4.99E−09 | ND | 1.0 |
| AB1170247 | 1.13E−08 | ND | 1.0 |
| AB1170248 | 1.58E−09 | ND | 1.0 |
| AB1170249 | 4.055E−10 | ND | 1 |

$IC_{50}$ values represent the geometric mean where n > 1.

SD = Standard deviation (SD) and n = number of experiments are also shown. Where n = 1, $IC_{50}$ values are the mean of duplicates or triplicates in one experiment.

ND = not done.

Specificity of IgGs Against Paralogues

Figure 1:
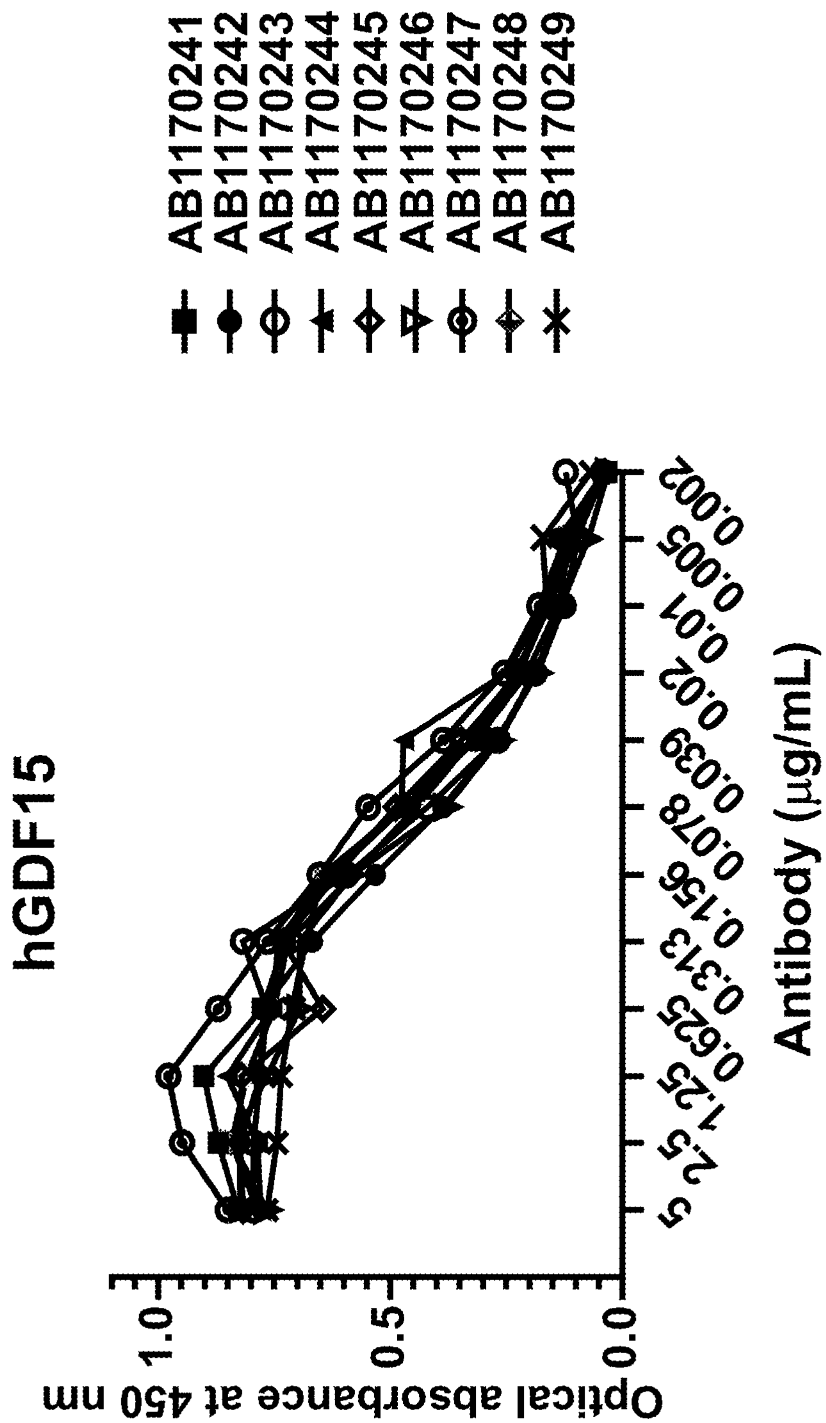
FIG. 1 shows the binding specificity of GDF-15 antibodies to human GDF-15 using a standard antigen presentation ELISA. (See Example 4.)
Figure 2:
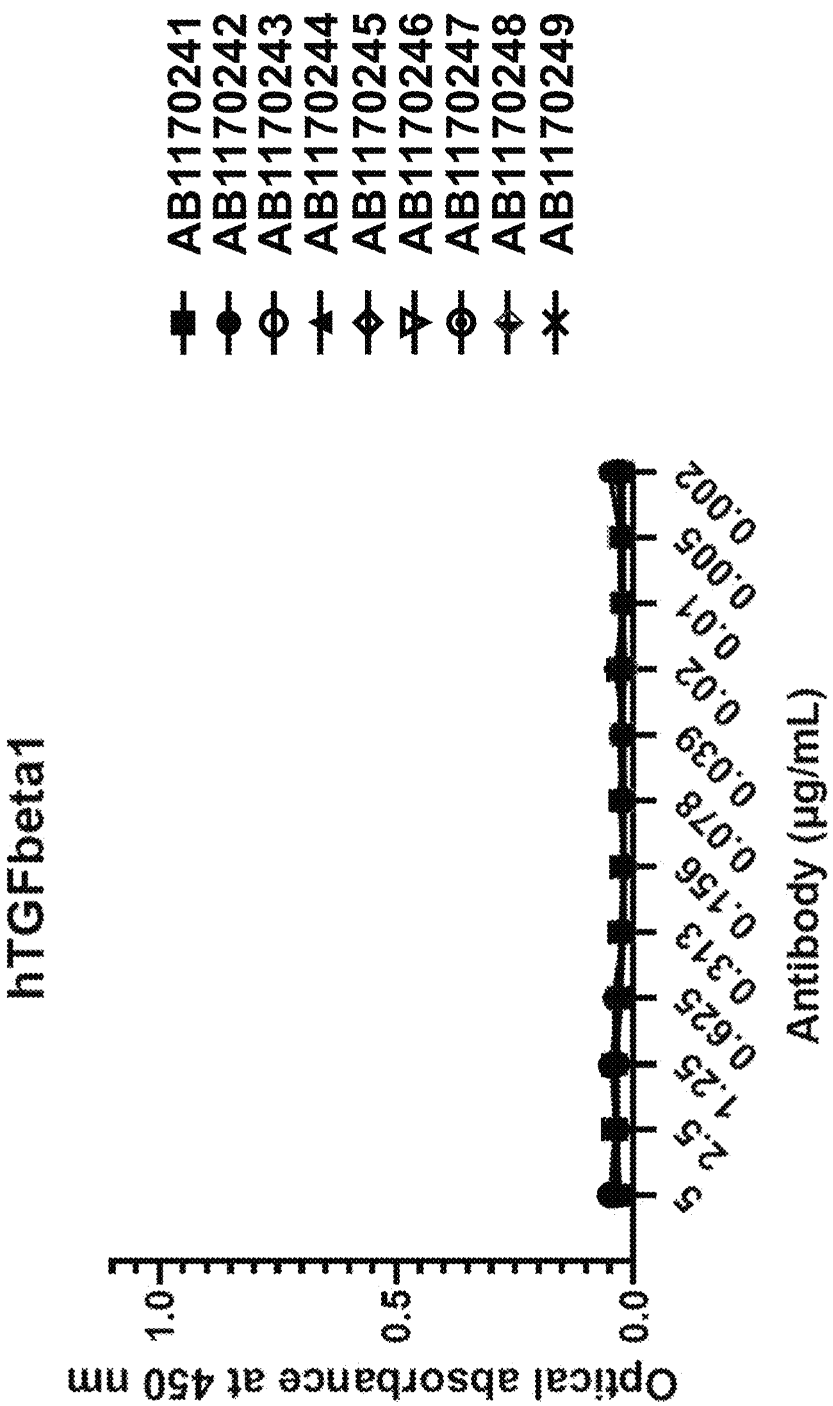
FIG. 2 shows the absence of binding of GDF-15 antibodies to TGFβ1 (R&D Systems 240-B) using a standard antigen presentation ELISA. (See Example 4.)
Figure 3:
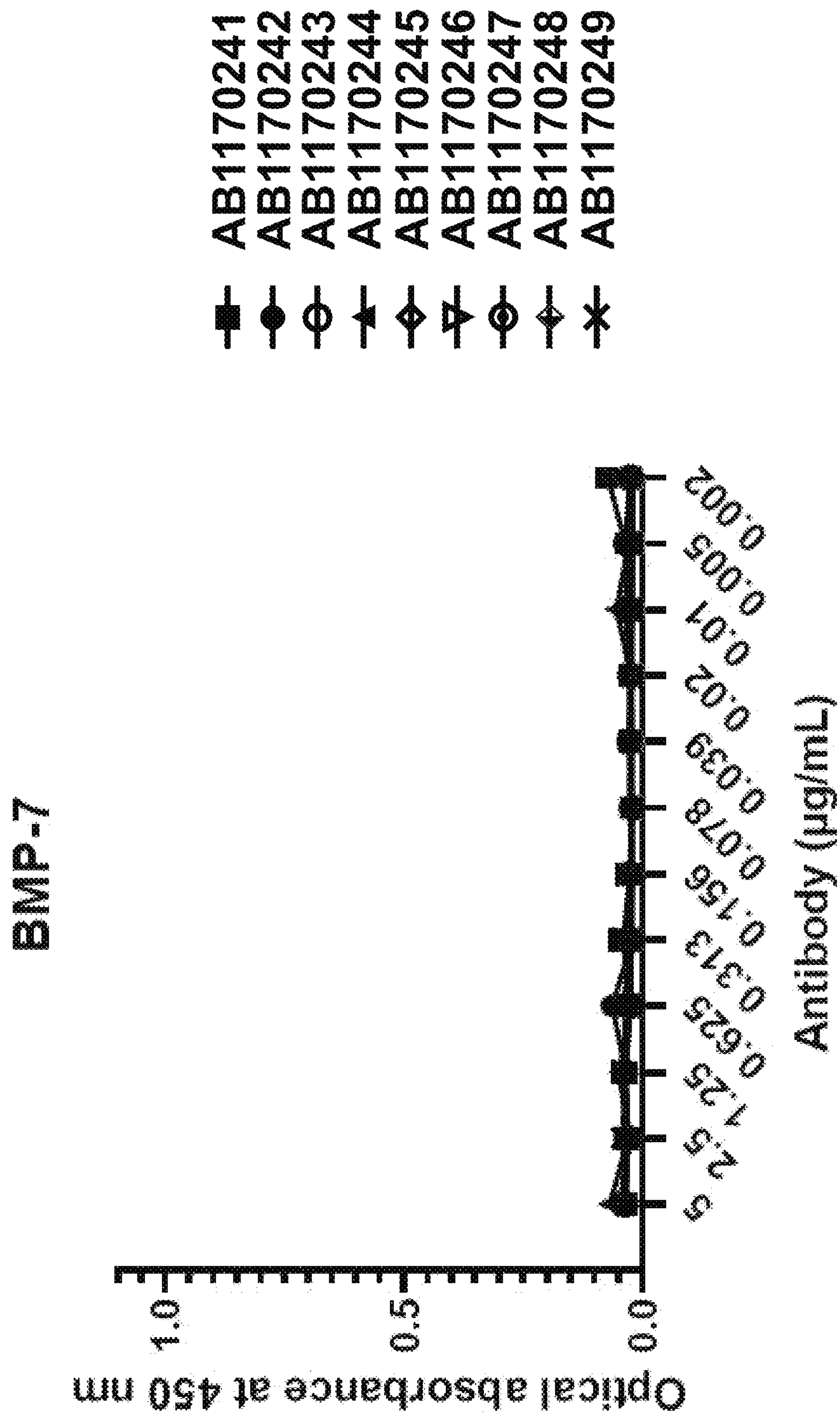
FIG. 3 shows the absence of binding of GDF-15 antibodies to BMP7 (R&D Systems 354-BP/CF) using a standard antigen presentation ELISA. (See Example 4.)

Purified humanized IgGs were screened for binding to human GDF-15 over two further members of the same family, TGFβ1 (R&D Systems 240-B) and BMP7 (R&D Systems 354-BP/CF), using a standard antigen presentation ELISA. Human GDF-15, human TGFβ1 or human BMP7 were adsorbed onto a Nunc Maxisorp™ plate. After removal of excess unbound antigen, a titration of test IgG was added to the plate. After a 1-hour incubation, the unbound IgG was removed. The extent of IgG binding was determined by addition of an anti-human IgG antibody conjugated to the horseradish peroxidase (HRP) enzyme and measuring the optical absorbance at 450 nm of the product of its reaction with the substrate TMB. Data are presented in FIGS. 1-3 and show that all antibodies tested bound to human GDF-15, but not to human TGFβ1 or human BMP7.

Screening Hybridoma IgGs for Binding to Recombinant Mouse GDF-15 Proteins in a Heterogenous (DELFIA) Assay Format Antibodies from the immunization with mouse GDF-15, in the form of crude supernatants from the immunization or in the form of purified IgGs, were triaged on the basis that they bind to immobilized mouse GDF-15 with differential affinity/binding strength.

Mouse GDF-15 was immobilized to the surface of high binding, ultra-low volume 384 well assay plates, for 1 hour at 37° C., followed by washing then blocking reactive sites with an excess of an irrelevant protein. Following further washing, titrations of test antibodies were allowed to bind to immobilized mouse GDF-15 for 1 hour at 37° C. This was followed by extensive washing to remove unbound IgG. Europium chelate labelled anti mouse IgG (Perkin Elmer) was used as a secondary detection reagent and was allowed to bind to test IgG bound to mouse GDF-15 for 1 hour at 37° C. Following more extensive washing, signal was developed by the addition of DELFIA enhancement solution (Perkin Elmer). Plates were left for 20 minutes at room temperature before reading on an Envision plate reader, and $EC_{50}$ values were determined by curve fitting the data to a four-parameter logistic equation using PRISM 6® software (GraphPad). Data for AB1520085 and AB1170119 antibodies are presented in Table 12.

Screening Hybridoma IgGs for Competitive Binding to Recombinant Mouse GDF-15 Proteins in Homogeneous Assay Format Antibodies from the immunization with mouse GDF-15, in the form of crude supernatants or purified IgGs, were chosen on the basis that they bind and compete with a desired epitope (based on functional screening assays) recognized by human anti-human GDF-15 IgG; AB 1170243. A biochemical epitope competition format was applied using an HTRF epitope competition assay that measured the binding of DyLight 650 labelled AB1170243 (energy acceptor) to Flag tagged mouse GDF-15. Europium labelled anti-Flag (Cis-Bio) was used as the energy donor. In the absence of labelled AB 1170243 binding, there is no detectable FRET fluorescence. When AB 1170243 binds to mouse GDF-15, the resulting physical proximity between the secondary reagent donor/acceptor pair results in FRET. Competition with an antibody that recognizes the same or similar epitope will result in a dose dependent reduction of the FRET signal. FRET was measured ratiometrically [665 nm (acceptor)/620 nm (donor)] on an Envision plate reader, and $IC_{50}$ values were determined by curve fitting the data to a four-parameter logistic equation using PRISM 6® software (Graphpad). Data for AB1520085 and AB 1170119 antibodies are presented in Table 12.

TABLE 12

| Purified mouse hybridoma antibody AB1520085 | | | | | | |
|---|---|---|---|---|---|---|
| | DELFIA Binding Assay | | | HTRF Competition Assay for AB1170243 Epitope | | |
| Antibody | Binding $EC_{50}$ | SD | n | $IC_{50}$ | SD | n |
| AB1520085 | 1.58E−10 | 3.59E−10 | 2 | 1.13E−10 | 9.81E−11 | 8 |
| AB1170019 | 2.837E−08 | 2.001E−08 | 3 | 7.099E−08 | 4.839E−08 | 6 |
| AB1170241 | ND | ND | ND | 7.53E−08 | ND | 1 |

$EC_{50}$ and $IC_{50}$ values represent the geometric mean.
SD = Standard deviation and n = number of experiments.
ND = not done.

Example 5: Biacore Affinity Analysis

Antigen binding fragments (Fabs) of the humanized anti-human GDF-15 antibodies or anti-mouse GDF-15 mouse IgG1 were expressed (Spooner et al. 2015), and the affinity was measured using the Biacore 8K at 25° C. The experiments were carried out using mature recombinant human GDF-15, human GDF-15 H202D variant, mouse GDF-15, and cynomolgus GDF-15 with an N-terminal Flag and His tag. All species were chemically biotinylated using EZ link Sulfo-NHS-LC-Biotin (Thermo).

Streptavidin was covalently immobilized to a C1 chip surface using standard amine coupling techniques at a concentration of 4 μg/ml in 10 mM Sodium acetate pH 4.5. Recombinant biotinylated GDF-15 species were titrated onto the streptavidin chip surface in HBS-EP+ buffer to enable Fab binding.

The anti-GDF-15 Fabs were serially diluted (0.0781-10 nM, 0.195-25 nM, 0.234-30 nM or 3.125-200 nM) in HBS-EP+ buffer pH 7.4 and flowed over the chip at 50 μl/min, with 3 minutes association and 10 minutes dissociation. Multiple buffer-only injections were made under the same conditions to allow for double reference subtraction of the final sensorgram sets, which were analyzed using Biacore 8K Evaluation Software. The chip surface was fully regenerated with pulses of 50 mM NaOH.

Biacore affinity results for select clones are provided in Tables 13-20.

TABLE 13

| AB1170241 Fab | | | | | | | |
|---|---|---|---|---|---|---|---|
| | $k_a$ ($M^{-1}$ $s^{-1}$) | | $k_d$ ($s^{-1}$) | | $K_D$ (nM) | | |
| Species | Mean | SD | Mean | SD | Mean | SD | n= |
| Human | 4.18E+06 | 1.56E+05 | 6.63E−04 | 1.05E−05 | 0.159 | 0.004 | 4 |
| Human H202D | 4.45E+06 | 3.17E05 | 6.96E−04 | 4.11E−05 | 0.156 | 0.004 | 4 |
| Cynomolgus | 5.87E+06 | 2.83E+05 | 2.79E−03 | 1.27E−04 | 0.476 | 0.013 | 6 |
| Mouse | 3.07E+06 | 2.58E+05 | 3.29E−01 | 4.64E−02 | 107 | 10 | 3 |

TABLE 14

| AB1170242 Fab | | | | | | | |
|---|---|---|---|---|---|---|---|
| | $k_a$ ($M^{-1}$ $s^{-1}$) | | $k_d$ ($s^{-1}$) | | $K_D$ (nM) | | |
| Species | Mean | SD | Mean | SD | Mean | SD | n= |
| Human | 7.68E+06 | 6.03E+05 | 2.47E−02 | 2.05E−03 | 3.22 | 0.09 | 7 |
| Human H202D | 7.47E+06 | 4.13E+05 | 2.33E−02 | 7.18E−04 | 3.13 | 0.25 | 5 |
| Cynomolgus | 8.50E+06 | 4.24E+05 | 2.45E−02 | 1.20E−03 | 2.88 | 0.09 | 7 |
| Mouse | 9.03E+05 | 6.78E+04 | 8.26E−01 | 1.76E−01 | 908 | 123 | 3 |

TABLE 15

| AB1170243 Fab | | | | | | | |
|---|---|---|---|---|---|---|---|
| | $k_a$ ($M^{-1}$ $s^{-1}$) | | $k_d$ ($s^{-1}$) | | $K_D$ (nM) | | |
| Species | Mean | SD | Mean | SD | Mean | SD | n= |
| Human | 4.74E+06 | 5.57E+05 | 4.22E−04 | 1.21E−05 | 0.090 | 0.009 | 15 |
| Human H202D | 4.85E+06 | 9.05E+05 | 4.25E−04 | 2.22E−05 | 0.090 | 0.014 | 13 |
| Cynomolgus | 6.23E+06 | 6.38E+05 | 1.69E−03 | 6.01E−05 | 0.273 | 0.023 | 17 |
| Mouse | 3.90E+06 | 8.45E+05 | 2.81E−01 | 1.74E−02 | 75.0 | 16 | 8 |

TABLE 16

| AB1170244 Fab | | | | | | | |
|---|---|---|---|---|---|---|---|
| | $k_a$ ($M^{-1}$ $s^{-1}$) | | $k_d$ ($s^{-1}$) | | $K_D$ (nM) | | |
| Species | Mean | SD | Mean | SD | Mean | SD | n= |
| Human | 2.39E+06 | 1.95E+05 | 5.58E−03 | 1.88E−04 | 2.35 | 0.17 | 7 |
| Human H202D | 2.49E+06 | 1.38E+05 | 5.95E−03 | 2.06E−04 | 2.39 | 0.13 | 5 |
| Cynomolgus | 2.64E+06 | 5.65E+04 | 1.45E−02 | 3.94E−04 | 5.47 | 0.15 | 8 |
| Mouse | 5.91E+05 | 7.31E+04 | 5.40E−01 | 7.09E−02 | 916 | 59 | 3 |

TABLE 17

| AB1170245 Fab | | | | | | | |
|---|---|---|---|---|---|---|---|
| | $k_a$ ($M^{-1}$ $s^{-1}$) | | $k_d$ ($s^{-1}$) | | $K_D$ (nM) | | |
| Species | Mean | SD | Mean | SD | Mean | SD | n= |
| Human | 3.10E+06 | 7.42E+04 | 3.15E−02 | 8.33E−04 | 10.2 | 0.3 | 7 |
| Human H202D | 3.07E+06 | 1.21E+05 | 3.21E−02 | 9.75E−04 | 10.5 | 0.4 | 6 |

TABLE 17-continued

| AB1170245 Fab | | | | | | | |
|---|---|---|---|---|---|---|---|
| | $k_a$ ($M^{-1}$ $s^{-1}$) | | $k_d$ ($s^{-1}$) | | $K_D$ (nM) | | |
| Species | Mean | SD | Mean | SD | Mean | SD | n= |
| Cynomolgus | 3.42E+06 | 3.45E+05 | 7.12E−02 | 7.14E−03 | 20.9 | 0.7 | 7 |
| Mouse | 6.43E+05 | 1.12E+05 | 1.50E+00 | 1.12E−01 | 2404 | 657 | 3 |

TABLE 18

| AB1170247 Fab | | | | | | | |
|---|---|---|---|---|---|---|---|
| | $k_a$ ($M^{-1}$ $s^{-1}$) | | $k_d$ ($s^{-1}$) | | $K_D$ (nM) | | |
| Species | Mean | SD | Mean | SD | Mean | SD | n= |
| Human | 4.18E+06 | 2.22E+05 | 3.86E−02 | 2.15E−03 | 9.24 | 0.32 | 6 |
| Human H202D | 4.06E+06 | 1.28E+05 | 3.85E−02 | 1.22E−03 | 9.50 | 0.10 | 3 |
| Cynomolgus | 4.58E+06 | 3.81E+05 | 6.86E−02 | 4.31E−03 | 15.0 | 0.5 | 6 |
| Mouse | | | | | —* | | 3 |

*= no binding

TABLE 19

| AB1170249 Fab | | | | | | | |
|---|---|---|---|---|---|---|---|
| | $k_a$ ($M^{-1}$ $s^{-1}$) | | $k_d$ ($s^{-1}$) | | $K_D$ (nM) | | |
| Species | Mean | SD | Mean | SD | Mean | SD | n= |
| Human | 3.63E+06 | 1.16E+05 | 1.14E−02 | 1.49E−04 | 3.13 | 0.08 | 6 |
| Human H202D | 3.72E+06 | 1.08E+05 | 1.13E−02 | 1.80E−04 | 3.04 | 0.11 | 5 |
| Cynomolgus | 4.15E+06 | 1.40E+05 | 1.29E−02 | 1.03E−04 | 3.11 | 0.09 | 6 |
| Mouse | 8.04E+05 | 6.65E+04 | 9.28E−01 | 3.04E−01 | 1139 | 293 | 3 |

TABLE 20

| AB1520085 Fab | | | | | | | |
|---|---|---|---|---|---|---|---|
| | $k_a$ ($M^{-1}$ $s^{-1}$) | | $k_d$ ($s^{-1}$) | | $K_D$ (nM) | | |
| Species | Mean | SD | Mean | SD | Mean | SD | n= |
| Human | 2.97E+06 | 3.34E+05 | 4.89E−03 | 5.02E−04 | 1.64 | 0.017 | 3 |
| Human H202D | 2.92E+06 | | 4.78E−03 | | 1.63 | | 1 |
| Cynomolgus | 2.79E+06 | | 7.80E−03 | | 2.80 | | 1 |
| Mouse | 1.75E+06 | 9.17E+04 | 2.44E−04 | 7.62E−06 | 0.140 | 0.012 | 4 |

Example 6: GDF-15 Antibodies Inhibit Proliferation of Prostate Cancer Cells

The results shown in FIG. 4 demonstrate that GDF-15 antibodies inhibit proliferation of LNCaP prostate cancer cells. LNCaP cells were plated at a density of 5000 cells/well in a 96-well plate and treated with the indicated antibodies diluted in a 2-fold dilution series from 400-25 nM. Cells were incubated for 3 days and viability was determined using Cell Titer Glo (Promega).

Example 7: GDF-15 Antibodies Promote Upregulation of Costimulatory Proteins on moDC The results shown in FIGS. 5A, 5B, and 5C demonstrate that GDF-15 antibodies promote upregulation of costimulatory proteins on monocyte-derived dendritic cells (moDC). Monocytes from healthy donors were isolated by Miltenyi kit (CD14 Microbeads, human catalog number 130-050-201) and plated at a density of 1 million cells/mL in a 6-well plate. They were treated for 6 days with 100 ng/ml IL-4 (R&D Systems) and 100 ng/mL GM-CSF (R&D Systems). After 6 days, 15 nM CD40L (Enzo Life Sciences INT Inc) with and without 400 ng/mL of recombinant hu-GDF15 (Prospec, Cat #CYT-335) was added to the wells and/or 10 μg/ml anti-GDF15 antibody. Two days later, cells were analyzed by flow cytometry for expression of CD14 (Biolegend) and CD1a (Biolegend) to confirm differentiation to dendritic cells as well as CD83 (BD Biosciences) and CD86 (BD Biosciences) to measure activation. IL-12p70 secretion was measured by ELISA. Data are presented as the percentage of the median fluorescence intensity (MFI) of cells activated in the absence of GDF15. Anti-GDF15 antibodies were able to restore the expression of CD83, CD86, and secretion of IL-12p70 to the level of expression observed in the absence of GDF15.

Example 8: GDF-15 Antibodies Reverse GDF15 Inhibition of T Cell Proliferation

The results, shown in FIGS. 6 and 7A, demonstrate that anti-GDF-15 antibodies reverse the anti-proliferative effects of GDF15. CD3 cells were isolated by EasySep Human T cell isolation kit (Stemcell Technologies) and plated at a density of 100,000 cells/well in a 96-well plate that was coated with 10 μg/ml anti-CD3 (ThermoFisher Scientific, cat #16-0037) and 10 μg/ml anti-CD28 antibody (Biolegend cat #302923, clone CD28.2). Recombinant hu-GDF15 was added at 400 ng/mL and antibodies were added from 33.3-0.05 nM in a 5-fold dilution series. Cell viability was determined using Cell Titer Glo (Promega) as measured by relative light units (RSU). The results in FIG. 7B demonstrates AB1520085 reverses the anti-proliferative effects of mouse GDF-15. Antibodies AB 1170241 and AB1520085 restored full proliferation to the T cells.

Example 9: GDF-15 Antibodies Reverse GDF-15 Inhibition of Th1 Differentiation

The results shown in FIG. 8 demonstrate that GDF-15 antibodies reverse GDF-15 inhibition of Th1 differentiation. CD4+ T-cells were isolated from healthy donors by EasySep human CD4+ T cell isolation kit (Stemcell Technologies). Cells were plated at a density of 250,000 cells/well in a 24-well plate coated with 10 mg/mL mouse Anti-Human CD3 antibody (R&D Systems). T-cells were skewed to a Th1 phenotype by CellXVivo™ Human Th1 Cell Differentiation Kit (R&D Systems) in the presence of 400 ng/mL recombinant Human GDF-15 protein and or 10 ug/mL anti human GDF-15 antibody for 5 days. At day 5, culture supernatants were collected and analyzed for Human TNF-alpha (R&D Systems) and Human IFNγ (R&D Systems) secretion by ELISA. The graph shows the level of secretion normalized to the levels observed without recombinant hu-GDF15. The GDF15 antibody AB1170241 restores the full level of cytokine secretion.

Example 10: GDF-15 Antibodies Reverse GDF-15 Downregulation of DC Activation Markers The results shown in FIG. 9 demonstrate that GDF-15 antibodies reverse GDF-15 downregulation of dendritic cell (DC) activation markers. Monocytes from healthy donors were isolated by Miltenyi kit (CD14 Microbeads, human catalog number 130-050-201) and plated at a density of 1 million cells/mL in a 6-well plate. They were treated for 6 days with 100 ng/ml IL-4 (R&D Systems, Cat #204-IL-050) and 100 ng/mL GM-CSF (R&D Systems, Act #215-GM-050). After 6 days, 15 nM CD40L (Enzo Life Sciences INT Inc, Cat #ALX-522-110-C010) with or without 400 ng/mL of recombinant hu-GDF15 (Prospec, Cat #CYT-335) and/or 10 μg/ml anti-GDF15 antibody was added to the wells. Two days later, cells were analyzed by flow cytometry for expression of CD14 (Biolegend, Cat #367116) and CD1a (Biolegend, Cat #300128) to confirm differentiation to dendritic cells as well as CD83 (BD Biosciences) and CD86 (BD Biosciences) to measure activation. Data was normalized to the median fluorescence intensity (MFI) obtained for samples activated in the absence of hu-GDF15. The anti-GDF15 antibody AB 1170241 restores full expression of both CD83 and CD86.

Example 11: GDF-15 Antibodies Lead to Tumor Regressions and have Anti-Tumor Activity in Anti-PD-L1 Refractory and MBT2 Syngeneic Tumors The results, shown in FIGS. 10 and 12, demonstrate that anti-GDF15 antibodies increase antigen presenting cells and activated T cells in the LL/2 syngeneic mouse model. LL/2 cells were injected, (500,000 per mouse) subcutaneously in the flanks of Balb/c mice. Tumors were allowed to grow to 150 $mm^3$ when they were randomized into treatment groups with 12 animals per arm. The various groups were treated with 10 mg/kg of the indicated antibody twice weekly for a total of 4 weeks. Tumors were measured twice weekly using calipers, and the resulting tumor growth curves are shown. Separate cohorts of mice (n=6) were treated with 10 mg/kg of the indicated antibodies twice weekly for one week. Tumors were harvested 24 hours post the second dose, dissociated by GentleMacs, and stained for flow cytometry. Antibodies used were CD45 BV785 (Biolegend), CD11c BV480 (BectonDickinson), CD86 APCR700 (Biolegend), CD103 PERCP-CY5.5 (ThermoFisher Scientific), CD8 BUV737 (BectonDickenson), CD69 BUV563 (Biolegend), and IFN gamma BV711 (Biolegend). DAPI was used for live/dead gating. All data is presented as percentage of CD45+ cells.

The results, shown in FIGS. 11 and 12, demonstrate that anti-GDF15 antibodies increase antigen presenting cells and activated T cells in the MBT2 syngeneic mouse model. MBT2 cells were injected ($2\times10^6$ per mouse) subcutaneously in the flanks of Balb/c mice. Tumors were allowed to grow to 150 $mm^3$ when they were randomized into treatment groups with 12 animals per arm. The various groups were treated with 10 mg/kg of the indicated antibody twice weekly for a total of 4 weeks. Tumors were measured twice weekly using calipers, and the resulting tumor growth curves are shown. Separate cohorts of mice (n=6) were treated with 10 mg/kg of the indicated antibodies twice weekly for one week. Tumors were harvested 24 hours post the second dose, dissociated by GentleMacs, and stained for flow cytometry. Antibodies used were CD45 BV785 (Biolegend), CD11c BV480 (BectonDickinson), CD86 APCR700 (Biolegend), CD103 PERCP-CY5.5 (ThermoFisher Scientific), CD8 BUV737 (BectonDickenson), CD69 BUV563 (Biolegend), and IFN gamma BV711 (Biolegend). DAPI was used for live/dead gating. All data is presented as percentage of CD45+ cells.

Example 12: AB1170241 Epitope Analysis

Expression and Purification of GDF15

The GDF15 protein was expressed and purified following a similar protocol as described by Bigalke et al. for Neurturin (Bigalke, Janna M., et al. "Cryo-EM structure of the activated RET signaling complex reveals the importance of its cysteine-rich domain." Science advances 5:7eaau4202 (2019)). Mature GDF15 residues, (residues Ala-197 to Ile-308 (SEQ ID NO: 479)), were cloned into a pET24a vector and expressed in *Escherichia coli* BL21 (DE3) Star via autoinduction at 25° C. The resulting inclusion bodies were dissolved in solubilization buffer (8 M Urea, 0.1 M $Na_2HPO_4$, 10 mM TCEP, 50 mM Tris-Cl pH 8.5) overnight at room temperature (RT) and slowly dripped into the refolding buffer (3 M Urea, 15% (w/v) glycerol, 75 mM $Na_2HPO_4$, 0.3 M NaCl, 20 mM glycine, 4 mM cysteine, 50 mM Tris-HCl, pH 8.5). Incubation at RT with slow stirring was done for three days. Ni-Sepharose FF washed in Buffer A (3 M Urea, 15% (w/v) glycerol, 75 mM $Na_2HPO_4$, 50 mM Tris-HCl, pH 8.5) was added to the refolded GDF15 and incubated overnight at RT with slow stirring. The resin was removed and washed with first Buffer A, then Buffer B (3 M Urea, 15% (w/v) glycerol, 75 mM $Na_2HPO_4$, 50 mM Tris-HCl, 0.3 M NaCl, 1% Triton X-100, pH 8.5) and finally Buffer A again. The resin was transferred to a column and washed with Buffer A with the addition of 1% Buffer C (3 M Urea, 15% (w/v) glycerol, 75 mM $Na_2HPO_4$, 50 mM Tris-HCl, 500 mM imidazole, pH 8.5) (end concentration of imidazole, 5 mM). The protein was then eluted in 40% Buffer A and 60% Buffer C (end concentration of imidazole, 300 mM). The collected sample was diluted in Buffer A to a final concentration of 1 M Urea and a protein concentration of 0.4 mg/ml. 3 mM reduced glutathione (GSH) and 0.3 mM glutathione disulfide (GSSG) were added to the protein, and then the HN-tag was cleaved off by TEV-protease at RT with slow stirring overnight. The next day, Urea powder was added to a final concentration of 3 M Urea. Precipitate was removed by centrifugation, and the material was loaded on a column containing Ni-Sepharose FF equilibrated in 96% Buffer A and 4% Buffer C (end 20 mM imidazole). The cleaved dimeric GDF15 was collected by washing the resin with buffer containing 50 mM imidazole. The pH was lowered to pH 4 by adding acetic acid. The protein solution was loaded on a HiTrap SP column equilibrated in 3 M Urea, 10% (w/v) glycerol, 25 mM NaAcetate, pH 4 (adjusted with acetic acid). The protein was eluted in 50% 3 M Urea, 10% (w/v) glycerol, 25 mM NaAcetate, 1 M NaCl, 1 M Arginine-Cl, pH 4 (adjusted with acetic acid). The concentrated protein was loaded on a Superdex 75 column equilibrated in 25 mM NaAcetate, 100 mM NaCl, pH 4.0 and the protein was flash-frozen in liquid nitrogen.

Formation of GDF1S-AB1170241 Fab Complex

GDF15 and AB1170241 Fab were mixed in a ratio of 1.2:1 and incubated overnight at 4° C. The mixture was run over a SEC column (Superdex 200 Increase 10/300 GL) in 0.025 M HEPES pH 7.5 and 0.150 M NaCl. The fractions containing the complex were pooled and concentrated.

Hydrogen Deuterium Exchange Mass Spectrometry (HDX-MS)

Elution Buffer (E-Buffer):

0.025 M HEPES pH 7.5 (Hampton Research) in $H_2O$ 0.15 M NaCl (Hampton Research) in $H_2O$ Labelling Buffer (L-Buffer):

0.025 M HEPES (Sigma) in $D_2O$ (Cambridge Isotope Laboratories Inc), measured value with pH-meter 7.1 (corresponding to pH 7.5 for non-deuterated buffers (Covington, Arthur K., et al. "Use of the glass electrode in deuterium oxide and the relation between the standardized pD (paD) scale and the operational pH in heavy water." Analytical Chemistry 40(4): 701 (1968)).

0.15 M NaCl (Sigma) in $D_2O$ (Cambridge Isotope Laboratories Inc)

Quench Buffer:

2 M Urea (Sigma)

0.4 M TCEP (Sigma)

pH 2.5 in $H_2O$

Hydrogen Deuterium Exchange Mass Spectrometry (HDX-MS) Data was Collected in Two Separate Experiments Experiment 1 (Results Summarized in FIG. 21)

GDF15 protein (9 μM) and preformed GDF15-AB1170241 Fab complex (11.2 μM) in E-buffer were thawed and filtered using a 0.22 μm spin filter (Amicon) just before starting the experiment. Exchange reactions were carried out using a CTC PAL sample handling robot (LEAP Technologies). Reactions were conducted by incubating 3 μL of protein samples with 57 μl of L-buffer (deuterated) for times of 0.5, 1, 10, and 30 min at 20° C.

Experiment 2 (Results Summarized in FIG. 22)

GDF15 protein (10 μM), preformed GDF15-AB1170241 Fab complex (9.6 μM), and AB1170241 Fab (10 μM) in E-buffer were thawed and filtered using a 0.22 μm spin filter (Amicon) just before starting the experiment. Exchange reactions were carried out using a CTC PAL sample handling robot (LEAP Technologies). Reactions were conducted by incubating 3 μL of protein samples with 57 μl of L-buffer (deuterated) for times of 0.5, 1, 5, and 30 min at 20° C.

Experiments 1 and 2 (Results Summarized in FIG. 22)

The exchange reactions in both experiments were stopped by the addition of 50 μL of quench solution (2 M Urea, 0.4 M TCEP pH 2.5) at 0° C. Samples were subsequently injected onto an online pepsin digestion system and subjected to digestion using a BEH pepsin column (Waters) 2.1×30 mm in 0.3% formic acid in water at 150 μL $min^{-1}$. The digested peptides were trapped using a 2.1×5 mm, 1.7 m, C18 trap (ACQUITY UPLC BEH C18 VanGuard Pre-Column, Waters) column for 3 min. The desalted peptides were separated and eluted using a C18 reverse phase column (ACQUITY UPLC BEH C18 Column, 1.7 m, 2.1×100 mm, Waters) with a 6-minute 5-40% (vol/vol) acetonitrile (containing 0.1% formic acid) gradient at 40 $\mu Lmin^{-1}$. The resulting peptides were ionized by electrospray onto SYNAPT XS mass spectrometer (Waters) acquiring in MSE mode for detection and mass measurements. Peptides from non-labelled protein were identified using Protein Lynx Global Server 2.0 searches of a protein database containing the GDF15 and AB 1170241 Fab sequences. Each deuterium labelling experiment was performed in at least triplicate. Relative deuterium levels for each peptide were calculated by subtracting the average mass of the deuterium labelled sample from that of the non-deuterated control sample. All mass spectra were processed with DynamX 3.0 (Waters). The normalized hydrogen-deuterium exchange data were mapped onto the crystal structure of GDF15 (5vz3) using Pymol (Schrödinger). The HDX-MS data were calculated using the mean deuteration level per amino acid, as reported in Klein, T. et al., "Structural and dynamic insights into the energetics of activation loop rearrangement in FGFR1 kinase," *Nat. Commun.* 6: 7877 (2015). A difference of 0.5 Da between labelled and non-labelled samples were considered significant.

Results

The sequence peptides that were detected after pepsin cleavage of GDF15 and GDF15-AB1170241 Fab complex resulted in a peptide coverage of 50% of the GDF15 sequence in experiment 1, and 49% in experiment 2. Some peptides are present in only one of the datasets, which means that the data sets combined have a total peptide coverage of 56%. The peptides that were not detected originated mainly from the cysteine knot at the center of the GDF15 protein and the N-terminus. The low degree of degradation of GDF15 has been observed for other cysteine knot proteins.

The difference in deuterium uptake between GDF15 alone and GDF15 in complex with the AB1170241 Fab was determined, and the normalized uptake data is plotted on the GDF15 crystal structure (PDB ID: 5VZ3) in FIGS. 13-19 and summarized in Table 20. The black/dark grey regions in FIGS. 13, 15-17, 19, and 20, indicate the GDF15 peptides that are more protected in the GDF15-AB 1170241 Fab complex compared to GDF15 alone, suggesting binding of the AB 1170241 Fab to these regions. The regions of mature GDF15 with the strongest protection are V33-Q40 (strongest) (SEQ ID NO:486) and I89-L105 (SEQ ID NO: 487). In experiment 2, E25-W32 (SEQ ID NO:485) showed protection (weaker, not detected in experiment 1). FIGS. 16 and 20 show areas of increased exposure of GDF15 peptides. This is seen for the alpha helix in the heel domain of GDF15, however, this effect is weaker.

The HDX protected areas are located on the extended finger domains and adjacent regions of GDF15. Since the protein is a symmetric homodimer, the epitope is present in both subunits. Therefore, it should be possible for two AB 1170241 copies to bind to the homodimer at the same time.

One of the protected regions is the I89-L105 stretch (SEQ ID NO: 487), which makes up the beta-hairpin structure that interacts with the GDNF family receptor alpha-like protein (GFRAL). 189 of SEQ ID NO: 479 has been demonstrated to be a key residues in the GDF15-GFRAL interaction surface by mutational studies (Hsu, Jer-Yuan, et al. "Non-homeostatic body weight regulation through a brainstem-restricted receptor for GDF15*." Nature* 550(7675): 255 (2017)). The stretch of GDF15 that displays the strongest degree of protection, V33-Q40 (SEQ ID NO: 486), is part of the interaction surface between GDF15 and Proto-oncogene tyrosine-protein kinase receptor Ret (RET) (Li, Jie, et al. "Cryo-EM analyses reveal the common mechanism and diversification in the activation of RET by different ligands." *Elife* 8:e47650 (2019)). The more weakly protected peptide E25-W32 (SEQ ID NO:486) bears the conserved residue W32, which has been demonstrated to be essential for the GDF15-RET interaction. Taken together, the HDX-MS data suggest that the AB1170241 epitope is located in two adjacent regions of the protein surface and is capable of interfering both with GFRAL and RET binding.

TABLE 21

Mature GDF15 (SEQ ID NO: 479) Residue Analysis

| GDF15 residues within 5Å of GDF15-GFRAL interface (PDB ID: 5VZ4) | Most protected by AB1170241 Fab in second dataset | GDF15 residues within 5Å of GDF15-RET interface (PDB ID: 6Q2J) |
|---|---|---|
| | 25(GLU) weak protection | |
| | 26(ASP) weak protection | |
| | 27(LEU) weak protection | |
| | 28(GLY) weak protection | |
| | 29(TRP) weak protection | |
| | 30(ALA) weak protection | |
| | 31(ASP) weak protection | 31(ASP) |
| | 32(TRP) medium protection | 32(TRP) |
| | 33(VAL) strong protection | |
| 34(LEU) | 34(LEU) strong protection | |
| 35(SER) | 35(SER) strong protection | |
| 36(PRO) | 36(PRO) strong protection | |
| | 37(ARG) strong protection | |
| | 38(GLU) strong protection | |
| | 39(VAL) very strong protection | |
| 40(GLN) | 40(GLN) very strong protection | |
| | ND | 51(GLN) |
| | ND | 53(ARG) |
| | ND | 54(ALA) |
| | ND | 55(ALA) |
| | ND | 56(ASN) |
| | ND | 57(MET) |
| | | 60(GLN) |
| 85(PRO) | ND | |
| 86(MET) | ND | |
| 87(VAL) | ND | |
| 89(ILE) | 89(ILE) strong protection | |
| | 90(GLN) strong protection | 90(GLN) |
| | 91(LYS) strong protection | 91(LYS) |
| | 92(THR) strong protection | 92(THR) |
| | 93(ASP) strong protection | 93(ASP) |
| 94(THR) | 94(THR) strong protection | |
| 95(GLY) | 95(GLY) strong protection | |
| 96(VAL) | 96(VAL) strong protection | |
| | 97(SER) strong protection | |
| 98(LEU) | 98(LEU) strong protection | |
| | 99(GLN) strong protection | 99(GLN) |
| 100(THR) | 100(THR) strong protection | |
| | 101(TYR) medium protection | 101(TYR) |
| 102(ASP) | 102(ASP) medium protection | |
| | 103(AS) medium protection | 103(ASP) |
| | 104(LEU) medium protection | |

ND—no peptide coverage. The Contact program from the CCP4 suite (Winn, M. D., et al. "Overview of the CCP4 suite and current developments." *Acta Crystallographica Section D: Biological Crystallography 67*: 235 (2011)) was used. In this table (dataset 2) values ≤0.1 are defined as very strong protection, ≤0.25 are defined as strong protection, 0.26-0.35 medium protection, 0.36-0.4 weak protection.

TABLE 22

Mature GDF15 (SEQ ID NO: 479) Residue Analysis

| Amino acid number | Amino acid type | Relative difference deuterium uptake per amino acid, dataset 1 | Relative difference deuterium uptake per amino acid, dataset 2 |
|---|---|---|---|
| 1 | A | ND | ND |
| 2 | R | ND | ND |
| 3 | N | ND | ND |
| 4 | G | ND | ND |
| 5 | D | ND | ND |
| 6 | H | ND | ND |
| 7 | C | ND | ND |
| 8 | P | ND | ND |
| 9 | L | ND | ND |
| 10 | G | ND | ND |
| 11 | P | ND | ND |
| 12 | G | ND | ND |
| 13 | R | ND | ND |
| 14 | C | ND | ND |
| 15 | C | ND | ND |
| 16 | R | ND | ND |
| 17 | L | ND | ND |
| 18 | H | 0.47 | 0.6 |
| 19 | T | 0.47 | 0.6 |
| 20 | V | 0.49 | 0.6 |
| 21 | R | 0.49 | 0.6 |
| 22 | A | 0.49 | 0.6 |
| 23 | S | 0.49 | 0.6 |
| 24 | L | 0.49 | 0.6 |
| 25 | E | 0.47 | 0.4 |
| 26 | D | 0.45 | 0.4 |
| 27 | L | 0.45 | 0.4 |
| 28 | G | 0.44 | 0.4 |
| 29 | W | 0.44 | 0.4 |
| 30 | A | 0.44 | 0.39 |
| 31 | D | 0.44 | 0.39 |
| 32 | W | 0.4 | 0.31 |
| 33 | V | 0.13 | 0.17 |

TABLE 22-continued

| Mature GDF15 (SEQ ID NO: 479) Residue Analysis | | | |
|---|---|---|---|
| Amino acid number | Amino acid type | Relative difference deuterium uptake per amino acid, dataset 1 | Relative difference deuterium uptake per amino acid, dataset 2 |
| 34 | L | 0 | 0.17 |
| 35 | S | 0 | 0.17 |
| 36 | P | 0 | 0.17 |
| 37 | R | 0 | 0.17 |
| 38 | E | 0 | 0.17 |
| 39 | V | 0.08 | 0 |
| 40 | Q | 0.08 | 0 |
| 41 | V | ND | ND |
| 42 | T | ND | ND |
| 43 | M | ND | ND |
| 44 | C | ND | ND |
| 45 | I | ND | ND |
| 46 | G | ND | ND |
| 47 | A | 0.47 | ND |
| 48 | C | 0.47 | ND |
| 49 | P | 0.47 | ND |
| 50 | S | 0.47 | ND |
| 51 | Q | 0.47 | ND |
| 52 | F | 0.47 | ND |
| 53 | R | 0.47 | ND |
| 54 | A | 0.47 | ND |
| 55 | A | ND | ND |
| 56 | N | ND | ND |
| 57 | M | ND | ND |
| 58 | H | 0.59 | 0.67 |
| 59 | A | 0.59 | 0.67 |
| 60 | Q | 0.6 | 0.67 |
| 61 | I | 0.6 | 0.67 |
| 62 | K | 0.6 | 0.67 |
| 63 | T | 0.6 | 0.67 |
| 64 | S | 0.6 | 0.67 |
| 65 | L | 0.6 | 0.67 |
| 66 | H | ND | ND |
| 67 | R | ND | ND |
| 68 | L | ND | ND |
| 69 | K | ND | ND |
| 70 | P | ND | ND |
| 71 | D | ND | ND |
| 72 | T | ND | ND |
| 73 | V | ND | ND |
| 74 | P | ND | ND |
| 75 | A | ND | ND |

TABLE 22-continued

| Mature GDF15 (SEQ ID NO: 479) Residue Analysis | | | |
|---|---|---|---|
| Amino acid number | Amino acid type | Relative difference deuterium uptake per amino acid, dataset 1 | Relative difference deuterium uptake per amino acid, dataset 2 |
| 76 | P | ND | ND |
| 77 | C | ND | ND |
| 78 | C | ND | ND |
| 79 | V | ND | ND |
| 80 | P | ND | ND |
| 81 | A | ND | ND |
| 82 | S | ND | ND |
| 83 | Y | ND | ND |
| 84 | N | ND | ND |
| 85 | P | ND | ND |
| 86 | M | ND | ND |
| 87 | V | ND | ND |
| 88 | L | ND | ND |
| 89 | I | 0.35 | 0.24 |
| 90 | Q | 0.35 | 0.24 |
| 91 | K | 0.35 | 0.24 |
| 92 | T | 0.35 | 0.24 |
| 93 | D | 0.35 | 0.24 |
| 94 | T | 0.35 | 0.24 |
| 95 | G | 0.35 | 0.24 |
| 96 | V | 0.35 | 0.22 |
| 97 | S | 0.35 | 0.22 |
| 98 | L | 0.36 | 0.23 |
| 99 | Q | 0.39 | 0.25 |
| 100 | T | 0.39 | 0.25 |
| 101 | Y | 0.41 | 0.31 |
| 102 | D | 0.41 | 0.31 |
| 103 | D | 0.41 | 0.31 |
| 104 | L | 0.41 | 0.31 |
| 105 | L | 0.36 | 0.52 |
| 106 | A | ND | 0.52 |
| 107 | K | ND | 0.52 |
| 108 | D | ND | 0.52 |
| 109 | C | ND | 0.52 |
| 110 | H | ND | 0.52 |
| 111 | C | ND | 0.52 |
| 112 | I | ND | 0.52 |

The table shows relative difference in deuterium uptake between AB1170241-GDF15 complex and GDF15 only. The data is normalised within one dataset. 0.5 equals no difference, <0.5 indicates increased protection in presence of Fab, >0.5 indicates increased exposure in presence of AB1170241, ND—no peptide coverage

What is claimed is:

1. An antibody or antigen-binding fragment thereof that specifically binds to human GDF-15 wherein the antibody or antigen-binding fragment comprises the VH CDR1, VH CDR2, VH CDR3, VL CDR1, VL CDR2, and VL CDR3 of AB1170241 wherein the CDRs are the Kabat-defined CDRs, the Chothia-defined CDRs, the IMGT-defined CDRs, or the AbM-defined CDRs.

2. The antibody or antigen-binding fragment thereof of claim 1, wherein the antibody or antigen-binding fragment thereof comprises a VH and a VL, wherein the VH comprises the amino acid sequence of SEQ ID NO:326, and wherein the VL comprises the amino acid sequence of SEQ ID NO:335.

3. The antibody or antigen-binding fragment thereof of claim 1, wherein the antibody or antigen-binding fragment comprises a heavy chain comprising a heavy chain constant domain and a light chain comprising a light chain constant domain, optionally wherein the heavy chain constant domain comprises the sequence of SEQ ID NO:474, and/or the light chain constant domain comprises the sequence of SEQ ID NO:475.

4. The antibody or antigen-binding fragment thereof of claim 3, wherein the heavy chain constant region is selected from the group consisting of human immunoglobulin $IgG_1$, $IgG_2$, $IgG_3$, $IgG_4$, $IgA_1$, and IgA2 heavy chain constant regions, and/or wherein the light chain constant region is selected from the group consisting of human immunoglobulin IgGκ and IgGλ light chain constant regions.

5. The antibody or antigen-binding fragment thereof of claim 1, wherein the antibody or antigen-binding fragment thereof comprises an Fc region that has been engineered to improve half-life, optionally wherein the antibody or antigen-binding fragment thereof comprises an Fc region with a YTE mutation, and/or the antibody or antigen-binding fragment thereof comprises an Fc region with a L234F/L235E/P331S triple mutation (TM).

6. An isolated polynucleotide comprising a nucleic acid molecule encoding the VH or heavy chain and/or the VL or light chain of the antibody or antigen-binding fragment thereof of claim 1.

7. The antibody or antigen-binding fragment thereof of claim 1 that binds to an epitope of GDF-15 comprising an amino acid in amino acids E25-W32 of GDF-15 (SEQ ID NO: 485), an amino acid in amino acids V33-Q40 of GDF-15 (SEQ ID NO: 486), and/or an amino acid in amino acids I89-L105 of GDF-15 (SEQ ID NO: 487).

8. The antibody or antigen-binding fragment thereof of claim 1, wherein the monoclonal antibody or antigen-binding fragment thereof inhibits the interaction of GDF-15 with GFRAL and inhibits the interaction of GDF-15 with RET.

9. The antibody or antigen-binding fragment thereof of claim 1, wherein the antibody or antigen-binding fragment thereof is capable of:

(a) inhibiting proliferation of cancer cells, optionally wherein the proliferation is inhibited by at least 25%, at least 50%, or at least 75% as compared to the proliferation in the absence of the antibody or antigen-binding fragment thereof, (b) activating dendritic cells, optionally wherein activation is doubled as compared to activation in the absence of the antibody or antigen-binding fragment thereof;

(c) increasing the proliferation of T cells, optionally wherein the increase is at least 25%, at least 30%, at least 35%, or at least 40% as compared to the proliferation in the absence of the antibody or antigen-binding fragment thereof, and/or (d) increasing differentiation of Th1 cells, optionally wherein the increase is at least 1.5-fold or by at least 2-fold as compared to the differentiation in the absence of the antibody or antigen-binding fragment thereof.

* * * * *

SEQUENCE LISTING

```
<160> NUMBER OF SEQ ID NOS: 487

<210> SEQ ID NO 1
<211> LENGTH: 354
<212> TYPE: DNA
<213> ORGANISM: Mus musculus

<400> SEQUENCE: 1

caggttactc tgaaagagtc tggccctggg atattgcagc cctcccagac cctcagtctg      60

acttgttctt tctctgggtt ttcactgagc acttatggta tgggtgtagg ttggattcgt     120

cagccttcag ggaagggtct ggagtggctg gccaacattt ggtggaatga tgataagtac     180

tataactcag ccctgaagag ccggctcaca atctccaagg atacctccaa caaccaggta     240

ttcctcaaga tctccagtgt ggacactgca gatactgtca catactactg tgctcaagta     300

ggctatgatt ggtttgctta ctggggccaa gggactctgg tcaccgtctc ctca           354


<210> SEQ ID NO 2
<211> LENGTH: 118
<212> TYPE: PRT
```

<213> ORGANISM: Mus musculus

<400> SEQUENCE: 2

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asn Ile Trp Trp Asn Asp Asp Lys Tyr Tyr Asn Ser Ala
    50                  55                  60

Leu Lys Ser Arg Leu Thr Ile Ser Lys Asp Thr Ser Asn Asn Gln Val
65                  70                  75                  80

Phe Leu Lys Ile Ser Ser Val Asp Thr Ala Asp Thr Val Thr Tyr Tyr
                85                  90                  95

Cys Ala Gln Val Gly Tyr Asp Trp Phe Ala Tyr Trp Gly Gln Gly Thr
            100                 105                 110

Leu Val Thr Val Ser Ser
        115
```

<210> SEQ ID NO 3
<211> LENGTH: 7
<212> TYPE: PRT
<213> ORGANISM: Mus musculus

<400> SEQUENCE: 3

```
Thr Tyr Gly Met Gly Val Gly
1               5
```

<210> SEQ ID NO 4
<211> LENGTH: 16
<212> TYPE: PRT
<213> ORGANISM: Mus musculus

<400> SEQUENCE: 4

```
Asn Ile Trp Trp Asn Asp Asp Lys Tyr Tyr Asn Ser Ala Leu Lys Ser
1               5                   10                  15
```

<210> SEQ ID NO 5
<211> LENGTH: 8
<212> TYPE: PRT
<213> ORGANISM: Mus musculus

<400> SEQUENCE: 5

```
Val Gly Tyr Asp Trp Phe Ala Tyr
1               5
```

<210> SEQ ID NO 6
<211> LENGTH: 30
<212> TYPE: PRT
<213> ORGANISM: Mus musculus

<400> SEQUENCE: 6

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser
            20                  25                  30
```

<210> SEQ ID NO 7
<211> LENGTH: 14
<212> TYPE: PRT

<213> ORGANISM: Mus musculus

<400> SEQUENCE: 7

```
Trp Ile Arg Gln Pro Ser Gly Lys Gly Leu Glu Trp Leu Ala
1               5                   10
```

<210> SEQ ID NO 8
<211> LENGTH: 32
<212> TYPE: PRT
<213> ORGANISM: Mus musculus

<400> SEQUENCE: 8

```
Arg Leu Thr Ile Ser Lys Asp Thr Ser Asn Asn Gln Val Phe Leu Lys
1               5                   10                  15

Ile Ser Ser Val Asp Thr Ala Asp Thr Val Thr Tyr Tyr Cys Ala Gln
            20                  25                  30
```

<210> SEQ ID NO 9
<211> LENGTH: 11
<212> TYPE: PRT
<213> ORGANISM: Mus musculus

<400> SEQUENCE: 9

```
Trp Gly Gln Gly Thr Leu Val Thr Val Ser Ser
1               5                   10
```

<210> SEQ ID NO 10
<211> LENGTH: 324
<212> TYPE: DNA
<213> ORGANISM: Mus musculus

<400> SEQUENCE: 10

```
gaaattgtgc tcacccagtc tccagcactc atggctgcat ctccagggga gaaggtcacc     60

atcacctgca gtgtcagctc aagtataagt tccagcaact tgcactggta ccagcagaag    120

tcagaaacct cccccaaacc ctggatttat ggcacatcca acctggcttc tggagtccct    180

gttcgcttca gtggcagtgg atctgggacc tcttattctc tcacaatcag cagcatggag    240

gctgaagatg ctgccactta ttactgtcaa cagtgcagta gttacccgct cacgttcggt    300

gctgggacca agctggagct gaaa                                           324
```

<210> SEQ ID NO 11
<211> LENGTH: 108
<212> TYPE: PRT
<213> ORGANISM: Mus musculus

<400> SEQUENCE: 11

```
Glu Ile Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
            20                  25                  30

Asn Leu His Trp Tyr Gln Gln Lys Ser Glu Thr Ser Pro Lys Pro Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Cys Ser Ser Tyr Pro
                85                  90                  95

Leu Thr Phe Gly Ala Gly Thr Lys Leu Glu Leu Lys
```

```
            100                 105


<210> SEQ ID NO 12
<211> LENGTH: 12
<212> TYPE: PRT
<213> ORGANISM: Mus musculus

<400> SEQUENCE: 12

Ser Val Ser Ser Ser Ile Ser Ser Ser Asn Leu His
1               5                   10


<210> SEQ ID NO 13
<211> LENGTH: 7
<212> TYPE: PRT
<213> ORGANISM: Mus musculus

<400> SEQUENCE: 13

Gly Thr Ser Asn Leu Ala Ser
1               5


<210> SEQ ID NO 14
<211> LENGTH: 9
<212> TYPE: PRT
<213> ORGANISM: Mus musculus

<400> SEQUENCE: 14

Gln Gln Cys Ser Ser Tyr Pro Leu Thr
1               5


<210> SEQ ID NO 15
<211> LENGTH: 23
<212> TYPE: PRT
<213> ORGANISM: Mus musculus

<400> SEQUENCE: 15

Glu Ile Val Leu Thr Gln Ser Pro Ala Leu Met Ala Ala Ser Pro Gly
1               5                   10                  15

Glu Lys Val Thr Ile Thr Cys
            20


<210> SEQ ID NO 16
<211> LENGTH: 15
<212> TYPE: PRT
<213> ORGANISM: Mus musculus

<400> SEQUENCE: 16

Trp Tyr Gln Gln Lys Ser Glu Thr Ser Pro Lys Pro Trp Ile Tyr
1               5                   10                  15


<210> SEQ ID NO 17
<211> LENGTH: 32
<212> TYPE: PRT
<213> ORGANISM: Mus musculus

<400> SEQUENCE: 17

Gly Val Pro Val Arg Phe Ser Gly Ser Gly Ser Gly Thr Ser Tyr Ser
1               5                   10                  15

Leu Thr Ile Ser Ser Met Glu Ala Glu Asp Ala Ala Thr Tyr Tyr Cys
            20                  25                  30


<210> SEQ ID NO 18
<211> LENGTH: 10
<212> TYPE: PRT
<213> ORGANISM: Mus musculus
```

<400> SEQUENCE: 18

```
Phe Gly Ala Gly Thr Lys Leu Glu Leu Lys
1               5                   10
```

<210> SEQ ID NO 19
<211> LENGTH: 357
<212> TYPE: DNA
<213> ORGANISM: Mus musculus

<400> SEQUENCE: 19

```
gaggtccagc tgcaacagtc tggacctgag ctggtgaagc ctggggcttc agtgaagata     60

ccctgcaagg cttctggata cacattcact gactacaaca tggactgggt gaagcagagc    120

catggaaaga gccttgagtg gattggagat attaatccta acaatggtgt tactatctac    180

aaccagaagt tcaagggcaa ggccacattg actgtagaca agtcctccag cacagcctac    240

atggagctcc gcagcctgac atctgaggac actgcagtct tttactgtgc tagagaggag    300

ctaactggga atgctatgga ctactggggt caaggaacct cagtcaccgt ctcctca       357
```

<210> SEQ ID NO 20
<211> LENGTH: 119
<212> TYPE: PRT
<213> ORGANISM: Mus musculus

<400> SEQUENCE: 20

```
Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro Asn Asn Gly Val Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Phe Tyr Cys
                85                  90                  95

Ala Arg Glu Glu Leu Thr Gly Asn Ala Met Asp Tyr Trp Gly Gln Gly
            100                 105                 110

Thr Ser Val Thr Val Ser Ser
        115
```

<210> SEQ ID NO 21
<211> LENGTH: 5
<212> TYPE: PRT
<213> ORGANISM: Mus musculus

<400> SEQUENCE: 21

```
Asp Tyr Asn Met Asp
1               5
```

<210> SEQ ID NO 22
<211> LENGTH: 17
<212> TYPE: PRT
<213> ORGANISM: Mus musculus

<400> SEQUENCE: 22

```
Asp Ile Asn Pro Asn Asn Gly Val Thr Ile Tyr Asn Gln Lys Phe Lys
1               5                   10                  15
```

Gly

<210> SEQ ID NO 23
<211> LENGTH: 10
<212> TYPE: PRT
<213> ORGANISM: Mus musculus

<400> SEQUENCE: 23

Glu Glu Leu Thr Gly Asn Ala Met Asp Tyr
1               5                   10

<210> SEQ ID NO 24
<211> LENGTH: 30
<212> TYPE: PRT
<213> ORGANISM: Mus musculus

<400> SEQUENCE: 24

Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr
            20                  25                  30

<210> SEQ ID NO 25
<211> LENGTH: 14
<212> TYPE: PRT
<213> ORGANISM: Mus musculus

<400> SEQUENCE: 25

Trp Val Lys Gln Ser His Gly Lys Ser Leu Glu Trp Ile Gly
1               5                   10

<210> SEQ ID NO 26
<211> LENGTH: 32
<212> TYPE: PRT
<213> ORGANISM: Mus musculus

<400> SEQUENCE: 26

Lys Ala Thr Leu Thr Val Asp Lys Ser Ser Ser Thr Ala Tyr Met Glu
1               5                   10                  15

Leu Arg Ser Leu Thr Ser Glu Asp Thr Ala Val Phe Tyr Cys Ala Arg
            20                  25                  30

<210> SEQ ID NO 27
<211> LENGTH: 11
<212> TYPE: PRT
<213> ORGANISM: Mus musculus

<400> SEQUENCE: 27

Trp Gly Gln Gly Thr Ser Val Thr Val Ser Ser
1               5                   10

<210> SEQ ID NO 28
<211> LENGTH: 321
<212> TYPE: DNA
<213> ORGANISM: Mus musculus

<400> SEQUENCE: 28
gacatccaga tgactcagtc tccagcctcc ctatctgtat ctgtgggaga aactgtcacc     60
atcacatgtc gagcaagtga gaatatttac agtcatttag catggtatca gcagaaacag    120
ggaaaatctc ctcagctcct ggtctatgct gcaacaaact tagcagatgg tgtgccatca    180
aggttcagtg gcagtggatc aggcacacag tattccctca agatcaacag cctgcagtct    240

```
gaagattttg ggagttatta ctgtcaacat tttggggta ctccgtggac gttcggtgga    300

ggcaccaagc tggaaatcaa a                                              321


<210> SEQ ID NO 29
<211> LENGTH: 107
<212> TYPE: PRT
<213> ORGANISM: Mus musculus

<400> SEQUENCE: 29

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser His
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Trp
                85                  90                  95

Thr Phe Gly Gly Gly Thr Lys Leu Glu Ile Lys
            100                 105


<210> SEQ ID NO 30
<211> LENGTH: 11
<212> TYPE: PRT
<213> ORGANISM: Mus musculus

<400> SEQUENCE: 30

Arg Ala Ser Glu Asn Ile Tyr Ser His Leu Ala
1               5                   10


<210> SEQ ID NO 31
<211> LENGTH: 7
<212> TYPE: PRT
<213> ORGANISM: Mus musculus

<400> SEQUENCE: 31

Ala Ala Thr Asn Leu Ala Asp
1               5


<210> SEQ ID NO 32
<211> LENGTH: 9
<212> TYPE: PRT
<213> ORGANISM: Mus musculus

<400> SEQUENCE: 32

Gln His Phe Trp Gly Thr Pro Trp Thr
1               5


<210> SEQ ID NO 33
<211> LENGTH: 23
<212> TYPE: PRT
<213> ORGANISM: Mus musculus

<400> SEQUENCE: 33

Asp Ile Gln Met Thr Gln Ser Pro Ala Ser Leu Ser Val Ser Val Gly
1               5                   10                  15

Glu Thr Val Thr Ile Thr Cys
```

20

<210> SEQ ID NO 34
<211> LENGTH: 15
<212> TYPE: PRT
<213> ORGANISM: Mus musculus

<400> SEQUENCE: 34

Trp Tyr Gln Gln Lys Gln Gly Lys Ser Pro Gln Leu Leu Val Tyr
1 5 10 15

<210> SEQ ID NO 35
<211> LENGTH: 32
<212> TYPE: PRT
<213> ORGANISM: Mus musculus

<400> SEQUENCE: 35

Gly Val Pro Ser Arg Phe Ser Gly Ser Gly Ser Gly Thr Gln Tyr Ser
1 5 10 15

Leu Lys Ile Asn Ser Leu Gln Ser Glu Asp Phe Gly Ser Tyr Tyr Cys
20 25 30

<210> SEQ ID NO 36
<211> LENGTH: 10
<212> TYPE: PRT
<213> ORGANISM: Mus musculus

<400> SEQUENCE: 36

Phe Gly Gly Gly Thr Lys Leu Glu Ile Lys
1 5 10

<210> SEQ ID NO 37
<211> LENGTH: 354
<212> TYPE: DNA
<213> ORGANISM: Mus musculus

<400> SEQUENCE: 37
caggttactc tgaaagagtc tggccctggg atattgcagc cctcccagac cctcagtctg 60
acttgttctt tctctgggtt ttcactgagc acttatggta tgggtgtagg ttggattcgt 120
cagccttcag ggaagggtct ggagtggctg gccaacattt ggtggaatga tgataagtac 180
tataactcag ccctgaagag ccggctcaca atctccaagg atacctccaa caaccaggta 240
ttcctcaaga tctccagtgt ggacactgca gatactgcca catactactg tgctcaagag 300
gtttacgggt ggtttgctta ctggggccaa gggactctgg tcaccgtctc ctca 354

<210> SEQ ID NO 38
<211> LENGTH: 118
<212> TYPE: PRT
<213> ORGANISM: Mus musculus

<400> SEQUENCE: 38

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Ser Thr Tyr
20 25 30

Gly Met Gly Val Gly Trp Ile Arg Gln Pro Ser Gly Lys Gly Leu Glu
35 40 45

Trp Leu Ala Asn Ile Trp Trp Asn Asp Asp Lys Tyr Tyr Asn Ser Ala
50 55 60

Leu Lys Ser Arg Leu Thr Ile Ser Lys Asp Thr Ser Asn Asn Gln Val

```
65                  70                  75                  80

Phe Leu Lys Ile Ser Ser Val Asp Thr Ala Asp Thr Ala Thr Tyr Tyr
                85                  90                  95

Cys Ala Gln Glu Val Tyr Gly Trp Phe Ala Tyr Trp Gly Gln Gly Thr
            100                 105                 110

Leu Val Thr Val Ser Ser
        115


<210> SEQ ID NO 39
<211> LENGTH: 7
<212> TYPE: PRT
<213> ORGANISM: Mus musculus

<400> SEQUENCE: 39

Thr Tyr Gly Met Gly Val Gly
1               5


<210> SEQ ID NO 40
<211> LENGTH: 16
<212> TYPE: PRT
<213> ORGANISM: Mus musculus

<400> SEQUENCE: 40

Asn Ile Trp Trp Asn Asp Asp Lys Tyr Tyr Asn Ser Ala Leu Lys Ser
1               5                   10                  15


<210> SEQ ID NO 41
<211> LENGTH: 8
<212> TYPE: PRT
<213> ORGANISM: Mus musculus

<400> SEQUENCE: 41

Glu Val Tyr Gly Trp Phe Ala Tyr
1               5


<210> SEQ ID NO 42
<211> LENGTH: 30
<212> TYPE: PRT
<213> ORGANISM: Mus musculus

<400> SEQUENCE: 42

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser
            20                  25                  30


<210> SEQ ID NO 43
<211> LENGTH: 14
<212> TYPE: PRT
<213> ORGANISM: Mus musculus

<400> SEQUENCE: 43

Trp Ile Arg Gln Pro Ser Gly Lys Gly Leu Glu Trp Leu Ala
1               5                   10


<210> SEQ ID NO 44
<211> LENGTH: 32
<212> TYPE: PRT
<213> ORGANISM: Mus musculus

<400> SEQUENCE: 44

Arg Leu Thr Ile Ser Lys Asp Thr Ser Asn Asn Gln Val Phe Leu Lys
1               5                   10                  15
```

```
Ile Ser Ser Val Asp Thr Ala Asp Thr Ala Thr Tyr Tyr Cys Ala Gln
            20                  25                  30


<210> SEQ ID NO 45
<211> LENGTH: 11
<212> TYPE: PRT
<213> ORGANISM: Mus musculus

<400> SEQUENCE: 45

Trp Gly Gln Gly Thr Leu Val Thr Val Ser Ser
1               5                   10


<210> SEQ ID NO 46
<211> LENGTH: 321
<212> TYPE: DNA
<213> ORGANISM: Mus musculus

<400> SEQUENCE: 46

gacattgtga tgacccagtc tcaaaaattc atgtccacat cagtaggaga cagggtcagc      60

gtcacctgca aggccagtca gaatgtgggt actaatgtag cctggtatca acagaaacca     120

gggcaatctc ctaaagcact gatttactcg gcatcctacc ggtacagtgg agtccctgat     180

cgcttcacag gcagtggatc tgggacagat ttcactctca ccatcagcaa tgtgcagtct     240

gaagacttgg cagagtattt ctgtcagcaa tataacagct atcctctcac gttcggaggg     300

gggaccaagc tggaaataaa a                                               321


<210> SEQ ID NO 47
<211> LENGTH: 107
<212> TYPE: PRT
<213> ORGANISM: Mus musculus

<400> SEQUENCE: 47

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Gly Gly Thr Lys Leu Glu Ile Lys
            100                 105


<210> SEQ ID NO 48
<211> LENGTH: 11
<212> TYPE: PRT
<213> ORGANISM: Mus musculus

<400> SEQUENCE: 48

Lys Ala Ser Gln Asn Val Gly Thr Asn Val Ala
1               5                   10


<210> SEQ ID NO 49
<211> LENGTH: 7
<212> TYPE: PRT
```

<213> ORGANISM: Mus musculus

<400> SEQUENCE: 49

Ser Ala Ser Tyr Arg Tyr Ser
1 5

<210> SEQ ID NO 50
<211> LENGTH: 9
<212> TYPE: PRT
<213> ORGANISM: Mus musculus

<400> SEQUENCE: 50

Gln Gln Tyr Asn Ser Tyr Pro Leu Thr
1 5

<210> SEQ ID NO 51
<211> LENGTH: 23
<212> TYPE: PRT
<213> ORGANISM: Mus musculus

<400> SEQUENCE: 51

Asp Ile Val Met Thr Gln Ser Gln Lys Phe Met Ser Thr Ser Val Gly
1 5 10 15

Asp Arg Val Ser Val Thr Cys
20

<210> SEQ ID NO 52
<211> LENGTH: 15
<212> TYPE: PRT
<213> ORGANISM: Mus musculus

<400> SEQUENCE: 52

Trp Tyr Gln Gln Lys Pro Gly Gln Ser Pro Lys Ala Leu Ile Tyr
1 5 10 15

<210> SEQ ID NO 53
<211> LENGTH: 32
<212> TYPE: PRT
<213> ORGANISM: Mus musculus

<400> SEQUENCE: 53

Gly Val Pro Asp Arg Phe Thr Gly Ser Gly Ser Gly Thr Asp Phe Thr
1 5 10 15

Leu Thr Ile Ser Asn Val Gln Ser Glu Asp Leu Ala Glu Tyr Phe Cys
20 25 30

<210> SEQ ID NO 54
<211> LENGTH: 10
<212> TYPE: PRT
<213> ORGANISM: Mus musculus

<400> SEQUENCE: 54

Phe Gly Gly Gly Thr Lys Leu Glu Ile Lys
1 5 10

<210> SEQ ID NO 55
<211> LENGTH: 360
<212> TYPE: DNA
<213> ORGANISM: Mus musculus

<400> SEQUENCE: 55
gaggtccagc tgcaacagtc tggacctgag ctggtgaagc ctggggcttc agtgaagata 60
ccctgcaagg cttctggata cacattcact gactacaaca tggactgggt gaagcagagc 120

```
catggaaaga gccttgagtg gattggagat attaatccta acaatggtgg tactttctac    180

aaccagaagt tcaaggacaa ggccacattg actgtagaca agtcctccag cacagcctac    240

atggagctcc gcagcctgac atctgaggac actgcagtct attactgtgc aagagaggag    300

aaactctact ttggccttat ggactactgg ggtcaaggaa cctcagtcac cgtctcctca    360


<210> SEQ ID NO 56
<211> LENGTH: 120
<212> TYPE: PRT
<213> ORGANISM: Mus musculus

<400> SEQUENCE: 56

Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro Asn Asn Gly Gly Thr Phe Tyr Asn Gln Lys Phe
    50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Glu Glu Lys Leu Tyr Phe Gly Leu Met Asp Tyr Trp Gly Gln
            100                 105                 110

Gly Thr Ser Val Thr Val Ser Ser
        115                 120


<210> SEQ ID NO 57
<211> LENGTH: 5
<212> TYPE: PRT
<213> ORGANISM: Mus musculus

<400> SEQUENCE: 57

Asp Tyr Asn Met Asp
1               5


<210> SEQ ID NO 58
<211> LENGTH: 17
<212> TYPE: PRT
<213> ORGANISM: Mus musculus

<400> SEQUENCE: 58

Asp Ile Asn Pro Asn Asn Gly Gly Thr Phe Tyr Asn Gln Lys Phe Lys
1               5                   10                  15

Asp


<210> SEQ ID NO 59
<211> LENGTH: 11
<212> TYPE: PRT
<213> ORGANISM: Mus musculus

<400> SEQUENCE: 59

Glu Glu Lys Leu Tyr Phe Gly Leu Met Asp Tyr
1               5                   10


<210> SEQ ID NO 60
<211> LENGTH: 30
```

```
<212> TYPE: PRT
<213> ORGANISM: Mus musculus

<400> SEQUENCE: 60

Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr
            20                  25                  30


<210> SEQ ID NO 61
<211> LENGTH: 14
<212> TYPE: PRT
<213> ORGANISM: Mus musculus

<400> SEQUENCE: 61

Trp Val Lys Gln Ser His Gly Lys Ser Leu Glu Trp Ile Gly
1               5                   10


<210> SEQ ID NO 62
<211> LENGTH: 32
<212> TYPE: PRT
<213> ORGANISM: Mus musculus

<400> SEQUENCE: 62

Lys Ala Thr Leu Thr Val Asp Lys Ser Ser Ser Thr Ala Tyr Met Glu
1               5                   10                  15

Leu Arg Ser Leu Thr Ser Glu Asp Thr Ala Val Tyr Tyr Cys Ala Arg
            20                  25                  30


<210> SEQ ID NO 63
<211> LENGTH: 11
<212> TYPE: PRT
<213> ORGANISM: Mus musculus

<400> SEQUENCE: 63

Trp Gly Gln Gly Thr Ser Val Thr Val Ser Ser
1               5                   10


<210> SEQ ID NO 64
<211> LENGTH: 321
<212> TYPE: DNA
<213> ORGANISM: Mus musculus

<400> SEQUENCE: 64

gacatccaga tgactcagtc tccagcctcc ctatctgcat ctgtgggaga aactgtcacc     60

atcacatgtc gagcaagtga gaatatttac agttatttag catggtatca gcagaaacag    120

ggaaaatctc ctcagctcct ggtctataat gcaaaaacct tagcagaagg tgtgccatca    180

aggttcagtg gcagtggatc aggcatacag ttttctctga agatcaacat cctgcagcct    240

gaagattttg ggaattatta ctgtcaacat cagtatggtt ctcctccgac gttcggtgga    300

ggcaccaagc tggaaatcaa a                                              321


<210> SEQ ID NO 65
<211> LENGTH: 107
<212> TYPE: PRT
<213> ORGANISM: Mus musculus

<400> SEQUENCE: 65

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
```

```
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Ile Gln Phe Ser Leu Lys Ile Asn Ile Leu Gln Pro
65                  70                  75                  80

Glu Asp Phe Gly Asn Tyr Tyr Cys Gln His Gln Tyr Gly Ser Pro Pro
                85                  90                  95

Thr Phe Gly Gly Gly Thr Lys Leu Glu Ile Lys
            100                 105


<210> SEQ ID NO 66
<211> LENGTH: 11
<212> TYPE: PRT
<213> ORGANISM: Mus musculus

<400> SEQUENCE: 66

Arg Ala Ser Glu Asn Ile Tyr Ser Tyr Leu Ala
1               5                   10


<210> SEQ ID NO 67
<211> LENGTH: 7
<212> TYPE: PRT
<213> ORGANISM: Mus musculus

<400> SEQUENCE: 67

Asn Ala Lys Thr Leu Ala Glu
1               5


<210> SEQ ID NO 68
<211> LENGTH: 9
<212> TYPE: PRT
<213> ORGANISM: Mus musculus

<400> SEQUENCE: 68

Gln His Gln Tyr Gly Ser Pro Pro Thr
1               5


<210> SEQ ID NO 69
<211> LENGTH: 23
<212> TYPE: PRT
<213> ORGANISM: Mus musculus

<400> SEQUENCE: 69

Asp Ile Gln Met Thr Gln Ser Pro Ala Ser Leu Ser Ala Ser Val Gly
1               5                   10                  15

Glu Thr Val Thr Ile Thr Cys
            20


<210> SEQ ID NO 70
<211> LENGTH: 15
<212> TYPE: PRT
<213> ORGANISM: Mus musculus

<400> SEQUENCE: 70

Trp Tyr Gln Gln Lys Gln Gly Lys Ser Pro Gln Leu Leu Val Tyr
1               5                   10                  15


<210> SEQ ID NO 71
<211> LENGTH: 32
<212> TYPE: PRT
```

<213> ORGANISM: Mus musculus

<400> SEQUENCE: 71

```
Gly Val Pro Ser Arg Phe Ser Gly Ser Gly Ser Gly Ile Gln Phe Ser
1               5                   10                  15

Leu Lys Ile Asn Ile Leu Gln Pro Glu Asp Phe Gly Asn Tyr Tyr Cys
            20                  25                  30
```

<210> SEQ ID NO 72
<211> LENGTH: 10
<212> TYPE: PRT
<213> ORGANISM: Mus musculus

<400> SEQUENCE: 72

```
Phe Gly Gly Gly Thr Lys Leu Glu Ile Lys
1               5                   10
```

<210> SEQ ID NO 73
<211> LENGTH: 354
<212> TYPE: DNA
<213> ORGANISM: Mus musculus

<400> SEQUENCE: 73

```
gacgtgaaac tggtggagtc tggggaaggc ttagtgaagc ctggagggtc cctgaaactc     60

tcctgtgcag cctctggatt cactttcagt agctttgcca tgtcttgggt tcgccagact    120

ccagagaaga ggctggagtg ggtcgcatac attactagtg gtggtgatta catcttctat    180

gcagacactg tgaagggccg attcaccatc tccagagaca atgccaggaa caccctgtac    240

ctgcaaatga gcagtctgaa gtctgaggac acagccatgt attactgtac aagagatgat    300

ggttacctct ggtttgctta ctggggccaa gggactctgg tcactgtctc tgca          354
```

<210> SEQ ID NO 74
<211> LENGTH: 118
<212> TYPE: PRT
<213> ORGANISM: Mus musculus

<400> SEQUENCE: 74

```
Asp Val Lys Leu Val Glu Ser Gly Glu Gly Leu Val Lys Pro Gly Gly
1               5                   10                  15

Ser Leu Lys Leu Ser Cys Ala Ala Ser Gly Phe Thr Phe Ser Ser Phe
            20                  25                  30

Ala Met Ser Trp Val Arg Gln Thr Pro Glu Lys Arg Leu Glu Trp Val
        35                  40                  45

Ala Tyr Ile Thr Ser Gly Gly Asp Tyr Ile Phe Tyr Ala Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Asp Asp Gly Tyr Leu Trp Phe Ala Tyr Trp Gly Gln Gly Thr
            100                 105                 110

Leu Val Thr Val Ser Ala
        115
```

<210> SEQ ID NO 75
<211> LENGTH: 5
<212> TYPE: PRT
<213> ORGANISM: Mus musculus

<400> SEQUENCE: 75

Ser Phe Ala Met Ser
1 5

<210> SEQ ID NO 76
<211> LENGTH: 17
<212> TYPE: PRT
<213> ORGANISM: Mus musculus

<400> SEQUENCE: 76

Tyr Ile Thr Ser Gly Gly Asp Tyr Ile Phe Tyr Ala Asp Thr Val Lys
1 5 10 15

Gly

<210> SEQ ID NO 77
<211> LENGTH: 9
<212> TYPE: PRT
<213> ORGANISM: Mus musculus

<400> SEQUENCE: 77

Asp Asp Gly Tyr Leu Trp Phe Ala Tyr
1 5

<210> SEQ ID NO 78
<211> LENGTH: 30
<212> TYPE: PRT
<213> ORGANISM: Mus musculus

<400> SEQUENCE: 78

Asp Val Lys Leu Val Glu Ser Gly Glu Gly Leu Val Lys Pro Gly Gly
1 5 10 15

Ser Leu Lys Leu Ser Cys Ala Ala Ser Gly Phe Thr Phe Ser
20 25 30

<210> SEQ ID NO 79
<211> LENGTH: 14
<212> TYPE: PRT
<213> ORGANISM: Mus musculus

<400> SEQUENCE: 79

Trp Val Arg Gln Thr Pro Glu Lys Arg Leu Glu Trp Val Ala
1 5 10

<210> SEQ ID NO 80
<211> LENGTH: 32
<212> TYPE: PRT
<213> ORGANISM: Mus musculus

<400> SEQUENCE: 80

Arg Phe Thr Ile Ser Arg Asp Asn Ala Arg Asn Thr Leu Tyr Leu Gln
1 5 10 15

Met Ser Ser Leu Lys Ser Glu Asp Thr Ala Met Tyr Tyr Cys Thr Arg
20 25 30

<210> SEQ ID NO 81
<211> LENGTH: 11
<212> TYPE: PRT
<213> ORGANISM: Mus musculus

<400> SEQUENCE: 81

Trp Gly Gln Gly Thr Leu Val Thr Val Ser Ala
1 5 10

<210> SEQ ID NO 82
<211> LENGTH: 321
<212> TYPE: DNA
<213> ORGANISM: Mus musculus

<400> SEQUENCE: 82
agtattgtga tgacccagac tcccaaattc ctgcctgtat cagcaggaga cagggttacc 60
atgacctgca aggccagtca gaatgtgggt aataatgtag cctggtacca acagaagcca 120
ggacagtctc ctaaactgct gatatactat gcatccaatc gctacactgg agtccctgat 180
cgcttcactg gcagtggatc tgggacagat ttcactttca ccatcagcag tgtgcaggtt 240
gaagacctgg cagtttattt ctgtcagcag cattatagct ctccgctcac gttcggtgct 300
gggaccaagc tggagctgaa a 321

<210> SEQ ID NO 83
<211> LENGTH: 107
<212> TYPE: PRT
<213> ORGANISM: Mus musculus

<400> SEQUENCE: 83

Ser Ile Val Met Thr Gln Thr Pro Lys Phe Leu Pro Val Ser Ala Gly
1 5 10 15

Asp Arg Val Thr Met Thr Cys Lys Ala Ser Gln Asn Val Gly Asn Asn
20 25 30

Val Ala Trp Tyr Gln Gln Lys Pro Gly Gln Ser Pro Lys Leu Leu Ile
35 40 45

Tyr Tyr Ala Ser Asn Arg Tyr Thr Gly Val Pro Asp Arg Phe Thr Gly
50 55 60

Ser Gly Ser Gly Thr Asp Phe Thr Phe Thr Ile Ser Ser Val Gln Val
65 70 75 80

Glu Asp Leu Ala Val Tyr Phe Cys Gln Gln His Tyr Ser Ser Pro Leu
85 90 95

Thr Phe Gly Ala Gly Thr Lys Leu Glu Leu Lys
100 105

<210> SEQ ID NO 84
<211> LENGTH: 11
<212> TYPE: PRT
<213> ORGANISM: Mus musculus

<400> SEQUENCE: 84

Lys Ala Ser Gln Asn Val Gly Asn Asn Val Ala
1 5 10

<210> SEQ ID NO 85
<211> LENGTH: 7
<212> TYPE: PRT
<213> ORGANISM: Mus musculus

<400> SEQUENCE: 85

Tyr Ala Ser Asn Arg Tyr Thr
1 5

<210> SEQ ID NO 86
<211> LENGTH: 9
<212> TYPE: PRT
<213> ORGANISM: Mus musculus

<400> SEQUENCE: 86

```
Gln Gln His Tyr Ser Ser Pro Leu Thr
1               5


<210> SEQ ID NO 87
<211> LENGTH: 23
<212> TYPE: PRT
<213> ORGANISM: Mus musculus

<400> SEQUENCE: 87

Ser Ile Val Met Thr Gln Thr Pro Lys Phe Leu Pro Val Ser Ala Gly
1               5                   10                  15

Asp Arg Val Thr Met Thr Cys
            20


<210> SEQ ID NO 88
<211> LENGTH: 15
<212> TYPE: PRT
<213> ORGANISM: Mus musculus

<400> SEQUENCE: 88

Trp Tyr Gln Gln Lys Pro Gly Gln Ser Pro Lys Leu Leu Ile Tyr
1               5                   10                  15


<210> SEQ ID NO 89
<211> LENGTH: 32
<212> TYPE: PRT
<213> ORGANISM: Mus musculus

<400> SEQUENCE: 89

Gly Val Pro Asp Arg Phe Thr Gly Ser Gly Ser Gly Thr Asp Phe Thr
1               5                   10                  15

Phe Thr Ile Ser Ser Val Gln Val Glu Asp Leu Ala Val Tyr Phe Cys
            20                  25                  30


<210> SEQ ID NO 90
<211> LENGTH: 10
<212> TYPE: PRT
<213> ORGANISM: Mus musculus

<400> SEQUENCE: 90

Phe Gly Ala Gly Thr Lys Leu Glu Leu Lys
1               5                   10


<210> SEQ ID NO 91
<211> LENGTH: 357
<212> TYPE: DNA
<213> ORGANISM: Mus musculus

<400> SEQUENCE: 91

gacgtgaagc tggtggagtc tggggaaggc ttagtgaagc ctggagggtc cctgaaactc      60

tcctgtgcag cctctggatt cactttcagt agctatgcca tgtcttgggt tcgccagact     120

ccagagaaga ggctggagtg ggtcgcatac attagtagtg gtggtgataa catctactat     180

gcagacactg tgaagggccg attcaccatc tccagagaca atgccaggaa caccctgtac     240

ctacaaatga gcagtctgaa gtctgaggac acagccatgt attactgtac aagagccttg     300

gttgaaaacg cgtactttga ctactggggc caaggcacca ctctcaccgt ctcctca        357


<210> SEQ ID NO 92
<211> LENGTH: 119
<212> TYPE: PRT
<213> ORGANISM: Mus musculus
```

<400> SEQUENCE: 92

Asp Val Lys Leu Val Glu Ser Gly Glu Gly Leu Val Lys Pro Gly Gly
1 5 10 15

Ser Leu Lys Leu Ser Cys Ala Ala Ser Gly Phe Thr Phe Ser Ser Tyr
20 25 30

Ala Met Ser Trp Val Arg Gln Thr Pro Glu Lys Arg Leu Glu Trp Val
35 40 45

Ala Tyr Ile Ser Ser Gly Gly Asp Asn Ile Tyr Tyr Ala Asp Thr Val
50 55 60

Lys Gly Arg Phe Thr Ile Ser Arg Asp Asn Ala Arg Asn Thr Leu Tyr
65 70 75 80

Leu Gln Met Ser Ser Leu Lys Ser Glu Asp Thr Ala Met Tyr Tyr Cys
85 90 95

Thr Arg Ala Leu Val Glu Asn Ala Tyr Phe Asp Tyr Trp Gly Gln Gly
100 105 110

Thr Thr Leu Thr Val Ser Ser
115

<210> SEQ ID NO 93
<211> LENGTH: 5
<212> TYPE: PRT
<213> ORGANISM: Mus musculus

<400> SEQUENCE: 93

Ser Tyr Ala Met Ser
1 5

<210> SEQ ID NO 94
<211> LENGTH: 17
<212> TYPE: PRT
<213> ORGANISM: Mus musculus

<400> SEQUENCE: 94

Tyr Ile Ser Ser Gly Gly Asp Asn Ile Tyr Tyr Ala Asp Thr Val Lys
1 5 10 15

Gly

<210> SEQ ID NO 95
<211> LENGTH: 10
<212> TYPE: PRT
<213> ORGANISM: Mus musculus

<400> SEQUENCE: 95

Ala Leu Val Glu Asn Ala Tyr Phe Asp Tyr
1 5 10

<210> SEQ ID NO 96
<211> LENGTH: 30
<212> TYPE: PRT
<213> ORGANISM: Mus musculus

<400> SEQUENCE: 96

Asp Val Lys Leu Val Glu Ser Gly Glu Gly Leu Val Lys Pro Gly Gly
1 5 10 15

Ser Leu Lys Leu Ser Cys Ala Ala Ser Gly Phe Thr Phe Ser
20 25 30

<210> SEQ ID NO 97
<211> LENGTH: 14
<212> TYPE: PRT

<213> ORGANISM: Mus musculus

<400> SEQUENCE: 97

```
Trp Val Arg Gln Thr Pro Glu Lys Arg Leu Glu Trp Val Ala
1               5                   10
```

<210> SEQ ID NO 98
<211> LENGTH: 32
<212> TYPE: PRT
<213> ORGANISM: Mus musculus

<400> SEQUENCE: 98

```
Arg Phe Thr Ile Ser Arg Asp Asn Ala Arg Asn Thr Leu Tyr Leu Gln
1               5                   10                  15

Met Ser Ser Leu Lys Ser Glu Asp Thr Ala Met Tyr Tyr Cys Thr Arg
            20                  25                  30
```

<210> SEQ ID NO 99
<211> LENGTH: 11
<212> TYPE: PRT
<213> ORGANISM: Mus musculus

<400> SEQUENCE: 99

```
Trp Gly Gln Gly Thr Thr Leu Thr Val Ser Ser
1               5                   10
```

<210> SEQ ID NO 100
<211> LENGTH: 333
<212> TYPE: DNA
<213> ORGANISM: Mus musculus

<400> SEQUENCE: 100

```
gacagtgttc tgacacagtc tcctgcttcc ttacttgtat ctctgggaca gagggccacc     60

atctcctgca gggccagcaa aagtgtcagt acatctacct atagttacat gcactggtac    120

caacagaaac caggacagcc acccaaactc ctcatcaagt atgcatccta cctagaatct    180

ggggttcctg ccaggttcag tggcagtggg tctgggacag acttcaccct caacatccat    240

cctgtggagg aggaggatgc tgcaacatat tactgtcagc acagtaggga gtttccgtgg    300

acgttcggtg gaggcaccaa gctggaaatc aaa                                 333
```

<210> SEQ ID NO 101
<211> LENGTH: 111
<212> TYPE: PRT
<213> ORGANISM: Mus musculus

<400> SEQUENCE: 101

```
Asp Ser Val Leu Thr Gln Ser Pro Ala Ser Leu Leu Val Ser Leu Gly
1               5                   10                  15

Gln Arg Ala Thr Ile Ser Cys Arg Ala Ser Lys Ser Val Ser Thr Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Phe Pro Trp Thr Phe Gly Gly Gly Thr Lys Leu Glu Ile Lys
```

```
            100                 105                 110


<210> SEQ ID NO 102
<211> LENGTH: 15
<212> TYPE: PRT
<213> ORGANISM: Mus musculus

<400> SEQUENCE: 102

Arg Ala Ser Lys Ser Val Ser Thr Ser Thr Tyr Ser Tyr Met His
1               5                   10                  15


<210> SEQ ID NO 103
<211> LENGTH: 7
<212> TYPE: PRT
<213> ORGANISM: Mus musculus

<400> SEQUENCE: 103

Tyr Ala Ser Tyr Leu Glu Ser
1               5


<210> SEQ ID NO 104
<211> LENGTH: 9
<212> TYPE: PRT
<213> ORGANISM: Mus musculus

<400> SEQUENCE: 104

Gln His Ser Arg Glu Phe Pro Trp Thr
1               5


<210> SEQ ID NO 105
<211> LENGTH: 23
<212> TYPE: PRT
<213> ORGANISM: Mus musculus

<400> SEQUENCE: 105

Asp Ser Val Leu Thr Gln Ser Pro Ala Ser Leu Leu Val Ser Leu Gly
1               5                   10                  15

Gln Arg Ala Thr Ile Ser Cys
            20


<210> SEQ ID NO 106
<211> LENGTH: 15
<212> TYPE: PRT
<213> ORGANISM: Mus musculus

<400> SEQUENCE: 106

Trp Tyr Gln Gln Lys Pro Gly Gln Pro Pro Lys Leu Leu Ile Lys
1               5                   10                  15


<210> SEQ ID NO 107
<211> LENGTH: 32
<212> TYPE: PRT
<213> ORGANISM: Mus musculus

<400> SEQUENCE: 107

Gly Val Pro Ala Arg Phe Ser Gly Ser Gly Ser Gly Thr Asp Phe Thr
1               5                   10                  15

Leu Asn Ile His Pro Val Glu Glu Glu Asp Ala Ala Thr Tyr Tyr Cys
            20                  25                  30


<210> SEQ ID NO 108
<211> LENGTH: 10
<212> TYPE: PRT
<213> ORGANISM: Mus musculus
```

<400> SEQUENCE: 108

Phe Gly Gly Gly Thr Lys Leu Glu Ile Lys
1 5 10

<210> SEQ ID NO 109
<211> LENGTH: 357
<212> TYPE: DNA
<213> ORGANISM: Mus musculus

<400> SEQUENCE: 109
gacgtgaagc tggtggagtc tggggaaggc ttagtgaagc ctggagggtc cctgaaactc 60
tcctgtgcag cctctggatt cactttcagt agctatgcca tgtcttgggt tcgccagact 120
ccagagaaga ggctggagtg ggtcgcatac attagtagtg gtggtgatta catctactat 180
gcagacactg tgaagggccg attcaccatc tccagagaca atgccaggaa caccctgtac 240
ctgcaaatga gcagtctgaa gtctgaggac acagccatgt attactgtac aagagccttg 300
gttgataacg cgtactttga ctactggggc caaggcacca ctctcaccgt ctcctca 357

<210> SEQ ID NO 110
<211> LENGTH: 119
<212> TYPE: PRT
<213> ORGANISM: Mus musculus

<400> SEQUENCE: 110

Asp Val Lys Leu Val Glu Ser Gly Glu Gly Leu Val Lys Pro Gly Gly
1 5 10 15

Ser Leu Lys Leu Ser Cys Ala Ala Ser Gly Phe Thr Phe Ser Ser Tyr
20 25 30

Ala Met Ser Trp Val Arg Gln Thr Pro Glu Lys Arg Leu Glu Trp Val
35 40 45

Ala Tyr Ile Ser Ser Gly Gly Asp Tyr Ile Tyr Tyr Ala Asp Thr Val
50 55 60

Lys Gly Arg Phe Thr Ile Ser Arg Asp Asn Ala Arg Asn Thr Leu Tyr
65 70 75 80

Leu Gln Met Ser Ser Leu Lys Ser Glu Asp Thr Ala Met Tyr Tyr Cys
85 90 95

Thr Arg Ala Leu Val Asp Asn Ala Tyr Phe Asp Tyr Trp Gly Gln Gly
100 105 110

Thr Thr Leu Thr Val Ser Ser
115

<210> SEQ ID NO 111
<211> LENGTH: 5
<212> TYPE: PRT
<213> ORGANISM: Mus musculus

<400> SEQUENCE: 111

Ser Tyr Ala Met Ser
1 5

<210> SEQ ID NO 112
<211> LENGTH: 17
<212> TYPE: PRT
<213> ORGANISM: Mus musculus

<400> SEQUENCE: 112

Tyr Ile Ser Ser Gly Gly Asp Tyr Ile Tyr Tyr Ala Asp Thr Val Lys
1 5 10 15

Gly

<210> SEQ ID NO 113
<211> LENGTH: 10
<212> TYPE: PRT
<213> ORGANISM: Mus musculus

<400> SEQUENCE: 113

Ala Leu Val Asp Asn Ala Tyr Phe Asp Tyr
1 5 10

<210> SEQ ID NO 114
<211> LENGTH: 30
<212> TYPE: PRT
<213> ORGANISM: Mus musculus

<400> SEQUENCE: 114

Asp Val Lys Leu Val Glu Ser Gly Glu Gly Leu Val Lys Pro Gly Gly
1 5 10 15

Ser Leu Lys Leu Ser Cys Ala Ala Ser Gly Phe Thr Phe Ser
20 25 30

<210> SEQ ID NO 115
<211> LENGTH: 14
<212> TYPE: PRT
<213> ORGANISM: Mus musculus

<400> SEQUENCE: 115

Trp Val Arg Gln Thr Pro Glu Lys Arg Leu Glu Trp Val Ala
1 5 10

<210> SEQ ID NO 116
<211> LENGTH: 32
<212> TYPE: PRT
<213> ORGANISM: Mus musculus

<400> SEQUENCE: 116

Arg Phe Thr Ile Ser Arg Asp Asn Ala Arg Asn Thr Leu Tyr Leu Gln
1 5 10 15

Met Ser Ser Leu Lys Ser Glu Asp Thr Ala Met Tyr Tyr Cys Thr Arg
20 25 30

<210> SEQ ID NO 117
<211> LENGTH: 11
<212> TYPE: PRT
<213> ORGANISM: Mus musculus

<400> SEQUENCE: 117

Trp Gly Gln Gly Thr Thr Leu Thr Val Ser Ser
1 5 10

<210> SEQ ID NO 118
<211> LENGTH: 333
<212> TYPE: DNA
<213> ORGANISM: Mus musculus

<400> SEQUENCE: 118
gacattgtgc tgacacagtc tcctgcttcc ttagctgtat ctctggggca gagggccacc 60
atctcctgca gggccagcaa aagtgtcagt acatctagct atagttacat gcactggtac 120
caacagaaac caggacagcc acccaaactc ctcatcaagt atgcatccta cctagaattt 180
ggggttcctg ccaggttcag tggcagtggg tctgggacag acttcaccct caacatccat 240
cctgtggagg aggaggatgc tgcaacatat tactgtcagc acagtaggga gtttccgtgg 300
acgttcggtg gaggcaccaa gctggaaatc aaa 333

<210> SEQ ID NO 119
<211> LENGTH: 111
<212> TYPE: PRT
<213> ORGANISM: Mus musculus

<400> SEQUENCE: 119

Asp Ile Val Leu Thr Gln Ser Pro Ala Ser Leu Ala Val Ser Leu Gly
1 5 10 15

Gln Arg Ala Thr Ile Ser Cys Arg Ala Ser Lys Ser Val Ser Thr Ser
20 25 30

Ser Tyr Ser Tyr Met His Trp Tyr Gln Gln Lys Pro Gly Gln Pro Pro
35 40 45

Lys Leu Leu Ile Lys Tyr Ala Ser Tyr Leu Glu Phe Gly Val Pro Ala
50 55 60

Arg Phe Ser Gly Ser Gly Ser Gly Thr Asp Phe Thr Leu Asn Ile His
65 70 75 80

Pro Val Glu Glu Glu Asp Ala Ala Thr Tyr Tyr Cys Gln His Ser Arg
85 90 95

Glu Phe Pro Trp Thr Phe Gly Gly Gly Thr Lys Leu Glu Ile Lys
100 105 110

<210> SEQ ID NO 120
<211> LENGTH: 15
<212> TYPE: PRT
<213> ORGANISM: Mus musculus

<400> SEQUENCE: 120

Arg Ala Ser Lys Ser Val Ser Thr Ser Ser Tyr Ser Tyr Met His
1 5 10 15

<210> SEQ ID NO 121
<211> LENGTH: 7
<212> TYPE: PRT
<213> ORGANISM: Mus musculus

<400> SEQUENCE: 121

Tyr Ala Ser Tyr Leu Glu Phe
1 5

<210> SEQ ID NO 122
<211> LENGTH: 9
<212> TYPE: PRT
<213> ORGANISM: Mus musculus

<400> SEQUENCE: 122

Gln His Ser Arg Glu Phe Pro Trp Thr
1 5

<210> SEQ ID NO 123
<211> LENGTH: 23
<212> TYPE: PRT
<213> ORGANISM: Mus musculus

<400> SEQUENCE: 123

Asp Ile Val Leu Thr Gln Ser Pro Ala Ser Leu Ala Val Ser Leu Gly
1 5 10 15

Gln Arg Ala Thr Ile Ser Cys

```
            20


<210> SEQ ID NO 124
<211> LENGTH: 15
<212> TYPE: PRT
<213> ORGANISM: Mus musculus

<400> SEQUENCE: 124

Trp Tyr Gln Gln Lys Pro Gly Gln Pro Pro Lys Leu Leu Ile Lys
1               5                   10                  15


<210> SEQ ID NO 125
<211> LENGTH: 32
<212> TYPE: PRT
<213> ORGANISM: Mus musculus

<400> SEQUENCE: 125

Gly Val Pro Ala Arg Phe Ser Gly Ser Gly Ser Gly Thr Asp Phe Thr
1               5                   10                  15

Leu Asn Ile His Pro Val Glu Glu Glu Asp Ala Ala Thr Tyr Tyr Cys
            20                  25                  30


<210> SEQ ID NO 126
<211> LENGTH: 10
<212> TYPE: PRT
<213> ORGANISM: Mus musculus

<400> SEQUENCE: 126

Phe Gly Gly Gly Thr Lys Leu Glu Ile Lys
1               5                   10


<210> SEQ ID NO 127
<211> LENGTH: 357
<212> TYPE: DNA
<213> ORGANISM: Mus musculus

<400> SEQUENCE: 127

caggttactc tgaaagagtc tggccctggg atattgcagt cctcccagac cctcagtctg      60

acttgttctt tctctgggtt ttcactgatc acttctggtt tgggtgtgag ctggattcgt     120

cagccttcag gaaagggtct ggagtggctg gcacacattt actgggatga tgacaagcgc     180

tataatccat ccctgaagag ccggctcaca atctccaagg atacctccag aaaccaggta     240

ttcctcaaga tcaccagtgt ggacactgca gatactgcca catactactg tgctcggggg     300

gggtatgatg gttactacga ctactggggc caaggcacca ctctcaccgt ctcctca        357


<210> SEQ ID NO 128
<211> LENGTH: 119
<212> TYPE: PRT
<213> ORGANISM: Mus musculus

<400> SEQUENCE: 128

Gln Val Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ile Thr Ser
            20                  25                  30

Gly Leu Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Asn Gln Val
```

```
65                  70                  75                  80

Phe Leu Lys Ile Thr Ser Val Asp Thr Ala Asp Thr Ala Thr Tyr Tyr
                85                  90                  95

Cys Ala Arg Gly Gly Tyr Asp Gly Tyr Tyr Asp Tyr Trp Gly Gln Gly
            100                 105                 110

Thr Thr Leu Thr Val Ser Ser
        115


<210> SEQ ID NO 129
<211> LENGTH: 7
<212> TYPE: PRT
<213> ORGANISM: Mus musculus

<400> SEQUENCE: 129

Thr Ser Gly Leu Gly Val Ser
1               5


<210> SEQ ID NO 130
<211> LENGTH: 16
<212> TYPE: PRT
<213> ORGANISM: Mus musculus

<400> SEQUENCE: 130

His Ile Tyr Trp Asp Asp Asp Lys Arg Tyr Asn Pro Ser Leu Lys Ser
1               5                   10                  15


<210> SEQ ID NO 131
<211> LENGTH: 9
<212> TYPE: PRT
<213> ORGANISM: Mus musculus

<400> SEQUENCE: 131

Gly Gly Tyr Asp Gly Tyr Tyr Asp Tyr
1               5


<210> SEQ ID NO 132
<211> LENGTH: 30
<212> TYPE: PRT
<213> ORGANISM: Mus musculus

<400> SEQUENCE: 132

Gln Val Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ile
            20                  25                  30


<210> SEQ ID NO 133
<211> LENGTH: 14
<212> TYPE: PRT
<213> ORGANISM: Mus musculus

<400> SEQUENCE: 133

Trp Ile Arg Gln Pro Ser Gly Lys Gly Leu Glu Trp Leu Ala
1               5                   10


<210> SEQ ID NO 134
<211> LENGTH: 32
<212> TYPE: PRT
<213> ORGANISM: Mus musculus

<400> SEQUENCE: 134

Arg Leu Thr Ile Ser Lys Asp Thr Ser Arg Asn Gln Val Phe Leu Lys
1               5                   10                  15
```

Ile Thr Ser Val Asp Thr Ala Asp Thr Ala Thr Tyr Tyr Cys Ala Arg
20 25 30

<210> SEQ ID NO 135
<211> LENGTH: 11
<212> TYPE: PRT
<213> ORGANISM: Mus musculus

<400> SEQUENCE: 135

Trp Gly Gln Gly Thr Thr Leu Thr Val Ser Ser
1 5 10

<210> SEQ ID NO 136
<211> LENGTH: 333
<212> TYPE: DNA
<213> ORGANISM: Mus musculus

<400> SEQUENCE: 136
gatgttgtga tgacccaaac tccactctcc ttgcctgtca gtcttggaga tcaagcctcc 60
atctcttgca gatctagtca gagcattgta catagtaatg gaaacaccaa tttagaatgg 120
tacctgcaga aaccaggcca gtctccaaag ctcctgatct acaaagtttc caaccgattg 180
tctggggtcc cagacaggtt cagtggcagt ggatcaggga cagacttcac actcaagatc 240
agcagagtgg aggctgagga tctgggagtt tattactgct ttcaaggttc acatgttcgg 300
acgttcggtg gaggcaccaa gctggaaatc aaa 333

<210> SEQ ID NO 137
<211> LENGTH: 111
<212> TYPE: PRT
<213> ORGANISM: Mus musculus

<400> SEQUENCE: 137

Asp Val Val Met Thr Gln Thr Pro Leu Ser Leu Pro Val Ser Leu Gly
1 5 10 15

Asp Gln Ala Ser Ile Ser Cys Arg Ser Ser Gln Ser Ile Val His Ser
20 25 30

Asn Gly Asn Thr Asn Leu Glu Trp Tyr Leu Gln Lys Pro Gly Gln Ser
35 40 45

Pro Lys Leu Leu Ile Tyr Lys Val Ser Asn Arg Leu Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser His Val Arg Thr Phe Gly Gly Gly Thr Lys Leu Glu Ile Lys
100 105 110

<210> SEQ ID NO 138
<211> LENGTH: 16
<212> TYPE: PRT
<213> ORGANISM: Mus musculus

<400> SEQUENCE: 138

Arg Ser Ser Gln Ser Ile Val His Ser Asn Gly Asn Thr Asn Leu Glu
1 5 10 15

<210> SEQ ID NO 139
<211> LENGTH: 7
<212> TYPE: PRT

<213> ORGANISM: Mus musculus

<400> SEQUENCE: 139

Lys Val Ser Asn Arg Leu Ser
1 5

<210> SEQ ID NO 140
<211> LENGTH: 8
<212> TYPE: PRT
<213> ORGANISM: Mus musculus

<400> SEQUENCE: 140

Phe Gln Gly Ser His Val Arg Thr
1 5

<210> SEQ ID NO 141
<211> LENGTH: 23
<212> TYPE: PRT
<213> ORGANISM: Mus musculus

<400> SEQUENCE: 141

Asp Val Val Met Thr Gln Thr Pro Leu Ser Leu Pro Val Ser Leu Gly
1 5 10 15

Asp Gln Ala Ser Ile Ser Cys
20

<210> SEQ ID NO 142
<211> LENGTH: 15
<212> TYPE: PRT
<213> ORGANISM: Mus musculus

<400> SEQUENCE: 142

Trp Tyr Leu Gln Lys Pro Gly Gln Ser Pro Lys Leu Leu Ile Tyr
1 5 10 15

<210> SEQ ID NO 143
<211> LENGTH: 32
<212> TYPE: PRT
<213> ORGANISM: Mus musculus

<400> SEQUENCE: 143

Gly Val Pro Asp Arg Phe Ser Gly Ser Gly Ser Gly Thr Asp Phe Thr
1 5 10 15

Leu Lys Ile Ser Arg Val Glu Ala Glu Asp Leu Gly Val Tyr Tyr Cys
20 25 30

<210> SEQ ID NO 144
<211> LENGTH: 10
<212> TYPE: PRT
<213> ORGANISM: Mus musculus

<400> SEQUENCE: 144

Phe Gly Gly Gly Thr Lys Leu Glu Ile Lys
1 5 10

<210> SEQ ID NO 145
<211> LENGTH: 354
<212> TYPE: DNA
<213> ORGANISM: Mus musculus

<400> SEQUENCE: 145
caggttcagc tgcagcagtc tggacctgag ctggtgaagc ctggggcttc agtgaagttg 60
tcctgcaagg cttctggcta caccttcaca agctacgata taaactgggt gaagcagagg 120

```
cctggacagg gacttgagtg gattggatgg atttatccta gagatggtat ttctaagtac    180

aatgagaagt tcaagggcaa ggccacattg actgtagaca catcctccag cacagcgtac    240

atggagctcc acagcctgac atctgaggac tctgcggtct atttctgtgc agggacctat    300

gaccccgcct actttgacta ctggggccaa ggcaccactc tcaccgtctc ctca          354


<210> SEQ ID NO 146
<211> LENGTH: 118
<212> TYPE: PRT
<213> ORGANISM: Mus musculus

<400> SEQUENCE: 146

Gln Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Tyr Pro Arg Asp Gly Ile Ser Lys Tyr Asn Glu Lys Phe
    50                  55                  60

Lys Gly Lys Ala Thr Leu Thr Val Asp Thr Ser Ser Ser Thr Ala Tyr
65                  70                  75                  80

Met Glu Leu His Ser Leu Thr Ser Glu Asp Ser Ala Val Tyr Phe Cys
                85                  90                  95

Ala Gly Thr Tyr Asp Pro Ala Tyr Phe Asp Tyr Trp Gly Gln Gly Thr
            100                 105                 110

Thr Leu Thr Val Ser Ser
        115


<210> SEQ ID NO 147
<211> LENGTH: 5
<212> TYPE: PRT
<213> ORGANISM: Mus musculus

<400> SEQUENCE: 147

Ser Tyr Asp Ile Asn
1               5


<210> SEQ ID NO 148
<211> LENGTH: 17
<212> TYPE: PRT
<213> ORGANISM: Mus musculus

<400> SEQUENCE: 148

Trp Ile Tyr Pro Arg Asp Gly Ile Ser Lys Tyr Asn Glu Lys Phe Lys
1               5                   10                  15

Gly


<210> SEQ ID NO 149
<211> LENGTH: 9
<212> TYPE: PRT
<213> ORGANISM: Mus musculus

<400> SEQUENCE: 149

Thr Tyr Asp Pro Ala Tyr Phe Asp Tyr
1               5


<210> SEQ ID NO 150
<211> LENGTH: 30
```

<212> TYPE: PRT
<213> ORGANISM: Mus musculus

<400> SEQUENCE: 150

Gln Val Gln Leu Gln Gln Ser Gly Pro Glu Leu Val Lys Pro Gly Ala
1 5 10 15

Ser Val Lys Leu Ser Cys Lys Ala Ser Gly Tyr Thr Phe Thr
20 25 30

<210> SEQ ID NO 151
<211> LENGTH: 14
<212> TYPE: PRT
<213> ORGANISM: Mus musculus

<400> SEQUENCE: 151

Trp Val Lys Gln Arg Pro Gly Gln Gly Leu Glu Trp Ile Gly
1 5 10

<210> SEQ ID NO 152
<211> LENGTH: 32
<212> TYPE: PRT
<213> ORGANISM: Mus musculus

<400> SEQUENCE: 152

Lys Ala Thr Leu Thr Val Asp Thr Ser Ser Ser Thr Ala Tyr Met Glu
1 5 10 15

Leu His Ser Leu Thr Ser Glu Asp Ser Ala Val Tyr Phe Cys Ala Gly
20 25 30

<210> SEQ ID NO 153
<211> LENGTH: 11
<212> TYPE: PRT
<213> ORGANISM: Mus musculus

<400> SEQUENCE: 153

Trp Gly Gln Gly Thr Thr Leu Thr Val Ser Ser
1 5 10

<210> SEQ ID NO 154
<211> LENGTH: 321
<212> TYPE: DNA
<213> ORGANISM: Mus musculus

<400> SEQUENCE: 154
gatattgtgc taactcagtc tccagccacc ctgtctgtga ctccaggaga tagagtcagt 60
ctttcctgca gggccagcca aagtattagc tactacctac actggtatca acaaaaatca 120
catgagtctc caaggcttct catcaagtat gcttcccagt ccatctctgg gatcccctcc 180
aggttcagtg gcagtggatc aggcacagat ttcactctca gtatcaacag tgtggagact 240
gaagattttg gaatgtattt ctgtcaacag agtaacagct ggccgtacac gttcggaggg 300
gggaccaagc tggaaataaa a 321

<210> SEQ ID NO 155
<211> LENGTH: 107
<212> TYPE: PRT
<213> ORGANISM: Mus musculus

<400> SEQUENCE: 155

Asp Ile Val Leu Thr Gln Ser Pro Ala Thr Leu Ser Val Thr Pro Gly
1 5 10 15

Asp Arg Val Ser Leu Ser Cys Arg Ala Ser Gln Ser Ile Ser Tyr Tyr

```
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Tyr
                85                  90                  95

Thr Phe Gly Gly Gly Thr Lys Leu Glu Ile Lys
            100                 105


<210> SEQ ID NO 156
<211> LENGTH: 11
<212> TYPE: PRT
<213> ORGANISM: Mus musculus

<400> SEQUENCE: 156

Arg Ala Ser Gln Ser Ile Ser Tyr Tyr Leu His
1               5                   10


<210> SEQ ID NO 157
<211> LENGTH: 7
<212> TYPE: PRT
<213> ORGANISM: Mus musculus

<400> SEQUENCE: 157

Tyr Ala Ser Gln Ser Ile Ser
1               5


<210> SEQ ID NO 158
<211> LENGTH: 9
<212> TYPE: PRT
<213> ORGANISM: Mus musculus

<400> SEQUENCE: 158

Gln Gln Ser Asn Ser Trp Pro Tyr Thr
1               5


<210> SEQ ID NO 159
<211> LENGTH: 23
<212> TYPE: PRT
<213> ORGANISM: Mus musculus

<400> SEQUENCE: 159

Asp Ile Val Leu Thr Gln Ser Pro Ala Thr Leu Ser Val Thr Pro Gly
1               5                   10                  15

Asp Arg Val Ser Leu Ser Cys
            20


<210> SEQ ID NO 160
<211> LENGTH: 15
<212> TYPE: PRT
<213> ORGANISM: Mus musculus

<400> SEQUENCE: 160

Trp Tyr Gln Gln Lys Ser His Glu Ser Pro Arg Leu Leu Ile Lys
1               5                   10                  15


<210> SEQ ID NO 161
<211> LENGTH: 32
<212> TYPE: PRT
```

<213> ORGANISM: Mus musculus

<400> SEQUENCE: 161

Gly Ile Pro Ser Arg Phe Ser Gly Ser Gly Ser Gly Thr Asp Phe Thr
1               5                   10                  15

Leu Ser Ile Asn Ser Val Glu Thr Glu Asp Phe Gly Met Tyr Phe Cys
            20                  25                  30

<210> SEQ ID NO 162
<211> LENGTH: 10
<212> TYPE: PRT
<213> ORGANISM: Mus musculus

<400> SEQUENCE: 162

Phe Gly Gly Gly Thr Lys Leu Glu Ile Lys
1               5                   10

<210> SEQ ID NO 163
<211> LENGTH: 354
<212> TYPE: DNA
<213> ORGANISM: Mus musculus

<400> SEQUENCE: 163
caggttcagc tgcagcagtc tggacctgaa ctggtgaagc ctggggcttc agtgaagttg 60
tcctgcaagg cttctggcta caccttcaca agctacgata taaactgggt gaagcagagg 120
cctggacagg gacttgagtg gattggatgg atttatccta gagatggtat ttctaagtac 180
aatgagaagt tcgagggcaa ggccacattg actgtagaca catcctccag cacagcgtac 240
atggagctcc acagcctgac atctgaggac tctgcggtct atttctgtgc agggacctct 300
gaccccgcct actttgacta ctggggccaa ggcaccactc tcaccgtctc ctca 354

<210> SEQ ID NO 164
<211> LENGTH: 118
<212> TYPE: PRT
<213> ORGANISM: Mus musculus

<400> SEQUENCE: 164

Gln Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Tyr Pro Arg Asp Gly Ile Ser Lys Tyr Asn Glu Lys Phe
    50                  55                  60

Glu Gly Lys Ala Thr Leu Thr Val Asp Thr Ser Ser Ser Thr Ala Tyr
65                  70                  75                  80

Met Glu Leu His Ser Leu Thr Ser Glu Asp Ser Ala Val Tyr Phe Cys
                85                  90                  95

Ala Gly Thr Ser Asp Pro Ala Tyr Phe Asp Tyr Trp Gly Gln Gly Thr
            100                 105                 110

Thr Leu Thr Val Ser Ser
        115

<210> SEQ ID NO 165
<211> LENGTH: 5
<212> TYPE: PRT
<213> ORGANISM: Mus musculus

<400> SEQUENCE: 165

Ser Tyr Asp Ile Asn
1               5

<210> SEQ ID NO 166
<211> LENGTH: 17
<212> TYPE: PRT
<213> ORGANISM: Mus musculus

<400> SEQUENCE: 166

Trp Ile Tyr Pro Arg Asp Gly Ile Ser Lys Tyr Asn Glu Lys Phe Glu
1               5                   10                  15

Gly

<210> SEQ ID NO 167
<211> LENGTH: 9
<212> TYPE: PRT
<213> ORGANISM: Mus musculus

<400> SEQUENCE: 167

Thr Ser Asp Pro Ala Tyr Phe Asp Tyr
1               5

<210> SEQ ID NO 168
<211> LENGTH: 30
<212> TYPE: PRT
<213> ORGANISM: Mus musculus

<400> SEQUENCE: 168

Gln Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr
            20                  25                  30

<210> SEQ ID NO 169
<211> LENGTH: 14
<212> TYPE: PRT
<213> ORGANISM: Mus musculus

<400> SEQUENCE: 169

Trp Val Lys Gln Arg Pro Gly Gln Gly Leu Glu Trp Ile Gly
1               5                   10

<210> SEQ ID NO 170
<211> LENGTH: 32
<212> TYPE: PRT
<213> ORGANISM: Mus musculus

<400> SEQUENCE: 170

Lys Ala Thr Leu Thr Val Asp Thr Ser Ser Ser Thr Ala Tyr Met Glu
1               5                   10                  15

Leu His Ser Leu Thr Ser Glu Asp Ser Ala Val Tyr Phe Cys Ala Gly
            20                  25                  30

<210> SEQ ID NO 171
<211> LENGTH: 11
<212> TYPE: PRT
<213> ORGANISM: Mus musculus

<400> SEQUENCE: 171

Trp Gly Gln Gly Thr Thr Leu Thr Val Ser Ser
1               5                   10

<210> SEQ ID NO 172
<211> LENGTH: 321
<212> TYPE: DNA
<213> ORGANISM: Mus musculus

<400> SEQUENCE: 172
gatattgtgc taactcagtc tccagccacc ctgtctgtga ctccaggaga tagagtcagt 60
ctttcctgca gggccagcca aagtattagc tactacctac actggtatca acaaaaatca 120
catgagtctc caaggcttct catcaagtat gcttcccagt ccatctctgg gatcccctcc 180
aggttcagtg gcagtggatc aggcacagat ttcactctca gtatcaacag tgtggagact 240
gaagattttg gaatgtattt ctgtcaacag agtaacagct ggccgtacac gttcggaggg 300
gggaccaagc tggaaataaa a 321

<210> SEQ ID NO 173
<211> LENGTH: 107
<212> TYPE: PRT
<213> ORGANISM: Mus musculus

<400> SEQUENCE: 173

Asp Ile Val Leu Thr Gln Ser Pro Ala Thr Leu Ser Val Thr Pro Gly
1 5 10 15

Asp Arg Val Ser Leu Ser Cys Arg Ala Ser Gln Ser Ile Ser Tyr Tyr
20 25 30

Leu His Trp Tyr Gln Gln Lys Ser His Glu Ser Pro Arg Leu Leu Ile
35 40 45

Lys Tyr Ala Ser Gln Ser Ile Ser Gly Ile Pro Ser Arg Phe Ser Gly
50 55 60

Ser Gly Ser Gly Thr Asp Phe Thr Leu Ser Ile Asn Ser Val Glu Thr
65 70 75 80

Glu Asp Phe Gly Met Tyr Phe Cys Gln Gln Ser Asn Ser Trp Pro Tyr
85 90 95

Thr Phe Gly Gly Gly Thr Lys Leu Glu Ile Lys
100 105

<210> SEQ ID NO 174
<211> LENGTH: 11
<212> TYPE: PRT
<213> ORGANISM: Mus musculus

<400> SEQUENCE: 174

Arg Ala Ser Gln Ser Ile Ser Tyr Tyr Leu His
1 5 10

<210> SEQ ID NO 175
<211> LENGTH: 7
<212> TYPE: PRT
<213> ORGANISM: Mus musculus

<400> SEQUENCE: 175

Tyr Ala Ser Gln Ser Ile Ser
1 5

<210> SEQ ID NO 176
<211> LENGTH: 9
<212> TYPE: PRT
<213> ORGANISM: Mus musculus

<400> SEQUENCE: 176

```
Gln Gln Ser Asn Ser Trp Pro Tyr Thr
1               5


<210> SEQ ID NO 177
<211> LENGTH: 23
<212> TYPE: PRT
<213> ORGANISM: Mus musculus

<400> SEQUENCE: 177

Asp Ile Val Leu Thr Gln Ser Pro Ala Thr Leu Ser Val Thr Pro Gly
1               5                   10                  15

Asp Arg Val Ser Leu Ser Cys
            20


<210> SEQ ID NO 178
<211> LENGTH: 15
<212> TYPE: PRT
<213> ORGANISM: Mus musculus

<400> SEQUENCE: 178

Trp Tyr Gln Gln Lys Ser His Glu Ser Pro Arg Leu Leu Ile Lys
1               5                   10                  15


<210> SEQ ID NO 179
<211> LENGTH: 32
<212> TYPE: PRT
<213> ORGANISM: Mus musculus

<400> SEQUENCE: 179

Gly Ile Pro Ser Arg Phe Ser Gly Ser Gly Ser Gly Thr Asp Phe Thr
1               5                   10                  15

Leu Ser Ile Asn Ser Val Glu Thr Glu Asp Phe Gly Met Tyr Phe Cys
            20                  25                  30


<210> SEQ ID NO 180
<211> LENGTH: 10
<212> TYPE: PRT
<213> ORGANISM: Mus musculus

<400> SEQUENCE: 180

Phe Gly Gly Gly Thr Lys Leu Glu Ile Lys
1               5                   10


<210> SEQ ID NO 181
<211> LENGTH: 357
<212> TYPE: DNA
<213> ORGANISM: Mus musculus

<400> SEQUENCE: 181

gaggtccagc tgcaacagtc tggacctgag ctggtgaagc ctggggcttc agtgaagata     60

ccctgcaagg cttctggata cacattcact gactacaaca tggactgggt gaagcagagc    120

catggaaaga gccttgagtg gattggagat attaatcctt acaatggtat tactatctac    180

aaccagaagt tcaagggcaa ggccacattg actgtcgaca agtcctccag cacagcctac    240

atggagctcc gcagcctgac atctgaggac actgcggtct attactgtgc aagagaggag    300

aaactgggaa cctcctttga ctactggggc caaggcacca ctctcaccgt ctcctca       357


<210> SEQ ID NO 182
<211> LENGTH: 119
<212> TYPE: PRT
<213> ORGANISM: Mus musculus
```

<400> SEQUENCE: 182

Glu Val Gln Leu Gln Gln Ser Gly Pro Glu Leu Val Lys Pro Gly Ala
1 5 10 15

Ser Val Lys Ile Pro Cys Lys Ala Ser Gly Tyr Thr Phe Thr Asp Tyr
20 25 30

Asn Met Asp Trp Val Lys Gln Ser His Gly Lys Ser Leu Glu Trp Ile
35 40 45

Gly Asp Ile Asn Pro Tyr Asn Gly Ile Thr Ile Tyr Asn Gln Lys Phe
50 55 60

Lys Gly Lys Ala Thr Leu Thr Val Asp Lys Ser Ser Ser Thr Ala Tyr
65 70 75 80

Met Glu Leu Arg Ser Leu Thr Ser Glu Asp Thr Ala Val Tyr Tyr Cys
85 90 95

Ala Arg Glu Glu Lys Leu Gly Thr Ser Phe Asp Tyr Trp Gly Gln Gly
100 105 110

Thr Thr Leu Thr Val Ser Ser
115

<210> SEQ ID NO 183
<211> LENGTH: 5
<212> TYPE: PRT
<213> ORGANISM: Mus musculus

<400> SEQUENCE: 183

Asp Tyr Asn Met Asp
1 5

<210> SEQ ID NO 184
<211> LENGTH: 17
<212> TYPE: PRT
<213> ORGANISM: Mus musculus

<400> SEQUENCE: 184

Asp Ile Asn Pro Tyr Asn Gly Ile Thr Ile Tyr Asn Gln Lys Phe Lys
1 5 10 15

Gly

<210> SEQ ID NO 185
<211> LENGTH: 10
<212> TYPE: PRT
<213> ORGANISM: Mus musculus

<400> SEQUENCE: 185

Glu Glu Lys Leu Gly Thr Ser Phe Asp Tyr
1 5 10

<210> SEQ ID NO 186
<211> LENGTH: 30
<212> TYPE: PRT
<213> ORGANISM: Mus musculus

<400> SEQUENCE: 186

Glu Val Gln Leu Gln Gln Ser Gly Pro Glu Leu Val Lys Pro Gly Ala
1 5 10 15

Ser Val Lys Ile Pro Cys Lys Ala Ser Gly Tyr Thr Phe Thr
20 25 30

<210> SEQ ID NO 187
<211> LENGTH: 14
<212> TYPE: PRT

<213> ORGANISM: Mus musculus

<400> SEQUENCE: 187

Trp Val Lys Gln Ser His Gly Lys Ser Leu Glu Trp Ile Gly
1 5 10

<210> SEQ ID NO 188
<211> LENGTH: 32
<212> TYPE: PRT
<213> ORGANISM: Mus musculus

<400> SEQUENCE: 188

Lys Ala Thr Leu Thr Val Asp Lys Ser Ser Ser Thr Ala Tyr Met Glu
1 5 10 15

Leu Arg Ser Leu Thr Ser Glu Asp Thr Ala Val Tyr Tyr Cys Ala Arg
20 25 30

<210> SEQ ID NO 189
<211> LENGTH: 11
<212> TYPE: PRT
<213> ORGANISM: Mus musculus

<400> SEQUENCE: 189

Trp Gly Gln Gly Thr Thr Leu Thr Val Ser Ser
1 5 10

<210> SEQ ID NO 190
<211> LENGTH: 321
<212> TYPE: DNA
<213> ORGANISM: Mus musculus

<400> SEQUENCE: 190
gacatccaga tgactcagtc tccagcctcc ctatctgcat ctgtgggaga aactgtcacc 60
atcacatgtc gagcaagtga gaatatttac agtaatttag catggtatca gcagaaacag 120
ggaaaatctc ctcagctcct ggtctatgct gcaacaaatt tagcagatgg tgtgccatca 180
aggttcagtg gcagtggatc aggcacacag ttttctctga agatcaacag cctgcagcct 240
gaagattttg ggagttatta ctgtcaacat ttttatggta ctccgtggac gttcggtgga 300
ggcaccaagc tggaaatcaa a 321

<210> SEQ ID NO 191
<211> LENGTH: 107
<212> TYPE: PRT
<213> ORGANISM: Mus musculus

<400> SEQUENCE: 191

Asp Ile Gln Met Thr Gln Ser Pro Ala Ser Leu Ser Ala Ser Val Gly
1 5 10 15

Glu Thr Val Thr Ile Thr Cys Arg Ala Ser Glu Asn Ile Tyr Ser Asn
20 25 30

Leu Ala Trp Tyr Gln Gln Lys Gln Gly Lys Ser Pro Gln Leu Leu Val
35 40 45

Tyr Ala Ala Thr Asn Leu Ala Asp Gly Val Pro Ser Arg Phe Ser Gly
50 55 60

Ser Gly Ser Gly Thr Gln Phe Ser Leu Lys Ile Asn Ser Leu Gln Pro
65 70 75 80

Glu Asp Phe Gly Ser Tyr Tyr Cys Gln His Phe Tyr Gly Thr Pro Trp
85 90 95

Thr Phe Gly Gly Gly Thr Lys Leu Glu Ile Lys 100 105

<210> SEQ ID NO 192
<211> LENGTH: 11
<212> TYPE: PRT
<213> ORGANISM: Mus musculus

<400> SEQUENCE: 192

Arg Ala Ser Glu Asn Ile Tyr Ser Asn Leu Ala
1 5 10

<210> SEQ ID NO 193
<211> LENGTH: 7
<212> TYPE: PRT
<213> ORGANISM: Mus musculus

<400> SEQUENCE: 193

Ala Ala Thr Asn Leu Ala Asp
1 5

<210> SEQ ID NO 194
<211> LENGTH: 9
<212> TYPE: PRT
<213> ORGANISM: Mus musculus

<400> SEQUENCE: 194

Gln His Phe Tyr Gly Thr Pro Trp Thr
1 5

<210> SEQ ID NO 195
<211> LENGTH: 23
<212> TYPE: PRT
<213> ORGANISM: Mus musculus

<400> SEQUENCE: 195

Asp Ile Gln Met Thr Gln Ser Pro Ala Ser Leu Ser Ala Ser Val Gly
1 5 10 15

Glu Thr Val Thr Ile Thr Cys
20

<210> SEQ ID NO 196
<211> LENGTH: 15
<212> TYPE: PRT
<213> ORGANISM: Mus musculus

<400> SEQUENCE: 196

Trp Tyr Gln Gln Lys Gln Gly Lys Ser Pro Gln Leu Leu Val Tyr
1 5 10 15

<210> SEQ ID NO 197
<211> LENGTH: 32
<212> TYPE: PRT
<213> ORGANISM: Mus musculus

<400> SEQUENCE: 197

Gly Val Pro Ser Arg Phe Ser Gly Ser Gly Ser Gly Thr Gln Phe Ser
1 5 10 15

Leu Lys Ile Asn Ser Leu Gln Pro Glu Asp Phe Gly Ser Tyr Tyr Cys
20 25 30

<210> SEQ ID NO 198
<211> LENGTH: 10
<212> TYPE: PRT
<213> ORGANISM: Mus musculus

<400> SEQUENCE: 198

Phe Gly Gly Gly Thr Lys Leu Glu Ile Lys
1 5 10

<210> SEQ ID NO 199
<211> LENGTH: 354
<212> TYPE: DNA
<213> ORGANISM: Mus musculus

<400> SEQUENCE: 199
caggttactc tgaaagagtc tggccctggg atattgcagc cctcccagac cctcagtctg 60
acttgttctt tctctgggtt ttcactgagc acttatggta tgggtgtagg ttggattcgt 120
cagccttcag ggaagggtct ggagtggctg gccaacattt ggtggaatga tgataagtac 180
tataactcag ccctgaagag ccggctcaca atctccaagg atacctccaa caaccaggta 240
ttcctcaaga tctccagtgt ggacactgca gatactgcca catactactg tgctcaaatg 300
gcctactcct ggtttgctta ctggggccaa gggactctgg tcaccgtctc ctca 354

<210> SEQ ID NO 200
<211> LENGTH: 118
<212> TYPE: PRT
<213> ORGANISM: Mus musculus

<400> SEQUENCE: 200

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Ser Thr Tyr
20 25 30

Gly Met Gly Val Gly Trp Ile Arg Gln Pro Ser Gly Lys Gly Leu Glu
35 40 45

Trp Leu Ala Asn Ile Trp Trp Asn Asp Asp Lys Tyr Tyr Asn Ser Ala
50 55 60

Leu Lys Ser Arg Leu Thr Ile Ser Lys Asp Thr Ser Asn Asn Gln Val
65 70 75 80

Phe Leu Lys Ile Ser Ser Val Asp Thr Ala Asp Thr Ala Thr Tyr Tyr
85 90 95

Cys Ala Gln Met Ala Tyr Ser Trp Phe Ala Tyr Trp Gly Gln Gly Thr
100 105 110

Leu Val Thr Val Ser Ser
115

<210> SEQ ID NO 201
<211> LENGTH: 7
<212> TYPE: PRT
<213> ORGANISM: Mus musculus

<400> SEQUENCE: 201

Thr Tyr Gly Met Gly Val Gly
1 5

<210> SEQ ID NO 202
<211> LENGTH: 16
<212> TYPE: PRT
<213> ORGANISM: Mus musculus

<400> SEQUENCE: 202

Asn Ile Trp Trp Asn Asp Asp Lys Tyr Tyr Asn Ser Ala Leu Lys Ser
1 5 10 15

<210> SEQ ID NO 203
<211> LENGTH: 8
<212> TYPE: PRT
<213> ORGANISM: Mus musculus

<400> SEQUENCE: 203

```
Met Ala Tyr Ser Trp Phe Ala Tyr
1               5
```

<210> SEQ ID NO 204
<211> LENGTH: 30
<212> TYPE: PRT
<213> ORGANISM: Mus musculus

<400> SEQUENCE: 204

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser
            20                  25                  30
```

<210> SEQ ID NO 205
<211> LENGTH: 14
<212> TYPE: PRT
<213> ORGANISM: Mus musculus

<400> SEQUENCE: 205

```
Trp Ile Arg Gln Pro Ser Gly Lys Gly Leu Glu Trp Leu Ala
1               5                   10
```

<210> SEQ ID NO 206
<211> LENGTH: 32
<212> TYPE: PRT
<213> ORGANISM: Mus musculus

<400> SEQUENCE: 206

```
Arg Leu Thr Ile Ser Lys Asp Thr Ser Asn Asn Gln Val Phe Leu Lys
1               5                   10                  15

Ile Ser Ser Val Asp Thr Ala Asp Thr Ala Thr Tyr Tyr Cys Ala Gln
            20                  25                  30
```

<210> SEQ ID NO 207
<211> LENGTH: 11
<212> TYPE: PRT
<213> ORGANISM: Mus musculus

<400> SEQUENCE: 207

```
Trp Gly Gln Gly Thr Leu Val Thr Val Ser Ser
1               5                   10
```

<210> SEQ ID NO 208
<211> LENGTH: 321
<212> TYPE: DNA
<213> ORGANISM: Mus musculus

<400> SEQUENCE: 208

```
gacattgtga tgacccagtc tcaaaaattc atgtccacat cagtaggaga cagggtcagc     60

gtcacctgca aggccagtca gaatatggat actaatgtag cctggtatca acagaaacca    120

gggcaatctc ctaaagcact gatttactcg gcatcctacc ggtacagtgg agtccctgat    180

cgcttcacag gcagtggatc tgggacagat ttcactctca ccatcagcaa tgtgcagtct    240

gaagacttgg cagaatattt ctgtcagcaa tataacagct atccattcac gttcggctcg    300
```

gggacaaagt tggaaataaa a 321

<210> SEQ ID NO 209
<211> LENGTH: 107
<212> TYPE: PRT
<213> ORGANISM: Mus musculus

<400> SEQUENCE: 209

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Met Asp Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Phe
                85                  90                  95

Thr Phe Gly Ser Gly Thr Lys Leu Glu Ile Lys
            100                 105
```

<210> SEQ ID NO 210
<211> LENGTH: 11
<212> TYPE: PRT
<213> ORGANISM: Mus musculus

<400> SEQUENCE: 210

```
Lys Ala Ser Gln Asn Met Asp Thr Asn Val Ala
1               5                   10
```

<210> SEQ ID NO 211
<211> LENGTH: 7
<212> TYPE: PRT
<213> ORGANISM: Mus musculus

<400> SEQUENCE: 211

```
Ser Ala Ser Tyr Arg Tyr Ser
1               5
```

<210> SEQ ID NO 212
<211> LENGTH: 9
<212> TYPE: PRT
<213> ORGANISM: Mus musculus

<400> SEQUENCE: 212

```
Gln Gln Tyr Asn Ser Tyr Pro Phe Thr
1               5
```

<210> SEQ ID NO 213
<211> LENGTH: 23
<212> TYPE: PRT
<213> ORGANISM: Mus musculus

<400> SEQUENCE: 213

```
Asp Ile Val Met Thr Gln Ser Gln Lys Phe Met Ser Thr Ser Val Gly
1               5                   10                  15

Asp Arg Val Ser Val Thr Cys
            20
```

<210> SEQ ID NO 214
<211> LENGTH: 15
<212> TYPE: PRT
<213> ORGANISM: Mus musculus

<400> SEQUENCE: 214

Trp Tyr Gln Gln Lys Pro Gly Gln Ser Pro Lys Ala Leu Ile Tyr
1 5 10 15

<210> SEQ ID NO 215
<211> LENGTH: 32
<212> TYPE: PRT
<213> ORGANISM: Mus musculus

<400> SEQUENCE: 215

Gly Val Pro Asp Arg Phe Thr Gly Ser Gly Ser Gly Thr Asp Phe Thr
1 5 10 15

Leu Thr Ile Ser Asn Val Gln Ser Glu Asp Leu Ala Glu Tyr Phe Cys
20 25 30

<210> SEQ ID NO 216
<211> LENGTH: 10
<212> TYPE: PRT
<213> ORGANISM: Mus musculus

<400> SEQUENCE: 216

Phe Gly Ser Gly Thr Lys Leu Glu Ile Lys
1 5 10

<210> SEQ ID NO 217
<211> LENGTH: 357
<212> TYPE: DNA
<213> ORGANISM: Mus musculus

<400> SEQUENCE: 217
caggttactc tgaaagagtc tggcccgggg atattgcagc cctcccagac cctcagtctg 60
acttgttctt tctctgggtt ttcactgagc acttttggta tgggtgtagg ctggattcgt 120
cagccttcag ggaagggtct ggagtggctg gcacacattt ggtgggatga tgataagtac 180
tataatccag ccctgaagag tcggctcaca atctccaagg atacctccaa aaaccaggta 240
ttcctcaaga tcgccaatgt ggacactgca gatactgcca catactactg tgctcgaata 300
gcttatgatg gttacttgga ctactggggc caaggcacca cgctcaccgt ctcctca 357

<210> SEQ ID NO 218
<211> LENGTH: 119
<212> TYPE: PRT
<213> ORGANISM: Mus musculus

<400> SEQUENCE: 218

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Ser Thr Phe
20 25 30

Gly Met Gly Val Gly Trp Ile Arg Gln Pro Ser Gly Lys Gly Leu Glu
35 40 45

Trp Leu Ala His Ile Trp Trp Asp Asp Asp Lys Tyr Tyr Asn Pro Ala
50 55 60

Leu Lys Ser Arg Leu Thr Ile Ser Lys Asp Thr Ser Lys Asn Gln Val
65 70 75 80

```
Phe Leu Lys Ile Ala Asn Val Asp Thr Ala Asp Thr Ala Thr Tyr Tyr
                85                  90                  95

Cys Ala Arg Ile Ala Tyr Asp Gly Tyr Leu Asp Tyr Trp Gly Gln Gly
            100                 105                 110

Thr Thr Leu Thr Val Ser Ser
        115


<210> SEQ ID NO 219
<211> LENGTH: 7
<212> TYPE: PRT
<213> ORGANISM: Mus musculus

<400> SEQUENCE: 219

Thr Phe Gly Met Gly Val Gly
1               5


<210> SEQ ID NO 220
<211> LENGTH: 16
<212> TYPE: PRT
<213> ORGANISM: Mus musculus

<400> SEQUENCE: 220

His Ile Trp Trp Asp Asp Asp Lys Tyr Tyr Asn Pro Ala Leu Lys Ser
1               5                   10                  15


<210> SEQ ID NO 221
<211> LENGTH: 9
<212> TYPE: PRT
<213> ORGANISM: Mus musculus

<400> SEQUENCE: 221

Ile Ala Tyr Asp Gly Tyr Leu Asp Tyr
1               5


<210> SEQ ID NO 222
<211> LENGTH: 30
<212> TYPE: PRT
<213> ORGANISM: Mus musculus

<400> SEQUENCE: 222

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser
            20                  25                  30


<210> SEQ ID NO 223
<211> LENGTH: 14
<212> TYPE: PRT
<213> ORGANISM: Mus musculus

<400> SEQUENCE: 223

Trp Ile Arg Gln Pro Ser Gly Lys Gly Leu Glu Trp Leu Ala
1               5                   10


<210> SEQ ID NO 224
<211> LENGTH: 32
<212> TYPE: PRT
<213> ORGANISM: Mus musculus

<400> SEQUENCE: 224

Arg Leu Thr Ile Ser Lys Asp Thr Ser Lys Asn Gln Val Phe Leu Lys
1               5                   10                  15

Ile Ala Asn Val Asp Thr Ala Asp Thr Ala Thr Tyr Tyr Cys Ala Arg
```

20 25 30

<210> SEQ ID NO 225
<211> LENGTH: 11
<212> TYPE: PRT
<213> ORGANISM: Mus musculus

<400> SEQUENCE: 225

Trp Gly Gln Gly Thr Thr Leu Thr Val Ser Ser
1 5 10

<210> SEQ ID NO 226
<211> LENGTH: 321
<212> TYPE: DNA
<213> ORGANISM: Mus musculus

<400> SEQUENCE: 226
gacattgtga tgacccagtc tcaaaaattc atgtccacat cagtaggaga cagggtcagc 60
gtcacctgca aggccagtca gaatgtgggt actgatgtag cctggtatca acagaaacca 120
gggcaatctc ctaaatcact gatttactcg gcatcctacc ggtacagtgg agtccctgat 180
cgcttcacag gcagtggatc tgggacagat ttcactctca ccatcagcaa tgtgcagtct 240
gaagacttgg cagagtattt ctgtcagcaa tataacagct atccgtacac gttcggaggg 300
gggaccaagc tggaaataaa a 321

<210> SEQ ID NO 227
<211> LENGTH: 107
<212> TYPE: PRT
<213> ORGANISM: Mus musculus

<400> SEQUENCE: 227

Asp Ile Val Met Thr Gln Ser Gln Lys Phe Met Ser Thr Ser Val Gly
1 5 10 15

Asp Arg Val Ser Val Thr Cys Lys Ala Ser Gln Asn Val Gly Thr Asp
20 25 30

Val Ala Trp Tyr Gln Gln Lys Pro Gly Gln Ser Pro Lys Ser Leu Ile
35 40 45

Tyr Ser Ala Ser Tyr Arg Tyr Ser Gly Val Pro Asp Arg Phe Thr Gly
50 55 60

Ser Gly Ser Gly Thr Asp Phe Thr Leu Thr Ile Ser Asn Val Gln Ser
65 70 75 80

Glu Asp Leu Ala Glu Tyr Phe Cys Gln Gln Tyr Asn Ser Tyr Pro Tyr
85 90 95

Thr Phe Gly Gly Gly Thr Lys Leu Glu Ile Lys
100 105

<210> SEQ ID NO 228
<211> LENGTH: 11
<212> TYPE: PRT
<213> ORGANISM: Mus musculus

<400> SEQUENCE: 228

Lys Ala Ser Gln Asn Val Gly Thr Asp Val Ala
1 5 10

<210> SEQ ID NO 229
<211> LENGTH: 7
<212> TYPE: PRT
<213> ORGANISM: Mus musculus

<400> SEQUENCE: 229

Ser Ala Ser Tyr Arg Tyr Ser
1 5

<210> SEQ ID NO 230
<211> LENGTH: 9
<212> TYPE: PRT
<213> ORGANISM: Mus musculus

<400> SEQUENCE: 230

Gln Gln Tyr Asn Ser Tyr Pro Tyr Thr
1 5

<210> SEQ ID NO 231
<211> LENGTH: 23
<212> TYPE: PRT
<213> ORGANISM: Mus musculus

<400> SEQUENCE: 231

Asp Ile Val Met Thr Gln Ser Gln Lys Phe Met Ser Thr Ser Val Gly
1 5 10 15

Asp Arg Val Ser Val Thr Cys
20

<210> SEQ ID NO 232
<211> LENGTH: 15
<212> TYPE: PRT
<213> ORGANISM: Mus musculus

<400> SEQUENCE: 232

Trp Tyr Gln Gln Lys Pro Gly Gln Ser Pro Lys Ser Leu Ile Tyr
1 5 10 15

<210> SEQ ID NO 233
<211> LENGTH: 32
<212> TYPE: PRT
<213> ORGANISM: Mus musculus

<400> SEQUENCE: 233

Gly Val Pro Asp Arg Phe Thr Gly Ser Gly Ser Gly Thr Asp Phe Thr
1 5 10 15

Leu Thr Ile Ser Asn Val Gln Ser Glu Asp Leu Ala Glu Tyr Phe Cys
20 25 30

<210> SEQ ID NO 234
<211> LENGTH: 10
<212> TYPE: PRT
<213> ORGANISM: Mus musculus

<400> SEQUENCE: 234

Phe Gly Gly Gly Thr Lys Leu Glu Ile Lys
1 5 10

<210> SEQ ID NO 235
<211> LENGTH: 357
<212> TYPE: DNA
<213> ORGANISM: Mus musculus

<400> SEQUENCE: 235
gaggtccagc tgcagcagtc tggacgtgaa ctggtaaagc ctggggcttc agtgaagatg 60
tcctgcaagg cttctggata cacattcact aactatgtta tgcactgggt gaagcagaag 120
cctgggcagg gccttgagtg gattggatat attaatcctc acaatgatgg tactgaatac 180

```
agtgagaagt tcaaaggcaa ggccacactg acttcagaca aatcctccag cacagcctac    240

atggagctca gcagcctgac ctctgaggac tctgcggtct attactgtgc aagatggtac    300

tacgatggtg gttactttgc ttactggggc caagggactc tggtcactgt ctctgca       357
```

<210> SEQ ID NO 236
<211> LENGTH: 119
<212> TYPE: PRT
<213> ORGANISM: Mus musculus

<400> SEQUENCE: 236

```
Glu Val Gln Leu Gln Gln Ser Gly Arg Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Met His Trp Val Lys Gln Lys Pro Gly Gln Gly Leu Glu Trp Ile
        35                  40                  45

Gly Tyr Ile Asn Pro His Asn Asp Gly Thr Glu Tyr Ser Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Trp Tyr Tyr Asp Gly Gly Tyr Phe Ala Tyr Trp Gly Gln Gly
            100                 105                 110

Thr Leu Val Thr Val Ser Ala
        115
```

<210> SEQ ID NO 237
<211> LENGTH: 5
<212> TYPE: PRT
<213> ORGANISM: Mus musculus

<400> SEQUENCE: 237

```
Asn Tyr Val Met His
1               5
```

<210> SEQ ID NO 238
<211> LENGTH: 17
<212> TYPE: PRT
<213> ORGANISM: Mus musculus

<400> SEQUENCE: 238

```
Tyr Ile Asn Pro His Asn Asp Gly Thr Glu Tyr Ser Glu Lys Phe Lys
1               5                   10                  15

Gly
```

<210> SEQ ID NO 239
<211> LENGTH: 10
<212> TYPE: PRT
<213> ORGANISM: Mus musculus

<400> SEQUENCE: 239

```
Trp Tyr Tyr Asp Gly Gly Tyr Phe Ala Tyr
1               5                   10
```

<210> SEQ ID NO 240
<211> LENGTH: 30
<212> TYPE: PRT
<213> ORGANISM: Mus musculus

<400> SEQUENCE: 240

Glu Val Gln Leu Gln Gln Ser Gly Arg Glu Leu Val Lys Pro Gly Ala
1 5 10 15

Ser Val Lys Met Ser Cys Lys Ala Ser Gly Tyr Thr Phe Thr
20 25 30

<210> SEQ ID NO 241
<211> LENGTH: 14
<212> TYPE: PRT
<213> ORGANISM: Mus musculus

<400> SEQUENCE: 241

Trp Val Lys Gln Lys Pro Gly Gln Gly Leu Glu Trp Ile Gly
1 5 10

<210> SEQ ID NO 242
<211> LENGTH: 32
<212> TYPE: PRT
<213> ORGANISM: Mus musculus

<400> SEQUENCE: 242

Lys Ala Thr Leu Thr Ser Asp Lys Ser Ser Ser Thr Ala Tyr Met Glu
1 5 10 15

Leu Ser Ser Leu Thr Ser Glu Asp Ser Ala Val Tyr Tyr Cys Ala Arg
20 25 30

<210> SEQ ID NO 243
<211> LENGTH: 11
<212> TYPE: PRT
<213> ORGANISM: Mus musculus

<400> SEQUENCE: 243

Trp Gly Gln Gly Thr Leu Val Thr Val Ser Ala
1 5 10

<210> SEQ ID NO 244
<211> LENGTH: 321
<212> TYPE: DNA
<213> ORGANISM: Mus musculus

<400> SEQUENCE: 244
gacattgtga tgactcagtc tccagccacc ctgtctgtga ctccaggaga tagggtctct 60
ctttcctgca gggccagtca gagtattagc gactacttac actggtatca acaaaaatca 120
catgagtctc caaggcttct catcaagtat gcttcccaat ccatctctgg gatcccctcc 180
aggttcagtg gcagtggatc agggtcagat ttcactctca gtatcaacag tgtggaacct 240
gaagatgttg gagtgtatta ctgtcaaaat ggtcacagct ttccgctcac gttcggtgct 300
gggaccaagc tggagctgaa a 321

<210> SEQ ID NO 245
<211> LENGTH: 107
<212> TYPE: PRT
<213> ORGANISM: Mus musculus

<400> SEQUENCE: 245

Asp Ile Val Met Thr Gln Ser Pro Ala Thr Leu Ser Val Thr Pro Gly
1 5 10 15

Asp Arg Val Ser Leu Ser Cys Arg Ala Ser Gln Ser Ile Ser Asp Tyr
20 25 30

```
Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105


<210> SEQ ID NO 246
<211> LENGTH: 11
<212> TYPE: PRT
<213> ORGANISM: Mus musculus

<400> SEQUENCE: 246

Arg Ala Ser Gln Ser Ile Ser Asp Tyr Leu His
1               5                   10


<210> SEQ ID NO 247
<211> LENGTH: 7
<212> TYPE: PRT
<213> ORGANISM: Mus musculus

<400> SEQUENCE: 247

Tyr Ala Ser Gln Ser Ile Ser
1               5


<210> SEQ ID NO 248
<211> LENGTH: 9
<212> TYPE: PRT
<213> ORGANISM: Mus musculus

<400> SEQUENCE: 248

Gln Asn Gly His Ser Phe Pro Leu Thr
1               5


<210> SEQ ID NO 249
<211> LENGTH: 23
<212> TYPE: PRT
<213> ORGANISM: Mus musculus

<400> SEQUENCE: 249

Asp Ile Val Met Thr Gln Ser Pro Ala Thr Leu Ser Val Thr Pro Gly
1               5                   10                  15

Asp Arg Val Ser Leu Ser Cys
            20


<210> SEQ ID NO 250
<211> LENGTH: 15
<212> TYPE: PRT
<213> ORGANISM: Mus musculus

<400> SEQUENCE: 250

Trp Tyr Gln Gln Lys Ser His Glu Ser Pro Arg Leu Leu Ile Lys
1               5                   10                  15


<210> SEQ ID NO 251
<211> LENGTH: 32
<212> TYPE: PRT
<213> ORGANISM: Mus musculus
```

<400> SEQUENCE: 251

```
Gly Ile Pro Ser Arg Phe Ser Gly Ser Gly Ser Gly Ser Asp Phe Thr
1               5                   10                  15

Leu Ser Ile Asn Ser Val Glu Pro Glu Asp Val Gly Val Tyr Tyr Cys
            20                  25                  30
```

<210> SEQ ID NO 252
<211> LENGTH: 10
<212> TYPE: PRT
<213> ORGANISM: Mus musculus

<400> SEQUENCE: 252

```
Phe Gly Ala Gly Thr Lys Leu Glu Leu Lys
1               5                   10
```

<210> SEQ ID NO 253
<211> LENGTH: 357
<212> TYPE: DNA
<213> ORGANISM: Mus musculus

<400> SEQUENCE: 253

```
caggttactc tgaaagagtc tggccctggg atattgcagt cctcccagac cctcagtctg     60

acttgttctt tctctgggtt ttcactgagc acttctggta tgggtgtgag ctggattcgt    120

cagccttcag gaaagggtct ggagtggctg gcacacattt actgggatga tgacaagcgc    180

tataacccat ccctggagag ccggctcaca atctccaagg atacctccag aaaccaggta    240

ttcctcaaga tcaccagtgt ggacactaca gatactgcca catactactg tgctcggggg    300

gggtatgatg gctactacga ctactggggc caaggcacca ctctcaccgt ctcctca       357
```

<210> SEQ ID NO 254
<211> LENGTH: 119
<212> TYPE: PRT
<213> ORGANISM: Mus musculus

<400> SEQUENCE: 254

```
Gln Val Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Glu Ser Arg Leu Thr Ile Ser Lys Asp Thr Ser Arg Asn Gln Val
65                  70                  75                  80

Phe Leu Lys Ile Thr Ser Val Asp Thr Thr Asp Thr Ala Thr Tyr Tyr
                85                  90                  95

Cys Ala Arg Gly Gly Tyr Asp Gly Tyr Tyr Asp Tyr Trp Gly Gln Gly
            100                 105                 110

Thr Thr Leu Thr Val Ser Ser
        115
```

<210> SEQ ID NO 255
<211> LENGTH: 7
<212> TYPE: PRT
<213> ORGANISM: Mus musculus

<400> SEQUENCE: 255

```
Thr Ser Gly Met Gly Val Ser
1               5


<210> SEQ ID NO 256
<211> LENGTH: 16
<212> TYPE: PRT
<213> ORGANISM: Mus musculus

<400> SEQUENCE: 256

His Ile Tyr Trp Asp Asp Asp Lys Arg Tyr Asn Pro Ser Leu Glu Ser
1               5                   10                  15


<210> SEQ ID NO 257
<211> LENGTH: 9
<212> TYPE: PRT
<213> ORGANISM: Mus musculus

<400> SEQUENCE: 257

Gly Gly Tyr Asp Gly Tyr Tyr Asp Tyr
1               5


<210> SEQ ID NO 258
<211> LENGTH: 30
<212> TYPE: PRT
<213> ORGANISM: Mus musculus

<400> SEQUENCE: 258

Gln Val Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser
            20                  25                  30


<210> SEQ ID NO 259
<211> LENGTH: 14
<212> TYPE: PRT
<213> ORGANISM: Mus musculus

<400> SEQUENCE: 259

Trp Ile Arg Gln Pro Ser Gly Lys Gly Leu Glu Trp Leu Ala
1               5                   10


<210> SEQ ID NO 260
<211> LENGTH: 32
<212> TYPE: PRT
<213> ORGANISM: Mus musculus

<400> SEQUENCE: 260

Arg Leu Thr Ile Ser Lys Asp Thr Ser Arg Asn Gln Val Phe Leu Lys
1               5                   10                  15

Ile Thr Ser Val Asp Thr Thr Asp Thr Ala Thr Tyr Tyr Cys Ala Arg
            20                  25                  30


<210> SEQ ID NO 261
<211> LENGTH: 11
<212> TYPE: PRT
<213> ORGANISM: Mus musculus

<400> SEQUENCE: 261

Trp Gly Gln Gly Thr Thr Leu Thr Val Ser Ser
1               5                   10


<210> SEQ ID NO 262
<211> LENGTH: 333
<212> TYPE: DNA
```

<213> ORGANISM: Mus musculus

<400> SEQUENCE: 262

```
gatgttgtga tgacccaaac tccactctcc ctgcctgtca gtcttggaga tcaagcctcc      60

atctcttgca gatctagtca gagcattgta catagtaatg gaaacaccaa tttagaatgg     120

tacctgcaga aaccaggcca gtctccaaag ctcctgatct acaaagtttc caaccgattg     180

tctggggtcc cagacaggtt cagtggcagt ggatcaggga cagactccac actcaagatc     240

agcagagtgg aggctgagga tctgggagtt tattactgct ttcaaggttc acatgttcgg     300

acgttcggtg gaggcaccaa gctggaaatc aaa                                  333
```

<210> SEQ ID NO 263
<211> LENGTH: 111
<212> TYPE: PRT
<213> ORGANISM: Mus musculus

<400> SEQUENCE: 263

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Asn Leu Glu Trp Tyr Leu Gln Lys Pro Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Asp Ser Thr Leu Lys Ile
65                  70                  75                  80

Ser Arg Val Glu Ala Glu Asp Leu Gly Val Tyr Tyr Cys Phe Gln Gly
                85                  90                  95

Ser His Val Arg Thr Phe Gly Gly Gly Thr Lys Leu Glu Ile Lys
            100                 105                 110
```

<210> SEQ ID NO 264
<211> LENGTH: 16
<212> TYPE: PRT
<213> ORGANISM: Mus musculus

<400> SEQUENCE: 264

```
Arg Ser Ser Gln Ser Ile Val His Ser Asn Gly Asn Thr Asn Leu Glu
1               5                   10                  15
```

<210> SEQ ID NO 265
<211> LENGTH: 7
<212> TYPE: PRT
<213> ORGANISM: Mus musculus

<400> SEQUENCE: 265

```
Lys Val Ser Asn Arg Leu Ser
1               5
```

<210> SEQ ID NO 266
<211> LENGTH: 8
<212> TYPE: PRT
<213> ORGANISM: Mus musculus

<400> SEQUENCE: 266

```
Phe Gln Gly Ser His Val Arg Thr
1               5
```

<210> SEQ ID NO 267
<211> LENGTH: 23
<212> TYPE: PRT
<213> ORGANISM: Mus musculus

<400> SEQUENCE: 267

```
Asp Val Val Met Thr Gln Thr Pro Leu Ser Leu Pro Val Ser Leu Gly
1               5                   10                  15

Asp Gln Ala Ser Ile Ser Cys
            20
```

<210> SEQ ID NO 268
<211> LENGTH: 15
<212> TYPE: PRT
<213> ORGANISM: Mus musculus

<400> SEQUENCE: 268

```
Trp Tyr Leu Gln Lys Pro Gly Gln Ser Pro Lys Leu Leu Ile Tyr
1               5                   10                  15
```

<210> SEQ ID NO 269
<211> LENGTH: 32
<212> TYPE: PRT
<213> ORGANISM: Mus musculus

<400> SEQUENCE: 269

```
Gly Val Pro Asp Arg Phe Ser Gly Ser Gly Ser Gly Thr Asp Ser Thr
1               5                   10                  15

Leu Lys Ile Ser Arg Val Glu Ala Glu Asp Leu Gly Val Tyr Tyr Cys
            20                  25                  30
```

<210> SEQ ID NO 270
<211> LENGTH: 10
<212> TYPE: PRT
<213> ORGANISM: Mus musculus

<400> SEQUENCE: 270

```
Phe Gly Gly Gly Thr Lys Leu Glu Ile Lys
1               5                   10
```

<210> SEQ ID NO 271
<211> LENGTH: 363
<212> TYPE: DNA
<213> ORGANISM: Mus musculus

<400> SEQUENCE: 271

```
caggtccaac tgcagcagcc tggggctgag ctggtgaggc ctgggacttc agtgaagttg      60

tcctgcaagg cttctggcta caccttcacc agctactgga tgcactgggt aaagcagagg     120

cctagacaag gccttgaatg gatcggattg attgatcctt ctgataatta tactaactac     180

aatcaaaact tcaagggcaa ggccacattg actgtagaca catcctccag cacagcctac     240

atgcagctcg gcagcctgac atctgaggac tctgcggtct attactgtgc ctcctatgat     300

ggttactcta ccccctctgc tatggactac tggggtcaag gaacctcagt caccgtctcc     360

tca                                                                   363
```

<210> SEQ ID NO 272
<211> LENGTH: 121
<212> TYPE: PRT
<213> ORGANISM: Mus musculus

<400> SEQUENCE: 272

```
Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Arg Gln Gly Leu Glu Trp Ile
        35                  40                  45

Gly Leu Ile Asp Pro Ser Asp Asn Tyr Thr Asn Tyr Asn Gln Asn Phe
    50                  55                  60

Lys Gly Lys Ala Thr Leu Thr Val Asp Thr Ser Ser Ser Thr Ala Tyr
65                  70                  75                  80

Met Gln Leu Gly Ser Leu Thr Ser Glu Asp Ser Ala Val Tyr Tyr Cys
                85                  90                  95

Ala Ser Tyr Asp Gly Tyr Ser Thr Pro Ser Ala Met Asp Tyr Trp Gly
            100                 105                 110

Gln Gly Thr Ser Val Thr Val Ser Ser
        115                 120


<210> SEQ ID NO 273
<211> LENGTH: 5
<212> TYPE: PRT
<213> ORGANISM: Mus musculus

<400> SEQUENCE: 273

Ser Tyr Trp Met His
1               5


<210> SEQ ID NO 274
<211> LENGTH: 17
<212> TYPE: PRT
<213> ORGANISM: Mus musculus

<400> SEQUENCE: 274

Leu Ile Asp Pro Ser Asp Asn Tyr Thr Asn Tyr Asn Gln Asn Phe Lys
1               5                   10                  15

Gly


<210> SEQ ID NO 275
<211> LENGTH: 12
<212> TYPE: PRT
<213> ORGANISM: Mus musculus

<400> SEQUENCE: 275

Tyr Asp Gly Tyr Ser Thr Pro Ser Ala Met Asp Tyr
1               5                   10


<210> SEQ ID NO 276
<211> LENGTH: 30
<212> TYPE: PRT
<213> ORGANISM: Mus musculus

<400> SEQUENCE: 276

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr
            20                  25                  30


<210> SEQ ID NO 277
<211> LENGTH: 14
<212> TYPE: PRT
<213> ORGANISM: Mus musculus
```

<400> SEQUENCE: 277

Trp Val Lys Gln Arg Pro Arg Gln Gly Leu Glu Trp Ile Gly
1 5 10

<210> SEQ ID NO 278
<211> LENGTH: 32
<212> TYPE: PRT
<213> ORGANISM: Mus musculus

<400> SEQUENCE: 278

Lys Ala Thr Leu Thr Val Asp Thr Ser Ser Ser Thr Ala Tyr Met Gln
1 5 10 15

Leu Gly Ser Leu Thr Ser Glu Asp Ser Ala Val Tyr Tyr Cys Ala Ser
20 25 30

<210> SEQ ID NO 279
<211> LENGTH: 11
<212> TYPE: PRT
<213> ORGANISM: Mus musculus

<400> SEQUENCE: 279

Trp Gly Gln Gly Thr Ser Val Thr Val Ser Ser
1 5 10

<210> SEQ ID NO 280
<211> LENGTH: 318
<212> TYPE: DNA
<213> ORGANISM: Mus musculus

<400> SEQUENCE: 280
caaattgttc tctcccagtc tccagcaatc ctgtctgcat ctccagggga gaaggtcaca 60
atgacttgca gggccagctc aagtgtaaat tacatgcact ggtaccagca gaagccagga 120
tcctccccca aaccctggat ttatgccaca tccaacctgg cttctggagt ccctgctcgc 180
ttcagtggca gtgggtctgg gacctcttac tctctaataa tcagcagagt ggaggctgaa 240
gatgctgccg cttattactg ccagcagtgg agtagttacc cacccacgtt cggagggggg 300
accaagctgg aaataaaa 318

<210> SEQ ID NO 281
<211> LENGTH: 106
<212> TYPE: PRT
<213> ORGANISM: Mus musculus

<400> SEQUENCE: 281

Gln Ile Val Leu Ser Gln Ser Pro Ala Ile Leu Ser Ala Ser Pro Gly
1 5 10 15

Glu Lys Val Thr Met Thr Cys Arg Ala Ser Ser Ser Val Asn Tyr Met
20 25 30

His Trp Tyr Gln Gln Lys Pro Gly Ser Ser Pro Lys Pro Trp Ile Tyr
35 40 45

Ala Thr Ser Asn Leu Ala Ser Gly Val Pro Ala Arg Phe Ser Gly Ser
50 55 60

Gly Ser Gly Thr Ser Tyr Ser Leu Ile Ile Ser Arg Val Glu Ala Glu
65 70 75 80

Asp Ala Ala Ala Tyr Tyr Cys Gln Gln Trp Ser Ser Tyr Pro Pro Thr
85 90 95

Phe Gly Gly Gly Thr Lys Leu Glu Ile Lys
100 105

<210> SEQ ID NO 282
<211> LENGTH: 10
<212> TYPE: PRT
<213> ORGANISM: Mus musculus

<400> SEQUENCE: 282

Arg Ala Ser Ser Ser Val Asn Tyr Met His
1               5                   10

<210> SEQ ID NO 283
<211> LENGTH: 7
<212> TYPE: PRT
<213> ORGANISM: Mus musculus

<400> SEQUENCE: 283

Ala Thr Ser Asn Leu Ala Ser
1               5

<210> SEQ ID NO 284
<211> LENGTH: 9
<212> TYPE: PRT
<213> ORGANISM: Mus musculus

<400> SEQUENCE: 284

Gln Gln Trp Ser Ser Tyr Pro Pro Thr
1               5

<210> SEQ ID NO 285
<211> LENGTH: 23
<212> TYPE: PRT
<213> ORGANISM: Mus musculus

<400> SEQUENCE: 285

Gln Ile Val Leu Ser Gln Ser Pro Ala Ile Leu Ser Ala Ser Pro Gly
1               5                   10                  15

Glu Lys Val Thr Met Thr Cys
            20

<210> SEQ ID NO 286
<211> LENGTH: 15
<212> TYPE: PRT
<213> ORGANISM: Mus musculus

<400> SEQUENCE: 286

Trp Tyr Gln Gln Lys Pro Gly Ser Ser Pro Lys Pro Trp Ile Tyr
1               5                   10                  15

<210> SEQ ID NO 287
<211> LENGTH: 32
<212> TYPE: PRT
<213> ORGANISM: Mus musculus

<400> SEQUENCE: 287

Gly Val Pro Ala Arg Phe Ser Gly Ser Gly Ser Gly Thr Ser Tyr Ser
1               5                   10                  15

Leu Ile Ile Ser Arg Val Glu Ala Glu Asp Ala Ala Ala Tyr Tyr Cys
            20                  25                  30

<210> SEQ ID NO 288
<211> LENGTH: 10
<212> TYPE: PRT
<213> ORGANISM: Mus musculus

<400> SEQUENCE: 288

```
Phe Gly Gly Gly Thr Lys Leu Glu Ile Lys
1               5                   10


<210> SEQ ID NO 289
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 289

caggttcagc tgcaagaatc tggacccggc ctgctgaagc cctctcagac actgtctctg      60

acctgcaccg tgtccggctt ctccctgtct acctatggca tgggcgtcgg ctggatcaga     120

cagcctgctg gcaaaggact ggaatggctg gccaacatct ggtggaacga cgacaagtac     180

tacaacagcg ccctgaagtc ccggctgacc atctccaagg acacctccaa gaaccaggtg     240

tccctgaagc tgtcctctgt gaccgctgct gataccgccg tgtactactg tgcccaagag     300

gtgtacggat ggttcgccta ttggggccag ggaaccctag taaccgtctc ctca           354


<210> SEQ ID NO 290
<211> LENGTH: 118
<212> TYPE: PRT
<213> ORGANISM: Artificial Sequence
<220> FEATURE:
<223> OTHER INFORMATION: Synthetic Peptide

<400> SEQUENCE: 290

Gln Val Gln Leu Gln Glu Ser Gly Pro Gly Leu Leu Lys Pro Ser Gln
1               5                   10                  15

Thr Leu Ser Leu Thr Cys Thr Val Ser Gly Phe Ser Leu Ser Thr Tyr
            20                  25                  30

Gly Met Gly Val Gly Trp Ile Arg Gln Pro Ala Gly Lys Gly Leu Glu
        35                  40                  45

Trp Leu Ala Asn Ile Trp Trp Asn Asp Asp Lys Tyr Tyr Asn Ser Ala
    50                  55                  60

Leu Lys Ser Arg Leu Thr Ile Ser Lys Asp Thr Ser Lys Asn Gln Val
65                  70                  75                  80

Ser Leu Lys Leu Ser Ser Val Thr Ala Ala Asp Thr Ala Val Tyr Tyr
                85                  90                  95

Cys Ala Gln Glu Val Tyr Gly Trp Phe Ala Tyr Trp Gly Gln Gly Thr
            100                 105                 110

Leu Val Thr Val Ser Ser
        115


<210> SEQ ID NO 291
<211> LENGTH: 7
<212> TYPE: PRT
<213> ORGANISM: Mus musculus

<400> SEQUENCE: 291

Thr Tyr Gly Met Gly Val Gly
1               5


<210> SEQ ID NO 292
<211> LENGTH: 16
<212> TYPE: PRT
<213> ORGANISM: Mus musculus

<400> SEQUENCE: 292
```

Asn Ile Trp Trp Asn Asp Asp Lys Tyr Tyr Asn Ser Ala Leu Lys Ser
1 5 10 15

<210> SEQ ID NO 293
<211> LENGTH: 8
<212> TYPE: PRT
<213> ORGANISM: Mus musculus

<400> SEQUENCE: 293

Glu Val Tyr Gly Trp Phe Ala Tyr
1 5

<210> SEQ ID NO 294
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 294

Gln Val Gln Leu Gln Glu Ser Gly Pro Gly Leu Leu Lys Pro Ser Gln
1 5 10 15

Thr Leu Ser Leu Thr Cys Thr Val Ser Gly Phe Ser Leu Ser
20 25 30

<210> SEQ ID NO 295
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 295

Trp Ile Arg Gln Pro Ala Gly Lys Gly Leu Glu Trp Leu Ala
1 5 10

<210> SEQ ID NO 296
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 296

Arg Leu Thr Ile Ser Lys Asp Thr Ser Lys Asn Gln Val Ser Leu Lys
1 5 10 15

Leu Ser Ser Val Thr Ala Ala Asp Thr Ala Val Tyr Tyr Cys Ala Gln
20 25 30

<210> SEQ ID NO 297
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 297

Trp Gly Gln Gly Thr Leu Val Thr Val Ser Ser
1 5 10

<210> SEQ ID NO 298
<211> LENGTH: 321
<212> TYPE: DNA
<213> ORGANISM: Artificial Sequence
<220> FEATURE:
<223> OTHER INFORMATION: Synthetic Polynucleotide

<400> SEQUENCE: 298

```
gacatccaga tgacccagtc tccatccaca ctgtccgcct ctgtgggcga cagagtgacc     60
atcacatgca aggcctctca gaacgtgggc accaacgtgg cctggtatca gcagaaacct    120
ggccagcctc ctaaggctct gatctactcc gcctcctacc ggtactctgg cgtgcccgat    180
agattctccg gctctggctc tggcaccgac tttaccctga caatcagctc cctgcaggcc    240
gaggatgtgg ccgtgtacta ctgccagcag tacaacagct accctctgac ctttggccag    300
ggcaccaagc tcgagataaa a                                              321
```

<210> SEQ ID NO 299
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 299

```
Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Gln Pro Pro Lys Ala Leu Ile
        35                  40                  45

Tyr Ser Ala Ser Tyr Arg Tyr Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Asn Ser Tyr Pro Leu
                85                  90                  95

Thr Phe Gly Gln Gly Thr Lys Leu Glu Ile Lys
            100                 105
```

<210> SEQ ID NO 300
<211> LENGTH: 11
<212> TYPE: PRT
<213> ORGANISM: Mus musculus

<400> SEQUENCE: 300

```
Lys Ala Ser Gln Asn Val Gly Thr Asn Val Ala
1               5                   10
```

<210> SEQ ID NO 301
<211> LENGTH: 7
<212> TYPE: PRT
<213> ORGANISM: Mus musculus

<400> SEQUENCE: 301

```
Ser Ala Ser Tyr Arg Tyr Ser
1               5
```

<210> SEQ ID NO 302
<211> LENGTH: 9
<212> TYPE: PRT
<213> ORGANISM: Mus musculus

<400> SEQUENCE: 302

```
Gln Gln Tyr Asn Ser Tyr Pro Leu Thr
1               5
```

<210> SEQ ID NO 303
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 303

Asp Ile Gln Met Thr Gln Ser Pro Ser Thr Leu Ser Ala Ser Val Gly
1 5 10 15

Asp Arg Val Thr Ile Thr Cys
20

<210> SEQ ID NO 304
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 304

Trp Tyr Gln Gln Lys Pro Gly Gln Pro Pro Lys Ala Leu Ile Tyr
1 5 10 15

<210> SEQ ID NO 305
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 305

Gly Val Pro Asp Arg Phe Ser Gly Ser Gly Ser Gly Thr Asp Phe Thr
1 5 10 15

Leu Thr Ile Ser Ser Leu Gln Ala Glu Asp Val Ala Val Tyr Tyr Cys
20 25 30

<210> SEQ ID NO 306
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 306

Phe Gly Gln Gly Thr Lys Leu Glu Ile Lys
1 5 10

<210> SEQ ID NO 307
<211> LENGTH: 360
<212> TYPE: DNA
<213> ORGANISM: Artificial Sequence
<220> FEATURE:
<223> OTHER INFORMATION: Synthetic Polynucleotide

<400> SEQUENCE: 307
caggttcagt tggtgcagtc tggctccgag ctgaagaaac ctggcgcctc tgtgaaggtg 60
tcctgcaagg cttctggcta cacctttacc gactacaaca tggactggat ccggcagtcc 120
cctggcaaag gcctggaatg gatcggcgac atcaacccca acaacggcgg caccttctac 180
aaccagaagt tcaaggaccg ggctaccctg accgtggaca agtctacctc taccgcctac 240
atggaactgc ggtccctgag atctgacgac accgccgtgt actactgcgc cagagaggaa 300
aagctgtact tcggcctgat ggactactgg ggccagggaa caacagtaac cgtctcctca 360

<210> SEQ ID NO 308
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 308

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Ile Arg Gln Ser Pro Gly Lys Gly Leu Glu Trp Ile
        35                  40                  45

Gly Asp Ile Asn Pro Asn Asn Gly Gly Thr Phe Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Glu Lys Leu Tyr Phe Gly Leu Met Asp Tyr Trp Gly Gln
            100                 105                 110

Gly Thr Thr Val Thr Val Ser Ser
        115                 120
```

<210> SEQ ID NO 309
<211> LENGTH: 5
<212> TYPE: PRT
<213> ORGANISM: Mus musculus

<400> SEQUENCE: 309

```
Asp Tyr Asn Met Asp
1               5
```

<210> SEQ ID NO 310
<211> LENGTH: 17
<212> TYPE: PRT
<213> ORGANISM: Mus musculus

<400> SEQUENCE: 310

```
Asp Ile Asn Pro Asn Asn Gly Gly Thr Phe Tyr Asn Gln Lys Phe Lys
1               5                   10                  15

Asp
```

<210> SEQ ID NO 311
<211> LENGTH: 11
<212> TYPE: PRT
<213> ORGANISM: Mus musculus

<400> SEQUENCE: 311

```
Glu Glu Lys Leu Tyr Phe Gly Leu Met Asp Tyr
1               5                   10
```

<210> SEQ ID NO 312
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 312

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30


<210> SEQ ID NO 313
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 313

Trp Ile Arg Gln Ser Pro Gly Lys Gly Leu Glu Trp Ile Gly
1               5                   10


<210> SEQ ID NO 314
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 314

Arg Ala Thr Leu Thr Val Asp Lys Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30


<210> SEQ ID NO 315
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 315

Trp Gly Gln Gly Thr Thr Val Thr Val Ser Ser
1               5                   10


<210> SEQ ID NO 316
<211> LENGTH: 321
<212> TYPE: DNA
<213> ORGANISM: Artificial Sequence
<220> FEATURE:
<223> OTHER INFORMATION: Synthetic Polynucleotide

<400> SEQUENCE: 316

gacatccaga tgacccagtc tccatcctct ctgtccgcct ctgtgggcga cagagtgacc     60

atcacctgtc gggcctccga gaacatctac tcctacctgg cctggtatca gcagaagcct    120

ggcaaggctc ctaagctgct ggtgtacaac gctaagaccc tggctgaggg cgtgccctct    180

agatttctg gctccggctc tggcatcgac tttaccctga caatctccag cctgcagcct    240

gaggacttcg ccacctacta ctgccagcac cagtacggct ctccacctac ctttggccag    300

ggcaccaagc tcgagataaa a                                              321


<210> SEQ ID NO 317
<211> LENGTH: 107
<212> TYPE: PRT
<213> ORGANISM: Artificial Sequence
<220> FEATURE:
<223> OTHER INFORMATION: Synthetic Peptide
```

<400> SEQUENCE: 317

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Ala Lys Thr Leu Ala Glu Gly Val Pro Ser Arg Phe Ser Gly
    50                  55                  60

Ser Gly Ser Gly Ile Asp Phe Thr Leu Thr Ile Ser Ser Leu Gln Pro
65                  70                  75                  80

Glu Asp Phe Ala Thr Tyr Tyr Cys Gln His Gln Tyr Gly Ser Pro Pro
                85                  90                  95

Thr Phe Gly Gln Gly Thr Lys Leu Glu Ile Lys
            100                 105
```

<210> SEQ ID NO 318
<211> LENGTH: 11
<212> TYPE: PRT
<213> ORGANISM: Mus musculus

<400> SEQUENCE: 318

```
Arg Ala Ser Glu Asn Ile Tyr Ser Tyr Leu Ala
1               5                   10
```

<210> SEQ ID NO 319
<211> LENGTH: 7
<212> TYPE: PRT
<213> ORGANISM: Mus musculus

<400> SEQUENCE: 319

```
Asn Ala Lys Thr Leu Ala Glu
1               5
```

<210> SEQ ID NO 320
<211> LENGTH: 9
<212> TYPE: PRT
<213> ORGANISM: Mus musculus

<400> SEQUENCE: 320

```
Gln His Gln Tyr Gly Ser Pro Pro Thr
1               5
```

<210> SEQ ID NO 321
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 321

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 322
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 322

```
Trp Tyr Gln Gln Lys Pro Gly Lys Ala Pro Lys Leu Leu Val Tyr
1               5                   10                  15
```

<210> SEQ ID NO 323
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 323

```
Gly Val Pro Ser Arg Phe Ser Gly Ser Gly Ser Gly Ile Asp Phe Thr
1               5                   10                  15

Leu Thr Ile Ser Ser Leu Gln Pro Glu Asp Phe Ala Thr Tyr Tyr Cys
            20                  25                  30
```

<210> SEQ ID NO 324
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 324

```
Phe Gly Gln Gly Thr Lys Leu Glu Ile Lys
1               5                   10
```

<210> SEQ ID NO 325
<211> LENGTH: 360
<212> TYPE: DNA
<213> ORGANISM: Artificial Sequence
<220> FEATURE:
<223> OTHER INFORMATION: Synthetic Polynucleotide

<400> SEQUENCE: 325

```
caggttcagt tggtgcagtc tggctccgag ctgaagaaac ctggcgcctc tgtgaaggtg     60

tcctgcaagg cttctggcta cacctttacc gactacaaca tggactggat ccggcagtcc    120

cctggcaaag gcctggaatg gatcggcgac atcaacccca accagggcgg caccttctac    180

aaccagaagt tcaaggaccg ggctaccctg accgtggaca agtctacctc taccgcctac    240

atggaactgc ggtccctgag atctgacgac accgccgtgt actactgcgc cagagaggaa    300

aagctgtact tcggcctgat ggactactgg ggccagggaa caacagtaac cgtctcctca    360
```

<210> SEQ ID NO 326
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 326

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Ile Arg Gln Ser Pro Gly Lys Gly Leu Glu Trp Ile
        35                  40                  45

Gly Asp Ile Asn Pro Asn Gln Gly Gly Thr Phe Tyr Asn Gln Lys Phe
    50                  55                  60
```

```
Lys Asp Arg Ala Thr Leu Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Glu Lys Leu Tyr Phe Gly Leu Met Asp Tyr Trp Gly Gln
            100                 105                 110

Gly Thr Thr Val Thr Val Ser Ser
        115                 120


<210> SEQ ID NO 327
<211> LENGTH: 5
<212> TYPE: PRT
<213> ORGANISM: Mus musculus

<400> SEQUENCE: 327

Asp Tyr Asn Met Asp
1               5


<210> SEQ ID NO 328
<211> LENGTH: 17
<212> TYPE: PRT
<213> ORGANISM: Mus musculus

<400> SEQUENCE: 328

Asp Ile Asn Pro Asn Gln Gly Gly Thr Phe Tyr Asn Gln Lys Phe Lys
1               5                   10                  15

Asp


<210> SEQ ID NO 329
<211> LENGTH: 11
<212> TYPE: PRT
<213> ORGANISM: Mus musculus

<400> SEQUENCE: 329

Glu Glu Lys Leu Tyr Phe Gly Leu Met Asp Tyr
1               5                   10


<210> SEQ ID NO 330
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 330

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30


<210> SEQ ID NO 331
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 331

Trp Ile Arg Gln Ser Pro Gly Lys Gly Leu Glu Trp Ile Gly
1               5                   10


<210> SEQ ID NO 332
<211> LENGTH: 32
```

<212> TYPE: PRT
<213> ORGANISM: Artificial Sequence
<220> FEATURE:
<223> OTHER INFORMATION: Synthetic Peptide

<400> SEQUENCE: 332

Arg Ala Thr Leu Thr Val Asp Lys Ser Thr Ser Thr Ala Tyr Met Glu
1 5 10 15

Leu Arg Ser Leu Arg Ser Asp Asp Thr Ala Val Tyr Tyr Cys Ala Arg
20 25 30

<210> SEQ ID NO 333
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 333

Trp Gly Gln Gly Thr Thr Val Thr Val Ser Ser
1 5 10

<210> SEQ ID NO 334
<211> LENGTH: 321
<212> TYPE: DNA
<213> ORGANISM: Artificial Sequence
<220> FEATURE:
<223> OTHER INFORMATION: Synthetic Polynucleotide

<400> SEQUENCE: 334
gacatccaga tgacccagtc tccatcctct ctgtccgcct ctgtgggcga cagagtgacc 60
atcacctgtc gggcctccga gaacatctac tcctacctgg cctggtatca gcagaagcct 120
ggcaaggctc ctaagctgct ggtgtacaac gctaagaccc tggctgaggg cgtgccctct 180 agatttctg gctccggctc tggcatcgac tttaccctga caatctccag cctgcagcct 240
gaggacttcg ccacctacta ctgccagcac cagtacggct ctccacctac ctttggccag 300
ggcaccaagc tcgagataaa a 321

<210> SEQ ID NO 335
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 335

Asp Ile Gln Met Thr Gln Ser Pro Ser Ser Leu Ser Ala Ser Val Gly
1 5 10 15

Asp Arg Val Thr Ile Thr Cys Arg Ala Ser Glu Asn Ile Tyr Ser Tyr
20 25 30

Leu Ala Trp Tyr Gln Gln Lys Pro Gly Lys Ala Pro Lys Leu Leu Val
35 40 45

Tyr Asn Ala Lys Thr Leu Ala Glu Gly Val Pro Ser Arg Phe Ser Gly
50 55 60

Ser Gly Ser Gly Ile Asp Phe Thr Leu Thr Ile Ser Ser Leu Gln Pro
65 70 75 80

Glu Asp Phe Ala Thr Tyr Tyr Cys Gln His Gln Tyr Gly Ser Pro Pro
85 90 95

Thr Phe Gly Gln Gly Thr Lys Leu Glu Ile Lys
100 105

<210> SEQ ID NO 336
<211> LENGTH: 11
<212> TYPE: PRT
<213> ORGANISM: Mus musculus

<400> SEQUENCE: 336

Arg Ala Ser Glu Asn Ile Tyr Ser Tyr Leu Ala
1 5 10

<210> SEQ ID NO 337
<211> LENGTH: 7
<212> TYPE: PRT
<213> ORGANISM: Mus musculus

<400> SEQUENCE: 337

Asn Ala Lys Thr Leu Ala Glu
1 5

<210> SEQ ID NO 338
<211> LENGTH: 9
<212> TYPE: PRT
<213> ORGANISM: Mus musculus

<400> SEQUENCE: 338

Gln His Gln Tyr Gly Ser Pro Pro Thr
1 5

<210> SEQ ID NO 339
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 339

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 340
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 340

Trp Tyr Gln Gln Lys Pro Gly Lys Ala Pro Lys Leu Leu Val Tyr
1 5 10 15

<210> SEQ ID NO 341
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 341

Gly Val Pro Ser Arg Phe Ser Gly Ser Gly Ser Gly Ile Asp Phe Thr
1 5 10 15

Leu Thr Ile Ser Ser Leu Gln Pro Glu Asp Phe Ala Thr Tyr Tyr Cys
20 25 30

```
<210> SEQ ID NO 342
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 342

Phe Gly Gln Gly Thr Lys Leu Glu Ile Lys
1               5                   10


<210> SEQ ID NO 343
<211> LENGTH: 357
<212> TYPE: DNA
<213> ORGANISM: Artificial Sequence
<220> FEATURE:
<223> OTHER INFORMATION: Synthetic Polynucleotide

<400> SEQUENCE: 343

gaagtgcagt tggttgaatc tggcggcgga ctggttaagc ctggcggatc tctgagactg      60

tcttgtgccg cctccggctt caccttctcc tcttacgcta tgtcctgggt ccgacaggct     120

cctggcaaag gattggagtg ggtcgcctac atctcctccg gcggagacaa catctactac     180

gccgacaccg tgaagggcag attcaccatc tctcgggaca actccaagaa caccctgtac     240

ctgcagatga actccctgaa aaccgaggac accgccgtgt actactgcac aagagccctg     300

gtggaaaacg cctacttcga ctactggggc cagggaacaa cagtaaccgt ctcctca        357


<210> SEQ ID NO 344
<211> LENGTH: 119
<212> TYPE: PRT
<213> ORGANISM: Artificial Sequence
<220> FEATURE:
<223> OTHER INFORMATION: Synthetic Peptide

<400> SEQUENCE: 344

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Tyr Ile Ser Ser Gly Gly Asp Asn Ile Tyr Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Arg Ala Leu Val Glu Asn Ala Tyr Phe Asp Tyr Trp Gly Gln Gly
            100                 105                 110

Thr Thr Val Thr Val Ser Ser
        115


<210> SEQ ID NO 345
<211> LENGTH: 5
<212> TYPE: PRT
<213> ORGANISM: Mus musculus

<400> SEQUENCE: 345

Ser Tyr Ala Met Ser
1               5
```

<210> SEQ ID NO 346
<211> LENGTH: 17
<212> TYPE: PRT
<213> ORGANISM: Mus musculus

<400> SEQUENCE: 346

Tyr Ile Ser Ser Gly Gly Asp Asn Ile Tyr Tyr Ala Asp Thr Val Lys
1 5 10 15

Gly

<210> SEQ ID NO 347
<211> LENGTH: 10
<212> TYPE: PRT
<213> ORGANISM: Mus musculus

<400> SEQUENCE: 347

Ala Leu Val Glu Asn Ala Tyr Phe Asp Tyr
1 5 10

<210> SEQ ID NO 348
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 348

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser
20 25 30

<210> SEQ ID NO 349
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 349

Trp Val Arg Gln Ala Pro Gly Lys Gly Leu Glu Trp Val Ala
1 5 10

<210> SEQ ID NO 350
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 350

Arg Phe Thr Ile Ser Arg Asp Asn Ser Lys Asn Thr Leu Tyr Leu Gln
1 5 10 15

Met Asn Ser Leu Lys Thr Glu Asp Thr Ala Val Tyr Tyr Cys Thr Arg
20 25 30

<210> SEQ ID NO 351
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 351

Trp Gly Gln Gly Thr Thr Val Thr Val Ser Ser
1 5 10

<210> SEQ ID NO 352
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 352
gactctgtgc tgacccagtc tcctgactct ctggctgtgt ctctgggcga gagagccacc 60
atcaactgca gagcctccaa gtccgtgtcc acctccacct actcctacat gcactggtat 120
cagcagaagc ccggccagcc tcctaagctg ctgattaagt acgcctccta cctggaatcc 180
ggcgtgcccg atagattctc cggctctggc tctggcaccg acttcaccct gaagatctcc 240
agagtggaag ccgaggacgt gggcgtgtac tactgccagc actccagaga gttcccttgg 300
acctttggcg gaggcaccaa ggtggaaatc aaa 333

<210> SEQ ID NO 353
<211> LENGTH: 111
<212> TYPE: PRT
<213> ORGANISM: Artificial Sequence
<220> FEATURE:
<223> OTHER INFORMATION: Synthetic Peptide

<400> SEQUENCE: 353

Asp Ser Val Leu Thr Gln Ser Pro Asp Ser Leu Ala Val Ser Leu Gly
1 5 10 15

Glu Arg Ala Thr Ile Asn Cys Arg Ala Ser Lys Ser Val Ser Thr Ser
20 25 30

Thr Tyr Ser Tyr Met His Trp Tyr Gln Gln Lys Pro Gly Gln Pro Pro
35 40 45

Lys Leu Leu Ile Lys Tyr Ala Ser Tyr Leu Glu Ser Gly Val Pro Asp
50 55 60

Arg Phe Ser Gly Ser Gly Ser Gly Thr Asp Phe Thr Leu Lys Ile Ser
65 70 75 80

Arg Val Glu Ala Glu Asp Val Gly Val Tyr Tyr Cys Gln His Ser Arg
85 90 95

Glu Phe Pro Trp Thr Phe Gly Gly Gly Thr Lys Val Glu Ile Lys
100 105 110

<210> SEQ ID NO 354
<211> LENGTH: 15
<212> TYPE: PRT
<213> ORGANISM: Mus musculus

<400> SEQUENCE: 354

Arg Ala Ser Lys Ser Val Ser Thr Ser Thr Tyr Ser Tyr Met His
1 5 10 15

<210> SEQ ID NO 355
<211> LENGTH: 7
<212> TYPE: PRT
<213> ORGANISM: Mus musculus

<400> SEQUENCE: 355

Tyr Ala Ser Tyr Leu Glu Ser
1 5

<210> SEQ ID NO 356
<211> LENGTH: 9
<212> TYPE: PRT
<213> ORGANISM: Mus musculus

<400> SEQUENCE: 356

```
Gln His Ser Arg Glu Phe Pro Trp Thr
1               5
```

<210> SEQ ID NO 357
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 357

```
Asp Ser Val Leu Thr Gln Ser Pro Asp Ser Leu Ala Val Ser Leu Gly
1               5                   10                  15

Glu Arg Ala Thr Ile Asn Cys
            20
```

<210> SEQ ID NO 358
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 358

```
Trp Tyr Gln Gln Lys Pro Gly Gln Pro Pro Lys Leu Leu Ile Lys
1               5                   10                  15
```

<210> SEQ ID NO 359
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 359

```
Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30
```

<210> SEQ ID NO 360
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 360

```
Phe Gly Gly Gly Thr Lys Val Glu Ile Lys
1               5                   10
```

<210> SEQ ID NO 361
<211> LENGTH: 357
<212> TYPE: DNA
<213> ORGANISM: Artificial Sequence
<220> FEATURE:
<223> OTHER INFORMATION: Synthetic Polynucleotide

<400> SEQUENCE: 361

```
gaagtgcagt tggttgaatc tggcggcgga ctggttaagc ctggcggatc tctgagactg     60
```

```
tcttgtgccg cctccggctt caccttctcc tcttacgcta tgtcctgggt ccgacaggct    120

cctggcaaag gattggagtg ggtcgcctac atctcctccg gcggagacta catctactac    180

gccgacaccg tgaagggcag attcaccatc tctcgggaca actccaagaa caccctgtac    240

ctgcagatga actccctgaa aaccgaggac accgccgtgt actactgcac aagagccctg    300

gtggacaacg cctacttcga ctattggggc cagggaacaa ccgtaaccgt ctcctca       357


<210> SEQ ID NO 362
<211> LENGTH: 119
<212> TYPE: PRT
<213> ORGANISM: Artificial Sequence
<220> FEATURE:
<223> OTHER INFORMATION: Synthetic Peptide

<400> SEQUENCE: 362

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Tyr Ile Ser Ser Gly Gly Asp Tyr Ile Tyr Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Arg Ala Leu Val Asp Asn Ala Tyr Phe Asp Tyr Trp Gly Gln Gly
            100                 105                 110

Thr Thr Val Thr Val Ser Ser
        115


<210> SEQ ID NO 363
<211> LENGTH: 5
<212> TYPE: PRT
<213> ORGANISM: Mus musculus

<400> SEQUENCE: 363

Ser Tyr Ala Met Ser
1               5


<210> SEQ ID NO 364
<211> LENGTH: 17
<212> TYPE: PRT
<213> ORGANISM: Mus musculus

<400> SEQUENCE: 364

Tyr Ile Ser Ser Gly Gly Asp Tyr Ile Tyr Tyr Ala Asp Thr Val Lys
1               5                   10                  15

Gly


<210> SEQ ID NO 365
<211> LENGTH: 10
<212> TYPE: PRT
<213> ORGANISM: Mus musculus

<400> SEQUENCE: 365

Ala Leu Val Asp Asn Ala Tyr Phe Asp Tyr
1               5                   10
```

<210> SEQ ID NO 366
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 366

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser
20 25 30

<210> SEQ ID NO 367
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 367

Trp Val Arg Gln Ala Pro Gly Lys Gly Leu Glu Trp Val Ala
1 5 10

<210> SEQ ID NO 368
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 368

Arg Phe Thr Ile Ser Arg Asp Asn Ser Lys Asn Thr Leu Tyr Leu Gln
1 5 10 15

Met Asn Ser Leu Lys Thr Glu Asp Thr Ala Val Tyr Tyr Cys Thr Arg
20 25 30

<210> SEQ ID NO 369
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 369

Trp Gly Gln Gly Thr Thr Val Thr Val Ser Ser
1 5 10

<210> SEQ ID NO 370
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 370
gacatcgtgc tgacccagtc tccagactct ctggctgtgt ctctgggcga gagagccacc 60
atcaactgca gagcctccaa gtccgtgtcc acctcctcct actcctacat gcactggtat 120
cagcagaagc ccggccagcc tcctaagctg ctgattaagt acgcctccta cctggaattc 180
ggcgtgccct ctagattctc cggctctggc tctggcaccg actttaccct gacaatctcc 240
agcctgcagc ctgaggatgt ggccacctac tactgccagc actccagaga gttcccttgg 300

```
acctttggcg gaggcaccaa ggtggaaatc aaa                          333


<210> SEQ ID NO 371
<211> LENGTH: 111
<212> TYPE: PRT
<213> ORGANISM: Artificial Sequence
<220> FEATURE:
<223> OTHER INFORMATION: Synthetic Peptide

<400> SEQUENCE: 371

Asp Ile Val Leu Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Phe Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Gln His Ser Arg
                85                  90                  95

Glu Phe Pro Trp Thr Phe Gly Gly Gly Thr Lys Val Glu Ile Lys
            100                 105                 110


<210> SEQ ID NO 372
<211> LENGTH: 15
<212> TYPE: PRT
<213> ORGANISM: Mus musculus

<400> SEQUENCE: 372

Arg Ala Ser Lys Ser Val Ser Thr Ser Ser Tyr Ser Tyr Met His
1               5                   10                  15


<210> SEQ ID NO 373
<211> LENGTH: 7
<212> TYPE: PRT
<213> ORGANISM: Mus musculus

<400> SEQUENCE: 373

Tyr Ala Ser Tyr Leu Glu Phe
1               5


<210> SEQ ID NO 374
<211> LENGTH: 9
<212> TYPE: PRT
<213> ORGANISM: Mus musculus

<400> SEQUENCE: 374

Gln His Ser Arg Glu Phe Pro Trp Thr
1               5


<210> SEQ ID NO 375
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 375

Asp Ile Val Leu Thr Gln Ser Pro Asp Ser Leu Ala Val Ser Leu Gly
1               5                   10                  15
```

Glu Arg Ala Thr Ile Asn Cys
            20

<210> SEQ ID NO 376
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 376

Trp Tyr Gln Gln Lys Pro Gly Gln Pro Pro Lys Leu Leu Ile Lys
1               5                   10                  15

<210> SEQ ID NO 377
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 377

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 378
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 378

Phe Gly Gly Gly Thr Lys Val Glu Ile Lys
1               5                   10

<210> SEQ ID NO 379
<211> LENGTH: 357
<212> TYPE: DNA
<213> ORGANISM: Artificial Sequence
<220> FEATURE:
<223> OTHER INFORMATION: Synthetic Polynucleotide

<400> SEQUENCE: 379
caagtacagc tgcaagagtc tggacccggc ctgctgaagc cttctcagac cctgtctctg     60
acctgcaccg tgtctggctt ctccctgatc acctctggcc tgggcgtgtc ctggattaga    120
cagcctgctg gcaaaggcct ggaatggctg gctcacatct actgggacga cgacaagcgg    180
tacaacccca gcctgaagtc tcggctgacc atctccaagg acacctccaa gaaccaggtg    240
tccctgaagc tgtcctctgt gaccgctgct gataccgccg tgtactactg tgctagaggc    300
ggctacgacg gctactacga ttattggggc cagggaacaa ccgtaaccgt ctcctca       357

<210> SEQ ID NO 380
<211> LENGTH: 119
<212> TYPE: PRT
<213> ORGANISM: Artificial Sequence
<220> FEATURE:
<223> OTHER INFORMATION: Synthetic Peptide

<400> SEQUENCE: 380

Gln Val Gln Leu Gln Glu Ser Gly Pro Gly Leu Leu Lys Pro Ser Gln
1               5                   10                  15

```
Thr Leu Ser Leu Thr Cys Thr Val Ser Gly Phe Ser Leu Ile Thr Ser
            20                  25                  30

Gly Leu Gly Val Ser Trp Ile Arg Gln Pro Ala Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Lys Asn Gln Val
65                  70                  75                  80

Ser Leu Lys Leu Ser Ser Val Thr Ala Ala Asp Thr Ala Val Tyr Tyr
                85                  90                  95

Cys Ala Arg Gly Gly Tyr Asp Gly Tyr Tyr Asp Tyr Trp Gly Gln Gly
            100                 105                 110

Thr Thr Val Thr Val Ser Ser
        115


<210> SEQ ID NO 381
<211> LENGTH: 7
<212> TYPE: PRT
<213> ORGANISM: Mus musculus

<400> SEQUENCE: 381

Thr Ser Gly Leu Gly Val Ser
1               5


<210> SEQ ID NO 382
<211> LENGTH: 16
<212> TYPE: PRT
<213> ORGANISM: Mus musculus

<400> SEQUENCE: 382

His Ile Tyr Trp Asp Asp Asp Lys Arg Tyr Asn Pro Ser Leu Lys Ser
1               5                   10                  15


<210> SEQ ID NO 383
<211> LENGTH: 9
<212> TYPE: PRT
<213> ORGANISM: Mus musculus

<400> SEQUENCE: 383

Gly Gly Tyr Asp Gly Tyr Tyr Asp Tyr
1               5


<210> SEQ ID NO 384
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 384

Gln Val Gln Leu Gln Glu Ser Gly Pro Gly Leu Leu Lys Pro Ser Gln
1               5                   10                  15

Thr Leu Ser Leu Thr Cys Thr Val Ser Gly Phe Ser Leu Ile
            20                  25                  30


<210> SEQ ID NO 385
<211> LENGTH: 14
<212> TYPE: PRT
<213> ORGANISM: Artificial Sequence
<220> FEATURE:
<223> OTHER INFORMATION: Synthetic Peptide
```

<400> SEQUENCE: 385

Trp Ile Arg Gln Pro Ala Gly Lys Gly Leu Glu Trp Leu Ala
1 5 10

<210> SEQ ID NO 386
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 386

Arg Leu Thr Ile Ser Lys Asp Thr Ser Lys Asn Gln Val Ser Leu Lys
1 5 10 15

Leu Ser Ser Val Thr Ala Ala Asp Thr Ala Val Tyr Tyr Cys Ala Arg
20 25 30

<210> SEQ ID NO 387
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 387

Trp Gly Gln Gly Thr Thr Val Thr Val Ser Ser
1 5 10

<210> SEQ ID NO 388
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 388
gacgtggtca tgacacagtc tccactgagc ctgcctgtga cactgggaca gcctgcctcc 60
atctcctgca gatcctctca gtccatcgtg cattccaacg gcaacaccaa cctggaatgg 120
tatctgcaga agcccggcca gtctcctcag ctgctgatct acaaggtgtc caaccggctg 180
tctggcgtgc ccgatagatt ttccggctct ggctctggca ccgacttcac cctgaagatc 240
tccagagtgg aagccgagga cgtgggcgtg tactactgct tccaaggctc tcacgtgcgg 300
acctttggcc agggcacaaa gctggaaatc aaa 333

<210> SEQ ID NO 389
<211> LENGTH: 111
<212> TYPE: PRT
<213> ORGANISM: Artificial Sequence
<220> FEATURE:
<223> OTHER INFORMATION: Synthetic Peptide

<400> SEQUENCE: 389

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Ile Val His Ser
20 25 30

Asn Gly Asn Thr Asn Leu Glu Trp Tyr Leu Gln Lys Pro Gly Gln Ser
35 40 45

Pro Gln Leu Leu Ile Tyr Lys Val Ser Asn Arg Leu Ser Gly Val Pro
50 55 60

Asp Arg Phe Ser Gly Ser Gly Ser Gly Thr Asp Phe Thr Leu Lys Ile 65 70 75 80

Ser Arg Val Glu Ala Glu Asp Val Gly Val Tyr Tyr Cys Phe Gln Gly
85 90 95

Ser His Val Arg Thr Phe Gly Gln Gly Thr Lys Leu Glu Ile Lys
100 105 110

<210> SEQ ID NO 390
<211> LENGTH: 16
<212> TYPE: PRT
<213> ORGANISM: Mus musculus

<400> SEQUENCE: 390

Arg Ser Ser Gln Ser Ile Val His Ser Asn Gly Asn Thr Asn Leu Glu
1 5 10 15

<210> SEQ ID NO 391
<211> LENGTH: 7
<212> TYPE: PRT
<213> ORGANISM: Mus musculus

<400> SEQUENCE: 391

Lys Val Ser Asn Arg Leu Ser
1 5

<210> SEQ ID NO 392
<211> LENGTH: 8
<212> TYPE: PRT
<213> ORGANISM: Mus musculus

<400> SEQUENCE: 392

Phe Gln Gly Ser His Val Arg Thr
1 5

<210> SEQ ID NO 393
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 393

Asp Val Val Met Thr Gln Ser Pro Leu Ser Leu Pro Val Thr Leu Gly
1 5 10 15

Gln Pro Ala Ser Ile Ser Cys
20

<210> SEQ ID NO 394
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 394

Trp Tyr Leu Gln Lys Pro Gly Gln Ser Pro Gln Leu Leu Ile Tyr
1 5 10 15

<210> SEQ ID NO 395
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 395

```
Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30


<210> SEQ ID NO 396
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 396

Phe Gly Gln Gly Thr Lys Leu Glu Ile Lys
1               5                   10


<210> SEQ ID NO 397
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 397

caagttcagc tggtgcagtc tggctccgag ctgaagaaac ctggcgcctc tgtgaaggtg     60

tcctgcaagg cttccggcta cacctttacc agctacgaca tcaactgggt ccgacaggct    120

cctggacagg gactcgaatg gatcggctgg atctacccca gagatggcat ctccaagtac    180

aacgagaagt tcaagggcag agctaccctg accgtggaca cctctgcttc caccgcctac    240

atggaactgt ccagcctgag atctgaggac accgccgtgt actactgcgc cggcacatac    300

gatcctgcct acttcgatta ttggggccag ggaacaaccg taaccgtctc ctca          354


<210> SEQ ID NO 398
<211> LENGTH: 118
<212> TYPE: PRT
<213> ORGANISM: Artificial Sequence
<220> FEATURE:
<223> OTHER INFORMATION: Synthetic Peptide

<400> SEQUENCE: 398

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Ile
        35                  40                  45

Gly Trp Ile Tyr Pro Arg Asp Gly Ile Ser Lys Tyr Asn Glu Lys Phe
    50                  55                  60

Lys Gly Arg Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Thr Tyr Asp Pro Ala Tyr Phe Asp Tyr Trp Gly Gln Gly Thr
            100                 105                 110

Thr Val Thr Val Ser Ser
        115


<210> SEQ ID NO 399
<211> LENGTH: 5
```

<212> TYPE: PRT
<213> ORGANISM: Mus musculus

<400> SEQUENCE: 399

Ser Tyr Asp Ile Asn
1 5

<210> SEQ ID NO 400
<211> LENGTH: 17
<212> TYPE: PRT
<213> ORGANISM: Mus musculus

<400> SEQUENCE: 400

Trp Ile Tyr Pro Arg Asp Gly Ile Ser Lys Tyr Asn Glu Lys Phe Lys
1 5 10 15

Gly

<210> SEQ ID NO 401
<211> LENGTH: 9
<212> TYPE: PRT
<213> ORGANISM: Mus musculus

<400> SEQUENCE: 401

Thr Tyr Asp Pro Ala Tyr Phe Asp Tyr
1 5

<210> SEQ ID NO 402
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 402

Gln Val Gln Leu Val Gln Ser Gly Ser Glu Leu Lys Lys Pro Gly Ala
1 5 10 15

Ser Val Lys Val Ser Cys Lys Ala Ser Gly Tyr Thr Phe Thr
20 25 30

<210> SEQ ID NO 403
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 403

Trp Val Arg Gln Ala Pro Gly Gln Gly Leu Glu Trp Ile Gly
1 5 10

<210> SEQ ID NO 404
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 404

Arg Ala Thr Leu Thr Val Asp Thr Ser Ala Ser Thr Ala Tyr Met Glu
1 5 10 15

Leu Ser Ser Leu Arg Ser Glu Asp Thr Ala Val Tyr Tyr Cys Ala Gly
20 25 30

<210> SEQ ID NO 405

<211> LENGTH: 11
<212> TYPE: PRT
<213> ORGANISM: Artificial Sequence
<220> FEATURE:
<223> OTHER INFORMATION: Synthetic Peptide

<400> SEQUENCE: 405

```
Trp Gly Gln Gly Thr Thr Val Thr Val Ser Ser
1               5                   10
```

<210> SEQ ID NO 406
<211> LENGTH: 321
<212> TYPE: DNA
<213> ORGANISM: Artificial Sequence
<220> FEATURE:
<223> OTHER INFORMATION: Synthetic Polynucleotide

<400> SEQUENCE: 406

```
gaaatcgtgc tgacccagtc tcctgccaca ctgagtgtgt ctccaggcga gagagctacc     60

ctgtcctgta gagcctctca gtccatctcc tactacctgc actggtatca gcagaagccc    120

ggccaggctc ctcggctgct gattaagtac gccagccagt ctatctccgg cgtgcccgat    180

agattctccg gctctggctc tggcaccgac ttcaccctga agatctccag agtggaagcc    240

gaggacttcg gcgtgtacta ctgccagcag tccaactcct ggccttacac ctttggcgga    300

ggcaccaagg tggaaatcaa a                                              321
```

<210> SEQ ID NO 407
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 407

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Ile Ser Tyr Tyr
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Phe Gly Val Tyr Tyr Cys Gln Gln Ser Asn Ser Trp Pro Tyr
                85                  90                  95

Thr Phe Gly Gly Gly Thr Lys Val Glu Ile Lys
            100                 105
```

<210> SEQ ID NO 408
<211> LENGTH: 11
<212> TYPE: PRT
<213> ORGANISM: Mus musculus

<400> SEQUENCE: 408

```
Arg Ala Ser Gln Ser Ile Ser Tyr Tyr Leu His
1               5                   10
```

<210> SEQ ID NO 409
<211> LENGTH: 7
<212> TYPE: PRT

<213> ORGANISM: Mus musculus

<400> SEQUENCE: 409

Tyr Ala Ser Gln Ser Ile Ser
1 5

<210> SEQ ID NO 410
<211> LENGTH: 9
<212> TYPE: PRT
<213> ORGANISM: Mus musculus

<400> SEQUENCE: 410

Gln Gln Ser Asn Ser Trp Pro Tyr Thr
1 5

<210> SEQ ID NO 411
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 411

Glu Ile Val Leu Thr Gln Ser Pro Ala Thr Leu Ser Val Ser Pro Gly
1 5 10 15

Glu Arg Ala Thr Leu Ser Cys
20

<210> SEQ ID NO 412
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 412

Trp Tyr Gln Gln Lys Pro Gly Gln Ala Pro Arg Leu Leu Ile Lys
1 5 10 15

<210> SEQ ID NO 413
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 413

Gly Val Pro Asp Arg Phe Ser Gly Ser Gly Ser Gly Thr Asp Phe Thr
1 5 10 15

Leu Lys Ile Ser Arg Val Glu Ala Glu Asp Phe Gly Val Tyr Tyr Cys
20 25 30

<210> SEQ ID NO 414
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 414

Phe Gly Gly Gly Thr Lys Val Glu Ile Lys
1 5 10

<210> SEQ ID NO 415
<211> LENGTH: 357

```
<212> TYPE: DNA
<213> ORGANISM: Artificial Sequence
<220> FEATURE:
<223> OTHER INFORMATION: Synthetic Polynucleotide

<400> SEQUENCE: 415

caagttcagc tggtgcagtc tggctccgag ctgaagaaac ctggcgcctc tgtgaaggtg     60

tcctgcaagg cttctggcta cacctttacc gactacaaca tggactgggt ccgacaggct    120

cctggcaaag gcctggaatg gatcggcgac atcaacccct acaacggcat caccatctac    180

aaccagaagt tcaagggcag agctaccctg accgtggaca agtctacctc caccgcctac    240

atggaactgc ggtccctgag atctgacgac accgccgtgt actactgcgc cagagaggaa    300

aagctgggca cctccttcga ttactggggc cagggaacaa ccgtaaccgt ctcctca       357


<210> SEQ ID NO 416
<211> LENGTH: 119
<212> TYPE: PRT
<213> ORGANISM: Artificial Sequence
<220> FEATURE:
<223> OTHER INFORMATION: Synthetic Peptide

<400> SEQUENCE: 416

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Lys Gly Leu Glu Trp Ile
        35                  40                  45

Gly Asp Ile Asn Pro Tyr Asn Gly Ile Thr Ile Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Glu Lys Leu Gly Thr Ser Phe Asp Tyr Trp Gly Gln Gly
            100                 105                 110

Thr Thr Val Thr Val Ser Ser
        115


<210> SEQ ID NO 417
<211> LENGTH: 5
<212> TYPE: PRT
<213> ORGANISM: Mus musculus

<400> SEQUENCE: 417

Asp Tyr Asn Met Asp
1               5


<210> SEQ ID NO 418
<211> LENGTH: 17
<212> TYPE: PRT
<213> ORGANISM: Mus musculus

<400> SEQUENCE: 418

Asp Ile Asn Pro Tyr Asn Gly Ile Thr Ile Tyr Asn Gln Lys Phe Lys
1               5                   10                  15

Gly


<210> SEQ ID NO 419
```

<211> LENGTH: 10
<212> TYPE: PRT
<213> ORGANISM: Mus musculus

<400> SEQUENCE: 419

Glu Glu Lys Leu Gly Thr Ser Phe Asp Tyr
1 5 10

<210> SEQ ID NO 420
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 420

Gln Val Gln Leu Val Gln Ser Gly Ser Glu Leu Lys Lys Pro Gly Ala
1 5 10 15

Ser Val Lys Val Ser Cys Lys Ala Ser Gly Tyr Thr Phe Thr
20 25 30

<210> SEQ ID NO 421
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 421

Trp Val Arg Gln Ala Pro Gly Lys Gly Leu Glu Trp Ile Gly
1 5 10

<210> SEQ ID NO 422
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 422

Arg Ala Thr Leu Thr Val Asp Lys Ser Thr Ser Thr Ala Tyr Met Glu
1 5 10 15

Leu Arg Ser Leu Arg Ser Asp Asp Thr Ala Val Tyr Tyr Cys Ala Arg
20 25 30

<210> SEQ ID NO 423
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 423

Trp Gly Gln Gly Thr Thr Val Thr Val Ser Ser
1 5 10

<210> SEQ ID NO 424
<211> LENGTH: 321
<212> TYPE: DNA
<213> ORGANISM: Artificial Sequence
<220> FEATURE:
<223> OTHER INFORMATION: Synthetic Polynucleotide

<400> SEQUENCE: 424
gacatccaga tgacccagtc tccatcctct ctgtccgcct ctgtgggcga cagagtgacc 60

```
atcacctgtc gggcctccga gaacatctac tccaacctgg cctggtatca gcagaagcct    120

ggcaaggctc ctaagctgct ggtgtacgcc gctaccaatc tggctgatgg cgtgccctct    180

agattctccg gctctggctc tggcaccgac tttaccctga caatctccag cctgcagcct    240

gaggacttcg ccacctacta ctgccagcac ttctacggca ccccttggac ctttggccag    300

ggcaccaagc tggaaatcaa a                                               321


<210> SEQ ID NO 425
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 425

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Thr Pro Trp
                85                  90                  95

Thr Phe Gly Gln Gly Thr Lys Leu Glu Ile Lys
            100                 105


<210> SEQ ID NO 426
<211> LENGTH: 11
<212> TYPE: PRT
<213> ORGANISM: Mus musculus

<400> SEQUENCE: 426

Arg Ala Ser Glu Asn Ile Tyr Ser Asn Leu Ala
1               5                   10


<210> SEQ ID NO 427
<211> LENGTH: 7
<212> TYPE: PRT
<213> ORGANISM: Mus musculus

<400> SEQUENCE: 427

Ala Ala Thr Asn Leu Ala Asp
1               5


<210> SEQ ID NO 428
<211> LENGTH: 9
<212> TYPE: PRT
<213> ORGANISM: Mus musculus

<400> SEQUENCE: 428

Gln His Phe Tyr Gly Thr Pro Trp Thr
1               5


<210> SEQ ID NO 429
<211> LENGTH: 23
<212> TYPE: PRT
<213> ORGANISM: Artificial Sequence
```

<220> FEATURE:
<223> OTHER INFORMATION: Synthetic Peptide

<400> SEQUENCE: 429

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 430
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 430

Trp Tyr Gln Gln Lys Pro Gly Lys Ala Pro Lys Leu Leu Val Tyr
1 5 10 15

<210> SEQ ID NO 431
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 431

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 432
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 432

Phe Gly Gln Gly Thr Lys Leu Glu Ile Lys
1 5 10

<210> SEQ ID NO 433
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 433
caagttcagc tgcaagagtc tggacccggc ctgctgaagc cttctcagac cctgtctctg 60
acctgcaccg tgtctggctt ctccctgtct acctatggca tgggcgtcgg ctggatcaga 120
cagcctctcg gcaaaggact ggaatggctg gccaacatct ggtggaacga cgacaagtac 180
tacaacagcg ccctgaagtc ccggctgacc atctccaagg acacctccaa gaaccaggtg 240
tccctgaagc tgtcctctgt gaccgctgct gataccgccg tgtactactg tgcccagatg 300
gcctacagtt ggttcgccta ttggggccag ggaaccctcg taaccgtctc ctca 354

<210> SEQ ID NO 434
<211> LENGTH: 118
<212> TYPE: PRT

```
<213> ORGANISM: Artificial Sequence
<220> FEATURE:
<223> OTHER INFORMATION: Synthetic Peptide

<400> SEQUENCE: 434

Gln Val Gln Leu Gln Glu Ser Gly Pro Gly Leu Leu Lys Pro Ser Gln
1               5                   10                  15

Thr Leu Ser Leu Thr Cys Thr Val Ser Gly Phe Ser Leu Ser Thr Tyr
            20                  25                  30

Gly Met Gly Val Gly Trp Ile Arg Gln Pro Leu Gly Lys Gly Leu Glu
        35                  40                  45

Trp Leu Ala Asn Ile Trp Trp Asn Asp Asp Lys Tyr Tyr Asn Ser Ala
    50                  55                  60

Leu Lys Ser Arg Leu Thr Ile Ser Lys Asp Thr Ser Lys Asn Gln Val
65                  70                  75                  80

Ser Leu Lys Leu Ser Ser Val Thr Ala Ala Asp Thr Ala Val Tyr Tyr
                85                  90                  95

Cys Ala Gln Met Ala Tyr Ser Trp Phe Ala Tyr Trp Gly Gln Gly Thr
            100                 105                 110

Leu Val Thr Val Ser Ser
        115


<210> SEQ ID NO 435
<211> LENGTH: 7
<212> TYPE: PRT
<213> ORGANISM: Mus musculus

<400> SEQUENCE: 435

Thr Tyr Gly Met Gly Val Gly
1               5


<210> SEQ ID NO 436
<211> LENGTH: 16
<212> TYPE: PRT
<213> ORGANISM: Mus musculus

<400> SEQUENCE: 436

Asn Ile Trp Trp Asn Asp Asp Lys Tyr Tyr Asn Ser Ala Leu Lys Ser
1               5                   10                  15


<210> SEQ ID NO 437
<211> LENGTH: 8
<212> TYPE: PRT
<213> ORGANISM: Mus musculus

<400> SEQUENCE: 437

Met Ala Tyr Ser Trp Phe Ala Tyr
1               5


<210> SEQ ID NO 438
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 438

Gln Val Gln Leu Gln Glu Ser Gly Pro Gly Leu Leu Lys Pro Ser Gln
1               5                   10                  15

Thr Leu Ser Leu Thr Cys Thr Val Ser Gly Phe Ser Leu Ser
            20                  25                  30
```

<210> SEQ ID NO 439
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 439

Trp Ile Arg Gln Pro Leu Gly Lys Gly Leu Glu Trp Leu Ala
1               5                   10

<210> SEQ ID NO 440
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 440

Arg Leu Thr Ile Ser Lys Asp Thr Ser Lys Asn Gln Val Ser Leu Lys
1               5                   10                  15

Leu Ser Ser Val Thr Ala Ala Asp Thr Ala Val Tyr Tyr Cys Ala Gln
            20                  25                  30

<210> SEQ ID NO 441
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 441

Trp Gly Gln Gly Thr Leu Val Thr Val Ser Ser
1               5                   10

<210> SEQ ID NO 442
<211> LENGTH: 321
<212> TYPE: DNA
<213> ORGANISM: Artificial Sequence
<220> FEATURE:
<223> OTHER INFORMATION: Synthetic Polynucleotide

<400> SEQUENCE: 442
gacatccaga tgacccagtc tccatccttc ctgtccgcct ctgtgggcga cagagtgacc     60
atcacatgca aggccagcca gaacatggac accaacgtgg cctggtatca gcagaagcct    120
ggccagcctc ctaaggctct gatctactcc gcctcctacc ggtactctgg cgtgcccgat    180
agattctccg gctctggctc tggcaccgac tttaccctga caatcagctc cctgcaggcc    240
gaggatgtgg ccgtgtacta ctgccagcag tacaacagct acccctcac ctttggccag    300 ggcaccaagc tggaaatcaa a                                               321

<210> SEQ ID NO 443
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 443

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Met Asp Thr Asn
            20                  25                  30

```
Val Ala Trp Tyr Gln Gln Lys Pro Gly Gln Pro Pro Lys Ala Leu Ile
        35                  40                  45

Tyr Ser Ala Ser Tyr Arg Tyr Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Asn Ser Tyr Pro Phe
                85                  90                  95

Thr Phe Gly Gln Gly Thr Lys Leu Glu Ile Lys
            100                 105


<210> SEQ ID NO 444
<211> LENGTH: 11
<212> TYPE: PRT
<213> ORGANISM: Mus musculus

<400> SEQUENCE: 444

Lys Ala Ser Gln Asn Met Asp Thr Asn Val Ala
1               5                   10


<210> SEQ ID NO 445
<211> LENGTH: 7
<212> TYPE: PRT
<213> ORGANISM: Mus musculus

<400> SEQUENCE: 445

Ser Ala Ser Tyr Arg Tyr Ser
1               5


<210> SEQ ID NO 446
<211> LENGTH: 9
<212> TYPE: PRT
<213> ORGANISM: Mus musculus

<400> SEQUENCE: 446

Gln Gln Tyr Asn Ser Tyr Pro Phe Thr
1               5


<210> SEQ ID NO 447
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 447

Asp Ile Gln Met Thr Gln Ser Pro Ser Phe Leu Ser Ala Ser Val Gly
1               5                   10                  15

Asp Arg Val Thr Ile Thr Cys
            20


<210> SEQ ID NO 448
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 448

Trp Tyr Gln Gln Lys Pro Gly Gln Pro Pro Lys Ala Leu Ile Tyr
1               5                   10                  15
```

<210> SEQ ID NO 449
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 449

```
Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30
```

<210> SEQ ID NO 450
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 450

```
Phe Gly Gln Gly Thr Lys Leu Glu Ile Lys
1               5                   10
```

<210> SEQ ID NO 451
<211> LENGTH: 354
<212> TYPE: DNA
<213> ORGANISM: Mus musculus

<400> SEQUENCE: 451

```
caggtccaac tgcagcagcc tggggctgag cttgtgatgc ctggggcttc agtgaagatg     60

tcctgcaagg cttctggcta cacattcact gactattgga tgcactgggt gaagcagagg    120

cctggacaag gccttgagtg gatcggagtg attgatactt ctgaaagtta tactagctac    180

aatcaaaagt tcaagggcaa ggccacattg actgtagacg aatcctccag cacagcctac    240

atgcagctca gcagcctgac atctgaggac tctgcggtct atttctgtgc aagagggggt    300

actacggtag tactcgacta ctggggccaa ggcaccactc tcaccgtctc ctca          354
```

<210> SEQ ID NO 452
<211> LENGTH: 118
<212> TYPE: PRT
<213> ORGANISM: Mus musculus

<400> SEQUENCE: 452

```
Gln Val Gln Leu Gln Gln Pro Gly Ala Glu Leu Val Met Pro Gly Ala
1               5                   10                  15

Ser Val Lys Met Ser Cys Lys Ala Ser Gly Tyr Thr Phe Thr Asp Tyr
            20                  25                  30

Trp Met His Trp Val Lys Gln Arg Pro Gly Gln Gly Leu Glu Trp Ile
        35                  40                  45

Gly Val Ile Asp Thr Ser Glu Ser Tyr Thr Ser Tyr Asn Gln Lys Phe
    50                  55                  60

Lys Gly Lys Ala Thr Leu Thr Val Asp Glu Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Thr Thr Val Val Leu Asp Tyr Trp Gly Gln Gly Thr
            100                 105                 110

Thr Leu Thr Val Ser Ser
        115
```

<210> SEQ ID NO 453
<211> LENGTH: 5
<212> TYPE: PRT
<213> ORGANISM: Mus musculus

<400> SEQUENCE: 453

Asp Tyr Trp Met His
1               5

<210> SEQ ID NO 454
<211> LENGTH: 17
<212> TYPE: PRT
<213> ORGANISM: Mus musculus

<400> SEQUENCE: 454

Val Ile Asp Thr Ser Glu Ser Tyr Thr Ser Tyr Asn Gln Lys Phe Lys
1               5                   10                  15

Gly

<210> SEQ ID NO 455
<211> LENGTH: 9
<212> TYPE: PRT
<213> ORGANISM: Mus musculus

<400> SEQUENCE: 455

Gly Gly Thr Thr Val Val Leu Asp Tyr
1               5

<210> SEQ ID NO 456
<211> LENGTH: 30
<212> TYPE: PRT
<213> ORGANISM: Mus musculus

<400> SEQUENCE: 456

Gln Val Gln Leu Gln Gln Pro Gly Ala Glu Leu Val Met Pro Gly Ala
1               5                   10                  15

Ser Val Lys Met Ser Cys Lys Ala Ser Gly Tyr Thr Phe Thr
            20                  25                  30

<210> SEQ ID NO 457
<211> LENGTH: 14
<212> TYPE: PRT
<213> ORGANISM: Mus musculus

<400> SEQUENCE: 457

Trp Val Lys Gln Arg Pro Gly Gln Gly Leu Glu Trp Ile Gly
1               5                   10

<210> SEQ ID NO 458
<211> LENGTH: 32
<212> TYPE: PRT
<213> ORGANISM: Mus musculus

<400> SEQUENCE: 458

Lys Ala Thr Leu Thr Val Asp Glu Ser Ser Ser Thr Ala Tyr Met Gln
1               5                   10                  15

Leu Ser Ser Leu Thr Ser Glu Asp Ser Ala Val Tyr Phe Cys Ala Arg
            20                  25                  30

<210> SEQ ID NO 459
<211> LENGTH: 11
<212> TYPE: PRT

```
<213> ORGANISM: Mus musculus

<400> SEQUENCE: 459

Trp Gly Gln Gly Thr Thr Leu Thr Val Ser Ser
1               5                   10


<210> SEQ ID NO 460
<211> LENGTH: 321
<212> TYPE: DNA
<213> ORGANISM: Mus musculus

<400> SEQUENCE: 460

gacattgtga tgacccagtc tcaaaaattc atgtccacat cagtaggaga cagggtcagc      60

gtcacctgca aggccagtca gaatgtgggt actgctgtag cctggtatca aaagaaacca     120

ggacaatctc ctaaagcact gatttactcg gcatccaccc ggtacactgg agtccctgat     180

cgcttcacag gcagtggatc tgggacagat ttcactctca ccatcagcaa tgtgcagtct     240

gaagacttgg cagagtattt ctgtcagcaa tatagcagct ctccgtggac gttcggtgga     300

ggcaccaagc tggaactcaa a                                               321


<210> SEQ ID NO 461
<211> LENGTH: 107
<212> TYPE: PRT
<213> ORGANISM: Mus musculus

<400> SEQUENCE: 461

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Ala
            20                  25                  30

Val Ala Trp Tyr Gln Lys Lys Pro Gly Gln Ser Pro Lys Ala Leu Ile
        35                  40                  45

Tyr Ser Ala Ser Thr Arg Tyr Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Ser Ser Ser Pro Trp
                85                  90                  95

Thr Phe Gly Gly Gly Thr Lys Leu Glu Leu Lys
            100                 105


<210> SEQ ID NO 462
<211> LENGTH: 11
<212> TYPE: PRT
<213> ORGANISM: Mus musculus

<400> SEQUENCE: 462

Lys Ala Ser Gln Asn Val Gly Thr Ala Val Ala
1               5                   10


<210> SEQ ID NO 463
<211> LENGTH: 7
<212> TYPE: PRT
<213> ORGANISM: Mus musculus

<400> SEQUENCE: 463

Ser Ala Ser Thr Arg Tyr Thr
1               5
```

<210> SEQ ID NO 464
<211> LENGTH: 9
<212> TYPE: PRT
<213> ORGANISM: Mus musculus

<400> SEQUENCE: 464

Gln Gln Tyr Ser Ser Ser Pro Trp Thr
1 5

<210> SEQ ID NO 465
<211> LENGTH: 23
<212> TYPE: PRT
<213> ORGANISM: Mus musculus

<400> SEQUENCE: 465

Asp Ile Val Met Thr Gln Ser Gln Lys Phe Met Ser Thr Ser Val Gly
1 5 10 15

Asp Arg Val Ser Val Thr Cys
20

<210> SEQ ID NO 466
<211> LENGTH: 15
<212> TYPE: PRT
<213> ORGANISM: Mus musculus

<400> SEQUENCE: 466

Trp Tyr Gln Lys Lys Pro Gly Gln Ser Pro Lys Ala Leu Ile Tyr
1 5 10 15

<210> SEQ ID NO 467
<211> LENGTH: 32
<212> TYPE: PRT
<213> ORGANISM: Mus musculus

<400> SEQUENCE: 467

Gly Val Pro Asp Arg Phe Thr Gly Ser Gly Ser Gly Thr Asp Phe Thr
1 5 10 15

Leu Thr Ile Ser Asn Val Gln Ser Glu Asp Leu Ala Glu Tyr Phe Cys
20 25 30

<210> SEQ ID NO 468
<211> LENGTH: 10
<212> TYPE: PRT
<213> ORGANISM: Mus musculus

<400> SEQUENCE: 468

Phe Gly Gly Gly Thr Lys Leu Glu Leu Lys
1 5 10

<210> SEQ ID NO 469
<211> LENGTH: 308
<212> TYPE: PRT
<213> ORGANISM: Artificial Sequence
<220> FEATURE:
<223> OTHER INFORMATION: Synthetic Peptide

<400> SEQUENCE: 469

Met Pro Gly Gln Glu Leu Arg Thr Val Asn Gly Ser Gln Met Leu Leu
1 5 10 15

Val Leu Leu Val Leu Ser Trp Leu Pro His Gly Gly Ala Leu Ser Leu
20 25 30

Ala Glu Ala Ser Arg Ala Ser Phe Pro Gly Pro Ser Glu Leu His Ser
35 40 45

```
Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300

Cys His Cys Ile
305


<210> SEQ ID NO 470
<211> LENGTH: 308
<212> TYPE: PRT
<213> ORGANISM: Artificial Sequence
<220> FEATURE:
<223> OTHER INFORMATION: Synthetic Peptide

<400> SEQUENCE: 470

Met Pro Gly Gln Glu Leu Lys Thr Leu Asn Gly Ser Gln Met Leu Leu
1               5                   10                  15

Val Leu Leu Val Leu Leu Trp Pro Pro His Gly Gly Ala Val Ser Leu
            20                  25                  30

Ala Glu Ala Ser Arg Ala Ser Phe Pro Gly Pro Ser Asp Leu His Ser
        35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Ile Gln Ala Pro Glu Val Arg Ile Leu Thr Pro Glu Val Arg Leu Gly
                85                  90                  95
```

```
Ser Gly Gly His Leu His Leu Arg Ile Ser Arg Ala Val Leu Pro Glu
            100                 105                 110

Gly Leu Pro Glu Ala Cys Arg Ile His Arg Ala Leu Phe Arg Leu Ser
        115                 120                 125

Pro Thr Ala Ser Arg Ser Arg Asp Val Thr Arg Pro Leu Arg Arg Gln
    130                 135                 140

Leu Arg Leu Ala Arg Pro Gln Ala Pro Ala Leu His Leu Arg Leu Ser
145                 150                 155                 160

Pro Pro Pro Ser Gln Ser Asp Gln Leu Leu Val Lys Ser Ser Ser Ser
                165                 170                 175

Arg Pro Gln Leu Ala Leu His Leu Arg Pro Arg Ala Ser Arg Gly Arg
            180                 185                 190

Arg Arg Ala Arg Ala Arg Asn Gly Asp Arg Cys Pro Leu Gly Pro Gly
        195                 200                 205

Arg Cys Cys Arg Leu His Thr Val His Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Glu Ala Asn Met His Ala Gln
                245                 250                 255

Ile Lys Met Asn Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300

Cys His Cys Val
305


<210> SEQ ID NO 471
<211> LENGTH: 308
<212> TYPE: PRT
<213> ORGANISM: Artificial Sequence
<220> FEATURE:
<223> OTHER INFORMATION: Synthetic Peptide

<400> SEQUENCE: 471

Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Ser
        35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140
```

Leu Ser Leu Ala Arg Pro Gln Ala Pro Ala Leu His Leu Arg Leu Ser
145 150 155 160

Pro Pro Pro Ser Gln Ser Asp Gln Leu Leu Ala Glu Ser Ser Ser Ala
165 170 175

Arg Pro Gln Leu Glu Leu His Leu Arg Pro Gln Ala Ala Arg Gly Arg
180 185 190

Arg Arg Ala Arg Ala Arg Asn Gly Asp Asp Cys Pro Leu Gly Pro Gly
195 200 205

Arg Cys Cys Arg Leu His Thr Val Arg Ala Ser Leu Glu Asp Leu Gly
210 215 220

Trp Ala Asp Trp Val Leu Ser Pro Arg Glu Val Gln Val Thr Met Cys
225 230 235 240

Ile Gly Ala Cys Pro Ser Gln Phe Arg Ala Ala Asn Met His Ala Gln
245 250 255

Ile Lys Thr Ser Leu His Arg Leu Lys Pro Asp Thr Val Pro Ala Pro
260 265 270

Cys Cys Val Pro Ala Ser Tyr Asn Pro Met Val Leu Ile Gln Lys Thr
275 280 285

Asp Thr Gly Val Ser Leu Gln Thr Tyr Asp Asp Leu Leu Ala Lys Asp
290 295 300

Cys His Cys Ile
305

<210> SEQ ID NO 472
<211> LENGTH: 303
<212> TYPE: PRT
<213> ORGANISM: Artificial Sequence
<220> FEATURE:
<223> OTHER INFORMATION: Synthetic Peptide

<400> SEQUENCE: 472

Met Ala Pro Pro Ala Leu Gln Ala Gln Pro Pro Gly Gly Ser Gln Leu
1 5 10 15

Arg Phe Leu Leu Phe Leu Leu Leu Leu Leu Leu Leu Leu Ser Trp Pro
20 25 30

Ser Gln Gly Asp Ala Leu Ala Met Pro Glu Gln Arg Pro Ser Gly Pro
35 40 45

Glu Ser Gln Leu Asn Ala Asp Glu Leu Arg Gly Arg Phe Gln Asp Leu
50 55 60

Leu Ser Arg Leu His Ala Asn Gln Ser Arg Glu Asp Ser Asn Ser Glu
65 70 75 80

Pro Ser Pro Asp Pro Ala Val Arg Ile Leu Ser Pro Glu Val Arg Leu
85 90 95

Gly Ser His Gly Gln Leu Leu Leu Arg Val Asn Arg Ala Ser Leu Ser
100 105 110

Gln Gly Leu Pro Glu Ala Tyr Arg Val His Arg Ala Leu Leu Leu Leu
115 120 125

Thr Pro Thr Ala Arg Pro Trp Asp Ile Thr Arg Pro Leu Lys Arg Ala
130 135 140

Leu Ser Leu Arg Gly Pro Arg Ala Pro Ala Leu Arg Leu Arg Leu Thr
145 150 155 160

Pro Pro Pro Asp Leu Ala Met Leu Pro Ser Gly Gly Thr Gln Leu Glu
165 170 175

Leu Arg Leu Arg Val Ala Ala Gly Arg Gly Arg Arg Ser Ala His Ala
180 185 190

```
His Pro Arg Asp Ser Cys Pro Leu Gly Pro Gly Arg Cys Cys His Leu
        195                 200                 205

Glu Thr Val Gln Ala Thr Leu Glu Asp Leu Gly Trp Ser Asp Trp Val
    210                 215                 220

Leu Ser Pro Arg Gln Leu Gln Leu Ser Met Cys Val Gly Glu Cys Pro
225                 230                 235                 240

His Leu Tyr Arg Ser Ala Asn Thr His Ala Gln Ile Lys Ala Arg Leu
                245                 250                 255

His Gly Leu Gln Pro Asp Lys Val Pro Ala Pro Cys Cys Val Pro Ser
            260                 265                 270

Ser Tyr Thr Pro Val Val Leu Met His Arg Thr Asp Ser Gly Val Ser
        275                 280                 285

Leu Gln Thr Tyr Asp Asp Leu Val Ala Arg Gly Cys His Cys Ala
    290                 295                 300


<210> SEQ ID NO 473
<211> LENGTH: 330
<212> TYPE: PRT
<213> ORGANISM: Artificial Sequence
<220> FEATURE:
<223> OTHER INFORMATION: Human IgG1 (heavy)

<400> SEQUENCE: 473

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 474
<211> LENGTH: 330
<212> TYPE: PRT
<213> ORGANISM: Artificial Sequence
<220> FEATURE:
<223> OTHER INFORMATION: Human IgG1 TM F allotype (heavy)

<400> SEQUENCE: 474

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 475
<211> LENGTH: 107
<212> TYPE: PRT
<213> ORGANISM: Artificial Sequence
<220> FEATURE:
<223> OTHER INFORMATION: Human kappa (light)

<400> SEQUENCE: 475

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 476
<211> LENGTH: 324
<212> TYPE: PRT
<213> ORGANISM: Artificial Sequence
<220> FEATURE:
<223> OTHER INFORMATION: Murine IgG1 (heavy)

<400> SEQUENCE: 476

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160
```

```
Val His Thr Ala Gln Thr Lys Pro Arg Glu Glu Gln Ile Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys


<210> SEQ ID NO 477
<211> LENGTH: 324
<212> TYPE: PRT
<213> ORGANISM: Artificial Sequence
<220> FEATURE:
<223> OTHER INFORMATION: Murine D265A IgG1 (heavy)

<400> SEQUENCE: 477

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Ala Ile Ser
    130                 135                 140

Lys Asp Asp Pro Glu Val Gln Phe Ser Trp Phe Val Asp Asp Val Glu
145                 150                 155                 160

Val His Thr Ala Gln Thr Lys Pro Arg Glu Glu Gln Ile Asn Ser Thr
                165                 170                 175

Phe Arg Ser Val Ser Glu Leu Pro Ile Met His Gln Asp Trp Leu Asn
            180                 185                 190
```

```
Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys


<210> SEQ ID NO 478
<211> LENGTH: 107
<212> TYPE: PRT
<213> ORGANISM: Artificial Sequence
<220> FEATURE:
<223> OTHER INFORMATION: Murine kappa (light)

<400> SEQUENCE: 478

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105


<210> SEQ ID NO 479
<211> LENGTH: 112
<212> TYPE: PRT
<213> ORGANISM: Artificial Sequence
<220> FEATURE:
<223> OTHER INFORMATION: Mature GDF-15

<400> SEQUENCE: 479

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60
```

```
Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110


<210> SEQ ID NO 480
<211> LENGTH: 112
<212> TYPE: PRT
<213> ORGANISM: Artificial Sequence
<220> FEATURE:
<223> OTHER INFORMATION: Mature GDF-15 H202D

<400> SEQUENCE: 480

Ala Arg Asn Gly Asp Asp Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110


<210> SEQ ID NO 481
<211> LENGTH: 990
<212> TYPE: DNA
<213> ORGANISM: Artificial Sequence
<220> FEATURE:
<223> OTHER INFORMATION: Human IgG1 TM F allotype (heavy)

<400> SEQUENCE: 481

gcctccacca agggcccatc ggtcttcccc ctggcaccct cctccaagag cacctctggg      60

ggcacagcgg ccctgggctg cctggtcaag gactacttcc ccgaaccggt gacggtgtcg     120

tggaactcag gcgccctgac cagcggcgtg cacaccttcc cggctgtcct acagtcctca     180

ggactctact ccctcagcag cgtggtgaca gtgccctcca gcagcttggg cacccagacc     240

tacatctgca acgtgaatca caagcccagc aacaccaagg tggacaagag agttgagccc     300

aaatcttgtg acaaaactca cacatgccca ccgtgcccag cacctgaatt cgaggggggga     360

ccgtcagtct tcctcttccc cccaaaaccc aaggacaccc tcatgatctc ccggacccct     420

gaggtcacat gcgtggtggt ggacgtgagc cacgaagacc ctgaggtcaa gttcaactgg     480

tacgtggacg gcgtggaggt gcataatgcc aagacaaagc cgcgggagga gcagtacaac     540

agcacgtacc gtgtggtcag cgtcctcacc gtcctgcacc aggactggct gaatggcaag     600

gagtacaagt gcaaggtctc caacaaagcc ctcccagcct ccatcgagaa aaccatctcc     660

aaagccaaag ggcagccccg agaaccacag gtgtacaccc tgcccccatc ccgggaggag     720

atgaccaaga accaggtcag cctgacctgc ctggtcaaag gcttctatcc cagcgacatc     780

gccgtggagt gggagagcaa tgggcagccg gagaacaact acaagaccac gcctcccgtg     840

ctggactccg acggctcctt cttcctctat agcaagctca ccgtggacaa gagcaggtgg     900
```

cagcagggga acgtcttctc atgctccgtg atgcatgagg ctctgcacaa ccactacacg 960
cagaagagcc tctccctgtc tccgggtaaa 990

<210> SEQ ID NO 482
<211> LENGTH: 321
<212> TYPE: DNA
<213> ORGANISM: Artificial Sequence
<220> FEATURE:
<223> OTHER INFORMATION: Human kappa (light)

<400> SEQUENCE: 482
cgaactgtgg ctgcaccatc tgtcttcatc ttcccgccat ctgatgagca gttgaaatct 60
ggaactgcct ctgttgtgtg cctgctgaat aacttctatc ccagagaggc caaagtacag 120
tggaaggtgg ataacgccct ccaatcgggt aactcccagg agagtgtcac agagcaggac 180
agcaaggaca gcacctacag cctcagcagc accctgacgc tgagcaaagc agactacgag 240
aaacacaaag tctacgcctg cgaagtcacc catcagggcc tgagctcgcc cgtcacaaag 300
agcttcaaca ggggagagtg t 321

<210> SEQ ID NO 483
<211> LENGTH: 972
<212> TYPE: DNA
<213> ORGANISM: Artificial Sequence
<220> FEATURE:
<223> OTHER INFORMATION: Murine D265A IgG1 (heavy)

<400> SEQUENCE: 483
gccaaaacga cacccccttc cgtgtaccct ctggcccctg gctctgccgc ccagaccaac 60
tccatggtca cactgggctg cctggtcaag ggctacttcc ctgagcctgt gaccgtgacc 120
tggaactccg gctccctgtc ctccggcgtg catacccttcc ctgccgtgct gcagtccgac 180
ctgtacaccc tgtccagctc cgtgaccgtg ccttcctcca cctggccttc ccagaccgtg 240
acatgcaacg tggcccaccc tgccagcagc accaaggtgg acaagaaaat tgtgcccagg 300
gattgtggtt gtaagccttg catatgcaca gtcccagaag tatcatccgt ctttatcttc 360
cctcctaagc ctaaggacgt gctgaccatc accctgacac ctaaggtcac atgcgtggtg 420
gtggccatct ccaaggacga tcctgaggtg cagttcagtt ggttcgtgga cgacgtggag 480
gtccacaccg ctcagaccaa gcctcgggaa gagcagatca actccacctt cagatccgtg 540
tccgagctgc ctatcatgca ccaggactgg ctgaacggca aagagttcaa gtgcagagtc 600
aacagcgccg ccttccctgc tcccatcgag aaaaccatct ccaaaaccaa aggcagaccg 660
aaggctccac aggtgtacac cattccacct cctaaagagc agatggccaa ggacaaggtg 720
tccctgacct gcatgatcac cgatttcttc cctgaggaca tcaccgtgga gtggcagtgg 780
aacggccagc ctgccgagaa ctacaagaat acccagccca tcatggacac cgacggctcc 840
tacttcgtgt actccaagct gaacgtgcag aagtccaact gggaggccgg caacaccttc 900
acctgtagcg tgctgcacga gggcctgcac aaccaccaca ccgagaagtc cctgtcccac 960
tcccccggca ag 972

<210> SEQ ID NO 484
<211> LENGTH: 321
<212> TYPE: DNA
<213> ORGANISM: Artificial Sequence
<220> FEATURE:
<223> OTHER INFORMATION: Murine kappa (light)

-continued

```
<400> SEQUENCE: 484

cgggctgatg ctgcaccaac cgtgtccatc ttccctccct cctccgagca gctgacctct     60

ggcggcgctt ccgtcgtctg cttcctgaac aacttctacc ccaaggacat caacgtgaag    120

tggaagatcg acggctccga gcggcagaac ggcgtgctga actcctggac cgaccaggac    180

tccaaggaca gcacctactc catgtcctcc accctgaccc tgaccaagga cgagtacgag    240

cggcacaact cctacacctg cgaggccacc cacaagacct ccacctcccc catcgtgaag    300

tccttcaacc ggaacgagtg c                                              321


<210> SEQ ID NO 485
<211> LENGTH: 8
<212> TYPE: PRT
<213> ORGANISM: Artificial Sequence
<220> FEATURE:
<223> OTHER INFORMATION: Synthetic sequence

<400> SEQUENCE: 485

Glu Asp Leu Gly Trp Ala Asp Trp
1               5


<210> SEQ ID NO 486
<211> LENGTH: 8
<212> TYPE: PRT
<213> ORGANISM: Artificial Sequence
<220> FEATURE:
<223> OTHER INFORMATION: Synthetic sequence

<400> SEQUENCE: 486

Val Leu Ser Pro Arg Glu Val Gln
1               5


<210> SEQ ID NO 487
<211> LENGTH: 17
<212> TYPE: PRT
<213> ORGANISM: Artificial Sequence
<220> FEATURE:
<223> OTHER INFORMATION: Synthetic sequence

<400> SEQUENCE: 487

Ile Gln Lys Thr Asp Thr Gly Val Ser Leu Gln Thr Tyr Asp Asp Leu
1               5                   10                  15

Leu
```